US009040549B2

(12) United States Patent
Bourke et al.

(10) Patent No.: US 9,040,549 B2
(45) Date of Patent: May 26, 2015

(54) THIOPYRIMIDINE-BASED COMPOUNDS AND USES THEREOF

(71) Applicant: Cytopia Research Pty Ltd., Richmond, Victoria (AU)

(72) Inventors: David Gerard Bourke, Donvale (AU); Xianyong Bu, Parkville (AU); Christopher John Burns, Caulfield North (AU); Anthony Nicholas Cuzzupe, Parkville (AU); John Thomas Feutrill, Rosanna (AU); Tracy Leah Nero, St. Albans (AU); Beata Maria Blannin, Seabrook (AU); Jun Zeng, Scoresby (AU); Shaun Patrick Gaynor, Richmond (AU)

(73) Assignee: YM Biosciences Australia Pty Ltd., Foster City, CA (US)

( * ) Notice: Subject to any disclaimer, the term of this patent is extended or adjusted under 35 U.S.C. 154(b) by 0 days.

(21) Appl. No.: 13/861,344

(22) Filed: Apr. 11, 2013

(65) Prior Publication Data
US 2014/0051703 A1 Feb. 20, 2014

Related U.S. Application Data

(63) Continuation of application No. 12/524,849, filed as application No. PCT/AU2008/000103 on Jan. 31, 2008.

(60) Provisional application No. 60/898,898, filed on Jan. 31, 2007.

(51) Int. Cl.
| | | |
|---|---|---|
| *A61K 31/505* | (2006.01) | |
| *A61K 31/506* | (2006.01) | |
| *C07D 413/12* | (2006.01) | |
| *C07D 487/00* | (2006.01) | |
| *C07D 487/02* | (2006.01) | |
| *C07D 239/38* | (2006.01) | |
| *C07D 239/47* | (2006.01) | |
| *C07D 401/12* | (2006.01) | |
| *C07D 401/14* | (2006.01) | |
| *C07D 403/12* | (2006.01) | |
| *C07D 405/12* | (2006.01) | |
| *C07D 413/14* | (2006.01) | |
| *C07D 417/12* | (2006.01) | |
| *C07D 417/14* | (2006.01) | |

(52) U.S. Cl.
CPC ............. *C07D 413/12* (2013.01); *A61K 31/505* (2013.01); *C07D 487/00* (2013.01); *C07D 487/02* (2013.01); *A61K 31/506* (2013.01); *C07D 239/38* (2013.01); *C07D 239/47* (2013.01); *C07D 401/12* (2013.01); *C07D 401/14* (2013.01); *C07D 403/12* (2013.01); *C07D 405/12* (2013.01); *C07D 413/14* (2013.01); *C07D 417/12* (2013.01); *C07D 417/14* (2013.01)

(58) Field of Classification Search
CPC .. C07D 413/12; C07D 413/14; C07D 403/12; C07D 419/14; C07D 239/38; C07D 239/47; C07D 417/12; C07D 487/02
USPC ....................................................... 514/272
See application file for complete search history.

(56) References Cited

U.S. PATENT DOCUMENTS

| | | | |
|---|---|---|---|
| 3,974,162 A | 8/1976 | Santilli et al. | |
| 2004/0063737 A1 | 4/2004 | Lucking et al. | |
| 2010/0239631 A1 | 9/2010 | Bourke et al. | |
| 2014/0045848 A1* | 2/2014 | Bourke et al. ............. | 514/235.8 |

FOREIGN PATENT DOCUMENTS

| | | | | |
|---|---|---|---|---|
| AU | 545 178 B2 | 7/1985 | | |
| DE | 3205638 A1 | 8/1983 | | |
| DE | 3436380 A1 | 4/1986 | | |
| DE | 3625168 A1 | 1/1988 | | |
| DE | 37 23 041 A1 | 1/1989 | | |
| DE | 41 39 624 A1 | 6/1993 | | |
| EP | 0 665 224 A1 | 8/1995 | | |
| FR | 1 536 093 A | 8/1968 | | |
| GB | 1191178 A | 5/1970 | | |
| JP | S63-35565 A | 2/1988 | | |
| WO | WO 97/19065 * | 5/1997 | ........... | C07D 239/42 |
| WO | WO-97/19065 A1 | 5/1997 | | |
| WO | WO 98/41512 * | 9/1998 | ........... | C07D 239/46 |
| WO | WO-98/41512 A1 | 9/1998 | | |
| WO | WO-01/64653 A1 | 9/2001 | | |
| WO | WO-02/46172 A2 | 6/2002 | | |
| WO | WO-02/46172 A3 | 6/2002 | | |
| WO | WO-2005/016348 A1 | 2/2005 | | |

(Continued)

OTHER PUBLICATIONS

Sen, et al., Sustained Src Inhibition Results in Signal Transducer and Activator of Transcription 3 (STAT3) Activation and Cancer Cell Survival via Altered Janus-Activated Kinase-STAT3 Binding, Cancer Res, 69 (5), 1958-1965 (2009).*

(Continued)

Primary Examiner — Erich A Leeser
(74) Attorney, Agent, or Firm — Yu-Ming Dammann

(57) ABSTRACT

The present invention relates to thiopyrimidine-based compounds that are inhibitors of protein kinases including JAK kinases. In particular, the compounds are selective for JAK1, JAK2 or JAK3 kinases and combinations thereof such as JAK1 and JAK2. The kinase inhibitors can be used in the treatment of kinase associated diseases such as immunological and inflammatory diseases including organ transplants; hyperproliferative diseases including cancer and myeloproliferative diseases; viral diseases; metabolic diseases and vascular diseases.

10 Claims, 2 Drawing Sheets

(56) References Cited

FOREIGN PATENT DOCUMENTS

| WO | WO-2005/039506 A2 | 5/2005 |
|---|---|---|
| WO | WO-2006/059234 A2 | 6/2006 |
| WO | WO-2008/092199 A1 | 8/2008 |

OTHER PUBLICATIONS

Banker, G.S. et al., eds. (1996). *Modern Pharmaceutics*, Third Edition, Marcel Dekker, New York.
Buettner et al., "Activated STAT Signaling in Human Tumors Provides Novel Molecular Targets for Therapeutic Intervention," Clinical Cancer Research (2002) 3:945-954.
Duhe et al., "Negative Regulation of Janus Kinases," Cell Biochemistry and Biophysics (2001) 34:17-59.
Gust, R. et al. (2001). "Vascular Remodeling in Experimentally Induced Subacute Canine Pulmonary Hypertension," *Experimental Lung Research* 27:1-12.
Hirata, M. et al. (1972). Synthesis of N1-(5-Halogenopyrimidinyl)sulfanilamide Derivatives, *Yakugaku Zasshi* 92(3):288-298.
Ishihara et al., "IL-6 in autoimmune disease and chronic inflammatory proliferative disease," Cytokine & Growth Factor Reviews (2002) 13:357-368.
March, J. (1992). "Aliphatic Nucleophilic Substitution," in *Advanced Organic Chemistry: Reactions, Mechanisms, and Structure*, 4th Edition, John Wiley & Sons, New York, pp. 352-357.
Okajima, N., "Synthesis and reaction of 2-imino-1,3-thiazetidines and 2-imino-1,3-dithietanes," *J. Het. Chem.* 1991, 28(1), 177-185.
Radics, U. et al. (1986). "Synthesis of Substituted 2-Amino-4-Benzylthio-1,3,5-Triazines from Isothiuronium Salts and Carboxylic Anhydrides," *Zeitschrift fuer Chemie* 26(12):435-437, STN Database Accession No. 1987:598262. (Chemical Abstract only).
Sen, B. et al. (2009). "Sustained Src Inhibition Results in Signal Transducer and Activator of Transcription 3 (STAT3) Activation and Cancer Cell Survival via Altered Janus-Activated Kinase-STAT3 Binding," *Cancer Research* 69(5):1958-1965.
Tsujikawa, T. et al. (1975). "Studies on Heterocyclic Compounds. II. Syntheses of 1,3,5-Triazine Derivatives and Their Pharmacological Activities," *Yakugaku Zasshi* 95(5):512-520, STN Database accession No. 1975:593237. (Chemical Abstract and English Summary on p. 512).
Von Angerer, S. (2004). "Product Subclass 3: 1,3,5-Triazines and Phosphorus Analogues," vol. 17: Six-Membered Hetarenes with Two Unlike or More Than Two Heteroatoms and Fully Unsaturated Larger-Ring Heterocycles in *Science of Synthesis*: Houben-Weyl Methods of Molecular Transformations, Chapter 17.2.3, pp. 449-583.
Wolff, M.E ed. (1995). *Burger's Medicinal Chemistry and Drug Discovery*, Fifth Ed., vol. 1: Principles and Practice, John Wiley & Sons, p. 975.
Yadav, J.S. et al. (2007, e-pub. May 31, 2007). "Iodine/MeOH as a Novel and Versatile Reagent System for the Synthesis of α-ketothiocyanates," *Tetrahedron Letters* 48:5243-5246.
International Search Report for PCT/AU2008/000103, mailed on Apr. 9, 2008, 3 pages.
Written Opinion mailed on Apr. 9, 2008 for PCT Patent Application No. PCT/AU2008/000103, filed on Jan. 31, 2008, 5 pages.
Final Office Action mailed on Sep. 21, 2012 for U.S. Appl. No. 12/524,849, filed Nov. 20, 2009, 11 pages.
Non-Final Office Action mailed on Apr. 2, 2012 for U.S. Appl. No. 12/524,849, filed Nov. 20, 2009, 13 pages.
Notice of Allowance mailed on Jan. 14, 2013 for U.S. Appl. No. 12/524,849, filed Nov. 20, 2009, 7 pages.
Australian Office Action mailed on Apr. 5, 2012 for AU Patent Application No. 2008210266, filed on Jan. 31, 2008, 3 pages.
Canadian Office Action mailed on Dec. 16, 2013 for CA Patent Application No. 2,702,647 filed on Jan. 31, 2008, 3 pages.
Extended European Search Report mailed on Jan. 27, 2012 for EP Patent Application No. 08700399.2, filed on Jan. 31, 2008, 11 pages.
English Translation of Office Action in Japanese Patent Application No. 2009-547489 mailed Feb. 19, 2013.

\* cited by examiner

Figure 1

SEQUENCE LISTING

<160> NUMBER OF SEQ ID NOS: 18

<210> SEQ ID NO 1
<211> LENGTH: 300
<212> TYPE: PRT
<213> ORGANISM: Homo sapiens
<220> FEATURE:
<223> OTHER INFORMATION: JAK2 Kinase j2h

<400> SEQUENCE: 1

```
Ser Gly Ala Phe Glu Asp Arg Asp Pro Thr Gln Phe Glu Glu Arg His
1               5                   10                  15

Leu Lys Phe Leu Gln Gln Leu Gly Lys Gly Asn Phe Gly Ser Val Glu
            20                  25                  30

Met Cys Arg Tyr Asp Pro Leu Gln Asp Asn Thr Gly Glu Val Val Ala
        35                  40                  45

Val Lys Lys Leu Gln His Ser Thr Glu Glu His Leu Arg Asp Phe Glu
50                  55                  60

Arg Glu Ile Glu Ile Leu Lys Ser Leu Gln His Asp Asn Ile Val Lys
65                  70                  75                  80

Tyr Lys Gly Val Cys Tyr Ser Ala Gly Arg Arg Asn Leu Lys Leu Ile
                85                  90                  95

Met Glu Tyr Leu Pro Tyr Gly Ser Leu Arg Asp Tyr Leu Gln Lys His
            100                 105                 110

Lys Glu Arg Ile Asp His Ile Lys Leu Leu Gln Tyr Thr Ser Gln Ile
        115                 120                 125

Cys Lys Gly Met Glu Tyr Leu Gly Thr Lys Arg Tyr Ile His Arg Asp
130                 135                 140

Leu Ala Thr Arg Asn Ile Leu Val Glu Asn Glu Asn Arg Val Lys Ile
145                 150                 155                 160

Gly Asp Phe Gly Leu Thr Lys Val Leu Pro Gln Asp Lys Glu Tyr Tyr
                165                 170                 175

Lys Val Lys Glu Pro Gly Glu Ser Pro Ile Phe Trp Tyr Ala Pro Glu
            180                 185                 190

Ser Leu Thr Glu Ser Lys Phe Ser Val Ala Ser Asp Val Trp Ser Phe
        195                 200                 205

Gly Val Val Leu Tyr Glu Leu Phe Thr Tyr Ile Glu Lys Ser Lys Ser
210                 215                 220

Pro Pro Ala Glu Phe Met Arg Met Ile Gly Asn Asp Lys Gln Gly Gln
225                 230                 235                 240

Met Ile Val Phe His Leu Ile Glu Leu Leu Lys Asn Asn Gly Arg Leu
                245                 250                 255

Pro Arg Pro Asp Gly Cys Pro Asp Glu Ile Tyr Met Ile Met Thr Glu
            260                 265                 270

Cys Trp Asn Asn Asn Val Asn Gln Arg Pro Ser Phe Arg Asp Leu Ala
        275                 280                 285

Leu Arg Val Asp Gln Ile Arg Asp Asn Met Ala Gly
290                 295                 300

<210> SEQ ID NO 2
<211> LENGTH: 295
<212> TYPE: PRT
<213> ORGANISM: Homo sapiens
<220> FEATURE:
<223> OTHER INFORMATION: JAK1 Kinase j1h

<400> SEQUENCE: 2

Lys Asn Gln Pro Thr Glu Val Asp Pro Thr His Phe Glu Lys Arg Phe
1               5                   10                  15

Leu Lys Arg Ile Arg Asp Leu Gly Glu Gly His Phe Gly Lys Val Glu
            20                  25                  30

Leu Cys Arg Tyr Asp Pro Glu Asp Asn Thr Gly Glu Gln Val Ala Val
        35                  40                  45

Lys Ser Leu Lys Pro Glu Ser Gly Gly Asn His Ile Ala Asp Leu Lys
50                  55                  60
```

```
Lys Glu Ile Glu Ile Leu Arg Asn Leu Tyr His Asn Ile Val Lys
 65                  70                  75                  80

Tyr Lys Gly Ile Cys Thr Glu Asp Gly Gly Asn Gly Ile Lys Leu Ile
                 85                  90                  95

Met Glu Phe Leu Pro Ser Gly Ser Leu Lys Glu Tyr Leu Pro Lys Asn
            100                 105                 110

Lys Asn Lys Ile Asn Leu Lys Gln Gln Leu Lys Tyr Ala Val Gln Ile
        115                 120                 125

Cys Lys Gly Met Asp Tyr Leu Gly Ser Arg Gln Tyr Val His Arg Asp
    130                 135                 140

Leu Ala Ala Arg Asn Val Leu Val Glu Ser Glu His Gln Val Lys Ile
145                 150                 155                 160

Gly Asp Phe Gly Leu Thr Lys Ala Ile Glu Thr Asp Lys Glu Tyr Tyr
                165                 170                 175

Thr Val Lys Asp Asp Arg Asp Ser Pro Val Phe Trp Tyr Ala Pro Glu
            180                 185                 190

Cys Leu Met Gln Ser Lys Phe Tyr Ile Ala Ser Asp Val Trp Ser Phe
        195                 200                 205

Gly Val Thr Leu His Glu Leu Leu Thr Tyr Cys Asp Ser Asp Ser Ser
    210                 215                 220

Pro Met Ala Leu Phe Leu Lys Met Ile Gly Pro Thr His Gly Gln Met
225                 230                 235                 240

Thr Val Thr Arg Leu Val Asn Thr Leu Lys Glu Gly Lys Arg Leu Pro
                245                 250                 255

Cys Pro Pro Asn Cys Pro Asp Glu Val Tyr Gln Leu Met Arg Lys Cys
            260                 265                 270

Trp Glu Phe Gln Pro Ser Asn Arg Thr Ser Phe Gln Asn Leu Ile Glu
        275                 280                 285

Gly Phe Glu Ala Leu Leu Lys
    290                 295

<210> SEQ ID NO 3
<211> LENGTH: 299
<212> TYPE: PRT
<213> ORGANISM: Homo sapiens
<220> FEATURE:
<223> OTHER INFORMATION: JAK3 Kinase j3h

<400> SEQUENCE: 3

Ala Gln Leu Tyr Ala Cys Gln Asp Pro Thr Ile Phe Glu Glu Arg His
  1               5                  10                  15

Leu Lys Tyr Ile Ser Gln Leu Gly Lys Gly Asn Phe Gly Ser Val Glu
             20                  25                  30

Leu Cys Arg Tyr Asp Pro Leu Ala His Asn Thr Gly Ala Leu Val Ala
         35                  40                  45

Val Lys Gln Leu Gln His Ser Gly Pro Asp Gln Arg Asp Phe Gln
     50                  55                  60

Arg Glu Ile Gln Ile Leu Lys Ala Leu His Ser Asp Phe Ile Val Lys
 65                  70                  75                  80

Tyr Arg Gly Val Ser Tyr Gly Pro Gly Arg Pro Glu Leu Arg Leu Val
                 85                  90                  95

Met Glu Tyr Leu Pro Ser Gly Cys Leu Arg Asp Phe Leu Gln Arg His
            100                 105                 110

Arg Ala Arg Leu Asp Ala Ser Arg Leu Leu Leu Tyr Ser Ser Gln Ile
        115                 120                 125
```

```
Cys Lys Gly Met Glu Tyr Leu Gly Ser Arg Arg Cys Val His Arg Asp
130                 135                 140

Leu Ala Ala Arg Asn Ile Leu Val Glu Ser Glu Ala His Val Lys Ile
145                 150                 155                 160

Ala Asp Phe Gly Leu Ala Lys Leu Leu Pro Leu Asp Lys Asp Tyr Tyr
                165                 170                 175

Val Val Arg Glu Pro Gly Gln Ser Pro Ile Phe Trp Tyr Ala Pro Glu
            180                 185                 190

Ser Leu Ser Asp Asn Ile Phe Ser Arg Gln Ser Asp Val Trp Ser Phe
        195                 200                 205

Gly Val Val Leu Tyr Glu Leu Phe Thr Tyr Cys Asp Lys Ser Cys Ser
    210                 215                 220

Pro Ser Ala Glu Phe Leu Arg Met Met Gly Cys Glu Arg Asp Val Pro
225                 230                 235                 240

Ala Leu Cys Arg Leu Leu Glu Leu Leu Glu Glu Gly Gln Arg Leu Pro
                245                 250                 255

Ala Pro Pro Ala Cys Pro Ala Glu Val His Glu Leu Met Lys Leu Cys
            260                 265                 270

Trp Ala Pro Ser Pro Gln Asp Arg Pro Ser Phe Ser Ala Leu Gly Pro
        275                 280                 285

Gln Leu Asp Met Leu Trp Ser Gly Ser Arg Gly
    290                 295

<210> SEQ ID NO 4
<211> LENGTH: 296
<212> TYPE: PRT
<213> ORGANISM: Homo sapiens
<220> FEATURE:
<223> OTHER INFORMATION: TYK2 Kinase tyk2

<400> SEQUENCE: 4

Asn Arg Asp Ser Pro Ala Val Gly Pro Thr Thr Phe His Lys Arg Tyr
1               5                   10                  15

Leu Lys Lys Ile Arg Asp Leu Gly Glu Gly His Phe Gly Lys Val Ser
            20                  25                  30

Leu Tyr Cys Tyr Asp Pro Thr Asn Asp Gly Thr Gly Glu Met Val Ala
        35                  40                  45

Val Lys Ala Leu Lys Ala Asp Cys Gly Pro Gln His Arg Ser Gly Trp
    50                  55                  60

Lys Gln Glu Ile Asp Ile Leu Arg Thr Leu Tyr His Glu His Ile Ile
65                  70                  75                  80

Lys Tyr Lys Gly Cys Cys Glu Asp Gln Gly Glu Lys Ser Leu Gln Leu
                85                  90                  95

Val Met Glu Tyr Val Pro Leu Gly Ser Leu Arg Asp Tyr Leu Pro Arg
            100                 105                 110

His Ser Ile Gly Leu Ala Gln Leu Leu Leu Phe Ala Gln Gln Ile Cys
        115                 120                 125

Glu Gly Met Ala Tyr Leu His Ala His Asp Tyr Ile His Arg Asp Leu
    130                 135                 140

Ala Ala Arg Asn Val Leu Leu Asp Asn Asp Arg Leu Val Lys Ile Gly
145                 150                 155                 160

Asp Phe Gly Leu Ala Lys Ala Val Pro Glu Gly His Glu Tyr Tyr Arg
                165                 170                 175

Val Arg Glu Asp Gly Asp Ser Pro Val Phe Trp Tyr Ala Pro Glu Cys
            180                 185                 190
```

```
Leu Lys Glu Tyr Lys Phe Tyr Tyr Ala Ser Asp Val Trp Ser Phe Gly
        195                 200                 205

Val Thr Leu Tyr Glu Leu Leu Thr His Cys Asp Ser Ser Gln Ser Pro
    210                 215                 220

Pro Thr Lys Phe Leu Glu Leu Ile Gly Ile Ala Gln Gly Gln Met Thr
225                 230                 235                 240

Val Leu Arg Leu Thr Glu Leu Leu Glu Arg Gly Glu Arg Leu Pro Arg
            245                 250                 255

Pro Asp Lys Cys Pro Cys Glu Val Tyr His Leu Met Lys Asn Cys Trp
            260                 265                 270

Glu Thr Glu Ala Ser Phe Arg Pro Thr Phe Glu Asn Leu Ile Pro Ile
        275                 280                 285

Leu Lys Thr Val His Glu Lys Tyr
        290                 295

<210> SEQ ID NO 5
<211> LENGTH: 30
<212> TYPE: DNA
<213> ORGANISM: Artificial Sequence
<220> FEATURE:
<223> OTHER INFORMATION: Primer XHOI-J1

<400> SEQUENCE: 5
ccgctcgaga ctgaagtgga ccccacacat                                    30

<210> SEQ ID NO 6
<211> LENGTH: 30
<212> TYPE: DNA
<213> ORGANISM: Artificial Sequence
<220> FEATURE:
<223> OTHER INFORMATION: Primer J1-KPNI

<400> SEQUENCE: 6
cggggtacct tattttaaaa gtgcttcaaa                                    30

<210> SEQ ID NO 7
<211> LENGTH: 31
<212> TYPE: DNA
<213> ORGANISM: Artificial Sequence
<220> FEATURE:
<223> OTHER INFORMATION: Primer SALI-jk2

<400> SEQUENCE: 7
acgcgtcgac ggtgcctttg aagaccggga t                                  31

<210> SEQ ID NO 8
<211> LENGTH: 34
<212> TYPE: DNA
<213> ORGANISM: Artificial Sequence
<220> FEATURE:
<223> OTHER INFORMATION: Primer jk2-NOTI

<400> SEQUENCE: 8
atagtttagc ggccgctcag aatgaaggtc attt                               34

<210> SEQ ID NO 9
<211> LENGTH: 30
<212> TYPE: DNA
<213> ORGANISM: Artificial Sequence
<220> FEATURE:
<223> OTHER INFORMATION: Primer XHOI-J3

<400> SEQUENCE: 9
```

```
ccgctcgagt atgcctgcca agaccccacg                                         30
```

<210> SEQ ID NO 10
<211> LENGTH: 30
<212> TYPE: DNA
<213> ORGANISM: Artificial Sequence
<220> FEATURE:
<223> OTHER INFORMATION: Primer J3-KPNI

<400> SEQUENCE: 10

```
cggggtaccc tatgaaaagg acagggagtg                                         30
```

<210> SEQ ID NO 11

<400> SEQUENCE: 11

000

<210> SEQ ID NO 12

<400> SEQUENCE: 12

000

<210> SEQ ID NO 13
<211> LENGTH: 17
<212> TYPE: PRT
<213> ORGANISM: Artificial Sequence
<220> FEATURE:
<223> OTHER INFORMATION: biotinylated substrate
<220> FEATURE:
<221> NAME/KEY: misc_feature
<222> LOCATION: 17
<223> OTHER INFORMATION: Phe modified by NH2

<400> SEQUENCE: 13

Glu Gly Pro Trp Leu Glu Glu Glu Glu Ala Tyr Gly Trp Met Asp
 1               5                  10                  15

Phe

<210> SEQ ID NO 14
<211> LENGTH: 30
<212> TYPE: DNA
<213> ORGANISM: Artificial Sequence
<220> FEATURE:
<223> OTHER INFORMATION: 5TEL primer

<400> SEQUENCE: 14

```
ggaggatcct gatctctctc gctgtgagac                                         30
```

<210> SEQ ID NO 15
<211> LENGTH: 28
<212> TYPE: DNA
<213> ORGANISM: Artificil Sequence
<220> FEATURE:
<223> OTHER INFORMATION: 3TEL primer

<400> SEQUENCE: 15

```
aggcgtcgac ttcttcttca tggttctg                                           28
```

<210> SEQ ID NO 16
<211> LENGTH: 31
<212> TYPE: DNA
<213> ORGANISM: Artificial Sequence
<220> FEATURE:
<223> OTHER INFORMATION: JAK2F primer

```
<400> SEQUENCE: 16
acgcgtcgac ggtgcctttg aagaccggga t                              31

<210> SEQ ID NO 17
<211> LENGTH: 34
<212> TYPE: DNA
<213> ORGANISM: Artificial Sequence
<220> FEATURE:
<223> OTHER INFORMATION: JAK2R primer

<400> SEQUENCE: 17
atagtttagc ggccgctcag aatgaaggtc attt                           34

<210> SEQ ID NO 18
<211> LENGTH: 35
<212> TYPE: DNA
<213> ORGANISM: Artificial Sequence
<220> FEATURE:
<223> OTHER INFORMATION: JAK3F primer

<400> SEQUENCE: 18
gaagtcgact atgcctgcca agacccacg atctt                           35
```

THIOPYRIMIDINE-BASED COMPOUNDS AND USES THEREOF

CROSS-REFERENCE TO RELATED APPLICATIONS

This application is a continuation of, and claims priority to, U.S. patent application Ser. No. 12/524,849, filed Nov. 20, 2009, which is the national phase of PCT Appln. No. PCT/AU2008/000103, filed Jan. 31, 2008, which in turn claims priority to U.S. Provisional Appln. No. 60/898,898, filed Jan. 31, 2007. The content of each of these documents is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the sequence listing (file name: 699992001601_Sequence_Listing.txt, date recorded: Oct. 7, 2013, size: 13,042 bytes).

FIELD OF THE INVENTION

The present invention relates to thiopyrimidine-based compounds that are inhibitors of protein kinases including JAK kinases. In particular, the compounds are selective for JAK1, JAK2 or JAK3 kinases and combinations thereof such as JAK1 and JAK2. The kinase inhibitors can be used in the treatment of kinase associated diseases such as immunological and inflammatory diseases including organ transplants; hyperproliferative diseases including cancer and myeloproliferative diseases; viral diseases; metabolic diseases; and vascular diseases.

BACKGROUND OF THE INVENTION

JAKs are kinases which phosphorylate a group of proteins called Signal Transduction and Activators of Transcription or STATs. When phosphorylated, STATs dimerize, translocate to the nucleus and activate expression of genes which lead to, amongst other things, cellular proliferation such as proliferation of endothelial cells and smooth muscle cells, and cause hypertrophy of cardiac myocytes.

A review of the JAK/STAT literature offers strong support to the hypothesis that this pathway is important for the recruitment and marshalling of the host immune response to environmental insults, such as viral and bacterial infection. Information accumulated from gene knock-out experiments have underlined the importance of members of the JAK family to the intracellular signalling triggered by a number of important immune regulatory cytokines. The therapeutic possibilities stemming from inhibition (or enhancement) of the JAK/STAT pathway are thus in the sphere of immune modulation, and as such are likely to be promising drugs for the treatment of a range of pathologies in this area. In addition inhibitors of JAKs could be used for immunological and inflammatory diseases including organ transplants, asthma and chronic obstructive pulmonary disease (COPD) as well as autoimmune diseases such as systemic lupus erythematosus, mixed connective tissue disease, scleroderma, autoimmune vasculitides, multiple sclerosis, rheumatoid arthritis, Crohns disease, Type I diabetes and autoimmune thyroid disorders.

The central role played by the JAK family of protein tyrosine kinases in the cytokine dependent regulation of both proliferation and end function of several important cell types indicates that agents capable of inhibiting the JAK kinases are useful in the prevention and chemotherapeutic treatment of disease states dependent on these enzymes. Potent and specific inhibitors of each of the currently known four JAK family members will provide a means of inhibiting the action of the cytokines that drive immunological and inflammatory diseases, such as those discussed above. Additionally, treatment of hyperproliferative disorders such as cancers including multiple myeloma; prostate, breast and lung cancer; Hodgkin's Lymphoma; B-cell Chronic Lymphocytic Leukemia; metastatic melanoma; glioma; and hepatoma, by JAK inhibitors is indicated. Additionally the use of JAK kinase inhibitors for the treatment of viral diseases and metabolic diseases is indicated.

Potent inhibitors of JAK2, in addition to the above, will also be useful in vascular disease such as hypertension, hypertrophy, cardiac ischemia, heart failure (including systolic heart failure and diastolic heart failure), migraine and related cerebrovascular disorders, stroke, Raynaud's phenomenon, POEMS syndrome, Prinzmetal's angina, vasculitides, such as Takayasu's arteritis and Wegener's granulomatosis, peripheral arterial disease, heart disease and pulmonary arterial hypertension. JAK2 inhibitors will also be useful in myeloproliferatve disorders (MPD) such as polycythemia rubra vera (PCV).

Potent and specific inhibitors of both JAK1 and JAK2 will be useful in the treatment of cancers including multiple myeloma; prostate, breast and lung cancer; Hodgkin's Lymphoma; B-cell Chronic Lymphocytic Leukemia; metastatic melanoma; glioma; and hepatoma.

Potent and specific inhibitors of JAK3 will be useful as immunosuppressive agents for, amongst others, organ transplants, and immunological and inflammatory diseases such as asthma and chronic obstructive pulmonary disease as well as autoimmune diseases such as systemic lupus erythematosus, mixed connective tissue disease, scleroderma, autoimmune vasculitides, multiple sclerosis, rheumatoid arthritis, Crohn's disease, Type I diabetes and complications from diabetes, metabolic diseases, and other indications where immunosuppression may be desirable. Furthermore specific inhibitors of JAK3 may find application for therapeutic treatments for proliferative diseases such as leukaemia and lymphoma where JAK3 is hyperactivated.

Although the other members of the JAK family are expressed by essentially all tissues, JAK3 expression appears to be limited to hematopoetic cells. This is consistent with its essential role in signalling through the receptors for IL-2, IL4, IL-7, IL-9 and IL-15 by non-covalent association of JAK3 with the gamma chain common to these multichain receptors. Males with X-linked severe combined immunodeficiency (XSCID) have defects in the common cytokine receptor gamma chain (gamma c) gene that encodes a shared, essential component of the receptors of interleukin-2 (IL-2), IL-4, IL-7, IL-9, and IL-15. An XSCID syndrome in which patients with either mutated or severely reduced levels of JAK3 protein has been identified, suggesting that immunosuppression should result from blocking signalling through the JAK3 pathway. Gene Knock out studies in mice have suggested that JAK3 not only plays a critical role in B and T lymphocyte maturation, but that JAK3 is constitutively required to maintain T cell function. Taken together with the biochemical evidence for the involvement of JAK3 in signalling events downstream of the IL-2 and IL-4 receptor, these human and mouse mutation studies suggest that modulation of immune activity through the inhibition of JAK3 could prove useful in the treatment of T-cell and B-cell proliferative disorders such as transplant rejection and autoimmune diseases.

Prolonged immunomodulation through inhibition of JAK3 signalling should have great therapeutic potential for chronic diseases as long as JAK3 inhibition was achieved selectively and not accompanied by inhibition of other kinase-dependent signalling processes. In particular, the high degree of sequence identity held in common by members of the JAK family of kinases raises the possibility that a compound which inhibits JAK3 would also inhibit other members of the family with detrimental long term consequences. For example, prolonged inhibition of JAK2 is likely to lead to erythropenia and thrombocytopenia, since the receptors for both erythropoietin and thrombopoietin use only JAK2 for intracellular transmission of signals.

Compounds of the present invention may also be useful in targeting other kinases of therapeutic relevance, such as the Aurora kinases. The Aurora family of serine/threonine protein kinases are critical for the proper regulation of mitosis. Mammals express three Aurora kinase paralogs, and at least two Aurora kinases (Aurora A and B) are commonly overexpressed in human tumours including breast, lung, colon, ovarian, and pancreatic cancers. The Aurora A gene is amplified in many tumours, indicating that overexpression of Aurora A may confer a selective advantage for the growth of these tumours. Overexpression of Aurora B has also been reported to produce multi-nuclearity and induce aggressive metastasis, suggestion that the overexpression of Aurora kinase B has multiple functions in cancer development. Recent clinical experience and subsequent approvals of kinase inhibitors such as Imatinib, Gefitinib and Erlotinib illustrate that this class of enzymes will be useful for anticancer drug development. Aurora A itself has been identified as a particularly attractive drug target through observations that it can act as an oncogene and transform cells when ectopically expressed. VX-680, a potent inhibitor of Aurora A and B kinases, has been shown to suppress tumour growth in vivo. These findings highlight the desirability of identifying Aurora kinase inhibitors for use in cancer treatment.

Other kinases which may be useful therapeutic targets include CK2, TBK1, NEK9, LCK, ACK1, p38 kinase, FAK, CAK, CDK4, GSK-3, Abl, PDGF-R, PLK1, PLK2, PLK3, PYK2, c-Kit, NPM-ALK, Flt-3, c-Met, KDR, EGFR, TIE-2, VEGFR-2, VEGFR-3, FMS, HCK, Blk, Bmx, BTK, Flt-1 and Flt-4.

Although the inhibition of various types of protein kinases, targeting a range of disease states, is clearly beneficial, it has been to date demonstrated that the identification of a compound which is selective for a protein kinase of interest, and has good "drug like" properties such as high oral bioavailability, is a challenging goal. In addition, it is well established that the predictability of inhibition, or selectivity, in the development of kinase inhibitors is quite low, regardless of the level sequence similarity between the enzymes being targeted.

The challenges in developing a therapeutically appropriate JAK1, JAK2 or JAK3 inhibitors or combinations thereof for use in treatment of kinase associated diseases such as immunological and inflammatory diseases including organ transplants; hyperproliferative diseases including cancer and myeloproliferative diseases; viral diseases; metabolic diseases; and vascular diseases, include designing a compound with appropriate specificity which also has good drug likeness.

There is therefore a continuing need to design and/or identify compounds which specifically inhibit the JAK family of kinases, and particularly compounds which may preferentially inhibit one or more of the JAK kinases relative to the other JAK kinases. There is a need for such compounds for the treatment of a range of disease states.

SUMMARY OF THE INVENTION

The present inventors have found that a group of thiopyrimidine-based compounds (and analogues thereof such as thiopyridines and thiotriazines), which may include an alkylating group such as a Michael acceptor, are inhibitors of the enzyme Janus Kinase 3.

Accordingly, in a first aspect, the present invention provides a compound of the general formula I:

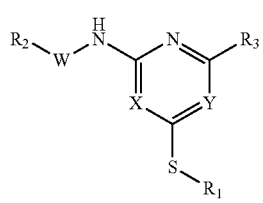

or salts, isomers and/or prodrugs thereof, wherein:

X and Y are independently selected from N and $CR_3$;

each $R_3$ is independently selected from hydrogen, $C_{1-6}$alkyl, $C_{2-6}$alkenyl, hydroxyl, halogen, nitro, substituted or unsubstituted amino, cyano, nitro, trifluoromethyl, methoxy, trifluoromethoxy, aryl and substituted or unsubstituted 5 or 6 membered heterocyclyl containing 1 to 2 N atoms;

$R_1$ is selected from hydrogen, $C_{1-6}$alkyl, $C_{1-6}$alkylCN, $C_{3-8}$cycloalkyl, $C_{1-6}$alkylenecycloalkyl, aryl, $C_{1-6}$alkylenearyl, heterocyclyl and $C_{1-6}$alkyleneheterocyclyl, wherein $C_{1-6}$alkyl, $C_{3-8}$cycloalkyl, heterocyclyl and aryl may be optionally substituted with 1 to 3 substituents selected from R or $R_9$;

$R_9$ is independently selected from halogen, substituted or unsubstituted $C_{1-6}$alkyl, OH, (O), OCN, substituted or unsubstituted $OC_{1-6}$alkyl, CN, $CF_3$,$CF_2$CN, SCN, $SO_2NR_5R_6$, $SR_7$, CHO, $CO_2R_7$, $COR^7$, $CONR_5R_6$, $CONR_5R_7$, $NR_5COR_7$, $NO_2$, $NR_5R_6$, $NR_5CN$, CH(CN)$NR_5R_6$, $NR_5SO_2R_7$, $COCF_3$, $COCH_2F$, $NR_5COCR_7$, $NR_5COOR_7$,$NR_5CONR_6R_7$, heterocyclyl and COheterocyclyl, wherein each heterocyclyl may be optionally substituted with 1 to 4 substituents selected from $NH_2$, CN, OH, $CO_2R_7$, $CH_2CN$ and 5 membered N-containing heterocyclyl;

R is $C_{1-6}$alkyleneR$_9$, $OC_{1-6}$alkyleneR$_9$ (except when $R_9$ is $NR_5R_6$ or $OC_{1-6}$alkyl, then R is $OC_{2-6}$alkyleneR$_9$); or $R_9$ and R together with the groups to which they are attached form a substituted or unsubstituted 5 or 6 membered N-containing heterocyclyl;

$R_5$ and $R_6$ are each independently selected from H, $C_{1-6}$alkyl, $C_{1-6}$alkylCN, $C_{3-8}$cycloalkyl, aryl, heterocyclyl, $C_{1-6}$alkylene, cycloalkyl, substituted or unsubstituted $C_{1-6}$alkylene, $SO_2C_{1-6}$alkyl and $C_{1-6}$alkylene heterocyclyl; or $R_5$ and $R_6$ together with the nitrogen to which they are attached form a 4-8 membered ring having 1 to 3 heteroatoms independently selected from $NR_8$, O, $S(O)_m$ wherein m is 0, 1 or 2 and wherein the ring may be optionally substituted with $C_{1-6}$alkyl or $NR_5R_6$;

$R_8$ is selected from H, $C_{1-6}$alkyl, $C_{2-6}$alkyleneOH, $C_{2-6}$alkyleneNR$_5R_6$, $C_{3-8}$cycloalkyl, aryl, heterocyclyl, $C_{1-6}$alkylenecycloalkyl, $C_{1-6}$alkylenearyl, $C_{1-6}$alkyleneheterocyclyl and $C_{1-6}$alkyleneCN, $R_7$ is selected from H, substituted or unsubstituted $C_{1-6}$alkyl, substituted or unsubstituted $OC_{1-6}$alkyl, substituted or unsubstituted $SC_{1-6}$alkyl, CNOH, $C_{1-6}$alkyleneCN, substituted or unsubstituted $C_{3-8}$cycloalkyl, substituted or unsubstituted aryl, substituted or unsubstituted heterocyclyl, $C_{1-6}$alkylenecycloalkyl, $C_{1-6}$alkylenearyl, $C_{1-6}$alkyleneheterocyclyl, $C_{2-6}$alkenyl, $C_{2-6}$alkynyl, $NR_5R_6$, $C_{1-6}$alkyleneNR$_5$R$_6$ and $C_{1-6}$alkyleneOR$_5$;

W is absent, CO, $SO_2$ or $C_{1-6}$alkylene;

$R_2$ is selected from H, $C_{1-6}$alkyl, $C_{3-8}$cycloalkyl, aryl and heterocyclyl, each of which may be optionally substituted with 1 to 4 substituents selected from R and $R_9$; and wherein each alkenyl and alkynyl may be optionally substituted with 1 to 3 substituents independently selected from $C_{1-6}$alkyl, $CO_2R_7$, $CONR_5R_6$, aryl, heterocyclyl, $C_{1-6}$alklene OH and $C_{1-6}$alkyleneNH$_2$;

In a second aspect, there is provided a process for the preparation of the compound of formula I defined above which comprises the steps of:

(a) adding S—$R_1$ wherein $R_1$ is as defined in formula I above to a compound of formula II

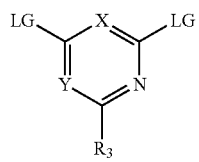

II wherein X, Y and $R_3$ are as defined in formula I above and LG is a leaving group to prepare a compound of formula III

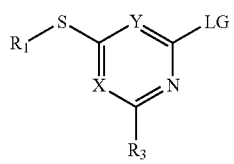

III wherein X, Y, LG, $R_1$ and $R_3$ are as defined above; and (b) coupling the compound of formula III with a source of NH—W—$R_2$ wherein W and $R_2$ are as defined in formula I above.

The compounds of formula I are kinase inhibitors, preferably JAK inhibitors, more preferably JAK2 or JAK3 inhibitors. These compounds are useful in the treatment of a kinase associated disease, preferably a JAK kinase associated disease such as immunological and inflammatory diseases; hyperproliferative diseases including myeloproliferative diseases; vascular diseases such as pulmonary arterial hypertension (PAH); viral diseases and metabolic diseases.

In a third aspect, there is provided a kinase inhibitor comprising the compound formula I defined above.

There is also provided use of the compound of formula I defined above as a kinase inhibitor.

There is further provided the compound of formula I defined above for use as a kinase inhibitor.

The compounds of formula I preferably act as selective JAK2 inhibitors, selective JAK3 inhibitors or selective JAK1 and JAK2 inhibitors.

The compound of formula I may also be administered in the form of a pharmaceutical composition together with a pharmaceutically acceptable carrier.

In a fourth aspect, there is provided a pharmaceutical composition comprising the compound of formula I defined above and a pharmaceutically acceptable carrier.

In one embodiment, the pharmaceutical composition also comprises one or more additional therapeutic agents.

The compound of formula I may be contained within or attached to an implant, such as a drug eluting stent. For example, when the compound is used for the treatment of PAH, the compound may be contained within or attached to a pulmonary artery stent, which may act locally, or be released from the stent into the pulmonary circulation where the compound exerts its therapeutic activity in the pulmonary vasculature.

In a fifth aspect, there is provided an implant which comprises the compound of formula I defined above.

In a sixth aspect, there is provided a method for the treatment of a kinase associated disease such as immunological and inflammatory diseases including organ transplants; hyperproliferative diseases including cancer and myeloproliferative diseases; viral diseases; metabolic diseases; and vascular diseases which comprises administering a therapeutically effective amount of the compound of formula I or a pharmaceutical composition defined above to a subject in need thereof.

There is also provided use of the compound of formula I or a pharmaceutical composition as defined above in the manufacture of a medicament for the treatment of a kinase associated disease such as immunological and inflammatory diseases including organ transplants; hyperproliferative diseases including cancer and myeloproliferative diseases; viral diseases; metabolic diseases; and vascular diseases.

There is further provided use of the compound of formula I or a pharmaceutical composition as defined above in the treatment of a kinase associated disease such as immunological and inflammatory diseases including organ transplants; hyperproliferative diseases including cancer and myeloproliferative diseases; viral diseases; metabolic diseases; and vascular diseases.

There is still further provided the compound of formula I or a pharmaceutical composition defined above for use in the treatment of a kinase associated disease such as immunological and inflammatory diseases including organ transplants; hyperproliferative diseases including cancer and myeloproliferative diseases; viral diseases; metabolic diseases; and vascular diseases.

In a seventh aspect, there is provided a method for suppressing the immune system of a subject which comprises administering a therapeutically effective amount of the compound of formula I or a pharmaceutical composition defined above to the subject in need thereof.

There is also provided use of the compound of formula I or a pharmaceutical composition as defined above in the manufacture of a medicament for suppressing the immune system of a subject.

There is further provided use of the compound of formula I or a pharmaceutical composition as defined about in suppressing the immune system of a subject.

There is still further provided the compound of formula I or a pharmaceutical composition defined above for use in suppressing the immune system of a subject.

In an eighth aspect, there is provided a method of inhibiting a kinase in a cell comprising contacting the cell with the compound of formula I defined above.

BRIEF DESCRIPTION OF THE FIGURES

Figure 1:
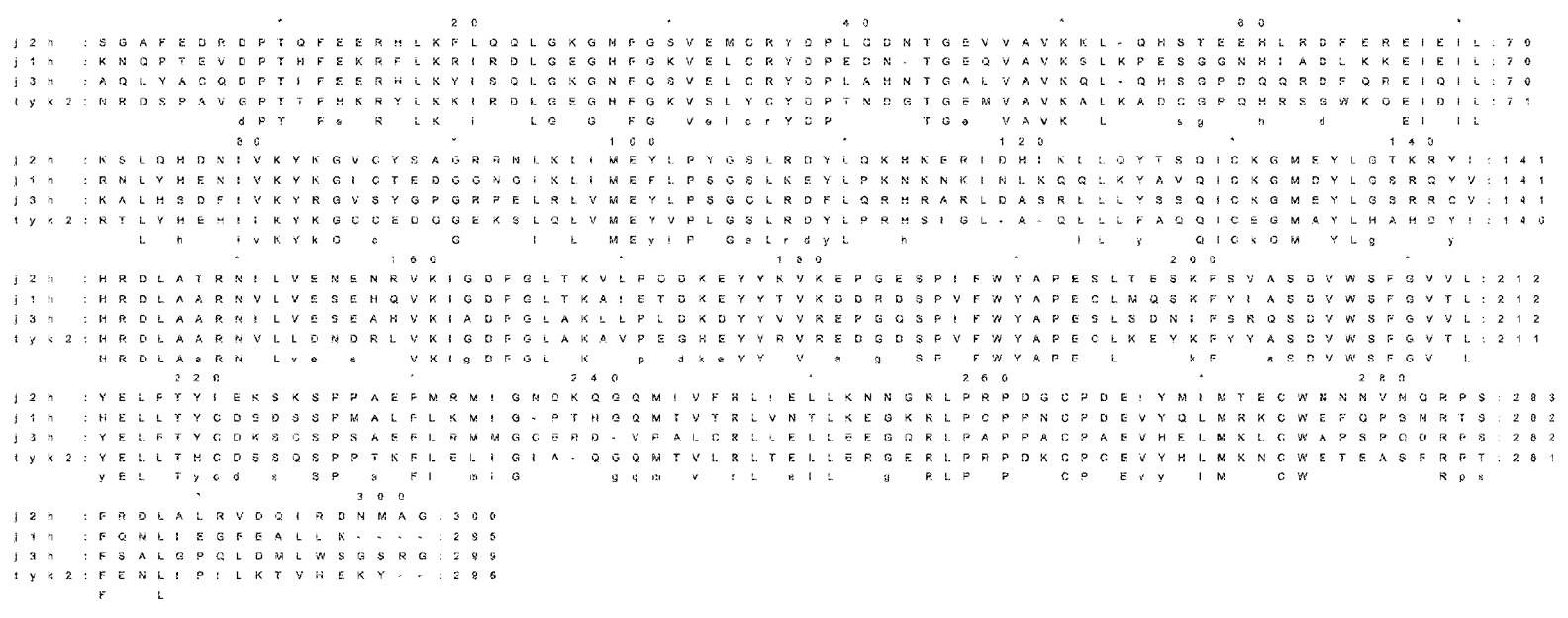

FIG. 1 shows the amino acid sequence alignment of selected JAK Kinases (SEQ ID NOS:1-4 in order of appearance).

DETAILED DESCRIPTION

Figure 2:
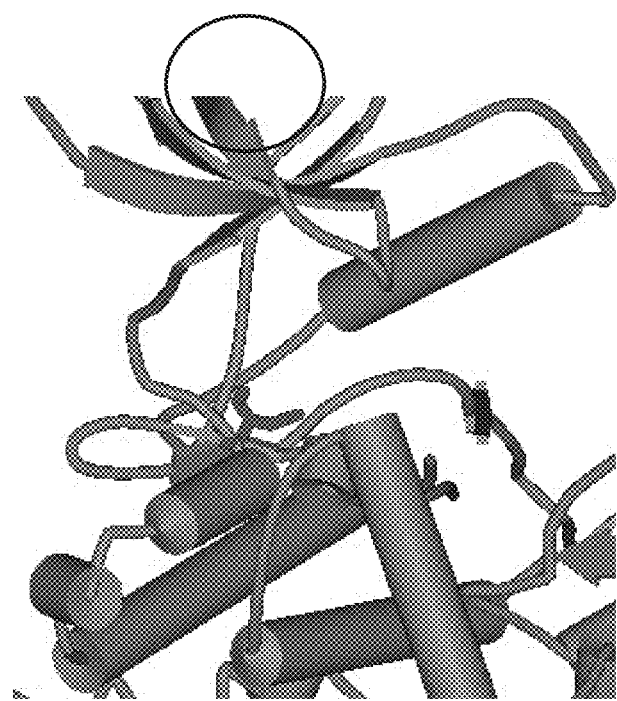
FIG. 2 shows a model of the JAK3 kinase ATP binding pocket displaying the Cysteine residue.

The present invention relates to compounds of formula I that inhibit kinases, in particular JAK kinases such as JAK2 or JAK3 kinases and are useful in the treatment of kinase associated diseases such as immunological and inflammatory diseases including organ transplants; hyperproliferative diseases including cancer and myeloproliferative diseases; viral diseases; metabolic diseases; and vascular diseases.

Accordingly, in a first aspect, the present invention provides a compound of the general formula I:

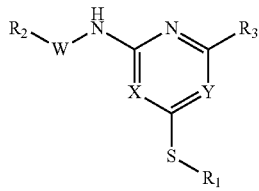

I or salts, isomers and/or prodrugs thereof, wherein:
X and Y are independently selected from N and $CR_3$;
each $R_3$ is independently selected from hydrogen, $C_{1-6}$alkyl, $C_{2-6}$alkenyl, hydroxyl, halogen, nitro, substituted or unsubstituted amino, cyano, nitro, trifluoromethyl, methoxy, trifluoromethoxy, aryl and substituted or unsubstituted 5 or 6 membered heterocyclyl containing 1 to 2 N atoms;
$R_1$ is selected from hydrogen, $C_{1-6}$alkyl, $C_{1-6}$alkylCN, $C_{3-8}$cycloalkyl, $C_{1-6}$alkylenecycloalkyl, aryl, $C_{1-6}$alkylenearyl, heterocyclyl and $C_{1-6}$alkyleneheterocyclyl, wherein $C_{1-6}$alkyl, $C_{3-8}$cycloalkyl, heterocyclyl and aryl may be optionally substituted with 1 to 3 substituents selected from R or $R_9$;
$R_9$ is independently selected from halogen, substituted or unsubstituted $C_{1-6}$alkyl, OH, (O), OCN, substituted or unsubstituted $OC_{1-6}$alkyl, CN, $CF_3$, $CF_2CN$, SCN, $SO_2NR_5R_6$, $SR_7$, CHO, $CO_2R_7$, $COR^7$, $CONR_5R_6$, $CONR_5R_7$, $NR_5COR_7$, $NO_2$, $NR_5R_6$, $NR_5CN$, CH(CN)$NR_5R_6$, $NR_5SO_2R_7$, $COCF_3$, $COCH_2F$, $NR_5COCOR_7$, $NR_5COOR_7$, $NR_5CONR_6R_7$, heterocyclyl and COheterocyclyl, wherein each heterocyclyl may be optionally substituted with 1 to 4 substituents selected from $NH_2$, CN, OH, $CO_2R_7$, $CH_2CN$ and 5 membered N-containing heterocyclyl;
R is $C_{1-6}$alkyleneR_9$, $OC_{1-6}$alkyleneR_9$ (except when $R_9$ is $NR_5R_6$ or $OC_{1-6}$alkyl, then R is $OC_{2-6}$alkyleneR_9$); or
$R_9$ and R together with the groups to which they are attached form a substituted or unsubstituted 5 or 6 membered N-containing heterocyclyl;
$R_5$ and $R_6$ are each independently selected from H, $C_{1-6}$alkyl, $C_{1-6}$alkylCN, $C_{3-8}$cycloalkyl, aryl, heterocyclyl, $C_{1-6}$alkylene, cycloalkyl, substituted or unsubstituted $C_{1-6}$alkylene, $SO_2C_{1-6}$alkyl and $C_{1-6}$alkylene heterocyclyl; or
$R_5$ and $R_6$ together with the nitrogen to which they are attached form a 4-8 membered ring having 1 to 3 heteroatoms independently selected from $NR_8$, O, $S(O)_m$ wherein m is 0, 1 or 2 and wherein the ring may be optionally substituted with $C_{1-6}$alkyl or $NR_5R_6$;
$R_8$ is selected from H, $C_{1-6}$alkyl, $C_{2-6}$alkyleneOH, $C_{2-6}$alkyleneNR_5R_6$, $C_{3-8}$cycloalkyl, aryl, heterocyclyl, $C_{1-6}$alkylenecycloalkyl, $C_{1-6}$alkylenearyl, $C_{1-6}$alkyleneheterocyclyl and $C_{1-6}$alkyleneCN,
$R_7$ is selected from H, substituted or unsubstituted $C_{1-6}$alkyl, substituted or unsubstituted $OC_{1-6}$alkyl, substituted or unsubstituted $SC_{1-6}$alkyl, CNOH, $C_{1-6}$alkyleneCN, substituted or unsubstituted $C_{3-8}$cycloalkyl, substituted or unsubstituted aryl, substituted or unsubstituted heterocyclyl, $C_{1-6}$alkylenecycloalkyl, $C_{1-6}$alkylenearyl, $C_{1-6}$alkyleneheterocyclyl, $C_{2-6}$alkenyl, $C_{2-6}$alkynyl, $NR_5R_6$, $C_{1-6}$alkyleneNR_5R_6$ and $C_{1-6}$alkyleneOR_5$;
W is absent, CO, $SO_2$ or $C_{1-6}$alkylene;
$R_2$ is selected from H, $C_{1-6}$alkyl, $C_{3-8}$cycloalkyl, aryl and heterocyclyl, each of which may be optionally substituted with 1 to 4 substituents selected from R and $R_9$; and
wherein each alkenyl and alkynyl may be optionally substituted with 1 to 3 substituents independently selected from $C_{1-6}$alkyl, $CO_2R_7$, $CONR_5R_6$, aryl, heterocyclyl, $C_{1-6}$alklene OH and $C_{1-6}$alkyleneNH_2$;

In one embodiment, the compound of formula I selectively inhibits JAK 3 with respect to JAK 1 or JAK 2. The term "selectively inhibits" is defined to mean that the apparent $IC_{50}$ of the compound for JAK 3 is more than ten-fold lower (i.e. more potent) than the $IC_{50}$ for JAK 1 or JAK 2.

The compounds of formula I which inhibit JAK3 may either reversibly or irreversibly inhibit JAK 3. Generally, the strength of binding of reversible inhibitors of an enzyme is measured by the $IC_{50}$ value which is a reflection of the equilibrium constant of the interaction between the inhibitor and the active site of the enzyme. Irreversible inhibitors display an apparent $IC_{50}$ because once the inhibitor is bound it will not leave the active site and the measured $IC_{50}$ will therefore improve (i.e. number will decrease) over time.

In the compounds of formula I, X is preferably N and Y is preferably $CR_3$ wherein $R_3$ is as defined above.

Thus, in one embodiment, the compounds of formula I have the formula Ia

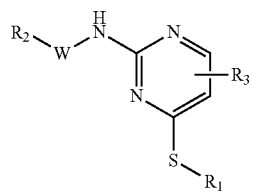

Ia wherein W, $R_1$, $R_2$ and $R_3$ are as defined above.

In another embodiment, the compounds of formula I and Ia have the formula Ib

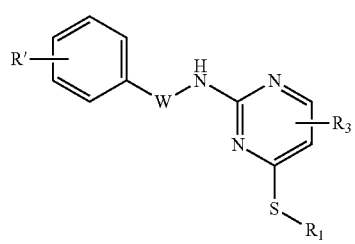

Ib wherein W, $R_1$ and $R_3$ are as defined above; and
R' is H, R or $R_9$ as defined above.

In a further embodiment, the compounds of formula I, Ia and Ib have the formula Ic

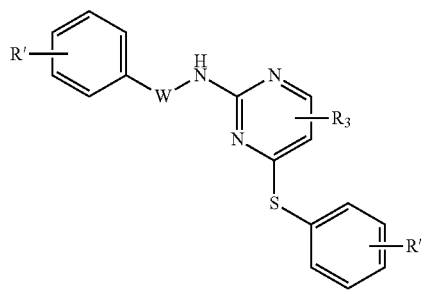

wherein W, $R_3$ and R' are as defined above.

W is preferably absent, CO or $C_{1-6}$alkylene.

$R_1$ is preferably aryl such as phenyl; heterocyclyl such as a N-containing heterocyclyls for example indolinyl; $C_{1-6}$ alkyl; or aryl substituted with one or more substituents selected from $NR_5R_6$, $NR_5COR_7$, CN, $OC_{1-6}$alkyl, OH, $CO_2R_7$, $CONR_5R_7$, $CONR_5R_6$, $NR_5CO_2R_7$, substituted or unsubstituted $C_{1-6}$alkyl, $SR_5$, CHO, substituted or unsubstituted heterocyclyl such as thiomorpholin-3-one, tetrazole pyrrolidine-2,5-dione, $CF_3$, OCN and $COR_7$ wherein $R_5$ to $R_7$ are as defined above.

$R_2$ is preferably aryl such as phenyl; imidazolyl; methylene dioxy phenyl; or aryl substituted with one or more substituents selected from an N-containing 5 or 6 membered heterocyclyl such as morpholinyl, piperidinyl, piperazinyl, pyrrolidinyl or 1,3-thiazolidine 1,1-dioxide; substituted or unsubstituted $OC_{1-6}$alkyl such as methoxy; $NR_5COR_7$ wherein $R_5$ is H and $R_7$ is $C_{1-6}$alkyl, $C_{2-6}$alkenyl, $C_{2-6}$alkynyl or CN; $NH_2$; halo such as chloro or fluoro; $CO_2R_7$; $SO_2NR_5R_6$; $NO_2$; $NHSO_2Me$; $CHOHCF_3CH_3$; $CH_2NHSO_2Me$; OH and SH wherein $R_5$ to $R_7$ are as defined above.

$R_3$ is preferably H; $C_{1-6}$alkyl; halo such as bromo, fluoro or iodo; $C_{2-6}$alkenyl; amino which may be substituted with $C_{2-6}$alkenyl; cyano; nitro; methoxy; aryl such as phenyl; or 5 or 6 membered heterocyclyl containing 1 or 2 N atoms such as pyrazolyl, 1,2,3,6-tetrahydropyridine and pyridinyl, wherein the heterocyclyl may be substituted with trimethylcarboxy.

Where the compounds of formulae I and Ia inhibit JAK3 kinases, a substituent of one of $R_1$ and $R_2$ is preferably selected from groups that can react reversibly or irreversibly with a thiol moiety such as the thiol groups of the Cys963 residue of JAK3. Similarly, where the compounds of formulae Ib inhibit JAK3 kinases, one of R' and a substituent of $R_2$ is preferably selected from groups that can react reversibly or irreversibly with a thiol moiety such as the thiol groups of the Cys963 residue of JAK3. Additionally where the compounds of formulae Ic inhibit JAK3 kinases, one of the R' substituents is preferably selected from groups that can react reversibly or irreversibly with a thiol moiety such as the thiol groups of the Cys963 residue of JAK3. Examples of such groups include Michael acceptors.

Michael acceptors are α,β-unsaturated carbonyl or thiocarbonyl compounds and selected examples are shown below.

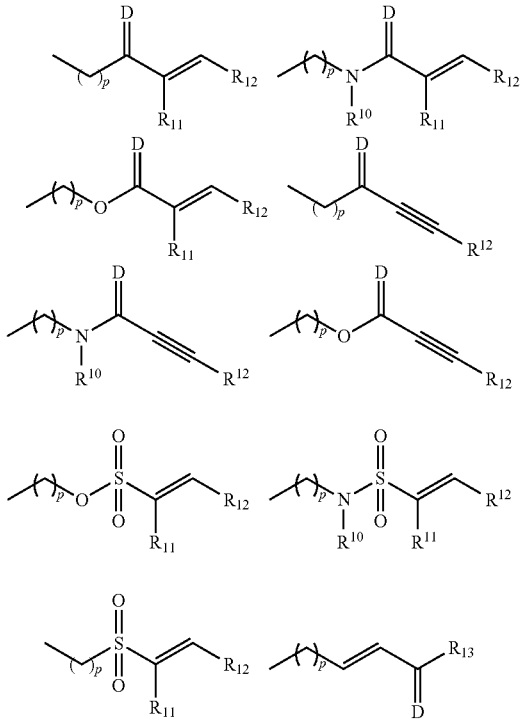

wherein

D is O or N;

$R_{10}$ is selected from H and substituted or unsubstituted $C_{1-4}$alkyl;

$R_{11}$ and $R_{12}$ are independently selected from H, substituted or unsubstituted $C_{1-4}$alkyl, $C_{1-4}$alkyl$NR_{14}R_{15}$, $C_{1-4}$alkyl$OR^8$, substituted or unsubstituted aryl or may be joined to form a substituted or unsubstituted 5 to 8 membered ring optionally containing one or more heteroatoms selected from O, S, $SO_2$ and $NR_{10}$;

$R_{13}$ is selected from OH, $OC_{1-4}$alkyl, $NR_{14}R_{15}$;

p is 0 to 4; and $R_{14}$ and $R_{15}$ are independently selected from H, substituted or unsubstituted $C_{1-4}$alkyl or may be joined to form a substituted 3-8 membered ring optionally containing one or more heteroatoms selected from O, S, $SO_2$ and $NR_{10}$.

Other groups which can undergo reversible or irreversible reaction with thiol moieties include, ketones, aldehydes, α-acyloxy ketones, α-phenoxy ketones, halomethyl ketones, maleimides, nitriles, 1,2,4-thiadiazoles, 2-vinyl oxazoles, 2-alkynyl-oxazoles, keto-oxazoles, cyclic disulfides, epoxides and O-acyl hydroxamates.

Examples of compounds of formula I include, but are not limited to, the following:

TABLE 1

| Compound number | Structure | Exact mass | Name | LCMS method | retention time (min) | Observed m/z | ¹H NMR |
|---|---|---|---|---|---|---|---|
| 1 | 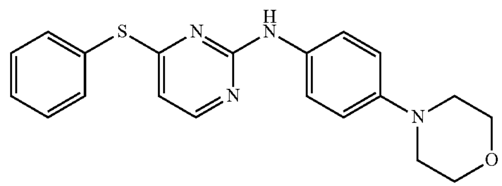 [SMILES: c1ccc(Sc2ccnc(Nc3ccc(N4CCOCC4)cc3)n2)cc1] | 364.14 | N-(4-morpholino-phenyl)-4-(phenylthio)pyrimidin-2-amine | C | 7.3 | m/z 365.1 [M + H]+ | ¹H NMR (CDCl₃) δ 3.08 (m, 4H), 3.86 (m, 4H), 6.25 (d, J = 5.35 Hz, 1H), 6.79 (d, J = 8.94 Hz, 2H), 6.95 (br s, 1H), 7.30 (d, J = 8.93 Hz, 2H), 7.46-7.50 (m, 3H), 7.62 (dd, J = 7.04, 1.64 Hz, 2H), 8.01 (d, J = 5.35 Hz, 1H) |
| 2 | 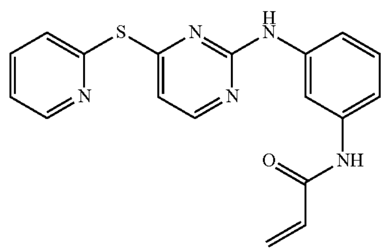 [SMILES: C=CC(=O)Nc1cccc(Nc2nccc(Sc3ccccn3)n2)c1] | 349.10 | N-(3-(4-(pyridin-2-ylthio)pyrimidin-2-ylamino)phenyl)acrylamide | B | 7.7 | m/z 349.3 M+ | ¹H NMR (CDCl₃) δ 5.74 (dd, J = 10.13, 1.26 Hz, 1H), 6.19-6.28 (m, 1H), 6.42 (dd, J = 16.79, 1.21 Hz, 1H), 6.64 (d, J = 5.29 Hz, 1H), 7.10-7.19 (m, 2H), 7.24 (br s, 1H), 7.30-7.34 (m, 1H), 7.39 (br s, 1H), 7.69-7.75 (m, 3H), 8.14 (d, J = 5.25 Hz, 1H), 8.66-8.68 (m, 1H) |
| 3 | 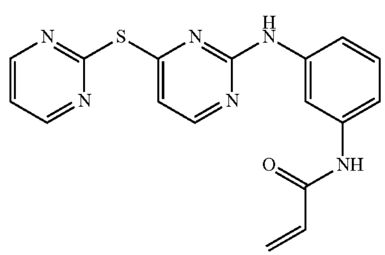 [SMILES: C=CC(=O)Nc1cccc(Nc2nccc(Sc3ncccn3)n2)c1] | 350.09 | N-(3-(4-(pyrimidin-2-ylthio)pyrimidin-2-ylamino)phenyl)acrylamide | C | 5.8 | m/z 351.0 [M + H]+ | |

TABLE 1-continued

| Compound number | Structure | Exact mass | Name | LCMS method | retention time (min) | Observed m/z | 1H NMR |
|---|---|---|---|---|---|---|---|
| 4 | 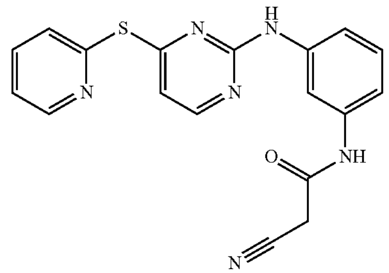 | 362.09 | 2-cyano-N-(3-(4-(pyridin-2-ylthio)pyrimidin-2-ylamino)phenyl)acetamide | C | 5.9 | m/z 363.0 [M + H]+ | |
| 5 | 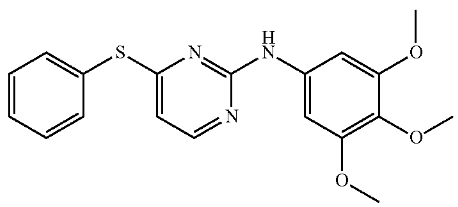 [SMILES: COc1cc(Nc2nccc(Sc3ccccc3)n2)cc(OC)c1OC] | 369.11 | 4-(phenylthio)-N-(3,4,5-trimethoxyphenyl)pyrimidin-2-amine | B | 9.7 | m/z 369.4 M+ | 1H NMR (CDCl3) δ 3.82 (s, 3H), 3.84 (s, 6H), 6.18 (d, J = 5.39 Hz, 1H), 6.88 (s, 2H), 7.01 (br s, 1H), 7.42-7.50 (m, 3H), 7.59-7.63 (m, 2H), 8.04 (d, J = 5.39 Hz, 1H) |
| 6 | 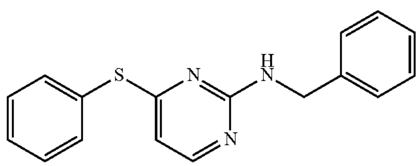 [SMILES: c1ccc(CNc2nccc(Sc3ccccc3)n2)cc1] | 293.10 | N-benzyl-4-(phenylthio)pyrimidin-2-amine | B | 10.1 | m/z 293.2 M+ | 1H NMR (CDCl3) δ 4.54 (d, J = 5.97 Hz, 2H), 5.41 (br s, 1H), 6.08 (d, J = 5.37 Hz, 1H), 7.24-7.31 (m, 5H), 7.41-7.44 (m, 3H), 7.57-7.60 (m, 2H), 7.92 (d, J = 5.37 Hz, 1H) |
| 7 | 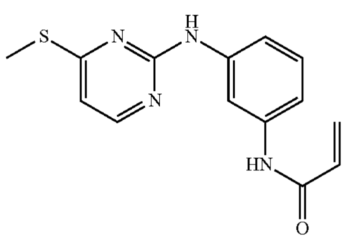 [SMILES: C=CC(=O)Nc1cccc(Nc2nccc(SC)n2)c1] | 286.09 | N-(3-(4-(methylthio)pyrimidin-2-ylamino) | H | NA | m/z 286.2 M+ | 1H NMR (300 MHz, CDCl3) δ 8.06 (d, J = 5.4, 1H); 8.00 (brs, 1H); 7.38-7.42 (m, 1H); 7.13-7.30 (m, 4H); 6.63 (d, J = 5.4, 1H); 6.43 (dd, J = 16.8, 1.5, 1H); 6.24 (dd, J = 16.9, 1.5, 1H); 5.76 (dd, J = 9.9, 1.5 H, 1H); 2.55 (s, 3H) |

TABLE 1-continued

| Compound number | Structure | Exact mass | Name | LCMS method | retention time (min) | Observed m/z | $^1$H NMR |
|---|---|---|---|---|---|---|---|
| 8 | 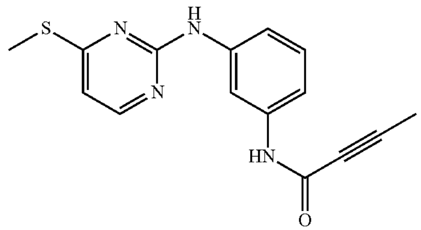 [SMILES: CC#CC(=O)Nc1cccc(Nc2nccc(SC)n2)c1] | 298.09 | phenyl)acrylamideN-(3-(4-(methylthio)pyrimidin-2-ylamino)phenyl)but-2-ynamide | H | NA | m/z 298.3 M+ | $^1$H NMR (300 MHz, CDCl$_3$) δ 8.06 (d, J = 5.4, 1H); 7.96 (s, 1H); 7.37-7.40 (m, 1H); 7.26 (t, J = 8.1, 1H); 7.08-7.15 (m, 2H); 6.63 (d, J = 5.4, 1H); 2.55 (s, 3H); 2.00 (s, 3H) |
| 9 | 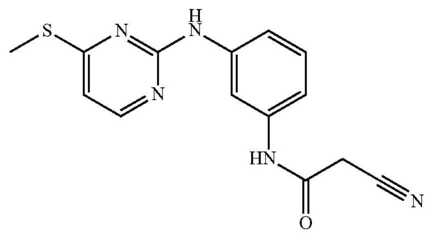 [SMILES: CSc1ccnc(Nc2cccc(NC(=O)CC#N)c2)n1] | 299.08 | 2-cyano-N-(3-(4-(methylthio)pyrimidin-2-ylamino)phenyl)acetamide | H | NA | m/z 299.3 M+ | |
| 10 | 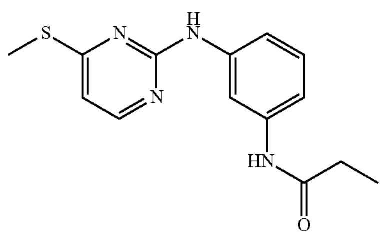 [SMILES: CCC(=O)Nc1cccc(Nc2nccc(SC)n2)c1] | 288.10 | N-(3-(4-(methylthio)pyrimidin-2-ylamino)phenyl)propionamide | H | NA | m/z 288.3 M+ | |
| 11 | 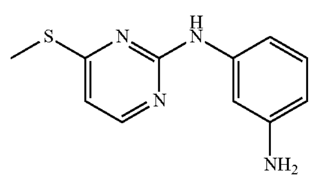 [SMILES: CSc1ccnc(Nc2cccc(N)c2)n1] | 232.08 | N1-(4-(methylthio)pyrimidin-2-yl)benzene-1,3-diamine | H | NA | m/z 232.3 M+ | $^1$H NMR (300 MHz, CDCl$_3$) δ 8.04 (d, J = 5.4 1H); 7.15 (t, J = 2.1, 1H); 7.09 (t, J = 7.8, 1H); 7.05 (brs, 1H); 6.88-6.92 (m, 1H); 6.60 (d, J = 5.7, 1H); 6.36-6.39 (m, 2H); 3.67 (brs, 2H); 2.55 (s, 3H) |

TABLE 1-continued

| Compound number | Structure | Exact mass | Name | LCMS method | retention time (min) | Observed m/z | ¹H NMR |
|---|---|---|---|---|---|---|---|
| 12 | 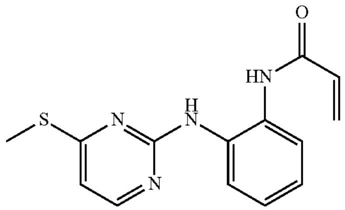 [SMILES: C=CC(=O)Nc1ccccc1Nc1nccc(SC)n1] | 286.09 | N-(2-(4-(methylthio)pyrimidin-2-ylamino)phenyl)acrylamide | B | 8.0 | m/z 286.1 M+ | ¹H NMR (300 MHz, CDCl3) δ 8.43 (brs, 1H); 8.01 (d, J = 5.4, 1H); 7.86 (brs, 1H); 7.44 (brs, 1H); 7.18-7.20 (m, 3H); 6.62 (d, J = 5.4, 1H); 6.14-6.39 (m, 2H); 5.69-5.74 (m, 1H); 2.46 (s, 3H) |
| 13 | 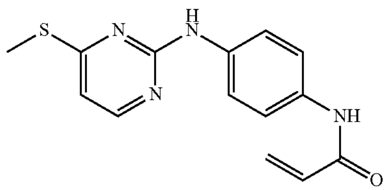 [SMILES: C=CC(=O)Nc1ccc(Nc2nccc(SC)n2)cc1] | 286.09 | N-(4-(4-(methylthio)pyrimidin-2-ylamino)phenyl)acrylamide | B | 7.8 | m/z 286.1 M+ | ¹H NMR (300 MHz, CD₃OD/CDCl₃) δ 8.01 (d, J = 5.4, 1H); 7.58 (brm, 4H); 6.61 (d, J = 5.4, 1H); 6.26-6.39 (m, 2H); 5.73 (d, J = 9.9, 1H); 2.54 (s, 3H) |
| 14 | 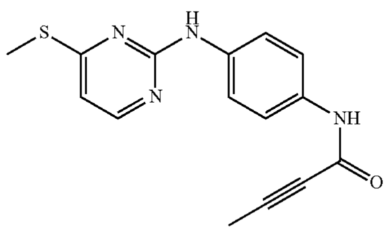 [SMILES: CC#CC(=O)Nc1ccc(Nc2nccc(SC)n2)cc1] | 298.09 | N-(4-(4-(methylthio)pyrimidin-2-ylamino)phenyl)but-2-ynamide | B | 8.1 | m/z 298.1 M+ | |
| 15 | 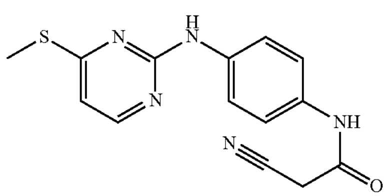 [SMILES: CSc1ccnc(Nc2ccc(NC(=O)CC#N)cc2)n1] | 299.08 | 2-cyano-N-(4-(4-(methylthio)pyrimidin-2-ylamino)phenyl)acetamide | B | 7.6 | m/z 299.1 M+ | |

TABLE 1-continued

| Compound number | Structure | Exact mass | Name | LCMS method | retention time (min) | Observed m/z | ¹H NMR |
|---|---|---|---|---|---|---|---|
| 16 | 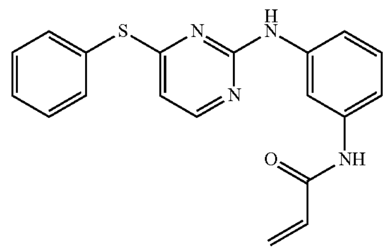 [SMILES: C=CC(=O)Nc1cccc(Nc2nccc(Sc3ccccc3)n2)c1] | 348.10 | N-(3-(4-(phenylthio)pyrimidin-2-ylamino)phenyl)acrylamide | B | 9.1 | m/z 348.4 M+ | ¹H NMR(CDCl₃) δ 5.77 (dd, J = 10.1, 1.13 Hz, 1H), 6.24 (m, 1H), 6.37 (d, J = 5.41 Hz, 1H), 6.42 (dd, J = 16.8, 1.17 Hz, 1H), 7.09 (br s, 1H), 7.14-7.16 (m, 3H), 7.31 (br s, 1H), 7.45-7.51 (m, 3H), 7.61-7.65 (m, 2H), 7.69 (br s, 1H), 8.07 (d, J = 5.38 Hz, 1H) |
| 17 | 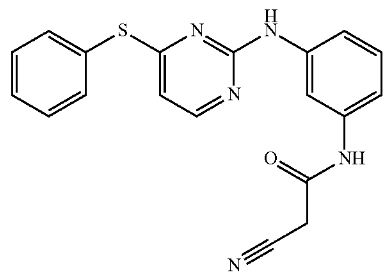 [SMILES: N#CCC(=O)Nc1cccc(Nc2nccc(Sc3ccccc3)n2)c1] | 361.10 | 2-cyano-N-(3-(4-(phenylthio)pyrimidin-2-ylamino)phenyl)acetamide | B | 8.9 | m/z 361.4 M+ | ¹H NMR (CDCl₃) δ 3.54 (s, 2H), 6.33 (d, J = 5.43 Hz, 1H), 7.16-7.22 (m, 3H), 7.25 (br s, 1H), 7.47-7.52 (m, 3H), 7.61-7.64 (m, 2H), 7.69 (br s, 1H), 8.06 (d, J = 5.37 Hz, 1H) |
| 18 | 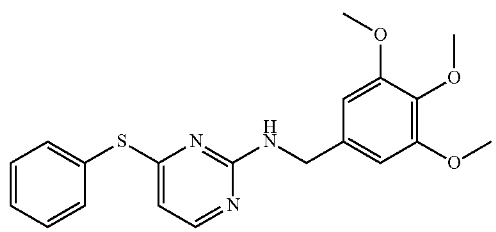 [SMILES: COc1cc(CNc2nccc(Sc3ccccc3)n2)cc(OC)c1OC] | 383.13 | 4-(phenylthio)-N-(3,4,5-trimethoxybenzyl)pyrimidin-2-amine | B | 9.5 | m/z 383.1 M+ | ¹H NMR (CDCl₃) δ 3.83 (s, 3H), 3.84 (s, 2H), 4.49 (d, J = 5.92 Hz, 2H), 5.37-5.41 (m, 1H), 6.07 (d, J = 5.37 Hz, 1H), 6.55 (s, 2H), 7.41-7.46 (m, 3H), 7.57-7.61 (m, 2H), 7.94 (d, J = 5.37 Hz, 1H) |
| 19 | 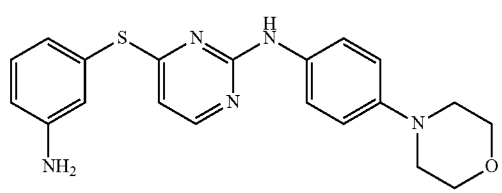 | 379.15 | 4-(3-aminophenylthio)-N-(4-morpholinophenyl)pyrimidin-2-amine | C | 6.6 | m/z 380 [M + H]+ | |

TABLE 1-continued

| Compound number | Structure | Name | Exact mass | LCMS method | retention time (min) | Observed m/z | ¹H NMR |
|---|---|---|---|---|---|---|---|
| 20 | 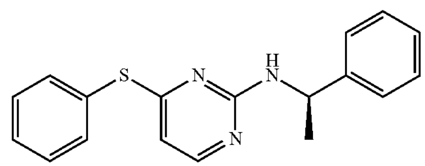 [SMILES: C[C@@H](Nc1nccc(Sc2ccccc2)n1)c1ccccc1] | (R)-N-(1-phenyl-ethyl)-4-(phenyl-thio)pyrimidin-2-amine | 307.11 | B | 10.4 | m/z 307.5 M+ | ¹H NMR (CDCl₃) δ 1.48 (d, J = 6.86 Hz, 3H), 5.01-5.10 (m,1H), 5.32 (d, J = 7.61 Hz, 1H), 6.05 (d, J = 5.33 Hz, 1H), 7.19-7.32 (m, 5H), 7.38-7.47 (m, 3H), 7.54-7.57 (m, 2H), 7.89 (d, J = 5.21 Hz, 1H) |
| 21 | 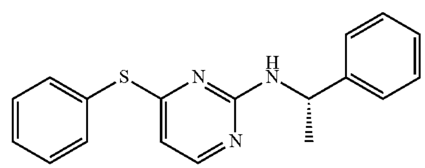 [SMILES: C[C@H](Nc1nccc(Sc2ccccc2)n1)c1ccccc1] | (S)-N-(1-phenyl-ethyl)-4-(phenyl-thio)pyrimidin-2-amine | 307.11 | B | 10.4 | m/z 307.5 M+ | ¹H NMR (CDCl₃) δ 1.48 (d, J = 6.86 Hz, 3H), 5.01-5.10 (m, 1H), 5.30 (d, J = 7.61 Hz, 1H), 6.04 (d, J = 5.33 Hz, 1H), 7.19-7.32 (m, 5H), 7.37-7.46 (m, 3H), 7.54-7.57 (m, 2H), 7.89 (d, J = 5.35 Hz, 1H) |
| 22 | 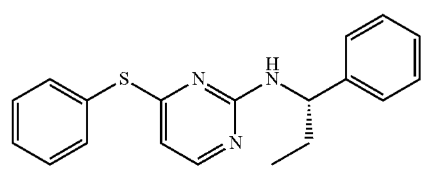 [SMILES: CC[C@H](Nc1nccc(Sc2ccccc2)n1)c1ccccc1] | (S)-N-(1-phenyl-propyl)-4-(phenyl-thio)pyrimidin-2-amine | 321.13 | B | 10.7 | m/z 321.5 M+ | ¹H NMR (CDCl₃) δ 0.88 (t, J = 7.36 Hz, 3H), 1.73-1.88 (m, 2H), 4.75-4.88 (m, 1H), 5.30-5.39 (m, 1H), 6.03 (d, J = 5.40 Hz, 1H), 7.19-7.32 (m, 5H), 7.39-7.47 (m, 3H), 7.54-7.57 (m, 2H), 7.88 (d, J = 5.35 Hz, 1H) |
| 23 | 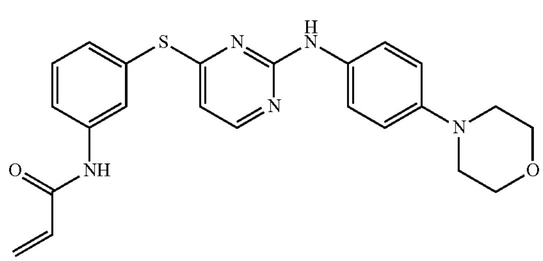 [SMILES: C=CC(=O)Nc1cccc(Sc2ccnc(Nc3ccc(N4CCOCC4)cc3)n2)c1] | N-(3-(2-(4-morpholino-phenylamino)pyrimidin-4-ylthio)phenyl)acrylamide | 433.16 | B | 8.5 | m/z 433.5 M+ | ¹H NMR (CDCl₃) δ 3.06-3.09 (m, 4H), 3.83-3.86 (m, 4H), 5.79 (dd, J = 10.18, 1.26 Hz, 1H), 6.21 (dd, J = 16.82, 10.18 Hz, 1H), 6.36 (d, J = 5.35 Hz, 1H), 6.44 (dd, J = 16.82, 1.26 Hz, 1H), 6.77 (d, J = 9.01 Hz, 2H), 6.96 (br s, 1H), 7.24-7.47 (m, 5H), 7.68-7.73 (m, 1H), 7.95 (d, J = 6.99 Hz, 1H), 8.02 (d, J = 5.35 Hz, 1H) |

TABLE 1-continued

| Compound number | Structure | Exact mass | Name | LCMS method | retention time (min) | Observed m/z | ¹H NMR |
|---|---|---|---|---|---|---|---|
| 24 | 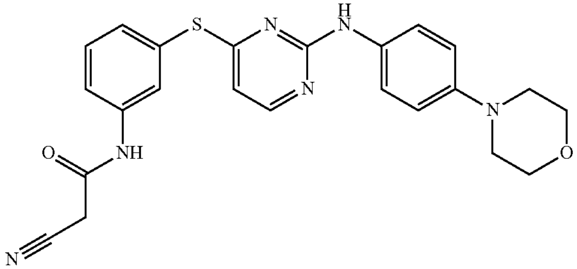 [SMILES: N#CCC(=O)Nc1cccc(Sc2ccnc(Nc3ccc(N4CCOCC4)cc3)n2)c1] | 446.15 | 2-cyano-N-(3-(2-(4-morpholino-phenylamino)pyrimidin-4-ylthio)phenyl)acetamide | B | 8.3 | m/z 446.4 M+ | ¹H NMR (CDCl₃) δ 3.06-3.09 (m, 4H), 3.83-3.85 (m, 4H), 3.48 (s, 2H), 6.32 (br s, 1H), 6.75 (br s, 2H), 7.19-7.25 (m, 3H), 7.37-7.40 (m, 1H), 7.43 (t, J = 7.71 Hz, 1H), 7.78 (d, J = 7.54 Hz, 1H), 7.98 (d, J = 5.21 Hz, 1H), 8.19 (s, 1H) |
| 25 | 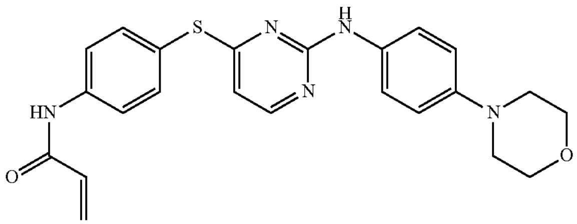 [SMILES: C=CC(=O)Nc1ccc(Sc2ccnc(Nc3ccc(N4CCOCC4)cc3)n2)cc1] | 433.16 | N-(4-(2-(4-morpholino-phenylamino)pyrimidin-4-ylthio)phenyl)acrylamide | B | 8.5 | m/z 433.6 M+ | ¹H NMR (d₆-DMSO) δ 2.91-2.94 (m, 4H), 3.66-3.69 (m, 4H), 8.53 (dd, J = 9.90, 2.02 Hz, 1H), 6.32 (dd, J = 16.95, 1.99 Hz, 1H), 6.44-6.53 (m, 2H), 6.62 (d, J = 9.06 Hz, 2H), 7.19 (d, J = 8.65 Hz, 2H), 7.57 (d, J = 8.58 Hz, 2H), 7.82 (d, J = 8.58 Hz, 2H), 8.10 (d, J = 5.24 Hz, 1H), 9.32 (s, 1H), 10.47 (s, 1H) |
| 26 | 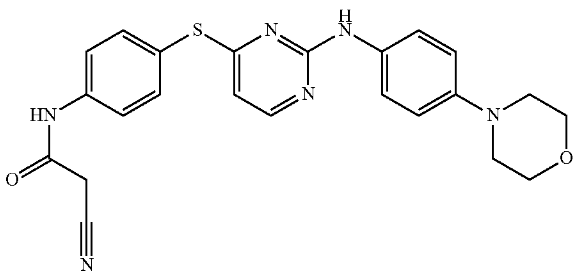 [SMILES: N#CCC(=O)Nc1ccc(Sc2ccnc(Nc3ccc(N4CCOCC4)cc3)n2)cc1] | 446.15 | 2-cyano-N-(4-(2-(4-morpholino-phenylamino)pyrimidin-4-ylthio)phenyl)acetamide | B | 8.2 | m/z 446.6 M+ | ¹H NMR (d₆-DMSO) δ 2.96 (m, 4H), 3.96 (s, 2H), 6.38 (d, J = 4.81 Hz, 1H), 6.68 (d, J = 8.87 Hz, 2H), 7.28 (d, J = 8.53 Hz, 2H), 7.73 (d, J = 8.59 Hz, 2H), 8.10 (d, J = 5.25 Hz, 1H), 9.34 (s, 1H), 10.59 (s, 1H) |
| 27 | 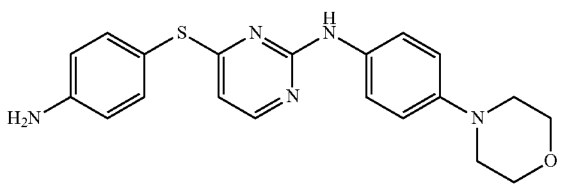 [SMILES: Nc1ccc(Sc2ccnc(Nc3ccc(N4CCOCC4)cc3)n2)cc1] | 379.15 | 4-(4-aminophenyl-thio)-N-(4-morpholino-phenyl)pyrimidin-2-amine | B | 8.4 | m/z 379.1 M+ | ¹H NMR (CDCl₃) δ 3.08-3.12 (m, 4H), 3.84-3.87 (m, 4H), 3.93 (br s, 2H), 6.22 (d, J = 5.38 Hz, 1H), 6.74 (d, J = 8.63 Hz, 2H), 6.83 (d, J = 9.03 Hz, 2H), 6.89 (br s, 1H), 7.34 (d, J = 8.63 Hz, 2H), 7.98 (d, J = 9.08 Hz, 2H), 7.36 (d, J = 5.38 Hz, 1H) |

TABLE 1-continued

| Compound number | Structure | Exact mass | Name | LCMS method | retention time (min) | Observed m/z | ¹H NMR |
|---|---|---|---|---|---|---|---|
| 28 | 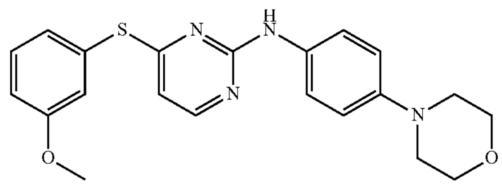 [SMILES: COc1cccc(Sc2ccnc(Nc3ccc(N4CCOCC4)cc3)n2)c1] | 394.15 | 4-(3-methoxyphenylthio)-N-(4-morpholinophenyl)pyrimidin-2-amine | B | 9.5 | m/z 394.2 M+ | ¹H NMR (CDCl₃) δ 3.09-3.12 (m, 4H), 3.81 (s, 3H), 3.86-3.89 (m, 4H), 6.29 (d, J = 5.35 Hz, 1H), 6.82 (d, J = 9.02 Hz, 2H), 6.89 (brs, 1H), 7.04 (ddd, J = 8.30, 2.59, 0.98 Hz, 1H), 7.16 (dd, J = 2.51, 1.68 Hz, 1H), 7.21 (ddd, J = 7.59, 1.55, 1.02 Hz, 1H), 7.32 (d, J = 9.02 Hz, 2H), 7.38 (t, J = 7.86 Hz, 1H), 8.03 (d, J = 5.36 Hz, 1H) |
| 29 | 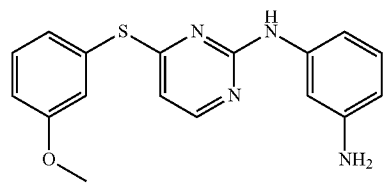 [SMILES: COc1cccc(Sc2ccnc(Nc3cccc(N)c3)n2)c1] | 324.10 | N1-(4-(3-methoxyphenylthio)pyrimidin-2-yl)benzene-1,3-diamine | B | 8.9 | m/z 324.3 M+ | ¹H NMR (CDCl₃) δ 3.81 (s, 3H), 6.31-6.32 (m, 1H), 6.34 (d, J = 5.40 Hz, 1H), 6.34-6.35 (m, 1H), 6.69 (ddd, J = 8.03, 2.07, 0.84 Hz, 1H), 6.96-7.08 (m, 4H), 7.17 (dd, J = 2.51, 1.63 Hz, 1H), 7.22 (ddd, J = 7.58, 1.57, 1.024 Hz, 1H), 7.38 (t, J = 7.83 Hz, 1H), 8.05 (d, J = 5.40 Hz, 1H) |
| 30 | 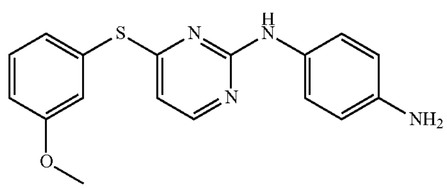 [SMILES: COc1cccc(Sc2ccnc(Nc3ccc(N)cc3)n2)c1] | 324.10 | N1-(4-(3-methoxyphenylthio)pyrimidin-2-yl)benzene-1,4-diamine | B | 8.6 | m/z 324.3 M+ | ¹H NMR (CDCl₃) δ 3.54 (brs, 2H), 3.81 (s, 3H), 6.24 (d, J = 5.35 Hz, 1H), 6.59 (d, J = 8.75 Hz, 2H), 6.82 (brs, 1H), 7.03 (ddd, J = 8.31, 2.58, 0.99 Hz, 1H), 7.13-7.22 (m, 4H), 7.36 (t, J = 7.85 Hz, 1H), 7.99 (d, J = 5.35 Hz, 1H) |
| 31 | 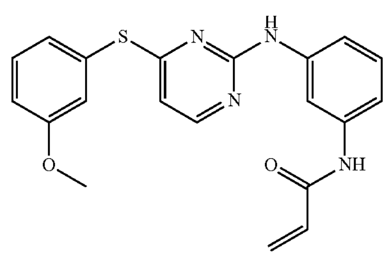 [SMILES: C=CC(=O)Nc1cccc(Nc2nccc(Sc3cccc(OC)c3)n2)c1] | 378.12 | N-(3-(4-(3-methoxyphenylthio)pyrimidin-2-ylamino)phenyl)acrylamide | B | 9 | m/z 378.3 M+ | ¹H NMR (CDCl₃) δ 3.80 (s, 3H), 5.77 (dd, J = 10.09, 1.43 Hz, 1H), 6.25 (dd, J = 16.87, 10.09 Hz, 1H), 6.39 (d, J = 5.44 Hz, 1H), 6.44 (dd, J = 16.84, 1.42 Hz, 1H), 7.04 (ddd, J = 8.30, 2.56, 0.91 Hz, 1H), 7.11-7.18 (m, 3H), 7.19-7.23 (m, 1H), 7.28-7.41 (m, 3H), 7.69 (brs, 1H), 8.06 (d, J = 5.36 Hz, 1H) |

TABLE 1-continued

| Compound number | Structure | Exact mass | Name | LCMS method | retention time (min) | Observed m/z | $^1$H NMR |
|---|---|---|---|---|---|---|---|
| 32 | 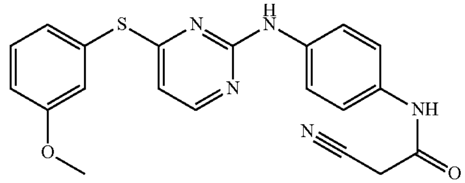 [SMILES: COc1cccc(Sc2ccnc(Nc3ccc(NC(=O)CC#N)cc3)n2)c1] | 391.11 | 2-cyano-N-(4-(4-(3-methoxyphenylthio)pyrimidin-2-ylamino)phenyl)acetamide | B | 8.6 | m/z 391.2 M+ | $^1$H NMR (CDCl$_3$) δ 3.54 (s, 2H), 3.83 (s, 3H), 6.33 (d, J = 5.34 Hz, 1H), 7.07 (ddd, J = 8.33, 2.59, 0.97 Hz, 1H), 7.16 (dd, J = 2.48, 1.73 Hz, 1H), 7.20 (ddd, J = 8.09, 1.58, 1.05 Hz, 1H), 7.39-7.44 (m, 4H), 7.67 (s, 1H), 8.05 (d, J = 5.53 Hz, 1H), 9.55 (brs, 1H) |
| 33 | 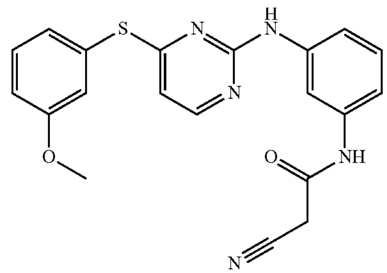 [SMILES: COc1cccc(Sc2ccnc(Nc3cccc(NC(=O)CC#N)c3)n2)c1] | 391.11 | 2-cyano-N-(3-(4-(3-methoxyphenylthio)pyrimidin-2-ylamino)phenyl)acetamide | B | 8.8 | m/z 391.2 M+ | $^1$H NMR (CDCl$_3$) δ 3.57 (s, 2H), 3.82 (s, 3H), 6.29 (d, J = 5.36 Hz, 1H), 7.04 (ddd, J = 8.32, 2.59, 0.94 Hz, 1H), 7.13-7.16 (m, 2H), 7.18-7.19 (m, 1H), 7.231 (dd, J = 1.48, 0.95 Hz, 1H), 7.34-7.39 (m, 3H), 7.76 (m, 1H), 7.91 (brs, 1H), 8.07 (d, J = 5.36 Hz, 1H), 9.70 (brs, 1H) |
| 34 | 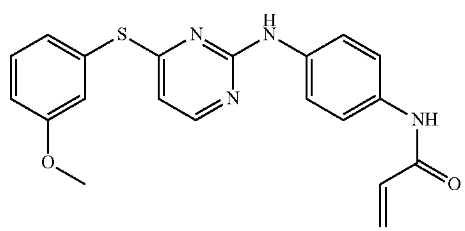 [SMILES: C=CC(=O)Nc1ccc(Nc2nccc(Sc3cccc(OC)c3)n2)cc1] | 378.12 | N-(4-(4-(3-methoxyphenyl)thio-2-ylamino)phenyl)acrylamide | B | 8.7 | m/z 378.2 M+ | $^1$H NMR (CDCl$_3$) δ 3.82 (s, 3H), 5.68 (dd, J = 11.86, 2.17 Hz, 1H), 6.31 (d, J = 5.35 Hz, 1H), 6.37 (d, J = 2.88 Hz, 1H), 6.39 (s, 1H), 7.07 (ddd, J = 8.35, 2.64, 0.96 Hz, 1H), 7.15-7.16 (m, 1H), 7.20 (ddd, J = 7.58, 1.55, 1.03 Hz, 1H), 7.41 (d, J = 8.93 Hz, 2H), 7.53 (d, J = 8.95 Hz, 2H), 7.75 (brs, 1H), 8.05 (d, J = 5.35 Hz, 1H), 8.96 (brs, 1H) |
| 35 | 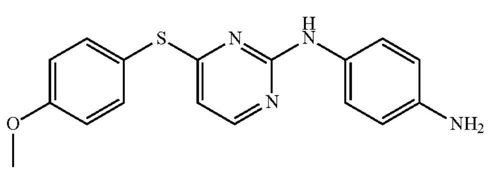 [SMILES: COc1ccc(Sc2ccnc(Nc3ccc(N)cc3)n2)cc1] | 324.10 | N1-(4-(4-methoxyphenyl)thio-2-yl)benzene-1,4-diamine | B | 8.6 | m/z 324.1 M+ | $^1$H NMR (CDCl$_3$) δ 3.61 (brs, 2H), 3.87 (s, 3H), 6.16 (d, J = 5.35 Hz, 1H), 6.58 (d, J = 8.74 Hz, 2H), 6.97 (d, J = 8.88 Hz, 2H), 7.19 (d, J = 8.71 Hz, 2H), 7.19 (d, J = 8.71 Hz, 1H), 7.51 (d, J = 8.88 Hz, 2H), 7.98 (d, J = 5.35 Hz, 1H) |

TABLE 1-continued

| Compound number | Structure | Exact mass | Name | LCMS method | retention time (min) | Observed m/z | 1H NMR |
|---|---|---|---|---|---|---|---|
| 36 | 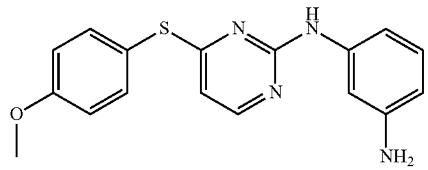 [SMILES: COc1ccc(Sc2ccnc(Nc3cccc(N)c3)n2)cc1] | 324.10 | N1-(4-(4-methoxyphenylthio)pyrimidin-2-yl)benzene-1,3-diamine | B | 8.9 | m/z 324.4 M+ | 1H NMR (CDCl3) δ 3.68 (brs, 2H), 3.87 (s, 3H), 6.25 (d, J = 5.36 Hz, 1H), 6.30 (ddd, J = 7.90, 2.18, 0.87 Hz, 1H), 6.72-6.76 (m, 1H), 6.94-7.01 (m, 4H), 7.35 (brs, 1H), 7.53 (d, J = 8.88 Hz, 2H), 8.03 (d, J = 5.36 Hz, 1H) |
| 37 | 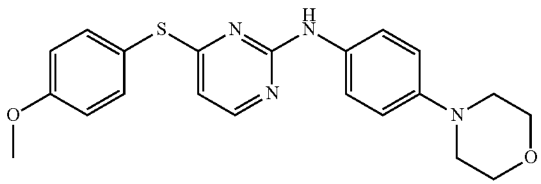 [SMILES: COc1ccc(Sc2ccnc(Nc3ccc(N4CCOCC4)cc3)n2)cc1] | 394.15 | 4-(4-methoxyphenylthio)-N-(4-morpholinophenyl)pyrimidin-2-amine | H | NA | m/z 394.4 M+ | 1H NMR (d6-DMSO) δ 2.98-3.01 (m, 4H), 3.72-3.75 (m, 4H), 3.85 (s, 3H), 6.27 (d, J = 5.06 Hz, 1H), 6.72 (d, J = 9.04 Hz, 2H), 7.10 (d, J = 8.88 Hz, 2H), 7.32 (d, J = 8.90 Hz, 2H), 7.54 (d, J = 8.85 Hz, 2H), 8.09 (d, J = 5.29 Hz, 1H), 9.35 (s, 1H) |
| 38 | 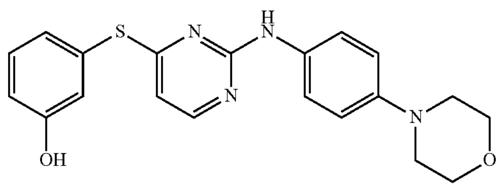 [SMILES: Oc1cccc(Sc2ccnc(Nc3ccc(N4CCOCC4)cc3)n2)c1] | 380.13 | 3-(2-(4-morpholinophenylamino)pyrimidin-4-ylthio)phenol | B | 8.3 | m/z 380.2 M+ | 1H NMR (d6-DMSO) δ 2.99-3.02 (m, 4H), 3.72-3.75(m, 4H), 6.28 (d, J = 5.29 Hz, 1H), 6.78 (d, J = 9.17 Hz, 2H), 6.95-7.06 (m, 3H), 7.34 (t, J = 7.81 Hz, 1H), 7.38 (d, J = 9.07 Hz, 2H), 8.11 (d, J = 5.29 Hz, 1H), 9.38 (s, 1H) |
| 39 | 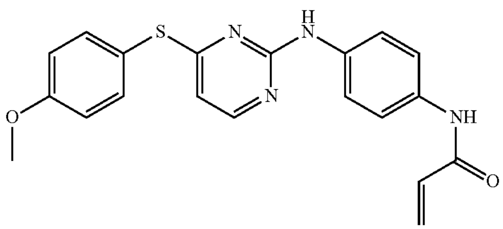 [SMILES: C=CC(=O)Nc1ccc(Nc2nccc(Sc3ccc(OC)cc3)n2)cc1] | 378.12 | N-4-(4-(4-methoxyphenylthio)pyrimidin-2-ylaminophenyl)acrylamide | B | 8.9 | m/z 378.1 M+ | 1H NMR (d6-DMSO) δ 3.86 (s, 3H), 5.71 (dd, J = 5.22, 7.42 Hz, 1H), 6.23 (dd, J = 2.18, 17.01 Hz, 1H), 6.29 (d, J = 5.40 Hz, 1H), 6.42 (dd, J = 10.04, 16.94 Hz, 1H), 7.09 (d, J = 8.88 Hz, 2H), 7.44 (s, 4H), 7.56 (d, J = 8.85 Hz, 2H), 8.13 (d, J = 5.31 Hz, 1H), 9.56 (s, 1H), 9.98 (s, 1H) |
| 40 | 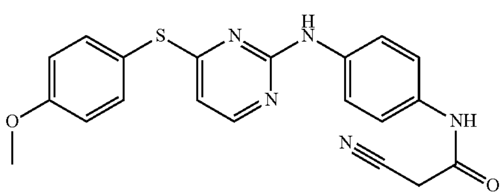 [SMILES: COc1ccc(Sc2ccnc(Nc3ccc(NC(=O)CC#N)cc3)n2)cc1] | 391.11 | 2-cyano-N-(4-(4-(4-methoxyphenylthio)pyrimidin-2-ylamino)phenyl)acetamide | B | 8.6 | m/z 391 M+ | 1H NMR (d6-DMSO) δ 3.84 (s, 2H), 3.86 (s, 3H), 6.31 (d, J = 5.38 Hz, 1H), 7.10 (d, J = 8.88 Hz, 2H), 7.31 (d, J = 9.02 Hz, 2H), 7.44 (d, J = 9.00 Hz, 2H), 7.56 (d, J = 8.84 Hz, 2H), 8.13 (d, J = 5.31 Hz, 1H), 9.58 (s, 1H), 10.13 (s, 1H) |

TABLE 1-continued

| Compound number | Structure | Exact mass | Name | LCMS method | retention time (min) | Observed m/z | 1H NMR |
|---|---|---|---|---|---|---|---|
| 41 | (structure) | 392.13 | N-(4-(4-methoxyphenyl-thio)pyrimidin-2-ylamino)phenyl)methacrylamide | B | 9.2 | m/z 392 M+ | 1H NMR (d6-DMSO) δ 1.94 (s, 3H), 3.84 (s, 3H), 5.45-5.46 (m, 1H), 5.74-5.77 (m, 1H), 6.27 (d, J = 5.26 Hz, 1H), 7.09 (d, J = 8.84 Hz, 2H), 7.43 (s, 4H), 7.55 (d, J = 8.84 Hz, 2H), 8.13 (d, J = 5.31 Hz, 1H), 9.54 (s, 1H), 9.61 (s, 1H) |
| 42 | (structure) | 378.12 | N-(3-(4-(4-methoxyphenyl-thio)pyrimidin-2-ylamino)phenyl acrylamide | B | 9 | m/z 378.1 M+ | 1H NMR (d6-DMSO) δ 3.84 (s, 3H), 5.73 (dd, J = 2.14, 10.06 Hz, 1H), 6.21 (d, J = 5.29 Hz, 1H), 6.25 (dd, J = 2.10, 14.82 Hz, 1H), 6.46 (dd, J = 10.04, 16.92 Hz, 1H), 7.04-7.12 (m, 3H), 7.28-7.33 (m, 2H), 7.57 (d, J = 8.84 Hz, 2H), 7.81-7.87 (m, 1H), 8.15 (d, J = 5.35 Hz, 1H), 9.65 (s, 1H), 10.04 (s, 1H) |
| 43 | (structure) | 391.11 | 2-cyano-N-(3-(4-(4-methoxyphenylthio)pyrimidin-2-ylamino)phenyl)acetamide | B | 8.8 | m/z 391 M+ | 1H NMR (d6-DMSO) δ 3.84 (s, 3H), 3.87 (s, 2H), 6.21 (d, J = 5.34 Hz, 1H), 7.05-7.12 (m, 3H), 7.17-7.22 (m, 1H), 7.28-7.35 (m, 1H), 7.57 (d, J = 8.84 Hz, 2H), 8.72-8.76 (m, 1H), 8.16 (d, J = 5.35 Hz, 1H), 9.69 (s, 1H), 10.19 (s, 1H) |

TABLE 1-continued

| Compound number | Structure | Exact mass | Name | LCMS method | retention time (min) | Observed m/z | ¹H NMR |
|---|---|---|---|---|---|---|---|
| 45 | 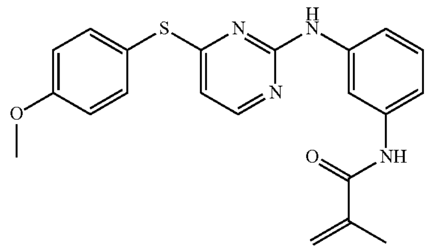 [SMILES: C=C(C)C(=O)Nc1cccc(Nc2nccc(Sc3ccc(OC)cc3)n2)c1] | 392.13 | N-(3-(4-(4-methoxyphenyl-thio)pyrimidin-2-ylamino)phenyl)methacrylamide | B | 9.4 | m/z 392.2 M+ | ¹H NMR (d₆-DMSO) δ 1.94 (s, 3H), 3.83 (s, 3H), 5.48-5.49 (m, 1H), 5.78 (s, 1H), 6.21 (d, J = 5.33 Hz, 1H), 7.05 (t, J = 8.06 Hz, 1H), 7.09 (d, J = 8.92 Hz, 2H), 7.16-7.22 (m, 1H), 7.27-7.33 (m, 1H), 7.57 (d, J = 9.21 Hz, 2H), 7.83-7.87 (m, 1H), 8.14 (d, J = 5.33 Hz, 1H), 9.60 (s, 1H), 9.69 (s, 1H) |
| 46 | 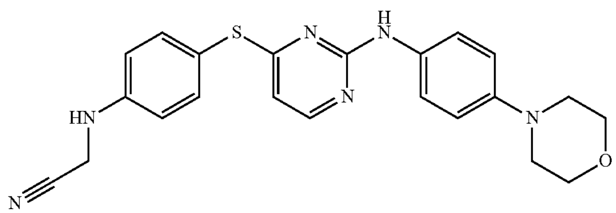 [SMILES: N#CCNc1ccc(Sc2ccnc(Nc3ccc(N4CCOCC4)cc3)n2)cc1] | 418.16 | 2-(4-(2-(4-morpholino-phenylamino)pyrimidin-4-ylthio)phenyl-aminoacetonitrile | B | 8.5 | m/z 418.4 M+ | ¹H NMR (d₆-DMSO) δ 2.98-3.01 (m, 4H), 3.71-3.74 (m, 4H), 4.36 (d, J = 6.56 Hz, 2H), 6.23 (d, J = 5.23 Hz, 1H), 6.75 (d, J = 9.03 Hz, 2H), 6.81 (d, J = 6.65 Hz, 1H), 6.85 (d, J = 8.69 Hz, 2H), 7.36 (d, J = 9.07 Hz, 2H), 7.41 (d, J = 8.64 Hz, 2H), 8.08 (d, J = 5.29 Hz, 1H), 9.34 (s, 1H) |
| 47 | 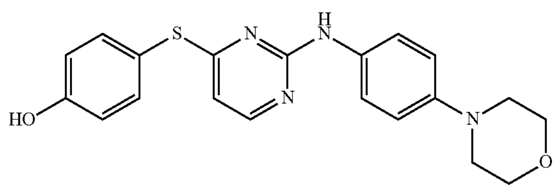 [SMILES: Oc1ccc(Sc2ccnc(Nc3ccc(N4CCOCC4)cc3)n2)cc1] | 380.13 | 4-(2-(4-morpholino-phenylamino)pyrimidin-4-ylthio)phenol | B | 8.3 | m/z 380 M+ | ¹H NMR (d₆-DMSO) δ 2.99-3.02 (m, 4H), 3.71-3.74 (m, 4H), 6.24 (d, J = 5.48 Hz, 1H), 6.75 (d, J = 9.09 Hz, 2H), 6.92 (d, J = 8.68 Hz, 2H), 7.35 (d, J = 8.94 Hz, 2H), 7.41 (d, J = 8.68 Hz, 2H), 8.07 (d, J = 5.29 Hz, 1H), 9.34 (s, 1H), 10.06 (s, 1H) |
| 48 | 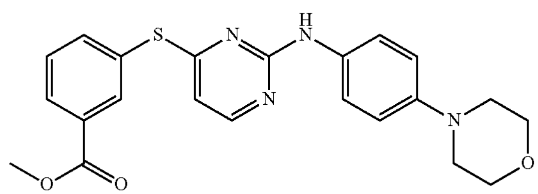 [SMILES: COC(=O)c1cccc(Sc2ccnc(Nc3ccc(N4CCOCC4)cc3)n2)c1] | 422.14 | methyl 3-(2-(4-morpholino-phenylamino)pyrimidin-4-ylthio)benzoate | B | 9.4 | m/z 422.2 M+ | ¹H NMR (CDCl₃) δ 3.06-3.09 (m, 4H), 3.85-3.88 (m, 4H), 3.92 (s, 3H), 6.33-6.35 (d, J = 5.36 Hz, 1H), 6.74 (d, J = 9.01 Hz, 2H), 7.04 (br s, 1H), 7.20 (d, J = 8.97 Hz, 2H), 7.54 (t, J = 7.78 Hz, 1H), 7.79 (ddd, J = 1.23, 1.80, 7.72 Hz, 1H), 8.02 (d, J = 5.36 Hz, 1H), 8.15-8.19 (m, 1H), 8.28-8.29 (m, 1H) |

TABLE 1-continued

| Compound number | Structure | Exact mass | Name | LCMS method | retention time (min) | Observed m/z | ¹H NMR |
|---|---|---|---|---|---|---|---|
| 49 | 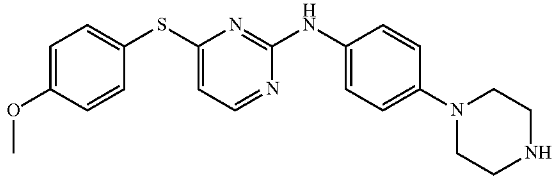 [SMILES: COc1ccc(Sc2ccnc(Nc3ccc(N4CCNCC4)cc3)n2)cc1] | 393.16 | 4-(4-methoxyphenylthio)-N-(4-(piperazin-1-yl)phenyl)pyrimidin-2-amine | B | 9 | m/z 393.5 M+ | ¹H NMR (CDCl₃) δ 3.02-3.05 (m, 4H), 3.87-3.90 (m, 4H), 3.85 (s, 3H), 5.97 (d, J = 5.31 Hz, 1H), 6.65 (d, J = 8.84 Hz, 2H), 6.84 (d, J = 8.83 Hz, 2H), 6.95 (d, J = 8.89 Hz, 2H), 7.51 (d, J = 8.87 Hz, 2H), 7.95 (d, J = 5.32 Hz, 1H) |
| 50 | 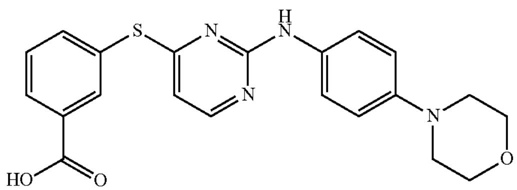 [SMILES: O=C(O)c1cccc(Sc2ccnc(Nc3ccc(N4CCOCC4)cc3)n2)c1] | 408.13 | 3-(2-(4-morpholinophenylamino)pyrimidin-4-ylthio)benzoic acid | B | 8.2 | m/z 408.2 M+ | ¹H NMR (d₆-DMSO) δ 2.97-3.01 (m, 4H), 3.71-3.75 (m, 4H), 6.47 (d, J = 4.67 Hz, 1H), 6.66 (d, J = 8.99 Hz, 2H), 7.22 (d, J = 8.14 Hz, 2H), 7.67 (t, J = 7.76 Hz, 1H), 7.86 (dd, J = 1.22, 1.71, 7.70 Hz, 1H), 8.11-8.17 (m, 2H), 8.14 (d, J = 5.24 Hz, 1H) |
| 51 | 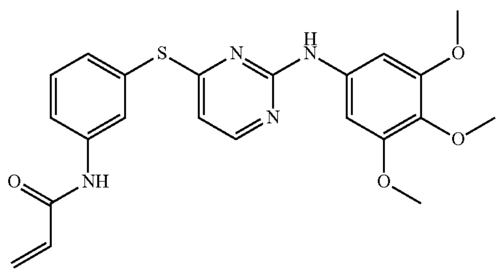 [SMILES: C=CC(=O)Nc1cccc(Sc2ccnc(Nc3cc(OC)c(OC)c(OC)c3)n2)c1] | 438.14 | N-(3-(2-(3,4,5-trimethoxyphenylamino)pyrimidin-4-ylthio)phenyl)acrylamide | B | 8.7 | m/z 438.4 M+ | ¹H NMR (CDCl₃) δ 3.81-3.85 (m, 9H), 5.80 (dd, J = 1.34, 10.13 Hz, 1H), 6.21-6.30 (m, 2H), 6.45 (dd, J = 1.35, 16.83 Hz, 1H), 6.86-6.92 (m, 2H), 7.12 (br s, 1H), 7.32-7.36 (m, 1H), 7.41 (t, 7.74 Hz, 1H), 7.52 (br s, 1H), 7.69-7.72 (m, 1H), 7.90 (s, 1H), 8.05 (d, J = 5.39 Hz, 1H) |
| 52 | 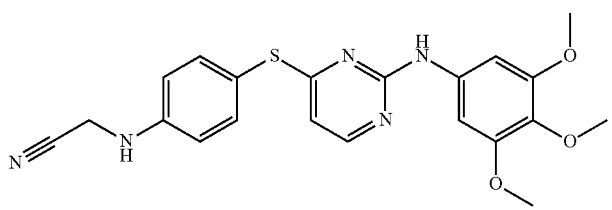 [SMILES: COc1cc(Nc2nccc(Sc3ccc(NCC#N)cc3)n2)cc(OC)c1OC] | 423.14 | 2-(4-(2-(3,4,5-trimethoxyphenylaminopyrimidin-4-ylthio)phenylamino)acetonitrile | B | 8.7 | m/z 423.2 M+ | ¹H NMR (CDCl₃) δ 3.82 (s, 3H), 3.85 (s, 6H), 4.17 (d, J = 6.97 Hz, 2H), 6.16 (d, J = 5.38 Hz, 1H), 6.76 (d, J = 8.75 Hz, 2H), 6.89 (s, 2H), 6.94 (br s, 1H), 7.49 (d, J = 8.68 Hz, 2H), 8.03 (d, J = 5.39 Hz, 1H) |

TABLE 1-continued

| Compound number | Structure | Exact mass | Name | LCMS method | retention time (min) | Observed m/z | ¹H NMR |
|---|---|---|---|---|---|---|---|
| 53 | 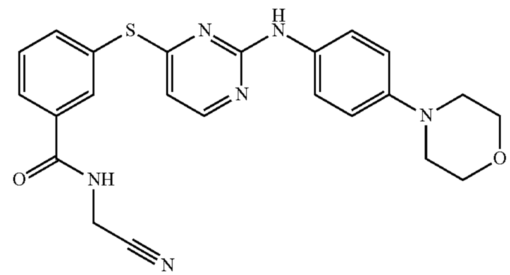 [SMILES: N#CCNC(=O)c1cccc(Sc2ccnc(Nc3ccc(N4CCOCC4)cc3)n2)c1] | 446.15 | N-(cyanomethyl) 3-(2-(4-morpholinophenyl aminopyrimidin-4-ylthio)benzamide | C | 6.4 | m/z 447.1 [M + H]+ | ¹H NMR (CDCl₃) δ 3.06-3.10 (m, 4H), 3.85-3.88 (m, 4H), 4.31 (d, J = 5.77 Hz, 2H), 6.25-6.32 (m, 1H), 6.41 (d, J = 5.27 Hz, 1H), 6.72 (d J = 8.96 Hz, 2H), 6.85 (br s, 1H), 7.15 (d, J = 8.79 Hz, 2H), 7.58 (t, J = 8.25 Hz, 1H), 7.77-7.81 (m, 1H), 7.93-7.97 (m, 2H), 8.08 (d, J = 5.32 Hz, 1H) |
| 54 | 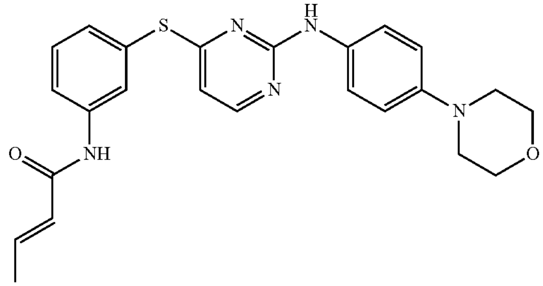 [SMILES: C/C=C/C(=O)Nc1cccc(Sc2ccnc(Nc3ccc(N4CCOCC4)cc3)n2)c1] | 447.17 | (E)-N-(3-(2-(4-morpholinophenyl aminopyrimidin-4-ylthio)phenyl) but-2-enamide | B | 8.8 | m/z 447.2 M+ | ¹H NMR (CDCl₃) δ 1.90 (dd, J = 1.65, 6.90 Hz, 3H), 3.06-3.09 (m, 4H), 3.85-3.88 (m, 4H), 5.95 (dd, J = 1.67, 15.09 Hz, 1H), 6.35 (d, J = 5.43 Hz, 1H), 6.78 (d, J = 9.02 Hz, 2H), 6.93-7.05 (m, 1H), 7.25 (d, J = 9.20 Hz, 2H), 7.30-7.34 (m, 1H), 7.42 (t, J = 7.82 Hz, 1H), 7.45 (br s, 1H), 7.57 (br s, 1H), 7.71 (br s, 1H), 7.71 (br s, 1H), 7.94 (br s, 1H), 7.97 (d, J = 5.40 Hz, 1H) |
| 55 | 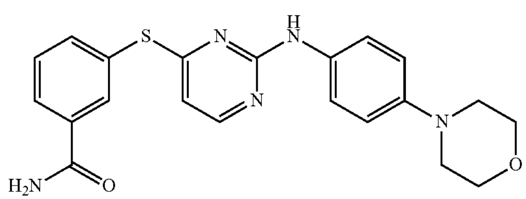 [SMILES: NC(=O)c1cccc(Sc2ccnc(Nc3ccc(N4CCOCC4)cc3)n2)c1] | 407.14 | 3-(2-(4-morpholinophenyl aminopyrimidin-4-ylthio)benzamide | B | 7.6 | m/z 407.1 M+ | ¹H NMR (d₆-DMSO) δ 2.97-3.00 (m, 4H), 3.71-3.74 (m, 4H), 6.41 (d, J = 4.88 Hz, 1H), 6.69 (d, J = 8.97 Hz, 2H), 7.24 (d, J = 9.02 Hz, 2H), 7.50 (br s, 1H), 7.62 (t, J = 7.72 Hz, 1H), 7.76-7.79 (m, 1H), 8.09-8.16 (m, 4H), 9.37 (s, 1H) |

TABLE 1-continued

| Compound number | Structure | Exact mass | Name | LCMS method | retention time (min) | Observed m/z | 1H NMR |
|---|---|---|---|---|---|---|---|
| 56 | 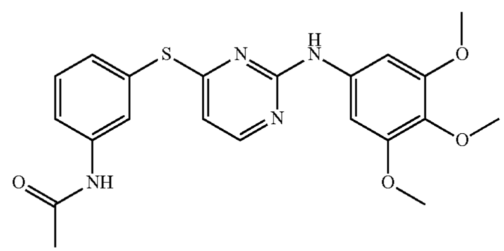 [SMILES: COc1cc(Nc2nccc(Sc3cccc(NC(C)=O)c3)n2)cc(OC)c1OC] | 426.14 | N-(3-(2-(3,4,5-trimethoxyphenyl-aminopyrimidin-4-ylthio)phenyl)acetamide | B | 8.3 | m/z 426.2 M+ | 1H NMR (CDCl3) δ 2.18 (s, 3H), 3.81 (s, 3H), 3.83 (s, 6H), 6.26 (d, J = 5.37 Hz, 1H), 6.88 (s, 2H), 7.10 (s, 1H), 7.29-7.34 (m, 1H), 7.39 (t, J = 7.88 Hz, 1H), 7.44 (br s, 1H), 7.63-7.68 (m, 1H), 7.78 (br s, 1H), 8.05 (d, J = 5.38 Hz, 1H) |
| 57 | 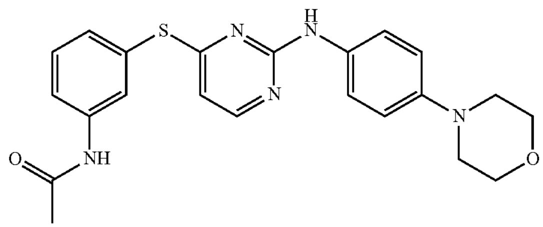 [SMILES: CC(=O)Nc1cccc(Sc2ccnc(Nc3ccc(N4CCOCC4)cc3)n2)c1] | 421.16 | N-(3-(2-(4-morpholinophenyl-aminopyrimidin-4-ylthio)phenyl)acetamide | B | 8.2 | m/z 421.1 M+ | 1H NMR (CDCl3) δ 2.17 (s, 3H), 3.08-3.11 (m, 4H), 3.87-3.90 (m, 4H), 6.34 (d, J = 5.40 Hz, 1H), 6.82 (d, J = 8.99 Hz, 2H), 7.22 (br s, 1H), 7.26 (d, J = 8.94 Hz, 2H), 7.29-7.36 (m, 1H), 7.42 (t, J = 7.80 Hz, 1H), 7.53 (br s, 1H), 7.67 (br s, 1H), 7.85 (d, J = 7.52 Hz, 1H), 8.05 (d, J = 5.38 Hz, 1H) |
| 58 | 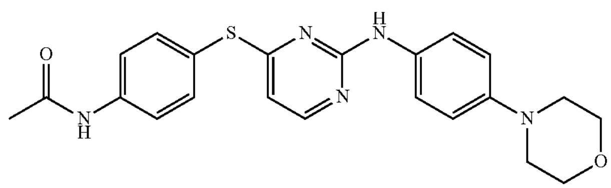 [SMILES: CC(=O)Nc1ccc(Sc2ccnc(Nc3ccc(N4CCOCC4)cc3)n2)cc1] | 421.16 | N-(4-(2-(4-morpholinophenyl-aminopyrimidin-4-ylthio)phenyl)acetamide | B | 8.2 | m/z 421.2 M+ | 1H NMR (d6-DMSO) δ 2.11 (s, 3H), 3.16-3.27 (m, 4H), 3.83-3.92 (m, 4H), 6.49 (d, J = 5.10 Hz, 1H), 7.03 (br s, 2H), 7.37 (d, J = 8.68 Hz, 2H), 7.53 (d, J = 6.86 Hz, 2H), 7.77 (d, J = 8.71 Hz, 2H), 8.14 (d, J = 5.41 Hz, 1H), 9.69 (s, 1H), 10.34 (s, 1H) |
| 59 | 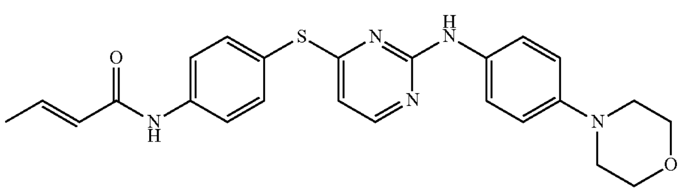 [SMILES: C/C=C/C(=O)Nc1ccc(Sc2ccnc(Nc3ccc(N4CCOCC4)cc3)n2)cc1] | 447.17 | (E)-N-(4-(2-(4-morpholinophenyl-aminopyrimidin-4-ylthio)phenyl)but-2-enamide | B | 8.9 | m/z 447.2 M+ | 1H NMR (d6-DMSO) δ 1.99 (dd, J = 1.55, 6.90 Hz, 3H), 3.04-3.14 (m, 4H), 3.72-3.78 (m, 4H), 6.19 (dd, J = 1.68, 15.24 Hz, 1H), 6.55 (d, J = 5.34 Hz, 1H), 6.83-6.91 (m, 3H), 7.27 (d, J = 8.72 Hz, 2H), 7.55 (d, J = 8.68 Hz, 2H), 7.84 (d, J = 8.72 Hz, 2H), 8.12 (d, J = 5.37 Hz, 1H), 9.58 (s, 1H), 10.33 (s, 1H) |

TABLE 1-continued

| Compound number | Structure | Exact mass | Name | LCMS method | retention time (min) | Observed m/z | ¹H NMR |
|---|---|---|---|---|---|---|---|
| 60 | 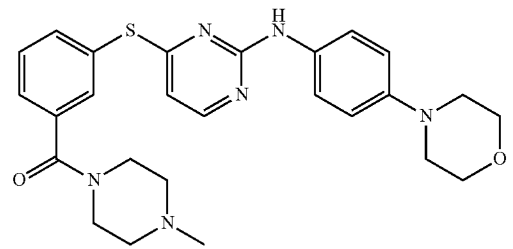 [SMILES: CN1CCN(C(=O)c2cccc(Sc3ccnc(Nc4ccc(N5CCOCC5)cc4)n3)c2)CC1] | 490.22 | (4-methylpiperazin-1-yl)(3-(2-(4-morpholinophenyl-aminopyrimidin-4-ylthio)phenyl)methanone | B | 8 | m/z 490.3 M+ | ¹H NMR (CDCl₃) δ 1.25 (m, 4H), 1.56 (s, 4H), 2.28 (s, 3H), 3.07-3.10 (m, 4H), 3.84-3.87 (m, 4H), 6.34 (d, J = 5.31 Hz, 1H), 6.78 (d, J = 9.01 Hz, 2H), 6.84 (s, 1H), 7.23 (d, J = 9.02 Hz, 2H), 7.49-7.63 (m, 3H), 7.66-7.69 (m, 1H), 8.04 (d, J = 5.33 Hz, 1H) |
| 61 | 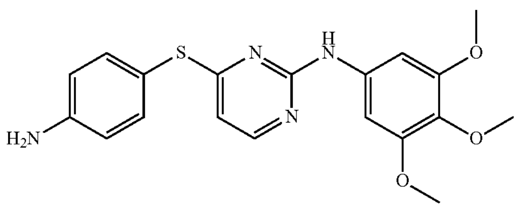 [SMILES: COc1cc(Nc2nccc(Sc3ccc(N)cc3)n2)cc(OC)c1OC] | 384.13 | 4-(4-aminophenyl-thio)-N-(3,4,5-trimethoxy-phenyl)pyrimidin-2-amine | B | 8.6 | m/z 384.4 M+ | ¹H NMR (CDCl₃) δ 3.82 (s, 3H), 3.86 (s, 6H), 3.93 (br s, 1H), 6.15 (d, J = 5.39 Hz, 1H), 6.73 (d, J = 8.65 Hz, 2H), 6.90 (s, 2H), 6.92 (br s, 1H), 7.36 (d, J = 8.65 Hz, 2H), 8.01 (d, J = 5.39 Hz, 1H) |
| 62 | 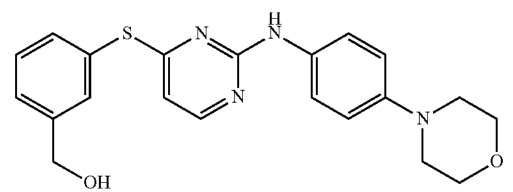 [SMILES: OCc1cccc(Sc2ccnc(Nc3ccc(N4CCOCC4)cc3)n2)c1] | 394.15 | (3-(2-(4-morpholinophenyl-aminopyrimidin-4-ylthio)phenyl)methanol | B | 8.2 | m/z 394.4 M+ | ¹H NMR (CDCl₃) δ 3.07-3.10 (m, 4H), 3.84-3.88 (m, 4H), 4.65 (s, 1H), 4.70 (s, 2H), 6.30 (d, J = 5.37 Hz, 1H), 6.77 (d, J = 9.02 Hz, 2H), 7.24 (d, J = 8.70 Hz, 2H), 7.42-7.59 (m, 5H), 8.01 (d, J = 5.37 Hz, 1H) |
| 63 | 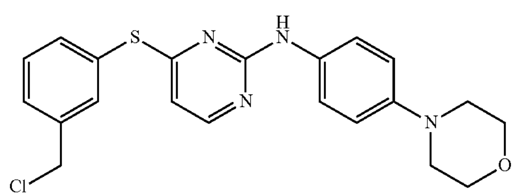 [SMILES: ClCc1cccc(Sc2ccnc(Nc3ccc(N4CCOCC4)cc3)n2)c1] | 412.11 | 4-(3-(chloromethyl)phenylthio)-N-(4-morpholino-phenyl)pyrimidin-2-amine | B | 9.9 | m/z 411.9/ 413.8 M+ | ¹H NMR (CDCl₃) δ 3.07-3.10 (m, 4H), 3.84-3.87 (m, 4H), 4.59 (s, 2H), 6.30 (d, J = 5.37 Hz, 1H), 6.78 (d, J = 9.06 Hz, 2H), 7.01 (br s, 1H), 7.25 (d, J = 8.98 Hz, 2H), 7.42-7.59 (m, 3H), 7.61-7.65 (m, 1H), 8.03 (d, J = 5.34 Hz, 1H) |

TABLE 1-continued

| Compound number | Structure | Exact mass | Name | LCMS method | retention time (min) | Observed m/z | ¹H NMR |
|---|---|---|---|---|---|---|---|
| 64 | 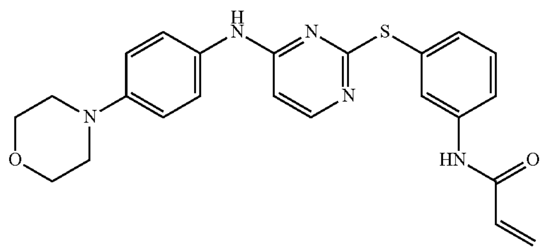 [SMILES: C=CC(=O)Nc1cccc(Sc2nccc(Nc3ccc(N4CCOCC4)cc3)n2)c1] | 433.16 | N-(3-(4-(4-morpholinophenyl-aminopyrimidin-2-ylthio)phenyl)acrylamide | B | 8.0 | m/z 432.9 M+ | ¹H NMR (CDCl$_3$) δ 3.10-3.14 (m, 4H), 3.84-3.87 (4H), 5.73 (dd, J = 1.39, 10.16 Hz, 1H), 6.16 (d, J = 16.88 Hz, 1H), 6.23 (d, J = 5.86 Hz, 1H), 6.4 (dd, J = 1.40, 16.82 Hz, 1H), 6.78 (br s, 1H), 6.82 (d, J = 8.90 Hz, 2H), 7.10 (d, J = 8.92 Hz, 2H), 7.35-7.37 (m, 2H), 7.66 (br s, 1H), 7.71 (br s, 1H), 7.82 (br s, 1H), 7.98 (d, J = 5.88 Hz, 1H) |
| 65 | 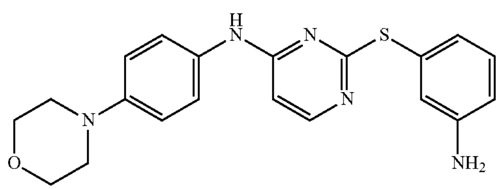 [SMILES: Nc1cccc(Sc2nccc(Nc3ccc(N4CCOCC4)cc3)n2)c1] | 379.15 | 2-(3-aminophenyl-thio)-N-(4-morpholino-phenyl)pyrimidin-4-amine | B | 7.8 | m/z 379.4 M+ | ¹H NMR (CDCl$_3$) δ 3.10-3.14 (m, 4H), 3.85-3.88 (m, 4H), 6.23 (d, J = 5.93 Hz, 1H), 6.75 (ddd, J = 0.99, 2.36, 7.99 Hz, 1H), 6.83 (d, J = 9.05 Hz, 2H), 6.99-7.01 (m, 1H), 7.04 (ddd, J = 1.09, 1.62, 7.58 Hz, 1H), 7.13 (d, J = 9.12 Hz, 2H), 7.21 (t, J = 7.97 Hz, 1H), 7.97 (d, J = 5.93 Hz, 1H) |
| 66 | 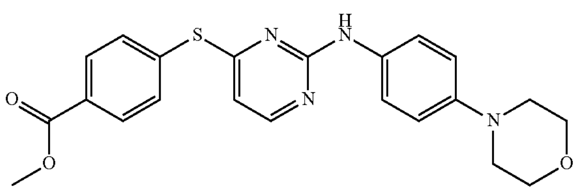 [SMILES: COC(=O)c1ccc(Sc2ccnc(Nc3ccc(N4CCOCC4)cc3)n2)cc1] | 422.14 | methyl 4-(2-(4-morpholinophenyl-aminopyrimidin-4-ylthio)benzoate | B | 9.6 | m/z 422.5 M+ | ¹H NMR (d$_6$-DMSO) δ 2.93-2.96 (m, 4H), 3.71-3.74 (m, 4H), 3.91 (s, 3H), 6.56-6.61 (m, 3H), 7.18 (d, J = 7.76 Hz, 2H), 7.77 (d, J = 8.61 Hz, 2H), 8.07 (d, J = 8.62 Hz, 2H), 8.15 (d, J = 5.25 Hz, 1H), 9.39 (s, 1H) |
| 67 | 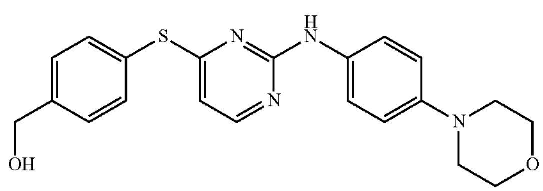 [SMILES: OCc1ccc(Sc2ccnc(Nc3ccc(N4CCOCC4)cc3)n2)cc1] | 394.15 | (4-(2-(4-morpholinophenyl-aminopyrimidin-4-ylthio)phenyl)methanol | B | 8.2 | m/z 394.4 M+ | ¹H NMR (d$_6$-DMSO) δ 2.98-3.02 (m, 4H), 3.71-3.74 (m, 4H), 4.62 (s, 2H), 6.28 (d, J = 5.44 Hz, 1H), 6.73 (d, J = 9.08 Hz, 2H), 7.32 (d, J = 8.91 Hz, 2H), 7.48 (d, J = 8.47 Hz, 2H), 7.59 (d, J = 8.30 Hz, 2H), 8.10 (d, J = 5.298 Hz, 1H), 9.37 (s, 1H) |

TABLE 1-continued

| Compound number | Structure | Exact mass | Name | LCMS method | retention time (min) | Observed m/z | ¹H NMR |
|---|---|---|---|---|---|---|---|
| 68 | 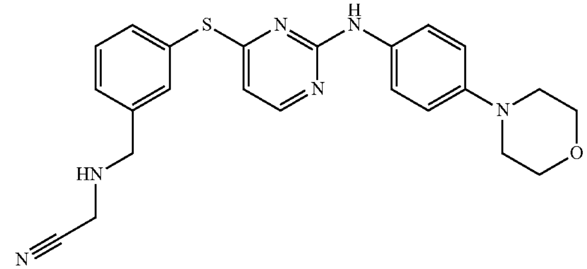 [SMILES: N#CCNCc1cccc(Sc2ccnc(Nc3ccc(N4CCOCC4)cc3)n2)c1] | 432.17 | 2-(3-(2-(4-morpholinophenyl-amino)pyrimidin-4-ylthio)benzyl-amino)acetonitrile | B | 8.6 | m/z 432.2 M+ | ¹H NMR (d₆-DMSO) δ 2.98-3.01 (m, 4H), 3.55 (d, J = 7.12 Hz, 2H), 3.70-3.74 (m, 4H), 3.79 (d, J = 5.83 Hz, 2H), 6.28 (d, J = 5.20 Hz, 1H), 6.73 (d, J = 9.05 Hz, 2H), 7.33 (d, J = 8.87 Hz, 2H), 7.51-7.58 (m, 4H), 8.09 (d, J = 5.29 Hz, 1H), 9.37 (s, 1H) |
| 69 | 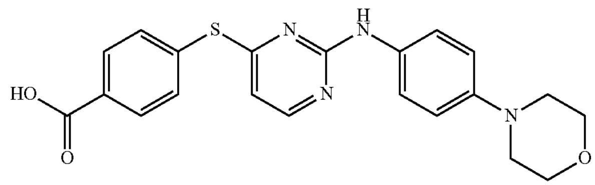 [SMILES: O=C(O)c1ccc(Sc2ccnc(Nc3ccc(N4CCOCC4)cc3)n2)cc1] | 408.13 | 4-(2-(4-morpholinophenyl-amino)pyrimidin-4-ylthio)benzoic acid | B | 9.0 (broad) | m/z 408.2 M+ | ¹H NMR (d₆-DMSO) δ 2.95-3.04 (m,4H), 3.70-3.76 (m, 4H), 6.31 (d, J = 5.31 Hz, 1H), 6.73 (d, J = 8.76 Hz, 2H), 7.27 (d, J = 8.76 Hz, 2H), 7.93 (d, J = 8.38 Hz, 2H), 8.00 (d, J = 5.28 Hz, 1H), 9.34 (s, 1H) |
| 70 | 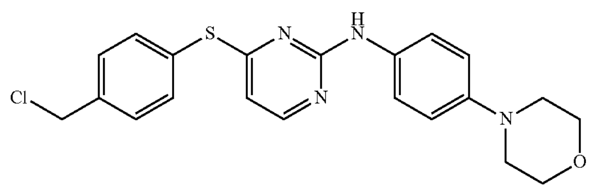 [SMILES: ClCc1ccc(Sc2ccnc(Nc3ccc(N4CCOCC4)cc3)n2)cc1] | 412.11 | 4-(4-(chloro-methyl)phenylthio)-N-(4-morpholino-phenyl)pyrimidin-2-amine | B | 9.9 | m/z 412.2/ 414.2 M+ | ¹H NMR (CDCl₃ + d₄-MeOH) δ 3.08-3.12 (m, 4H), 3.85-3.88 (m, 4H), 4.68 (s, 2H), 6.35 (d, J = 5.40 Hz, 1H), 6.81 (d, J = 9.13 Hz, 2H), 7.29 (d, J = 9.13 Hz, 2H), 7.51 (d, J = 8.47 Hz, 2H), 7.62 (d, J = 8.40 Hz, 2H), 8.00 (d, J = 5.39 Hz, 1H) |
| 71 | 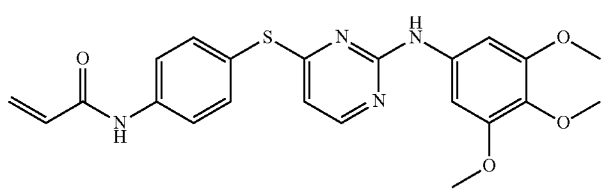 [SMILES: C=CC(=O)Nc1ccc(Sc2ccnc(Nc3cc(OC)c(OC)c(OC)c3)n2)cc1] | 438.14 | N-(4-(2-(3,4,5-trimethoxyphenyl-amino)pyrimidin-4-ylthio)phenyl)acrylamide | C | 6.8 | m/z 439.0 [M + H]+ | ¹H NMR (300 MHz, CDCl₃) δ 8.05 (d, J = 5.7, 1H), 7.69 (d, J = 8.7, 2H), 7.56 (d, J = 8.7, 2H), 7.52 (br s, 1H), 6.98 (br s, 1H), 6.86 (s, 2H), 6.50 (dd, J = 17.7, 1.5, 1H), 6.29 (dd, J = 17.1, 10.2, 1H), 6.21 (d, J = 5.4, 1H), 5.34 (dd, J = 10.2, 1.5, 1H), 3.84 (s, 6H), 3.82 (s, 3H) |

TABLE 1-continued

| Compound number | Structure | Exact mass | Name | LCMS method | retention time (min) | Observed m/z | ¹H NMR |
|---|---|---|---|---|---|---|---|
| 72 | 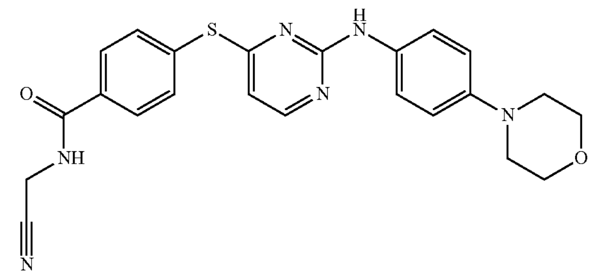 [SMILES: N#CCNC(=O)c1ccc(Sc2ccnc(Nc3ccc(N4CCOCC4)cc3)n2)cc1] | 446.15 | N-(cyanomethyl)-4-(2-(4-morpholinophenyl-aminopyrimidin-4-ylthio)benzamide | B | 8.1 | m/z 446.5 M+ | ¹H NMR (d₆-DMSO) δ 2.93-2.96 (m, 4H), 3.71-3.73 (m, 4H), 4.35 (d, J = 5.48 Hz, 1H), 6.51-6.61 (m, 3H), 7.17 (d, J = 8.68 Hz, 2H), 7.77 (d, J = 8.48 Hz, 2H), 8.2 (d, J = 8.42 Hz, 2H), 8.14 (d, J = 5.25 Hz, 1H), 9.46 (s, 1H), 9.43 (t, J = 5.84 Hz, 1H) |
| 73 | 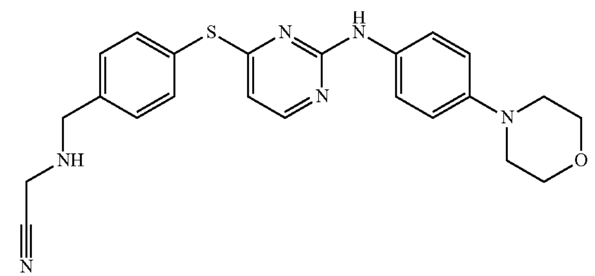 [SMILES: N#CCNCc1ccc(Sc2ccnc(Nc3ccc(N4CCOCC4)cc3)n2)cc1] | 432.17 | 2-(4-(2-(4-morpholinophenyl-aminopyrimidin-4-ylthio)benzyl-amino)acetonitrile | B | 8.6 | m/z 432.3 M+ | ¹H NMR (d₆-DMSO) δ 2.98-3.01 (m, 4H), 3.64 (d, J = 5.78 Hz, 2H), 3.71-3.74 (m, 4H), 3.85 (d, J = 4.28 Hz, 2H), 6.27 (d, J = 5.59 Hz, 1H), 6.74 (d, J = 9.08 Hz, 2H), 7.35 (d, J = 9.08 Hz, 2H), 7.50 (d, J = 7.94 Hz, 2H), 7.60 (d, J = 8.31 Hz, 2H), 8.10 (d, J = 5.31 Hz, 1H), 9.39 (s, 1H) |
| 74 | 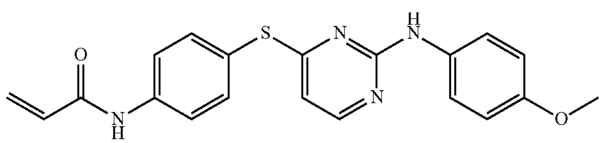 [SMILES: C=CC(=O)Nc1ccc(Sc2ccnc(Nc3ccc(OC)cc3)n2)cc1] | 378.12 | N-(4-(2-(4-methoxyphenyl-aminopyrimidin-4-ylthio)phenyl)acrylamide | B | 8.9 | m/z 378.1 M+ | ¹H NMR (300 MHz, CDCl₃) δ 7.98 (d, J = 5.4, 1H), 7.77 (d, J = 8.7, 2H), 7.56 (d, J = 8.7, 2H), 7.28 (s, 1H), 7.27 (d, J = 8.7, 2H), 6.76 (d, J = 8.7, 2H), 6.48 (dd, J = 16.8, 1.8, 1H), 6.35 (dd, J = 17.1, 10.2, 1H), 6.33 (d, J = 5.4, 1H), 5.80 (dd, J = 10.2, 1.8, 1H), 3.76 (s, 3H) |
| 75 | 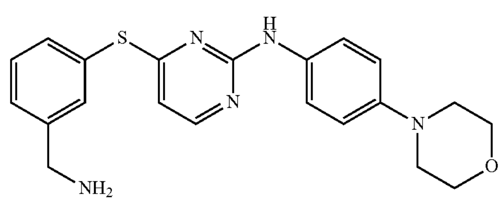 [SMILES: NCc1cccc(Sc2ccnc(Nc3ccc(N4CCOCC4)cc3)n2)c1] | 393.16 | 4-(3-(amino-methyl)phenylthio)-N-(4-morpholino-phenyl)pyrimidin-2-amine | A | 6.8 | m/z 393.2 M+ | ¹H NMR (CDCl₃) δ 3.07-3.10 (m, 4H), 3.84-3.88 (m, 4H), 3.91 (br s, 2H), 6.27 (d, J = 5.35 Hz, 1H), 6.78 (d, J = 9.06 Hz, 2H), 6.92 (br s, 1H), 7.27 (d, J = 9.09 Hz, 2H), 7.43-7.54 (m, 3H), 7.58-7.59 (m, 1H), 8.01 (d, J = 5.36 Hz, 1H) |

TABLE 1-continued

| Compound number | Structure | Exact mass | Name | LCMS method | retention time (min) | Observed m/z | 1H NMR |
|---|---|---|---|---|---|---|---|
| 76 | 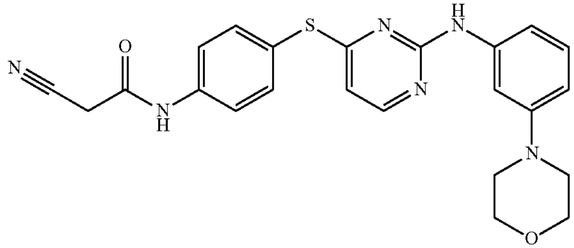 [SMILES: N#CCC(=O)Nc1ccc(Sc2ccnc(Nc3cccc(N4CCOCC4)c3)n2)cc1] | 446.15 | 2-cyano-N-(4-(2-(3-morpholinophenylamino)pyrimidin-4-ylthio)phenyl)acetamide | C | 6.6 | m/z 447.1 [M + H]+ | 1H NMR (300 MHz, CDCl3) δ 8.06 (d, J = 5.4, 1H), 7.82 (br s, 1H), 7.62 (s, 4H), 7.18 (t, J = 2.1, 1H), 7.13 (t, J = 8.1, 1H), 6.97 (br s, 1H), 6.95 (dd, J = 8.1, 2.4, 1H), 6.59 (dd, J = 8.1, 2.4, 1H), 6.26 (d, J = 5.4, 1H), 3.86 (t, J = 4.5, 4H), 3.60 (s, 2H), 3.15 (t, J = 4.5, 4H) |
| 77 | 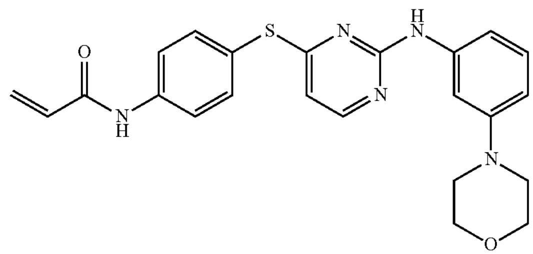 [SMILES: C=CC(=O)Nc1ccc(Sc2ccnc(Nc3cccc(N4CCOCC4)c3)n2)cc1] | 433.16 | N-(4-(2-(3-morpholinophenylamino)pyrimidin-4-ylthio)phenyl)acrylamide | B | 8.8 | m/z 433.4 M+ | 1H NMR (300 MHz, CDCl3) δ 8.05 (d, J = 5.6, 1H), 7.71 (d, J = 9.1, 2H), 7.58 (d, J = 8.7, 2H), 7.35 (br s, 1H), 7.21 (t, J = 2.2, 1H), 7.13 (t, J = 8.0, 1H), 6.98 (br s, 1H), 6.95-6.94 (m, 1H), 6.58 (dd, J = 8.2, 2.4, 1H), 6.52-6.47 (m, 1H), 6.30 (d, J = 10.1, 1H), 6.25-6.23 (m, 1H), 5.86-5.83 (m, 1H), 3.86 (t, J = 4.8, 4H), 3.16 (t, J = 4.8, 4H) |
| 78 | 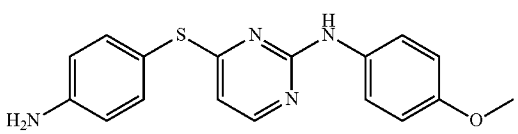 [SMILES: COc1ccc(Nc2nccc(Sc3ccc(N)cc3)n2)cc1] | 324.10 | 4-(4-aminophenylthio)-N-(4-methoxyphenyl)pyrimidin-2-amine | B | 8.8 | m/z 324.1 M+ | 1H NMR (300 MHz, CDCl3) δ 7.98 (d, J = 5.4, 1H), 7.36 (d, J = 8.7, 2H), 7.33 (d, J = 9.0, 2H), 6.98 (br s, 1H), 6.81 (d, J = 9.3, 2H), 6.74 (d, J = 8.7, 2H), 6.25 (d, J = 5.7, 1H), 3.98 (br s, 2H), 3.79 (s, 3H) |
| 79 | 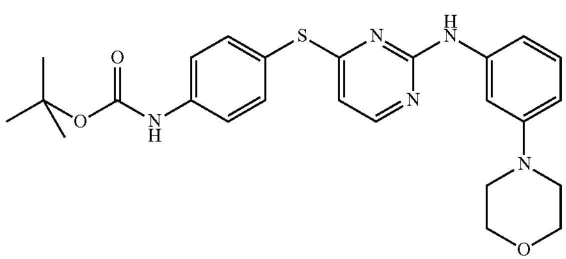 [SMILES: CC(C)(C)OC(=O)Nc1ccc(Sc2ccnc(Nc3cccc(N4CCOCC4)c3)n2)cc1] | 479.20 | tert-butyl 4-(2-(3-morpholinophenylamino)pyrimidin-4-ylthiophenyl-carbamate | C | 7.8 | m/z 480.1 [M + H]+ | 1H NMR (300 MHz, CDCl3) δ 8.03 (d, J = 5.0, 1H), 7.54-7.46 (m, 4H), 7.23 (t, J = 2.3, 1H), 7.14 (t, J = 8.1, 1H), 7.04 (br s, 1H), 6.98-6.95 (m, 1H), 6.66 (br s, 1H), 6.57 (dd, J = 8.3, 1.8, 1H), 6.20 (d, J = 5.3, 1H), 3.86 (t, J = 4.8, 4H), 3.64 (s, 2H), 3.16 (t, J = 4.8, 4H), 1.55 (s, 9H) |

TABLE 1-continued

| Compound number | Structure | Exact mass | Name | LCMS method | retention time (min) | Observed m/z | ¹H NMR |
|---|---|---|---|---|---|---|---|
| 80 | 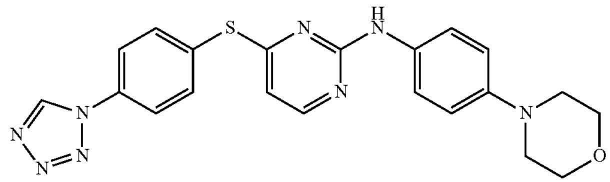 [SMILES: c1cc(Sc2ccc(-n3cnnn3)cc2)nc(Nc2ccc(N3CCOCC3)cc2)n1] | 432.15 | 4-(4-(1H-tetrazol-1-yl)phenylthio)-N-(4-morpholinophenyl)pyrimidin-2-amine | C | 6.6 | m/z 433 [M + H]+ | ¹H NMR (d₆-DMSO) δ 2.79-2.81 (m, 4H), 3.63-3.66 (m, 4H), 6.54-6.59 (m, 3H), 7.19 (d, J = 8.48 Hz, 2H), 7.91 (d, J = 8.81 Hz, 2H), 8.12 (d, J = 8.79 Hz, 2H), 8.16 (d, J = 5.24 Hz, 1H), 9.39 (s, 1H), 10.25 (s, 1H) |
| 81 | 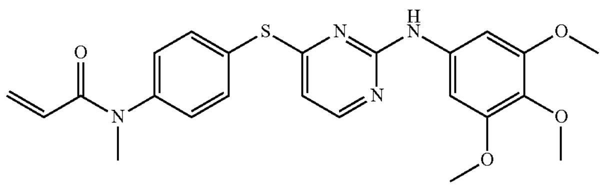 [SMILES: C=CC(=O)N(C)c1ccc(Sc2ccnc(Nc3cc(OC)c(OC)c(OC)c3)n2)cc1] | 452.15 | N-methyl-N-(4-(2-(3,4,5-trimethoxyphenylamino)pyrimidin-4-ylthio)phenyl)acrylamide | B | 8.8 | m/z 452.3 M+ | ¹H NMR (300 MHz, CDCl₃) δ 8.11 (d, J = 4.8, 1H), 7.65 (d, J = 8.4, 2H), 7.27 (d, J = 8.4, 2H), 6.97 (br s, 1H), 6.88 (s, 2H), 6.42 (dd, J = 16.8, 1.8, 1H), 6.27 (d, J = 5.4, 1H), 6.14 (dd, J = 17.1, 10.8, 1H), 5.61 (dd, J = 10.2, 1.8, 1H), 3.85 (s, 6H), 3.82 (s, 3H), 3.41 (s, 3H) |
| 82 | 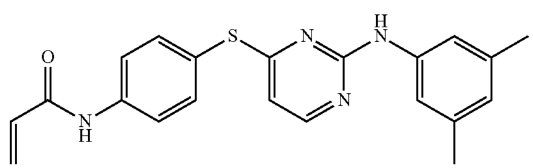 [SMILES: C=CC(=O)Nc1ccc(Sc2ccnc(Nc3cc(C)cc(C)c3)n2)cc1] | 376.14 | N-(4-(2-(3,5-dimethylphenylaminopyrimidin-4-ylthio)phenyl)acrylamide | B | 9.8 | m/z 376.3 M+ | |
| 83 | 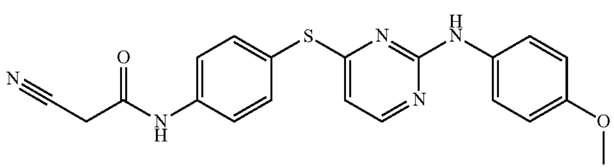 [SMILES: COc1ccc(Nc2nccc(Sc3ccc(NC(=O)CC#N)cc3)n2)cc1] | 391.11 | 2-cyano-N-(4-(2-(4-methoxyphenylamino)pyrimidin-4-ylthio)phenyl)acetamide | B | 8.3 (broad) | m/z 391.1 M+ | ¹H NMR (300 MHz, d₆-DMSO) δ 8.11 (d, J = 5.7, 1H), 7.75 (d, J = 8.7, 2H), 7.60 (d, J = 8.7, 2H), 7.36 (d, J = 9.3, 2H), 6.74 (d, J = 9.3, 2H), 6.37 (d, J = 5.7, 1H), 3.69 (s, 3H), 3.43 (s, 1H) |
| 84 | 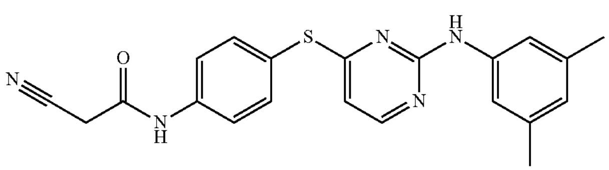 [SMILES: Cc1cc(C)cc(Nc2nccc(Sc3ccc(NC(=O)CC#N)cc3)n2)c1] | 389.13 | 2-cyano-N-(4-(2-(3,5-dimethylphenylamino)pyrimidin-4-ylthio)phenyl)acetamide | B | 9.4 | m/z 389.2 M+ | ¹H NMR (300 MHz, CDCl₃) δ 8.01 (d, J = 5.1, 1H), 7.69 (d, J = 8.7, 2H), 7.58 (d, J = 8.7, 2H), 7.13 (s, 2H), 6.77 (br s, 1H), 6.25 (d, J = 5.4, 1H), 2.26 (s, 6H) |

TABLE 1-continued

| Compound number | Exact mass | Name | Structure | LCMS method | retention time (min) | Observed m/z | ¹H NMR |
|---|---|---|---|---|---|---|---|
| 85 | 509.17 | 2-amino-1-(4-(2-(4-morpholino-phenylamino)pyrimidin-4-ylthio)benzyl)-1H-imidazole-4,5-dicarbonitrile | 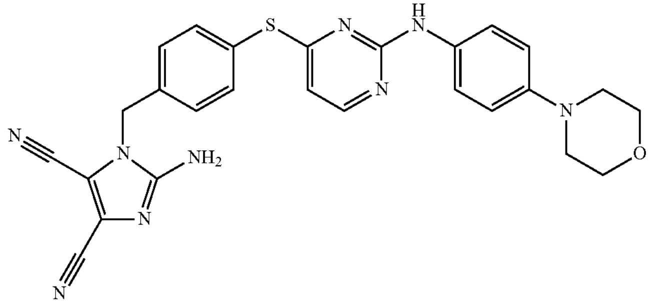 [SMILES: N#Cc1nc(N)n(Cc2ccc(Sc3ccnc(Nc4ccc(N5CCOCC5)cc4)n3)cc2)c1C#N] | A | 9.3 | m/z 509.1 M+ | ¹H NMR (d₆-DMSO) δ 3.00-3.03 (m, 4H), 3.71-3.74 (m, 4H), 5.27 (s, 2H) 6.19 (d, J = 5.30 Hz, 1H), 6.78 (d, J = 9.12 Hz, 2H), 7.23 (s, 2H), 7.37 (d, J = 8.34 Hz, 2H), 7.42 (d, J = 9.05 Hz, 2H), 7.69 (d, J = 8.34 Hz, 2H), 8.11 (d, J = 5.27 Hz, 1H), 9.39 (s, 1H) |
| 86 | 488.24 | N-(4-(2-(4-(4-(pyrrolidin-1-yl)piperidin-1-yl)phenylamino)pyrimidin-4-ylthio)phenyl)acetamide | 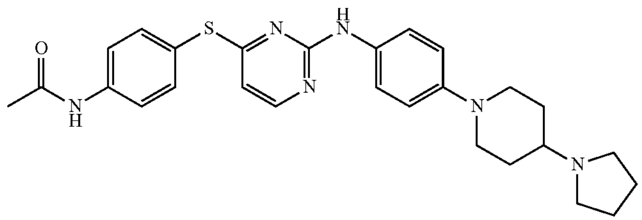 [SMILES: CC(=O)Nc1ccc(Sc2ccnc(Nc3ccc(N4CCC(N5CCCC5)CC4)cc3)n2)cc1] | B | 6.3 | m/z 488.3 M+ | ¹H NMR (DMSO-d₆, 300 MHz) δ 10.32 (s, 1H), 9.70 (br.s., 1H, TsOH), 8.15 (d, J = 5.7 Hz, 1H), 7.77 (d, J = 9.3 Hz, 2H), 7.56 (d, J = 8.4 Hz, 2H), 7.41-7.50 (m, 4H, TsOH), 7.20-7.05 (m, 4H, TsOH), 6.46 (d, J = 6.3 Hz, 1H), 3.82 (m, 1H), 3.70 (m, 2H), 3.57 (m, 2H), 3.08 (m, 4H), 2.29 (s, 3H, TsOH), 2.13 (s, 3H), 2.01 (m, 4H), 1.89 (m, 4H) |
| 87 | 500.24 | N-(4-(2-(4-(4-(pyrrolidin-1-yl)piperidin-1-yl)phenylamino)pyrimidin-4-ylthio)phenyl)acrylamide | 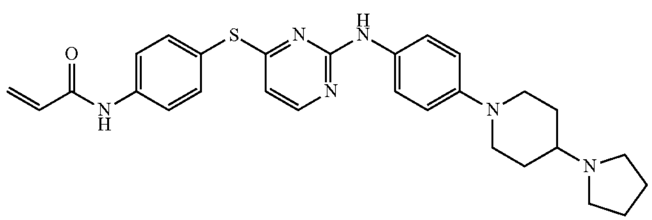 [SMILES: C=CC(=O)Nc1ccc(Sc2ccnc(Nc3ccc(N4CCC(N5CCCC5)CC4)cc3)n2)cc1] | B | 6.5 | m/z 500.2 M+ | ¹H NMR (DMSO-d₆, 300 MHz) δ 10.60 (s, 1H), 10.33 (br.s., 1H, TsOH), 9.78 (br.s., 1H), 8.17 (d, J = 5.4 Hz, 1H), 7.88 (d, J = 8.7 Hz, 2H), 7.60 (d, J = 8.4 Hz, 2H), 7.49 (m, 4H, TsOH), 7.11 (m, 4H, TsOH), 6.62-6.51 (m, 2H), 6.34 (dd, J = 17.1, 2.1 Hz, 1H), 5.86 (d, J = 9.9, 1.5 Hz, 1H), 3.70-3.65 (m, 3H), 3.36 (m, 2H), 3.06 (m, 4H), 2.28 (s, 3H, TsOH), 2.24-2.16 (m, 2H), 2.02 (m, 4H), 1.88 (m, 2H) |
| 88 | 513.23 | 2-cyano-N-(4-(2-(4-(4-(pyrrolidin-1-yl)piperidin-1-yl)phenylamino)pyrimidin-4-ylthio)phenyl)acetamide | 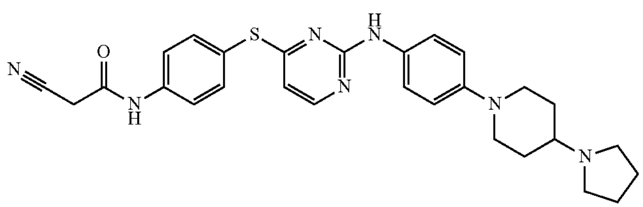 [SMILES: N#CCC(=O)Nc1ccc(Sc2ccnc(Nc3ccc(N4CCC(N5CCCC5)CC4)cc3)n2)cc1] | B | 6.4 | m/z 513.1 M+ | ¹H NMR (DMSO-d₆, 300 MHz) δ 10.74 (s, 1H), 10.19 (br.s., 1H, TsOH), 9.78 (br.s., 1H), 8.18 (d, J = 5.1 Hz, 1H), 7.73 (d, J = 8.7 Hz, 2H), 7.61 (d, J = 8.1 Hz, 2H), 7.52-7.45 (m, 4H, TsOH), 7.42 (br.d, J = 8.1 Hz, 1H), 7.20-7.08 (m, 4H, TsOH), 6.55 (br.d, J = 4.8 Hz, 1H), 4.06 (s, 2H), 3.70-3.64 (m, 4H), 3.36 (m, 1H), 3.10 (m, 4H), 2.28 (s, 3H, tsOH), 2.50-2.20 (m, 2H), 2.04-1.98 (m, 4H), 1.95-1.80 (m, 2H) |

TABLE 1-continued

| Compound number | Structure | Exact mass | Name | LCMS method | retention time (min) | Observed m/z | ¹H NMR |
|---|---|---|---|---|---|---|---|
| 89 | 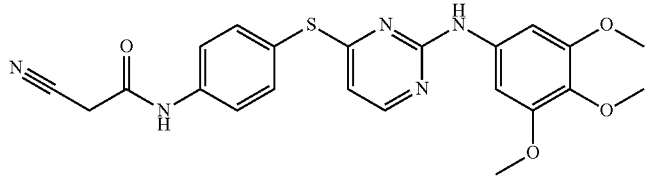 [SMILES: COc1cc(Nc2nccc(Sc3ccc(NC(=O)CC#N)cc3)n2)cc(OC)c1OC] | 451.13 | 2-cyano-N-(4-(2-(3,4,5-trimethoxyphenylamino)pyrimidin-4-ylthio)phenyl)acetamide | B | 7.9 | m/z 451.3 M+ | ¹H NMR (300 MHz, d₆-DMSO) δ 10.57 (s, 1H), 9.50 (s, 1H), 8.16 (d, J = 5.4, 1H), 7.71 (d, J = 9.1, 2H), 7.62 (d, J = 9.1, 2H), 7.13 (s, 2H), 6.12 (d, J = 4.8, 1H), 3.95 (s, 2H), 3.71 (s, 6H), 3.61 (s, 3H) |
| 90 | 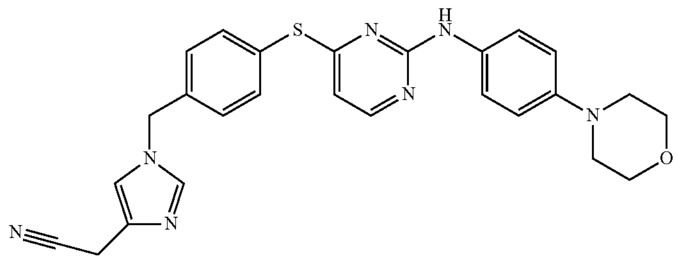 [SMILES: N#CCc1cn(Cc2ccc(Sc3ccnc(Nc4ccc(N5CCOCC5)cc4)n3)cc2)cn1] | 483.18 | 2-(1-(4-(2-(4-morpholinophenylamino)pyrimidin-4-ylthio)benzyl)-1H-imidazol-4-yl)acetonitrile | A | 8.3 | m/z 483.2 M+ | ¹H NMR (d₆-DMSO) δ 3.01-3.08 (m, 4H), 3.70 (d, J = 0.99 Hz, 2H), 3.84-3.88 (m, 4H), 5.15 (s, 2H), 6.21 (d, J = 5.33 Hz, 1H), 6.82-6.85 (m, 3H), 6.94-6.98 (m, 1H), 7.23 (d, J = 10.10 Hz, 2H), 7.37 (d, J = 9.08 Hz, 2H), 7.51-7.53 (m, 1H), 7.62 (d, J = 8.36 hz, 2H), 8.04 (d, J = 5.33 Hz, 1H) |
| 91 | 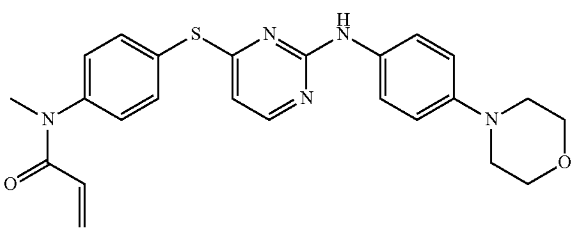 [SMILES: C=CC(=O)N(C)c1ccc(Sc2ccnc(Nc3ccc(N4CCOCC4)cc3)n2)cc1] | 447.17 | N-methyl-N-(2-(4-morpholinophenylamino)pyrimidin-4-ylthio)phenyl)acrylamide | B | 8.3 | m/z 447.5 M+ | (300 MHz, CDCl₃) δ 8.06 (d, J = 5.7 Hz, 1H), 7.66 (d, J = 8.7 Hz, 2H), 7.36 (d, J = 9.3 Hz, 2H), 7.27 (d, J = 8.7 Hz, 2H), 7.13 (s, 1H), 6.82 (d, J = 9.0 Hz, 2H), 6.43 (dd J = 15.0, 2.0 Hz, 1H), 6.33 (d, J = 5.4 Hz, 1H), 6.15 (dd J = 10.0, 1.7 Hz, 1H), 5.59 (dd J = 10.0, 1.7 Hz, 1H), 3.85 (m, 4H), 3.42 (s, 3H), 3.08 (m, 4H) |
| 92 | 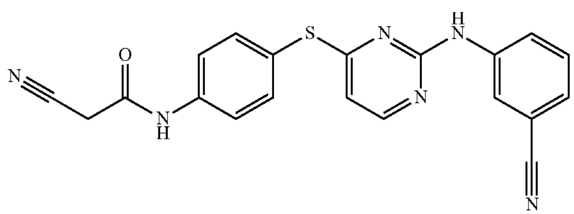 [SMILES: N#CCC(=O)Nc1ccc(Sc2ccnc(Nc3cccc(C#N)c3)n2)cc1] | 386.09 | 2-cyano-N-(4-(2-(3-cyanophenylamino)pyrimidin-4-ylthio)phenyl)acetamide | B | 8.1 | m/z 386.1 M+ | ¹H NMR (300 MHz, d₆-DMSO) δ 10.58 (s, 1H), 9.99 (s, 1H), 8.23 (d, J = 5.1, 1H), 7.99 (brs, 1H), 7.84-7.80 (m, 1H), 7.72 (d, J = 9.0, 2H), 7.62 (d, J = 8.7, 2H), 7.63-7.60 (m, 2H), 6.43 (d, J = 5.4, 1H), 3.96 (s, 2H) |

TABLE 1-continued

| Compound number | Structure | Exact mass | Name | LCMS method | retention time (min) | Observed m/z | 1H NMR |
|---|---|---|---|---|---|---|---|
| 93 | 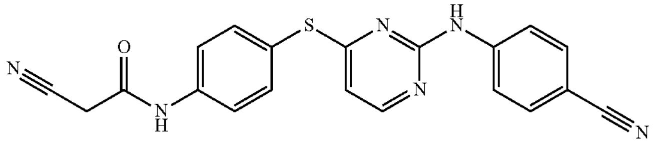 [SMILES: N#CCC(=O)Nc1ccc(Sc2ccnc(Nc3ccc(C#N)cc3)n2)cc1] | 386.09 | 2-cyano-N-(4-(2-(4-cyanophenylamino)pyrimidin-4-ylthio)phenyl)acetamide | B | 8.1 | m/z 386.1 M+ | 1H NMR (300 MHz, d6-DMSO) δ 10.62 (s, 1H), 10.17 (s, 1H), 8.25 (d, J = 5.3, 1H), 7.73 (d, J = 8.7, 2H), 7.67 (d, J = 9.1, 2H), 7.62 (d, J = 8.7, 2H), 7.54 (d, J = 9.1, 2H), 6.54 (d, J = 5.5, 1H), 3.96 (s, 3H). |
| 94 | 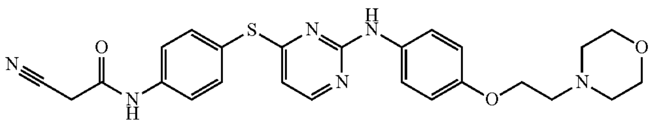 [SMILES: N#CCC(=O)Nc1ccc(Sc2ccnc(Nc3ccc(OCCN4CCOCC4)cc3)n2)cc1] | 490.18 | 2-cyano-N-(4-(2-(4-(2-morpholinoethoxy)phenylamino)pyrimidin-4-ylthio)phenyl)acetamide | A | 7.6 | m/z 490.3 M+ | 1H NMR (300 MHz, CDCl3) δ 8.03 (d, J = 5.5, 2H), 7.61 (m, 4H), 7.25 (d, J = 9.3, 2H), 6.89 (br s, 1H), 6.76 (d, J = 9.2, 2H), 6.32 (d, J = 5.2, 1H), 4.08 (t, J = 5.7, 2H), 3.75 (t, J = 4.7, 4H), 3.64 (s, 2H), 2.80 (t, J = 5.7, 2H), 2.59 (t, J = 4.8, 4H). |
| 95 | 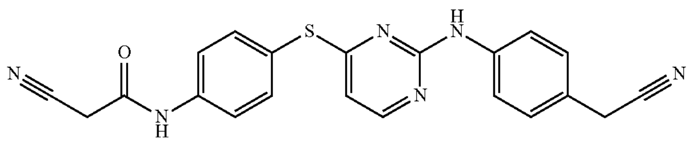 [SMILES: N#CCC(=O)Nc1ccc(Sc2ccnc(Nc3ccc(CC#N)cc3)n2)cc1] | 400.11 | 2-cyano-N-(4-(2-(4-(cyanomethyl)phenylamino)pyrimidin-4-ylthio)phenyl)acetamide | C | 6.6 | m/z 401.0 [M + H]+ | 1H-NMR (300 MHz, DMSO) δ 10.74 (s, 1H), 8.17 (d, J = 5.4, 1H), 7.74 (d, J = 8.7, 2H), 7.60 (d, J = 8.7, 2H), 7.43 (d, J = 8.6, 2H), 7.06 (d, J = 8.6, 2H), 6.48 (d, J = 5.3, 1H), 3.98 (s, 2H), 3.89 (s, 2H). |
| 96 | 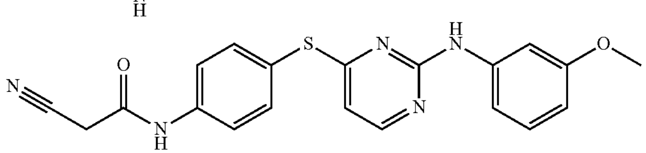 | 391.11 | 2-cyano-N-(4-(2-(3-methoxyphenylamino)pyrimidin-4-ylthio)phenyl)acetamide | C | 6.8 | m/z 392.0 [M + H]+ | 1H-NMR (300 MHz, DMSO) δ 10.68 (s, 1H), 9.63 (s, 1H), 8.16 (d, J = 5.4, 1H), 7.79-7.67 (m, 2H), 7.66-7.55 (m, 2H), 7.24 (t, J = 2.1, 1H), 7.13 (d, J = 8.2, 1H), 7.03 (t, J = 8.1, 1H), 6.54-6.44 (m, 1H), 6.31 (d, J = 5.4, 1H), 3.98 (s, 2H), 3.69 (s, 3H). |
| 97 | 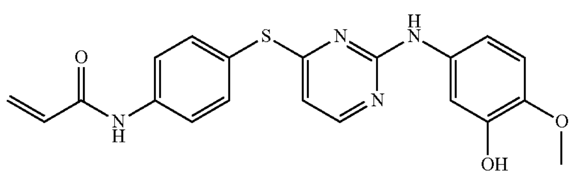 [SMILES: C=CC(=O)Nc1ccc(Sc2ccnc(Nc3ccc(OC)c(O)c3)n2)cc1] | 394.11 | N-(4-(2-(3-hydroxy-4-methoxyphenylamino)pyrimidin-4-ylthio)phenyl)acrylamide | B | 7.7 | m/z 394.3 M+ | 1H NMR (300 MHz, d6-DMSO) δ 10.43 (s, 1H), 9.30 (s, 1H), 8.78 (br s, 1H), 8.09 (d, J = 5.3, 1H), 7.85 (d, J = 8.7, 2H), 7.58 (d, J = 8.7, 2H), 6.97-6.96 (m, 1H), 6.88 (dd, J = 8.7, 2.9, 1H), 6.58 (d, J = 9.1, 1H), 6.48 (dd, J = 17.0, 10.0, 1H), 6.33-6.27 (m, 1H), 5.80 (dd, J = 10.1, 2.5, 1H), 5.74 (s, 1H), 3.56 (s, 3H). |
| 98 | 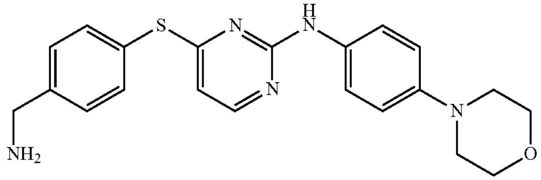 | 393.16 | 4-(4-(aminomethyl)phenylthio)-N-(4-morpholinophenyl)pyrimidin-2-amine | A | 7.1 | m/z not observed | 1H NMR (d6-DMSO) δ 3.32-3.43 (m, 4H), 3.91-4.01 (m, 4H), 4.15-4.25 (m, 2H), 6.46 (d, J = 5.39 Hz, 1H), 7.35 (d, J = 8.82 Hz, 2H), 7.52 (d, J = 8.99 Hz, 2H), 7.63-7.73 (m, 4H), 8.19 (d, J = 5.37 Hz, 1H), 8.54 (br s, 1H), 9.83 (s, 1H). |

TABLE 1-continued

| Compound number | Structure | Exact mass | Name | LCMS method | retention time (min) | Observed m/z | ¹H NMR |
|---|---|---|---|---|---|---|---|
| 99 | 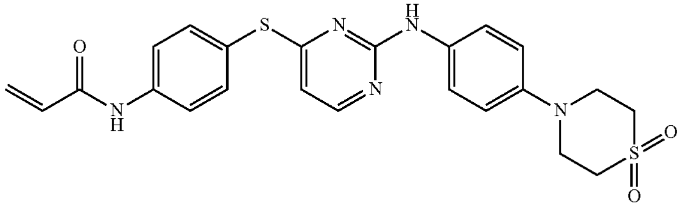 [SMILES: C=CC(=O)Nc1ccc(Sc2ccnc(Nc3ccc(N4CCS(=O)(=O)CC4)cc3)n2)cc1] | 481.12 | N-{4-[(2-{[4-(1,1-dioxo-1λ⁶,4-thiomorpholin-4-yl)phenyl]amino}pyrimidin-4-yl)sulfanyl]phenyl}prop-2-enamide | C | 6.6 | m/z 482.0 [M+H]+ | ¹H NMR (300 MHz, d₆-DMSO) δ 10.55 (s, 1H), 9.58 (s, 1H), 8.12 (d, J = 5.5, 1H), 7.87 (d, J = 8.7, 2H), 7.58 (d, J = 8.7, 2H), 7.25 (d, J = 8.2, 2H), 6.74 (d, J = 9.3, 2H), 6.57-6.48 (m, 2H), 6.37-6.30 (m, 1H), 5.84 (dd, J = 10.0, 2.2, 1H), 3.56-3.55 (m, 4H), 3.06-3.05 (m, 4H). |
| 100 | 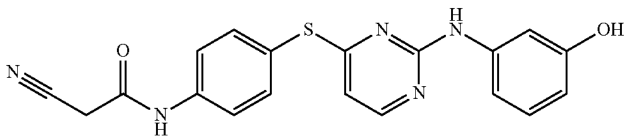 [SMILES: N#CCC(=O)Nc1ccc(Sc2ccnc(Nc3cccc(O)c3)n2)cc1] | 377.09 | 2-cyano-N-(4-(2-(3-hydroxyphenylamino)pyrimidin-4-ylthio)phenyl)acetamide | C | 6.3 | m/z 378.0 [M+H]+ | ¹H-NMR (300 MHz, DMSO) δ 10.57 (s, 1H), 9.49 (s, 1H), 9.17 (s, 1H), 8.14 (d, J = 5.3, 1H), 7.71 (d, J = 8.7, 2H), 7.61 (d, J = 8.8, 2H), 7.08 (t, J = 2.0, 1H), 7.04-6.95 (m, 1H), 6.89 (t, J = 8.0, 1H), 6.37-6.27 (m, 1H), 6.23 (d, J = 5.3, 1H), 3.96 (s, 2H). |
| 101 | 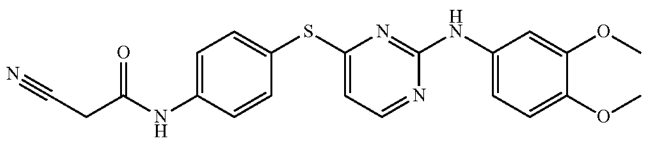 [SMILES: COc1ccc(Nc2nccc(Sc3ccc(NC(=O)CC#N)cc3)n2)cc1OC] | 421.12 | 2-cyano-N-(4-(2-(3,4-dimethoxyphenylamino)pyrimidin-4-ylthio)phenyl)acetamide | C | 6.5 | m/z 422.0 [M+H]+ | ¹H-NMR (300 MHz, CD₃OD) δ 8.02 (d, J = 5.4, 1H), 7.72 (d, J = 8.8, 2H), 7.58 (d, J = 8.8, 2H), 7.09 (d, J = 2.5, 1H), 6.97 (dd, J = 8.5, 8.7, 1H), 6.71 (d, J = 8.8, 1H), 6.38 (d, J = 5.4, 1H), 3.79 (s, 3H), 3.77 (s, 3H). |
| 102 | 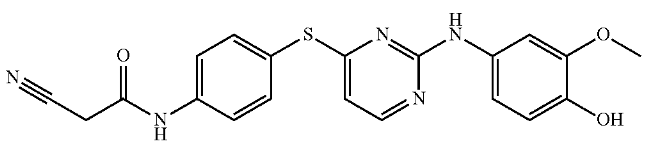 [SMILES: COc1cc(Nc2nccc(Sc3ccc(NC(=O)CC#N)cc3)n2)ccc1O] | 407.11 | 2-cyano-N-(4-(2-(4-hydroxy-3-methoxyphenylamino)pyrimidin-4-ylthio)phenyl)acetamide | C | 6.2 | m/z 408.0 [M+H]+ | ¹H-NMR (300 MHz, CD₃OD) δ 7.99 (d, J = 5.4, 1H), 7.72 (d, J = 8.8, 2H), 7.58 (d, J = 8.8, 2H), 6.91 (d, J = 2.5, 1H), 6.85 (dd, J = 2.6, 8.7, 1H), 6.68 (d, J = 8.8, 1H), 6.35 (d, J = 5.4, 1H), 3.81 (s, 3H). |
| 103 | 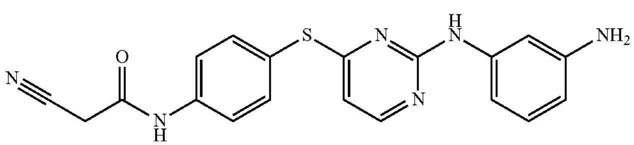 [SMILES: N#CCC(=O)Nc1ccc(Sc2ccnc(Nc3cccc(N)c3)n2)cc1] | 376.11 | N-(4-(2-(3-aminophenylaminopyrimidin-4-ylthio)phenyl)-2-cyanoacetamide | C | 6.2 | m/z 377.1 [M+H]+ | ¹H-NMR (300 MHz, DMSO) δ 10.56 (s, 1H), 9.30 (s, 1H), 8.11 (d, J = 5.3, 1H), 7.71 (d, J = 8.7, 2H), 7.60 (d, J = 8.7, 2H), 6.85-6.68 (m, 3H), 6.25-6.08 (m, 2H), 4.84 (s, 2H), 3.95 (s, 2H). |
| 104 | 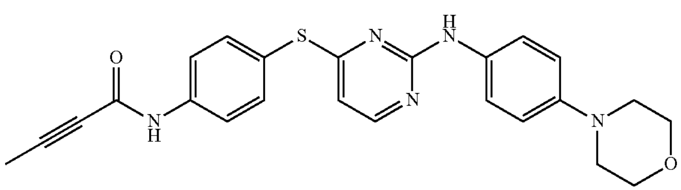 [SMILES: CC#CC(=O)Nc1ccc(Sc2ccnc(Nc3ccc(N4CCOCC4)cc3)n2)cc1] | 445.16 | N-(4-(2-(4-morpholinophenylaminopyrimidin-4-ylthio)phenyl)but-2-ynamide | C | 6.8 | m/z 446.1 [M+H]+ | (300 MHz, CDCl₃) δ 10.96 (s, 1H), 9.34 (s, 1H), 8.10 (d, J = 5.7 Hz, 1H), 7.78 (d, J = 8.7 Hz, 2H), 7.56 (d, J = 8.7 Hz, 2H), 7.18 (d, J = 8.7 Hz, 2H), 6.61 (d, J = 8.7 Hz, 2H), 6.47 (d, J = 4.8 Hz, 1H), 3.73 (m, 4H), 2.97 (m, 4H), 2.08 (s, 3H) |

TABLE 1-continued

| Compound number | Structure | Exact mass | Name | LCMS method | retention time (min) | Observed m/z | ¹H NMR |
|---|---|---|---|---|---|---|---|
| 105 | 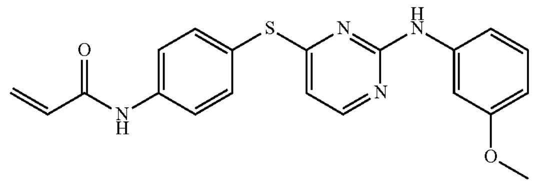 [SMILES: C=CC(=O)Nc1ccc(Sc2ccnc(Nc3cccc(OC)c3)n2)cc1] | 378.12 | N-(4-(2-(3-methoxyphenyl-amino)pyrimidin-4-ylthio)phenyl)acrylamide | B | 8.5 | m/z 378.4 M+ | ¹H NMR (300 MHz, CDCl₃) δ 8.05 (d, J = 4.9, 1H), 7.71 (d, J = 8.7, 2H), 7.58 (d, J = 8.7, 2H), 7.43 (br s, 1H), 7.14 (br s, 1H), 7.13 (t, J = 8.1, 1H), 7.01-6.98 (m, 1H), 6.57-6.52 (m, 1H), 6.46 (m, 1H), 6.31 (d, J = 10.5, 1H), 6.25 (d, J = 11.0, 1H), 5.85-5.82 (m, 1H), 3.78 (s, 3H) |
| 106 | 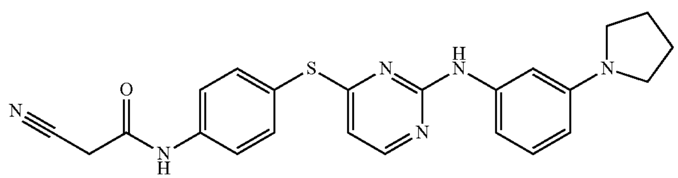 [SMILES: N#CCC(=O)Nc1ccc(Sc2ccnc(Nc3cccc(N4CCCC4)c3)n2)cc1] | 430.16 | 2-cyano-N-(4-(2-(3-(pyrrolidin-1-yl)phenylamino)pyrimidin-4-ylthio)phenyl)acetamide | C | 7.4 | m/z 431.1 [M + H]+ | ¹H-NMR (300 MHz, DMSO) δ 10.57 (s, 1H), 9.35 (s, 1H), 8.13 (d, J = 5.3, 1H), 7.71 (d, J = 8.8, 2H), 7.60 (d, J = 8.7, 2H), 6.99-6.78 (m, 3H), 6.21 (d, J = 5.3, 1H), 6.17-6.09 (m, 1H), 3.96 (s, 2H), 3.16 (t, J = 6.4, 4H), 1.92 (dd, J = 5.0, 8.0, 5H). |
| 107 | 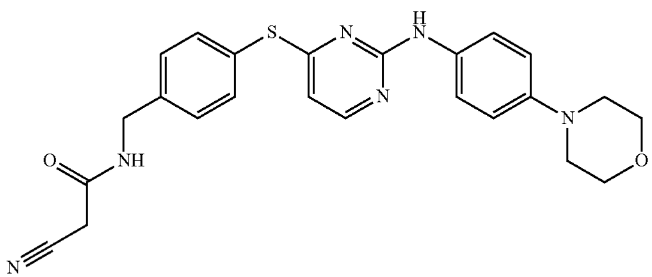 [SMILES: N#CCC(=O)NCc1ccc(Sc2ccnc(Nc3ccc(N4CCOCC4)cc3)n2)cc1] | 460.17 | 2-cyano-N-(4-(2-(4-morpholinophenylamino)pyrimidin-4-ylthio)benzyl)acetamide | B | 7.6 | m/z 460.1 M+ | ¹H NMR (d₆-DMSO) δ 2.99-3.02 (m, 4H), 3.71-3.73 (m, 4H), 3.74 (s, 2H), 4.39-4.41 (m, 2H), 6.22 (d, J = 4.93 Hz, 1H), 6.75 (d, J = 9.04 Hz, 2H), 7.37 (d, J = 8.62 Hz, 2H), 7.43 (d, J = 8.41 Hz, 2H), 7.60 (d, J = 8.23 Hz, 2H), 8.10 (d, J = 5.28 Hz, 1H), 8.67-8.82 (m, 1H), 9.38 (s, 1H) |
| 108 | 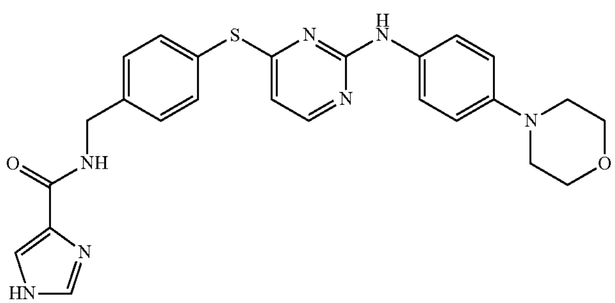 [SMILES: O=C(NCc1ccc(Sc2ccnc(Nc3ccc(N4CCOCC4)cc3)n2)cc1)c1c[nH]cn1] | 487.18 | N-(4-(2-(4-morpholinophenylamino)pyrimidin-4-ylthio)benzyl)-1H-imidazole-4-carboxamide | B | 7.2 | m/z 486.9 M+ | ¹H NMR (d₆-DMSO) δ 2.99-3.03 (m, 4H), 3.70-3.73 (m, 4H), 4.51 (d, J = 6.74 Hz, 2H), 6.21 (d, J = 5.34 Hz, 1H), 6.76 (d, J = 8.95 Hz, 2H), 7.38 (d, J = 8.74 Hz, 2H), 7.44 (d, J = 8.21 Hz, 2H), 7.57 (d, J = 8.28 Hz, 2H), 7.63 (s, 1H), 7.72 (s, 1H), 8.09 (d, J = 5.28 Hz, 1H), 8.51-8.59 (m, 1H), 12.47 (br s, 1H) |

TABLE 1-continued

| Compound number | Structure | Exact mass | Name | LCMS method | retention time (min) | Observed m/z | $^1$H NMR |
|---|---|---|---|---|---|---|---|
| 109 | 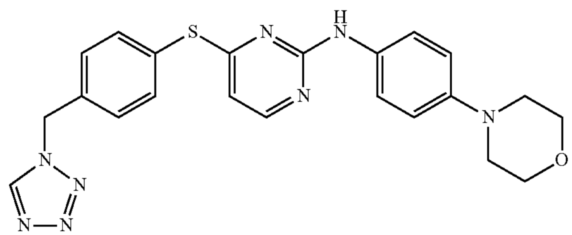 | 446.16 | 4-(4-((1H-tetrazol-1-yl)methyl)phenyl-thio)-N-(4-morpholinophenyl)pyrimidin-2-amine | B | 7.8 | m/z 446.1 M+ | $^1$H NMR (CDCl$_3$ + d$_4$-MeOH) δ 3.09-3.12 (m, 4H), 3.85-3.89 (m, 4H), 5.67 (s, 2H), 6.27 (d, J = 5.36 Hz, 1H), 6.82 (d, J = 9.10 Hz, 2H), 7.31-7.36 (m, 5H), 7.66 (d, J = 8.36 Hz, 2H), 8.08 (d, J = 5.35 Hz, 1H), 8.65 (s, 1H) |
| 110 | 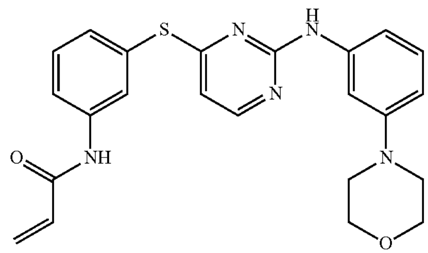 [SMILES: C=CC(=O)Nc1cccc(Sc2ccnc(Nc3cccc(N4CCOCC4)c3)n2)c1] | 433.16 | N-(3-(2-(3-morpholinophenyl-aminopyrimidin-4-ylthio)phenyl)acrylamide | B | 8.3 | m/z 433 M+ | $^1$H NMR (d$_6$-DMSO) δ 3.01-3.04 (m, 4H), 3.70-3.74 (m, 4H), 5.78 (dd, J = 2.11, 9.24 Hz, 1H), 6.26 (dd, J = 2.15, 16.96 Hz, 1H), 6.34 (d, J = 5.28 Hz, 1H), 6.45 (dd, J = 9.90, 16.92 Hz, 1H), 6.48-6.58 (m, 1H), 6.97 (t, J = 8.10Hz, 1H), 7.06-7.11 (m, 1H), 7.19-7.22 (m, 1H), 7.34 (ddd, J = 1.08, 7.71, 7.70 Hz, 1H), 7.50 (t, J = 7.87 Hz, 1H), 7.83 (ddd, J = 1.02, 2.09, 8.22 Hz, 1H), 7.98-8.01 (m, 1H), 8.17 (d, J = 5.31 Hz, 1H), 9.47 (s, 1H), 10.34 (s, 1H) |
| 111 | 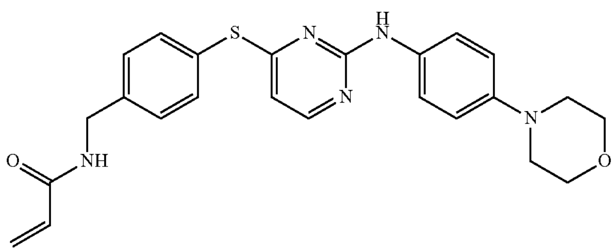 [SMILES: C=CC(=O)NCc1ccc(Sc2ccnc(Nc3ccc(N4CCOCC4)cc3)n2)cc1] | 447.17 | N-(4-(2-(4-morpholinophenyl-aminopyrimidin-4-ylthio)benzyl)acrylamide | B | 7.7 | m/z 447.4 M+ | $^1$H NMR (d$_6$-DMSO) δ 3.00-3.03 (m, 4H), 3.71-3.74 (m, 4H), 4.46 (d, J = 5.95 Hz, 2H), 5.64 (dd, J = 2.31, 9.99 Hz, 1H), 6.15 (dd, J = 2.30, 17.09 Hz, 1H), 6.23 (d, J = 4.99 Hz, 1H), 6.31 (d, J = 9.99 Hz, 1H), 6.75 (d, J = 9.14 Hz, 2H), 7.37 (d, J = 9.02 Hz, 2H), 7.43 (d, J = 8.42 Hz, 2H), 7.60 (d, J = 8.33 Hz, 2H), 8.10 (d, J = 5.27 Hz, 1H), 8.68 (t, J = 6.25 Hz, 1H), 9.38 (s, 1H) |

TABLE 1-continued

| Compound number | Structure | Exact mass | Name | LCMS method | retention time (min) | Observed m/z | ¹H NMR |
|---|---|---|---|---|---|---|---|
| 112 | 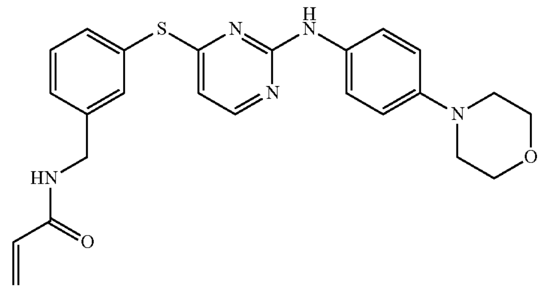 [SMILES: C=CC(=O)NCc1cccc(Sc2ccnc(Nc3ccc(N4CCOCC4)cc3)n2)c1] | 447.17 | N-(3-(2-(4-morpholinophenylamino)pyrimidin-4-ylthio)benzyl)acrylamide | B | 7.8 | m/z 447.4 M+ | ¹H NMR (d₆-DMSO) δ 2.99-3.02 (m, 4H), 3.71-3.74 (m, 4H), 4.41 (m, 4H), 5.62 (dd, J = 2.34, 9.96 Hz, 1H), 6.12 (dd, J = 2.34, 17.10 Hz, 1H), 6.27 (dd, J = 9.95, 17.07 Hz, 1H), 6.28 (d, J = 5.27 Hz, 1H), 6.74 (d, J = 9.07 Hz, 2H), 7.35 (d, J = 9.05 Hz, 2H), 7.43-7.53 (m, 4H), 8.12 (d, J = 5.29 Hz, 1H), 8.76 (t, J = 5.96 Hz, 1H), 9.37 (s, 1H) |
| 113 | 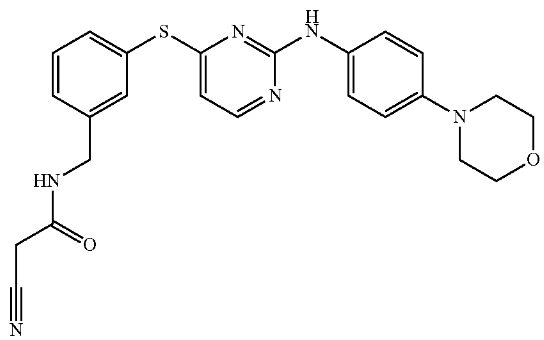 [SMILES: N#CCC(=O)NCc1cccc(Sc2ccnc(Nc3ccc(N4CCOCC4)cc3)n2)c1] | 460.17 | 2-cyano-N-(3-(2-(4-morpholinophenylamino)pyrimidin-4-ylthio)benzyl)acetamide | B | 7.7 | m/z 460.5 M+ | ¹H NMR (d₆-DMSO) δ 2.99-3.02 (m, 4H), 3.70 (s, 2H), 3.71-3.75 (m, 4H), 4.35 (d, J = 5.93 Hz, 2H), 6.27 (d, J = 5.52 Hz, 1H), 6.75 (d, J = 9.10 Hz, 2H), 7.35 (d, J = 8.68 Hz, 2H), 7.48-7.55 (m, 4H), 8.11(d, J = 5.29 Hz, 1H), 8.76 (t, J = 5.25 Hz, 1H), 9.38 (s, 1H) |
| 114 | 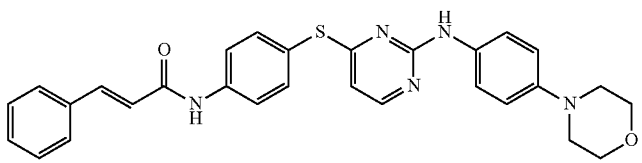 [SMILES: O=C(/C=C/c1ccccc1)Nc1ccc(Sc2ccnc(Nc3ccc(N4CCOCC4)cc3)n2)cc1] | 509.19 | N-(4-(2-(4-morpholinophenylamino)pyrimidin-4-ylthio)phenyl)cinnamamide | C | 7.5 | m/z 510.1 [M + H]+ | ¹H NMR (300 MHz, DMSO-d₆) δ 10.6 (br s, 1H), 9.34 (br s, 1H), 8.11 (d, J = 5.1, 1H), 7.91 (d, J = 8.7, 2H), 7.69-7.64 (m, 3H), 7.59 (d, J = 8.1, 2H), 7.51-7.44 (m, 3H), 7.18 (d, J = 8.7, 2H), 6.89 (d, J = 16.2, 1H), 6.62-6.53 (m, 3H), 3.59 (m, 4H), 2.91 (m, 4H) |

TABLE 1-continued

| Compound number | Structure | Exact mass | Name | LCMS method | retention time (min) | Observed m/z | 1H NMR |
|---|---|---|---|---|---|---|---|
| 115 | 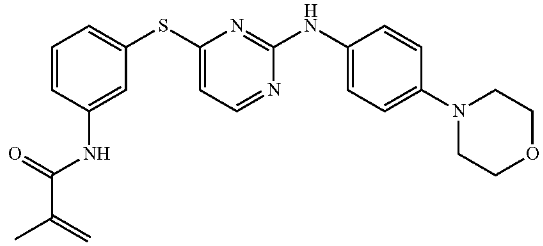 [SMILES: C=C(C)C(=O)Nc1cccc(Sc2ccnc(Nc3ccc(N4CCOCC4)cc3)n2)c1] | 447.17 | N-(3-(4-morpholinophenyl-aminopyrimidin-4-ylthio)phenyl)methacrylamide | C | 6.9 | m/z 448.1 [M+H]+ | 1H-NMR (300 MHz, CD3OD) δ 8.01 (d, J = 5.4, 1H), 7.98 (ddd, J = 1.1, 2.1, 8.2, 1H), 7.88 (t, J = 1.8, 1H), 7.47 (t, J = 7.9, 1H), 7.39-7.32 (m, 1H), 7.25 (d, J = 9.1, 2H), 6.77 (d, J = 9.0, 2H), 6.46 (d, J = 5.4, 1H), 5.78 (s, 1H), 5.51 (d, J = 0.9, 1H), 3.89-3.76 (m, 4H), 3.16-2.95 (m, 4H), 2.02 (s, 3H). |
| 116 | 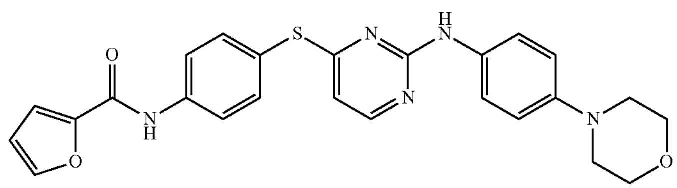 [SMILES: O=C(Nc1ccc(Sc2ccnc(Nc3ccc(N4CCOCC4)cc3)n2)cc1)c1ccco1] | 473.15 | N-(4-(2-(4-morpholinophenyl-aminopyrimidin-4-yl)thio)phenyl)furan-2-carboxamide | C | 6.9 | m/z 474 [M+H]+ | 1H NMR (300 MHz, DMSO-d6) δ 10.5 (brs, 1H), 9.34 (brs, 1H), 8.12 (d, J = 5.1, 1H), 8.02-7.98 (m, 3H), 7.59 (d, J = 8.7, 2H), 7.43 (dd, J = 3.6, 0.9, 1H), 7.17 (d, J = 9.0, 2H), 6.76 (dd, J = 3.6, 1.5, 1H), 6.60 (d, J = 9.0, 2H), 6.54 (d, J = 5.1, 1H), 3.52 (m, 4H), 2.87 (m, 4H) |
| 117 | 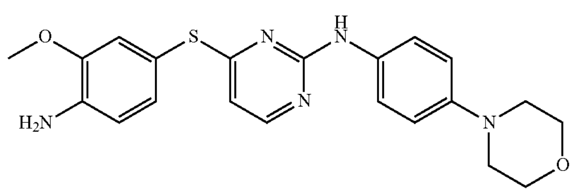 [SMILES: COc1cc(Sc2ccnc(Nc3ccc(N4CCOCC4)cc3)n2)ccc1N] | 409.16 | 4-(4-amino-3-methoxyphenyl)-thio-N-(4-morpholinophenyl)pyrimidin-2-amine | C | 6.8 | m/z 410 [M+H]+ | (300 MHz, CDCl3) δ 7.98 (d, J = 4.8, 1H), 7.33 (d, J = 8.4, 2H), 7.05 (dd, J = 1.8, 7.8, 1H), 6.97 (d, J = 1.8, 1H), 6.89 (brs, 1H), 6.83 (d, J = 9.3, 2H), 6.75 (d, J = 7.8, 1H), 6.24 (d, J = 5.4, 1H), 3.82-3.88 (m, 4H), 3.82 (s, 3H), 3.08-3.13 (m, 4H). |
| 118 | 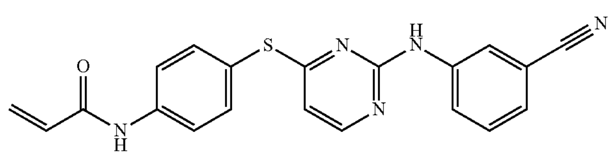 [SMILES: C=CC(=O)Nc1ccc(Sc2ccnc(Nc3cccc(C#N)c3)n2)cc1] | 373.10 | N-(4-(2-(3-cyanophenyl)amino)pyrimidin-4-ylthio)phenyl)acrylamide | C | 6.9 | m/z 374.1 [M+H]+ | 1H NMR (300 MHz, DMSO) δ 10.42 (s, 1H), 10.00 (s, 1H), 8.24 (d, J = 5.5, 1H), 8.01 (s, 1H), 7.85 (d, J = 8.7, 3H), 7.61 (d, J = 8.2, 2H) 7.33 (d, J = 5.0, 2H), 6.52-6.28 (m, 3H), 5.82 (dd, J = 10.0, 1.8, 1H) |

TABLE 1-continued

| Compound number | Structure | Exact mass | Name | LCMS method | retention time (min) | Observed m/z | $^1$H NMR |
|---|---|---|---|---|---|---|---|
| 119 | 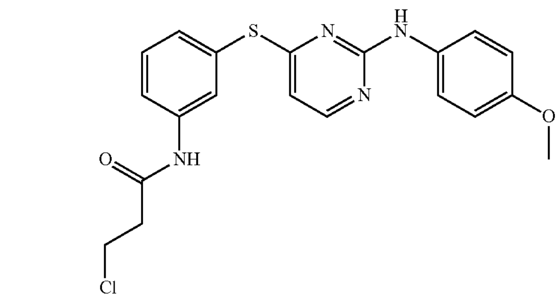 [SMILES: COc1ccc(Nc2nccc(Sc3cccc(NC(=O)CCCl)c3)n2)cc1] | 414.09 | 3-chloro-N-(3-(2-(4-methoxyphenylamino)pyrimidin-4-ylthio)phenyl)propanamide | C | 7.1 | m/z 415.0/417.0 [M + H]+ | $^1$H NMR (CDCl$_3$ + d$_4$-MeOH) δ 2.80 (t, J = 6.47 Hz, 2H), 3.78 (s, 3H), 3.86 (t, J = 6.50 Hz, 2H), 6.35 (d, J = 5.38 Hz, 1H), 6.76 (d, J = 9.10 Hz, 2H), 7.26 (d, J = 9.30 Hz, 2H), 7.32-7.36 (m, 1H), 7.42 (t, J = 7.76 Hz, 1H), 7.72-7.74 (m, 1H), 7.81 (m, 1H), 8.00 (d, J = 5.39 Hz, 1H) |
| 120 | 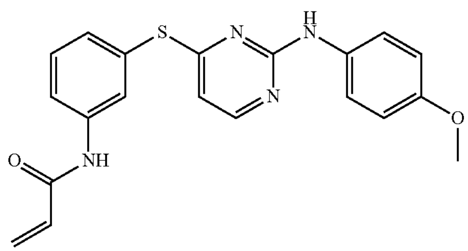 [SMILES: C=CC(=O)Nc1cccc(Sc2ccnc(Nc3ccc(OC)cc3)n2)c1] | 378.12 | N-(3-(2-(4-methoxyphenylamino)pyrimidin-4-ylthio)phenyl)acrylamide | C | 6.9 | m/z 379 [M + H]+ | $^1$H NMR (CDCl$_3$ + d$_4$-MeOH) δ 3.79 (s, 3H), 5.77 (dd, J = 1.45, 10.14 Hz, 1H), 6.25 (dd, J = 10.14, 16.87 Hz, 1H), 6.36 (d, J = 5.37 Hz, 1H), 6.44 (dd, J = 1.45, 16.87 Hz, 1H), 6.75 (d, J = 9.14 Hz, 2H), 7.26 (d, J = 9.00 Hz, 2H), 7.33-7.37 (m, 1H), 7.43 (t, J = 7.67 Hz, 1H), 7.77-7.78 (m, 1H), 7.91 (d, J = 7.04 Hz, 1H), 8.01 (d, J = 5.36 Hz, 1H) |
| 121 | 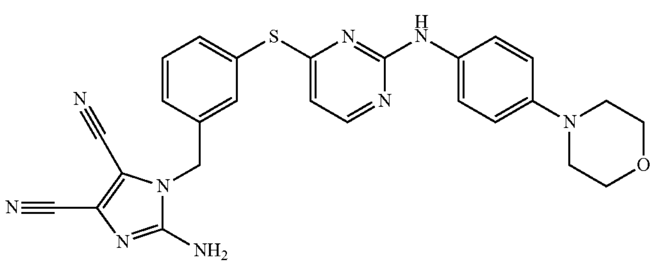 [SMILES: N#Cc1nc(N)n(Cc2cccc(Sc3ccnc(Nc4ccc(N5CCOCC5)cc4)n3)c2)c1C#N] | 509.17 | 2-amino-1-(3-(2-(4-morpholinophenylamino)pyrimidin-4-ylthio)benzyl)-1H-imidazole-4,5-dicarbonitrile | C | 6.7 | m/z 510.1 [M + H]+ | $^1$H NMR (d$_6$-DMSO) δ 2.98-3.10 (m, 4H), 3.71-3.74 (m, 4H), 5.22 (s, 2H), 6.29 (d, J = 5.17 Hz, 1H), 6.71 (d, J = 8.71 Hz, 2H), 7.21 (s, 2H), 7.30-7.39 (m, 3H), 7.54-7.64 (m, 3H), 8.11 (d, J = 5.27 Hz, 1H), 9.38 (s, 1H) |

TABLE 1-continued

| Compound number | Structure | Exact mass | Name | LCMS method | retention time (min) | Observed m/z | $^1$H NMR |
|---|---|---|---|---|---|---|---|
| 122 | 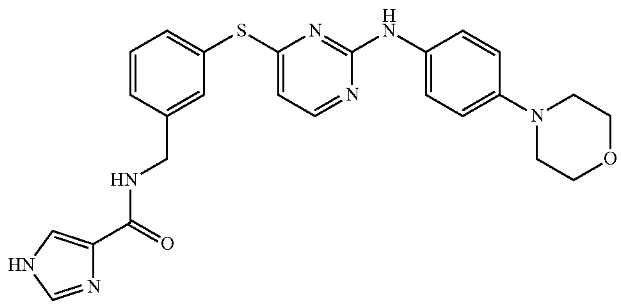 [SMILES: O=C(NCc1cccc(Sc2ccnc(Nc3ccc(N4CCOCC4)cc3)n2)c1)c1c[nH]cn1] | 487.18 | N-(3-(2-(4-morpholinophenylaminopyrimidin-4-ylthio)benzyl)-1H-imidazole-4-carboxamide | C | 6.1 | m/z 488.1 [M + H]+ | $^1$H NMR (CDCl$_3$ + d$_4$-MeOH) δ 3.07-3.10 (m, 4H), 3.84-3.87 (m, 4H), 4.64 (s, 2H), 6.28 (d, J = 5.40 Hz, 1H), 6.80 (d, J = 9.02 Hz, 2H), 7.33 (d, J = 9.16 Hz, 2H), 7.40-7.51 (m, 4H), 7.63 (m, 2H), 7.98 (d, J = 5.39 Hz, 1H) |
| 123 | 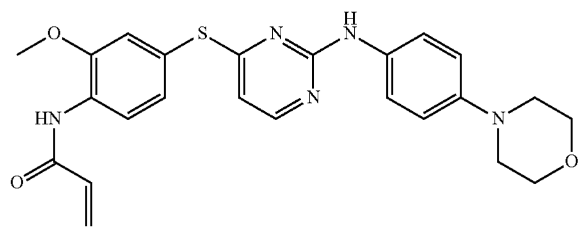 [SMILES: C=CC(=O)Nc1ccc(Sc2ccnc(Nc3ccc(N4CCOCC4)cc3)n2)cc1OC] | 463.17 | N-(2-methoxy-4-(2-(4-morpholinophenylamino)pyrimidin-4-ylthio)phenyl)acrylamide | C | 6.9 | m/z 464.1 [M + H]+ | (300 MHz, CDCl$_3$) δ 8.64 (d, J = 8.4 Hz, 1H), 8.02 (d, J = 5.1 Hz, 1H), 7.99 (br. s., 1H), 7.03 (d, J = 1.8 Hz, 1H), 7.22 (s, 1H), 7.09 (d, J = 1.8 Hz, 1H), 6.92 (br. s., 1H), 6.75 (d, J = 9.0 Hz, 2H), 6.48 (dd, J = 16.8, 1.2 Hz, 1H), 6.37-6.27 (m, 2H), 5.83 (dd, J = 9.9, 1.5 Hz, 1H), 3.86 (s, 3H), 3.83 (m, 4H), 3.06 (m, 4H) |
| 124 | 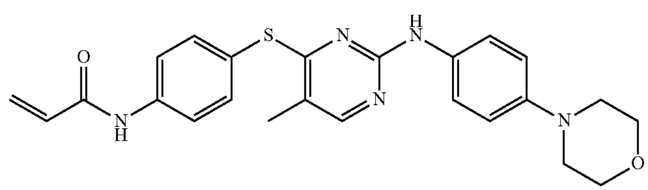 [SMILES: C=CC(=O)Nc1ccc(Sc2nc(Nc3ccc(N4CCOCC4)cc3)ncc2C)cc1] | 447.17 | N-(4-(5-methyl-2-(4-morpholinophenylamino)pyrimidin-4-ylthio)phenyl)acrylamide | C | 6.8 | m/z 448.2 [M + H]+ | $^1$H NMR (300 MHz, DMSO-d$_6$) δ 10.5 (br s, 1H), 9.11 (br s, 1H), 8.01 (s, 1H), 7.89 (d, J = 8.4 Hz, 2H), 7.55 (d, J = 9.0, 2H), 6.98 (d, J = 9.3, 2H), 6.52 (dd, J = 16.8, 10.2, 1H), 6.46 (d, J = 9.3, 2H), 6.34 (dd, J = 16.8, 2.1, 1H), 5.86 (dd, J = 9.9, 2.1, 1H), 3.64 (m, 4H), 2.85 (m, 4H), 2.13 (s, 3H) |
| 125 | 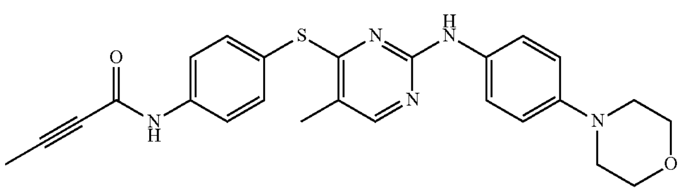 [SMILES: CC#CC(=O)Nc1ccc(Sc2nc(Nc3ccc(N4CCOCC4)cc3)ncc2C)cc1] | 459.17 | N-(4-(5-methyl-2-(4-morpholinophenylamino)pyrimidin-4-ylthio)phenyl)but-2-ynamide | C | 6.9 | m/z 460.2 [M + H]+ | $^1$H NMR (300 MHz, DMSO-d$_6$) δ 11.0 (br s, 1H), 9.11 (br s, 1H), 8.00 (s, 1H), 7.80 (d, J = 8.7, 2H), 7.53 (d, J = 8.7, 2H), 6.96 (d, J = 9.3, 2H), 6.46 (d, J = 9.0, 2H), 3.73 (m, 4H), 2.93 (m, 4H), 2.12 (s, 3H), 2.09 (s, 3H) |

TABLE 1-continued

| Compound number | Structure | Exact mass | Name | LCMS method | retention time (min) | Observed m/z | ¹H NMR |
|---|---|---|---|---|---|---|---|
| 126 | 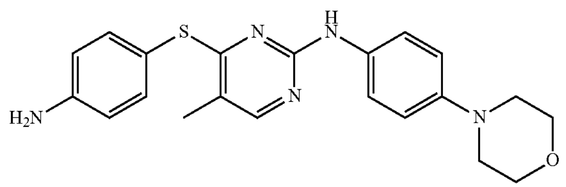 [SMILES: Cc1cnc(Nc2ccc(N3CCOCC3)cc2)nc1Sc1ccc(N)cc1] | 393.16 | 4-(4-aminophenyl-thio)-5-methyl-N-(4-morpholino-phenyl)pyrimidin-2-amine | C | 6.8 | m/z 394.2 [M + H]+ | ¹H NMR (300 MHz, DMSO-d₆) δ 9.02 (br s, 1H), 7.94 (s, 1H), 7.17 (d, J = 8.4, 2H), 7.12 (d, J = 9.3, 2H), 6.69 (d, J = 8.7, 2H), 6.64 (d, J = 9.0, 2H), 5.68 (br s, 2H), 3.72 (m, 4H), 2.99 (m, 4H), 2.09 (s, 3H) |
| 127 | 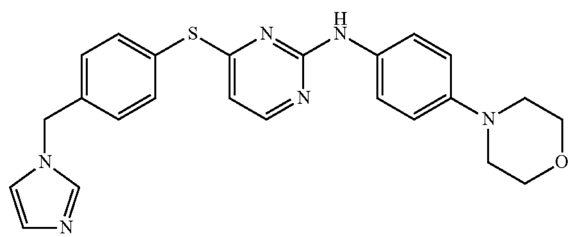 | 444.17 | 4-(4-((1H-imidazol-1-yl)methyl)phenyl-thio)-N-(4-morpholinophenyl)pyrimidin-2-amine | C | 6.3 | m/z 445.2 [M + H]+ | ¹H NMR (CDCl₃ + d₄-MeOH) δ 3.09-3.12 (m, 4H), 3.86-3.89 (m, 4H), 5.22 (s, 2H), 6.21 (d, J = 5.39 Hz, 1H), 6.84 (d, J = 9.02 Hz, 2H), 6.97-6.98 (m, 1H), 7.07-7.09 (m, 1H), 7.25 (d, J = 8.14 Hz, 2H), 7.37 (d, J = 8.87 Hz, 2H), 7.60-7.63 (m, 3H), 7.99 (d, J = 5.39 Hz, 1H) |
| 128 | 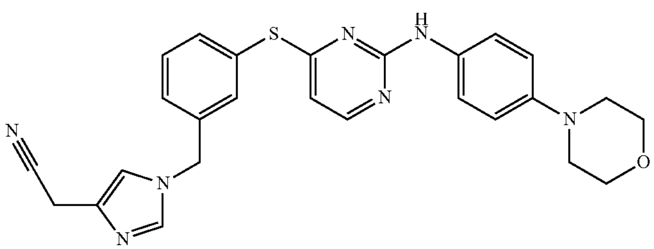 [SMILES: N#CCc1cn(Cc2cccc(Sc3ccnc(Nc4ccc(N5CCOCC5)cc4)n3)c2)cn1] | 483.18 | 2-(1-(3-(2-(4-morpholinophenyl-amino)pyrimidin-4-ylthio)benzyl)-1H-imidazol-4-yl)acetonitrile | C | 6.4 | m/z 484.2 [M + H]+ | ¹H NMR (CDCl₃ + d₄-MeOH) δ 3.07-3.10 (m, 4H), 3.65-3.66 (m, 2H), 3.86-3.89 (m, 4H), 5.11 9s, 2H), 6.31-6.33 (d, J = 5.40 Hz, 1H), 6.77 (d, J = 9.00 Hz, 2H), 6.87 (br s, 1H), 7.27 (d, J = 8.96 Hz, 2H), 7.29-7.36 (m, 1H), 7.40-7.42 (m, 1H), 7.49-7.54 (m, 2H), 7.60-7.64 (m, 1H), 8.01 (d, J = 5.35 Hz, 1H), |
| 129 | 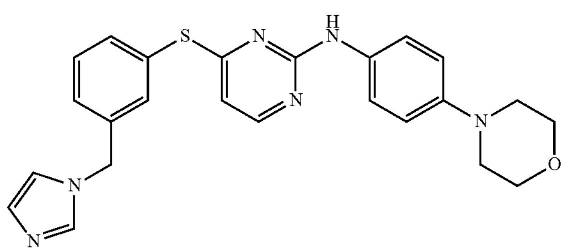 [SMILES: c1cc(Cn2cncn2)cc(Sc2ccnc(Nc3ccc(N4CCOCC4)cc3)n2)c1] | 444.17 | 4-(3-((1H-imidazol-1-yl)methyl)phenyl-thio)-N-(4-morpholinophenyl)pyrimidin-2-amine | C | 6.4 | m/z 445.2 [M + H]+ | ¹H NMR (CDCl₃ + d₄-MeOH) δ 3.06-3.09 (m, 4H), 3.86-3.89 (m, 4H), 5.14 (s, 2H), 6.30 (s, J = 5.37 Hz, 1H), 6.77 (d, J = 9.05 Hz, 2H), 6.87-6.91 (m, 1H), 7.03-7.06 (m, 1H), 7.22-7.29 (m, 1H), 7.29 (d, J = 9.09 Hz, 2H), 7.39-7.42 (m, 1H), 7.48 (t, J = 7.68 Hz, 1H), 7.56-7.57 (m, 1H), 7.57-7.61 (m, 1H), 8.01 (d, J = 5.36 Hz, 1H) |

| Compound number | Structure | Exact mass | Name | LCMS method | retention time (min) | Observed m/z | 1H NMR |
|---|---|---|---|---|---|---|---|
| 130 | 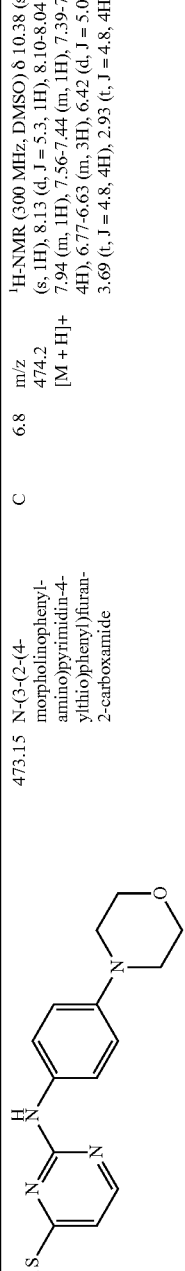 | 473.15 | N-(3-(2-(4-morpholinophenyl-amino)pyrimidin-4-ylthio)phenyl)furan-2-carboxamide | C | 6.8 | m/z 474.2 [M + H]+ | 1H-NMR (300 MHz, DMSO) δ 10.38 (s, 1H), 9.37 (s, 1H), 8.13 (d, J = 5.3, 1H), 8.10-8.04 (m, 2H), 7.94 (m, 1H), 7.56-7.44 (m, 1H), 7.39-7.23 (m, 4H), 6.77-6.63 (m, 3H), 6.42 (d, J = 5.0, 1H), 3.69 (t, J = 4.8, 4H), 2.93 (t, J = 4.8, 4H). |
| 131 | 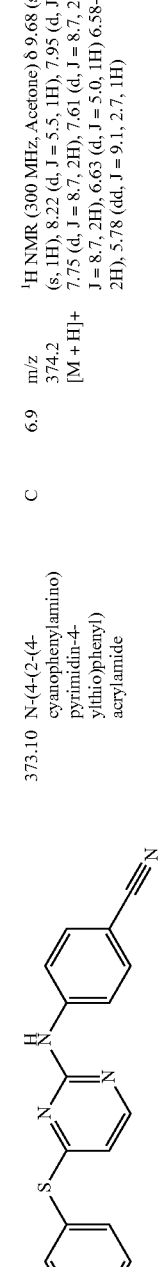 | 373.10 | N-(4-(2-(4-cyanophenylamino)pyrimidin-4-ylthio)phenyl)acrylamide | C | 6.9 | m/z 374.2 [M + H]+ | 1H NMR (300 MHz, Acetone) δ 9.68 (s, 1H), 9.06 (s, 1H), 8.22 (d, J = 5.5, 1H), 7.95 (d, J = 8.2, 2H), 7.75 (d, J = 8.7, 2H), 7.61 (d, J = 8.7, 2H) 7.51 (d, J = 8.7, 2H), 6.63 (d, J = 5.0, 1H) 6.58-6.38 (m, 2H), 5.78 (dd, J = 9.1, 2.7, 1H) |
| 132 | 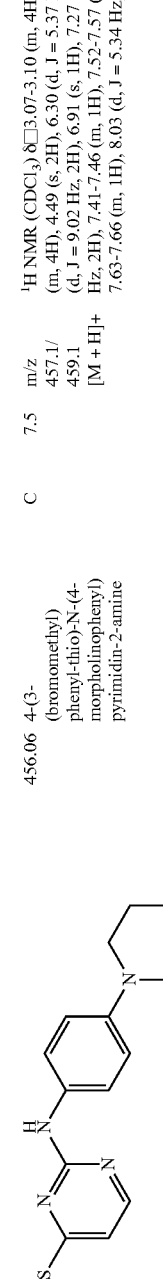 | 456.06 | 4-(3-(bromomethyl)phenyl-thio)-N-(4-morpholinophenyl)pyrimidin-2-amine | C | 7.5 | m/z 457.1/459.1 [M + H]+ | 1H NMR (CDCl3) δ 3.07-3.10 (m, 4H), 3.84-3.88 (m, 4H), 4.49 (s, 2H), 6.30 (d, J = 5.37 Hz, 1H), 6.79 (d, J = 9.02 Hz, 2H), 6.91 (s, 1H), 7.27 (d, J = 8.90 Hz, 2H), 7.41-7.46 (m, 1H), 7.52-7.57 (m, 2H), 7.63-7.66 (m, 1H), 8.03 (d, J = 5.34 Hz, 1H) |
| 133 | 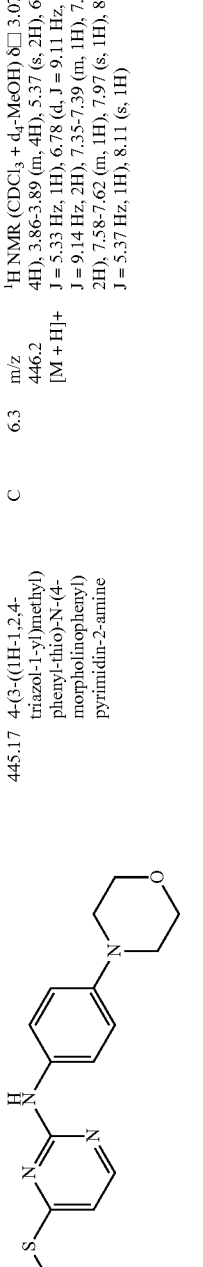 | 445.17 | 4-(3-((1H-1,2,4-triazol-1-yl)methyl)phenyl-thio)-N-(4-morpholinophenyl)pyrimidin-2-amine | C | 6.3 | m/z 446.2 [M + H]+ | 1H NMR (CDCl3 + d4-MeOH) δ 3.07-3.10 (m, 4H), 3.86-3.89 (m, 4H), 5.37 (s, 2H), 6.31 (d, J = 5.33 Hz, 1H), 6.78 (d, J = 9.11 Hz, 2H), 7.27 (d, J = 9.14 Hz, 2H), 7.35-7.39 (m, 1H), 7.46-7.52 (m, 2H), 7.58-7.62 (m, 1H), 7.97 (s, 1H), 8.01 (d, J = 5.37 Hz, 1H), 8.11 (s, 1H) |

| Compound number | Structure | Exact mass | Name | LCMS method | retention time (min) | Observed m/z | ¹H NMR |
|---|---|---|---|---|---|---|---|
| 134 | 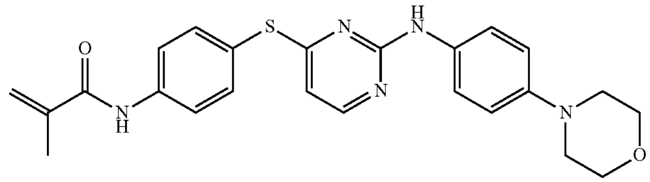 [SMILES: C=C(C)C(=O)Nc1ccc(Sc2ccnc(Nc3ccc(N4CCOCC4)cc3)n2)cc1] | 447.17 | N-(4-(2-(4-morpholinophenylaminopyrimidin-4-ylthio)phenyl)methacrylamide | C | 6.9 | m/z 448.3 [M + H]+ | ¹H NMR (300 MHz, CDCl₃/MeOD) δ 7.97 (d, J = 5.7, 1H), 7.79 (d, J = 8.7, 2H), 7.57 (d, J = 8.7, 2H), 7.28 (d, J = 9.0, 2H), 6.80 (d, J = 9.0, 2H), 6.35 (d, J = 5.4, 1H), 5.86 (s, 1H), 5.55 (s, 1H), 3.85 (m, 4H), 3.08 (m, 4H), 2.08 (s, 3H) |
| 135 | 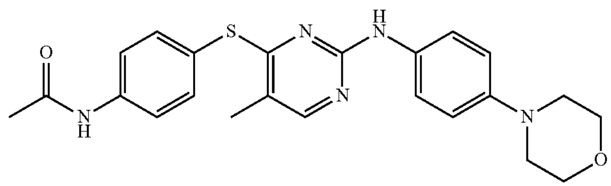 [SMILES: CC(=O)Nc1ccc(Sc2nc(Nc3ccc(N4CCOCC4)cc3)ncc2C)cc1] | 435.17 | N-(4-(5-methyl-2-(4-morpholinophenylaminopyrimidin-4-ylthio)phenyl)acetamide | C | 6.5 | m/z 436.4 [M + H]+ | ¹H NMR (300 MHz, DMSO-d₆) δ 10.3 (br s, 1H), 9.10 (br s, 1H), 8.00 (s, 1H), 7.78 (d, J = 8.7, 2H), 7.51 (d, J = 8.7, 2H), 7.00 (d, J = 8.7, 2H), 6.49 (d, J = 9.0, 2H), 3.72 (m, 4H), 2.92 (m, 4H), 2.13 (s, 3H), 2.10 (s, 3H) |
| 136 | 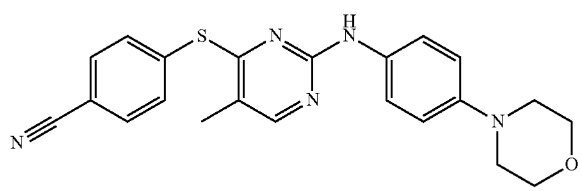 [SMILES: Cc1cnc(Nc2ccc(N3CCOCC3)cc2)nc1Sc1ccc(C#N)cc1] | 403.15 | 4-(5-methyl-2-(4-morpholinophenylaminopyrimidin-4-ylthio)benzonitrile | C | 7.3 | m/z 404.3 [M + H]+ | ¹H NMR (500 MHz, CDCl₃) δ 7.94 (d, J = 1.0, 1H), 7.71 (AB, J = 8.5, 2H), 7.69 (AB, J = 8.5, 2H), 6.93 (d, J = 9.0, 2H), 6.75 (br s, 1H), 6.64 (d, J = 9.0, 2H), 3.87 (m, 4H), 3.11 (m, 4H), 2.20 (d, J = 1.0, 3H) |
| 137 | 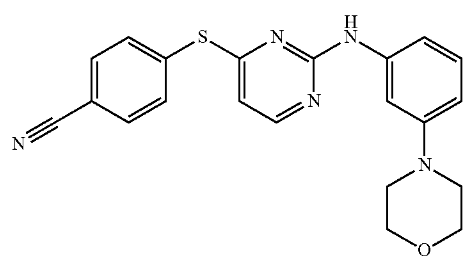 [SMILES: N#Cc1ccc(Sc2ccnc(Nc3cccc(N4CCOCC4)c3)n2)cc1] | 389.13 | 4-(2-(3-morpholinophenylaminopyrimidin-4-ylthio)benzonitrile | C | 7.1 | m/z 390.3 [M + H]+ | ¹H NMR (500 MHz, CDCl₃) δ 8.13 (d, J = 5.5, 1H), 7.71 (AB, J = 8.5, 2H), 7.69 (AB, J = 8.5, 2H), 7.08 (t, J = 8.0, 1H), 7.01 (br s, 1H), 6.99 (m, 1H), 6.86 (dd, J = 8.0, 2.0, 1H), 6.60 (dd, J = 8.0, 2.0, 1H), 6.46 (d, J = 5.5, 1H), 3.84 (m, 4H), 3.12 (m, 4H) |

| Compound number | Structure | Exact mass | Name | LCMS method | retention time (min) | Observed m/z | ¹H NMR |
|---|---|---|---|---|---|---|---|
| 138 | 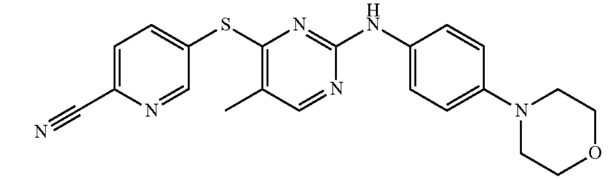 [SMILES: Cc1cnc(Nc2ccc(N3CCOCC3)cc2)nc1Sc1ccc(C#N)nc1] | 404.14 | 5-(5-methyl-2-(4-morpholinophenyl-aminopyrimidin-4-ylthio)picolinonitrile | C | 6.9 | m/z 405.3 [M + H]+ | ¹H NMR (300 MHz, CDCl₃) δ 8.83 (m, 1H), 8.01-7.97 (m, 2H), 7.68 (dd, J = 8.1, 0.9, 1H), 6.95 (d, J = 9.0, 2H), 6.73 (br s, 1H), 6.70 (d, J = 9.0, 2H), 3.14 (m, 4H), 2.21 (s, 3H), 3.88 (m, 4H) |
| 139 | 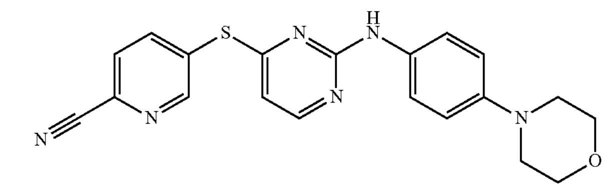 [SMILES: N#Cc1ccc(Sc2ccnc(Nc3ccc(N4CCOCC4)cc3)n2)cn1] | 390.13 | 5-(2-(4-morpholinophenyl-aminopyrimidin-4-ylthio)picolinonitrile | C | 6.6 | m/z 391.3 [M + H]+ | ¹H NMR (300 MHz, CDCl₃) δ 8.85 (dd, J = 2.4, 0.9, 1H), 8.13 (d, J = 5.4, 1H), 8.02 (dd, J = 7.5, 2.4, 1H), 7.69 (dd, J = 7.8, 0.9, 1H), 7.07 (d, J = 8.4, 2H), 6.92 (br s, 1H), 6.75 (d, J = 8.7, 2H), 6.58 (d, J = 5.1, 1H), 3.88 (m, 4H), 3.14 (m, 4H) |
| 140 | 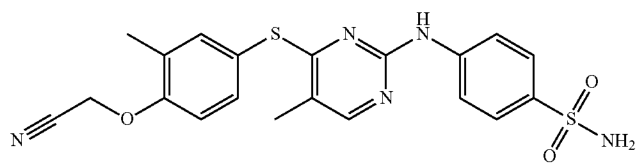 [SMILES: Cc1cc(Sc2nc(Nc3ccc(S(N)(=O)=O)cc3)ncc2C)ccc1OCC#N] | 441.09 | 4-(4-(cyanomethoxy)-3-methylphenylthio)-5-methyl-pyrimidin-2-ylamino)benzene-sulfonamide | C | 7.0 | m/z 442.3 [M + H]+ | ¹H NMR (500 MHz, DMSO-d₆) δ 9.75 (br s, 1H), 8.14 (s, 1H), 7.51 (m, 2H), 7.34 (d, J = 9.0, 2H), 7.29-7.23 (m, 3H), 7.04 (br s, 2H), 5.27 (s, 2H), 2.23 (s, 3H), 2.18 (s, 3H) |
| 141 | 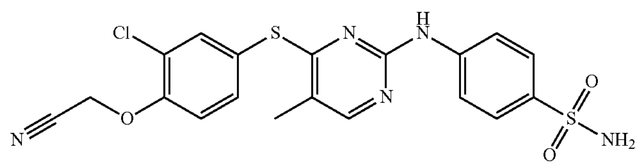 [SMILES: Cc1cnc(Nc2ccc(S(N)(=O)=O)cc2)nc1Sc1ccc(OCC#N)c(Cl)c1] | 461.04 | 4-(4-(3-chloro-4-(cyanomethoxy)phenylthio)-5-methylpyrimidin-2-ylamino)benzene-sulfonamide | C | 7.0 | m/z 462.3 [M + H]+ | ¹H NMR (500 MHz, DMSO-d₆) δ 9.78 (br s, 1H), 8.17 (s, 1H), 7.82 (d, J = 2.5, 1H), 7.66 (dd, J = 8.5, 2.0, 1H), 7.46 (d, J = 9.0, 1H), 7.40 (d, J = 9.5, 2H), 7.31 (d, J = 9.0, 2H), 7.06 (br s, 2H), 5.36 (s, 2H), 2.18 (s, 3H) |
| 142 | 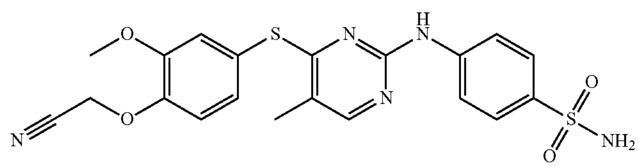 [SMILES: COc1cc(Sc2nc(Nc3ccc(S(N)(=O)=O)cc3)ncc2C)ccc1OCC#N] | 457.09 | 4-(4-(cyanomethoxy)-3-methoxy-phenylthio)-5-methylpyrimidin-2-ylamino)benzenesulfonamide | C | 6.6 | m/z 458.3 [M + H]+ | ¹H NMR (500 MHz, DMSO-d₆) δ 9.76 (br s, 1H), 8.15 (s, 1H), 7.40-7.20 (m, 7H), 7.05 (br s, 2H), 5.21 (s, 2H), 3.77 (s, 3H), 2.18 (s, 3H) |

| Compound number | Structure | Exact mass | Name | LCMS method | retention time (min) | Observed m/z | ¹H NMR |
|---|---|---|---|---|---|---|---|
| 143 | 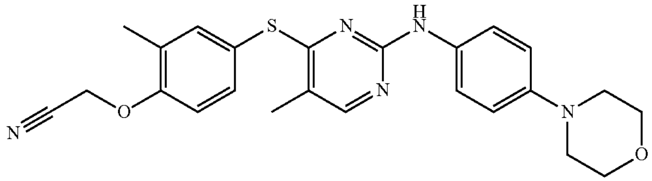 [SMILES: Cc1cc(Sc2nc(Nc3ccc(N4CCOCC4)cc3)ncc2C)ccc1OCC#N] | 447.17 | 2-(2-methyl-4-(5-methyl-2-(4-morpholinophenyl-aminopyrimidin-4-ylthio)phenoxy)acetonitrile | C | 7.5 | m/z 448.4 [M + H]+ | ¹H NMR (300 MHz, CDCl₃) δ 7.88 (s, 1H), 7.44 (m, 2H), 7.00-6.95 (m, 3H), 6.74 (br s, 1H), 6.59 (d, J = 9.3, 2H), 4.87 (s, 2H), 3.88 (m, 4H), 2.27 (s, 3H), 2.18 (s, 3H), 3.06 (m, 4H) |
| 144 | 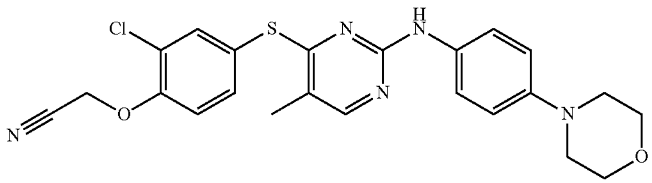 [SMILES: Cc1cnc(Nc2ccc(N3CCOCC3)cc2)nc1Sc1ccc(OCC#N)c(Cl)c1] | 467.12 | 2-(2-chloro-4-(5-methyl-2-(4-morpholinophenyl-aminopyrimidin-4-ylthio)phenoxy)acetonitrile | C | 7.5 | m/z 468.3 [M + H]+ | ¹H NMR (300 MHz, CDCl₃) δ 7.91 (s, 1H), 7.69 (d, J = 1.8, 1H), 7.49 (dd, J = 8.7, 1.8, 1H), 7.10 (d, J = 8.7, 1H), 7.00 (d, J = 9.0, 2H), 6.73 (br s, 1H), 6.66 (d, J = 9.0, 2H), 4.90 (s, 2H), 3.88 (m, 4H), 3.08 (m, 4H), 2.18 (s, 3H) |
| 145 | 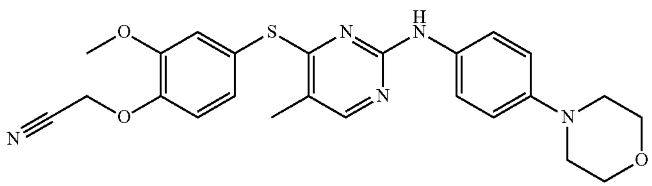 [SMILES: COc1cc(Sc2nc(Nc3ccc(N4CCOCC4)cc3)ncc2C)ccc1OCC#N] | 463.17 | 2-(2-methoxy-4-(5-methyl-2-(4-morpholinophenyl-aminopyrimidin-4-ylthio)phenoxy)acetonitrile | C | 7.0 | m/z 464.4 [M + H]+ | ¹H NMR (300 MHz, CDCl₃) δ 7.90 (s, 1H), 7.21-7.09 (m, 3H), 7.00 (d, J = 9.3, 2H), 6.78 (br s, 1H), 6.64 (d, J = 9.0, 2H), 4.89 (s, 2H), 3.87 (m, 4H), 3.77 (s, 3H), 3.08 (m, 4H), 2.19 (s, 3H) |
| 146 | 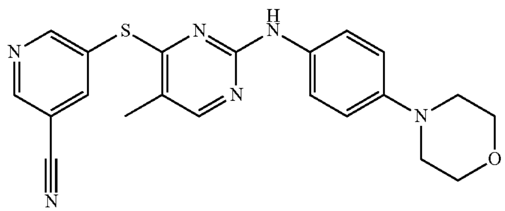 [SMILES: Cc1cnc(Nc2ccc(N3CCOCC3)cc2)nc1Sc1cncc(C#N)c1] | 404.14 | 5-(5-methyl-2-(4-morpholinophenyl-aminopyrimidin-4-ylthio)nicotinonitrile | C | 6.56 | m/z 405.3 [M + H]+ | ¹H NMR (300 MHz, DMSO-d₆) δ 9.26 (d, J = 1.8, 1H), 9.17 (br s, 1H), 8.99 (d, J = 2.7, 1H), 8.65 (t, J = 1.8, 1H), 8.10 (s, 1H), 6.95 (d, J = 8.4, 2H), 6.59 (d, J = 9.3, 2H), 3.74 (m, 4H), 3.00 (m, 4H), 2.17 (s, 3H) |
| 147 | 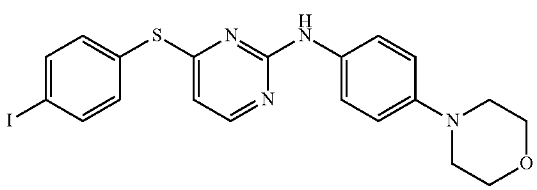 [SMILES: Ic1ccc(Sc2ccnc(Nc3ccc(N4CCOCC4)cc3)n2)cc1] | 490.03 | 4-(4-iodophenyl-thio)-N-(4-morpholinophenyl)pyrimidin-2-amine | C | 7.8 | m/z 491.2 [M + H]+ | ¹H NMR (300 MHz, DMSO-d₆) δ 9.40 (br s, 1H), 8.13 (d, J = 4.8, 1H), 7.91 (d, J = 8.4, 2H), 7.41 (d, J = 8.4, 2H), 7.21 (d, J = 9.0, 2H), 6.69 (d, J = 9.3, 2H), 6.51 (m, 1H), 3.74 (m, 4H), 3.04 (m, 4H) |

TABLE 1-continued

| Compound number | Structure | Exact mass | Name | LCMS method | retention time (min) | Observed m/z | ¹H NMR |
|---|---|---|---|---|---|---|---|
| 148 | 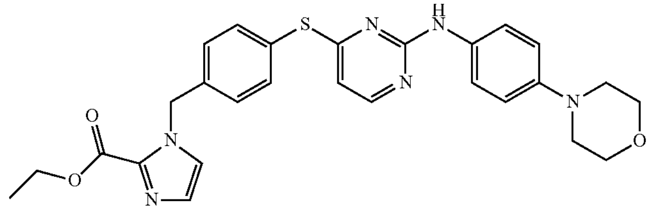 [SMILES: CCOC(=O)c1nccn1Cc1ccc(Sc2ccnc(Nc3ccc(N4CCOCC4)cc3)n2)cc1] | 516.19 | ethyl 1-(4-(2-(4-morpholinophenylaminopyrimidin-4-ylthio)benzyl)-1H-imidazole-2-carboxylate | E | 9.4 | m/z 517.4 [M + H]+ | ¹H NMR (300 MHz, CDCl₃) δ 8.02 (d, J = 5.4, 1H), 7.59 (d, J = 8.4, 2H), 7.35 (d, J = 9.3, 2H), 7.26 (d, J = 8.1, 2H), 7.23 (d, J = 0.9, 1H), 7.12 (d, J = 0.9, 1H), 6.95 (br s, 1H), 6.84 (d, J = 9.0, 2H), 6.21 (d, J = 5.7, 1H), 5.72 (s, 2H), 4.38 (q, J = 7.2, 2H), 3.87 (m, 4H), 3.11 (m, 4H), 1.41 (t, J = 7.2, 3H) |
| 149 | 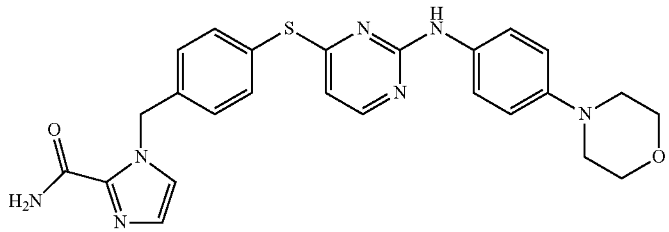 [SMILES: NC(=O)c1nccn1Cc1ccc(Sc2ccnc(Nc3ccc(N4CCOCC4)cc3)n2)cc1] | 487.18 | 1-(4-(2-(4-morpholinophenylaminopyrimidin-4-ylthio)benzyl)-1H-imidazole-2-carboxamide | C | 6.2 | m/z 488.3 [M + H]+ | ¹H NMR (300 MHz, DMSO-d₆) δ 9.41 (br s, 1H), 8.11 (d, J = 5.4, 1H), 7.83 (br s, 1H), 7.62 (d, J = 8.1, 2H), 7.48 (s, 1H), 7.37 (m, 4H), 7.05 (s, 1H), 6.77 (d, J = 9.3, 2H), 6.22 (d, J = 5.1, 1H), 5.79 (s, 2H), 5.30 (br s, 1H), 3.74 (m, 4H), 3.02 (m, 4H) |
| 150 | 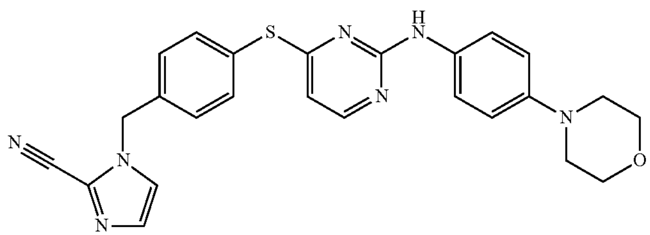 | 469.17 | 1-(4-(2-(4-morpholinophenylaminopyrimidin-4-ylthio)benzyl)-1H-imidazole-2-carbonitrile | C | 6.7 | m/z 470.3 [M + H]+ | ¹H NMR (300 MHz, CDCl₃) δ 8.04 (d, J = 5.7, 1H), 7.65 (d, J = 8.4, 2H), 7.36 (d, J = 8.7, 2H), 7.30 (d, J = 8.4, 2H), 7.26 (d, J = 1.2, 1H), 7.12 (d, J = 1.2, 1H), 6.90 (br s, 1H), 6.83 (d, J = 8.7, 2H), 6.25 (d, J = 5.4, 1H), 5.36 (s, 2H), 3.87 (m, 4H), 3.10 (m, 4H) |
| 151 | 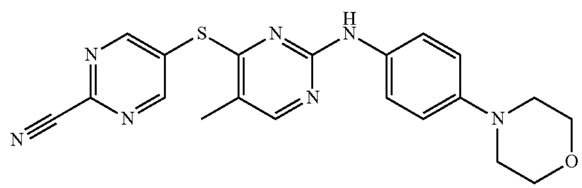 [SMILES: Cc1cnc(Nc2ccc(N3CCOCC3)cc2)nc1Sc1cnc(C#N)nc1] | 405.14 | 5-(5-methyl-2-(4-morpholinophenylaminopyrimidin-4-ylthio)pyridine-2-carbonitrile | C | 6.8 | m/z 406.2 [M + H]+ | ¹H NMR (300 MHz, DMSO-d₆) δ 9.22 (s, 2H), 9.20 (br s, 1H), 8.14 (s, 1H), 6.98 (d, J = 8.4, 2H), 6.65 (d, J = 9.0, 2H), 3.74 (m, 4H), 3.03 (m, 4H), 2.18 (s, 3H) |

TABLE 1-continued

| Compound number | Structure | Exact mass | Name | LCMS method | retention time (min) | Observed m/z | 1H NMR |
|---|---|---|---|---|---|---|---|
| 152 | 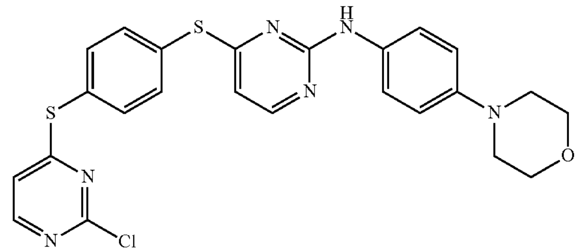 [SMILES: Clc1nccc(Sc2ccc(Sc3ccnc(Nc4ccc(N5CCOCC5)cc4)n3)cc2)n1] | 508.09 | 4-(2-chloropyrimidin-4-ylthio)phenylthio)-N-(4-morpholinophenyl)pyrimidin-2-amine | C | 7.4 | m/z 509.2 [M + H]+ | 1H NMR (300 MHz, CDCl3) δ 8.20 (d, J = 5.4, 1H), D8.09 (d, J = 5.4, 1H), 7.74 (AB, J = 8.4, 2H), 7.67 (AB, J = 8.4, 2H), 7.24 (d, J = 8.7, 2H), 6.94 (br s, 1H), 6.75 (d, J = 8.4, 2H), 6.75 (d, J = 5.4, 1H), 6.44 (d, J = 5.4, 1H), 3.84 (m, 4H), 3.05 (m, 4H) |
| 153 | 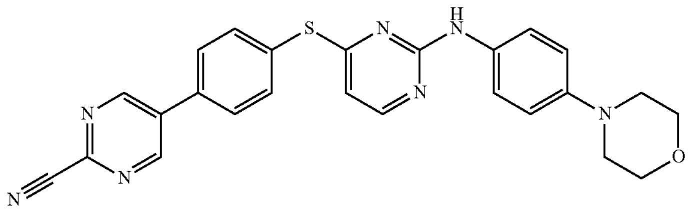 [SMILES: N#Cc1ncc(-c2ccc(Sc3ccnc(Nc4ccc(N5CCOCC5)cc4)n3)cc2)cn1] | 467.15 | 5-(4-(2-(4-morpholinophenylamino)pyrimidin-4-ylthio)phenyl)pyrimidine-2-carbonitrile | C | 7.1 | m/z 468.3 [M + H]+ | 1H NMR (300 MHz, DMSO-d6) δ 9.54 (s, 2H), 9.40 (br s, 1H), 8.16 (d, J = 5.4, 1H), 8.13 (d, J = 8.7, 2H), 7.84 (d, J = 8.7, 2H), 7.24 (d, J = 8.7, 2H), 6.57 (d, J = 9.0, 2H), 6.53 (d, J = 5.1, 1H), 3.64 (m, 4H), 2.79 (m, 4H) |
| 154 | 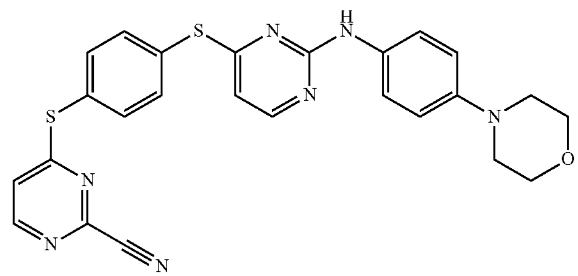 [SMILES: N#Cc1nccc(Sc2ccc(Sc3ccnc(Nc4ccc(N5CCOCC5)cc4)n3)cc2)n1] | 499.12 | 4-(4-(2-(4-morpholinophenylamino)pyrimidin-4-ylthio)phenyl)pyrimidine-2-carbonitrile | C | 7.4 | m/z 500.3 [M + H]+ | 1H NMR (300 MHz, CDCl3) δ 8.40 (d, J = 5.7, 1H), 8.10 (d, J = 5.4, 1H), 7.75 (AB, J = 8.4, 2H), 7.66 (AB, J = 8.4, 2H), 7.26 (d, J = 9.0, 2H), 7.03 (d, J = 5.7, 1H), 6.89 (br s, 1H), 6.76 (d, J = 9.0, 2H), 6.43 (d, J = 5.4, 1H), 3.86 (m, 4H), 3.06 (m, 4H) |
| 155 | 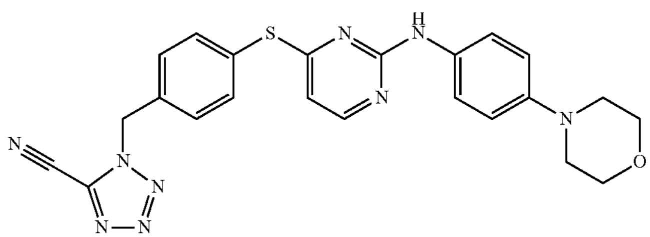 | 471.16 | 1-(4-(2-(4-morpholinophenylamino)pyrimidin-4-ylthio)benzyl)-1H-tetrazole-5-carbonitrile | C | 7.0 | m/z 472.3 [M + H]+ | 1H NMR (300 MHz, CDCl3) δ 8.06 (d, J = 5.1, 1H), 7.69 (d, J = 8.4, 2H), 7.46 (d, J = 8.4, 2H), 7.35 (d, J = 9.0, 2H), 6.86 (br s, 1H), 6.83 (d, J = 9.3, 2H), 6.29 (d, J = 5.7, 1H), 5.79 (s, 2H), 3.87 (m, 4H), 3.11 (m, 4H) |

TABLE 1-continued

| Compound number | Structure | Exact mass | Name | LCMS method | retention time (min) | Observed m/z | ¹H NMR |
|---|---|---|---|---|---|---|---|
| 156 | 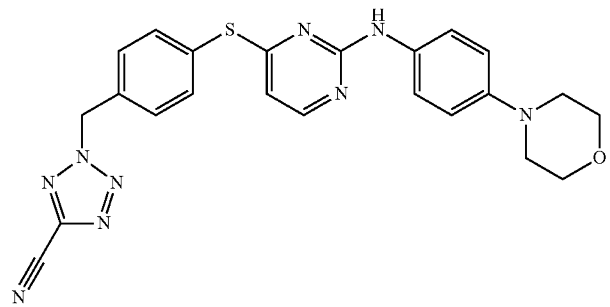 [SMILES: N#Cc1nnn(Cc2ccc(Sc3ccnc(Nc4ccc(N5CCOCC5)cc4)n3)cc2)n1] | 471.16 | 2-(4-(2-(4-morpholinophenylaminopyrimidin-4-ylthio)benzyl)-2H-tetrazole-5-carbonitrile | C | 7.1 | m/z 472.3 [M+H]+ | ¹H NMR (300 MHz, CDCl₃) δ 8.05 (d, J = 5.4, 1H), 7.67 (d, J = 8.4, 2H), 7.46 (d, J = 8.4, 2H), 7.33 (d, J = 9.0, 2H), 6.86 (br s, 1H), 6.82 (d, J = 9.0, 2H), 6.27 (d, J = 5.1, 1H), 5.91 (s, 2H), 3.87 (m, 4H), 3.11 (m, 4H) |
| 157 | 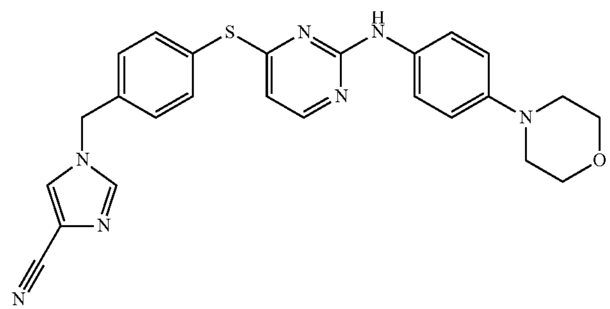 [SMILES: N#Cc1cn(Cc2ccc(Sc3ccnc(Nc4ccc(N5CCOCC5)cc4)n3)cc2)cn1] | 469.17 | 1-(4-(2-(4-morpholinophenylaminopyrimidin-4-ylthio)benzyl)-1H-imidazole-4-carbonitrile | C | 6.4 | m/z 470.3 [M+H]+ | ¹H NMR (300 MHz, CDCl₃) δ 8.05 (d, J = 5.1, 1H), 7.65 (d, J = 8.4, 2H), 7.60 (d, J = 1.2, 1H), 7.47 (d, J = 1.5, 1H), 7.36 (d, J = 9.0, 2H), 7.24 (d, J = 8.4, 2H), 6.88 (br s, 1H), 6.83 (d, J = 9.0, 2H), 6.24 (d, J = 5.4, 1H), 5.21 (s, 2H), 3.86 (m, 4H), 3.10 (m, 4H) |
| 158 | 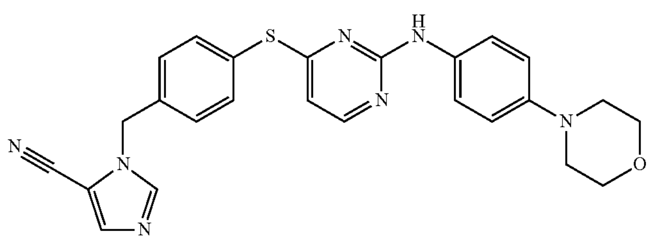 [SMILES: N#Cc1cncn1Cc1ccc(Sc2ccnc(Nc3ccc(N4CCOCC4)cc3)n2)cc1] | 469.17 | 1-(4-(2-(4-morpholinophenylaminopyrimidin-4-ylthio)benzyl)-1H-imidazole-5-carbonitrile | C | 6.4 | m/z 470.3 [M+H]+ | ¹H NMR (300 MHz, CDCl₃) δ 8.04 (d, J = 5.4, 1H), 7.22 (s, 1H), 7.71 (s, 1H), 7.65 (d, J = 8.1, 2H), 7.37 (d, J = 9.0, 2H), 7.30 (d, J = 8.1, 2H), 6.92 (br s, 1H), 6.84 (d, J = 9.0, 2H), 6.24 (d, J = 5.7, 1H), 5.31 (s, 2H), 3.86 (m, 4H), 3.10 (m, 4H) |

TABLE 1-continued

| Compound number | Structure | Exact mass | Name | LCMS method | retention time (min) | Observed m/z | ¹H NMR |
|---|---|---|---|---|---|---|---|
| 159 | 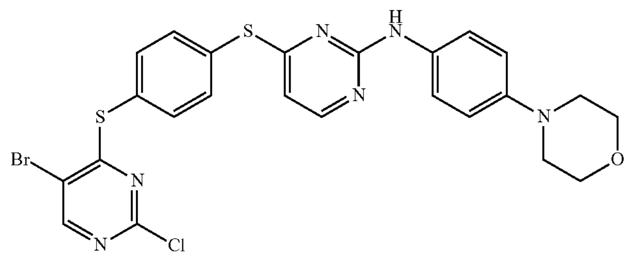 [SMILES: Clc1ncc(Br)c(Sc2ccc(Sc3ccnc(Nc4ccc(N5CCOCC5)cc4)n3)cc2)n1] | 586.00 | 4-(5-bromo-2-chloropyrimidin-4-ylthio)phenylthio)-N-(4-morpholinophenyl)pyrimidin-2-amine | C | 7.9 | m/z 587.0 [M + H]+ | ¹H NMR (300 MHz, CDCl₃) δ 8.41 (s, 1H), 8.06 (d, J = 5.4, 1H), 7.71 (AB, J = 8.7, 2H), 7.62 (AB, J = 8.7,2H), 7.24 (d, J = 8.4, 2H), 6.91 (br s, 1H), 6.77 (d, J = 9.0, 2H), 6.39 (d, J = 5.4, 1H), 3.85 (m, 4H), 3.09 (m, 4H) |
| 160 | 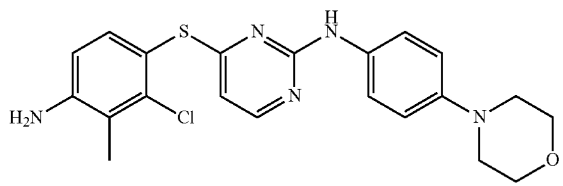 [SMILES: Cc1c(N)ccc(Sc2ccnc(Nc3ccc(N4CCOCC4)cc3)n2)c1Cl] | 427.12 | 4-(4-amino-2-chloro-3-methylphenylthio)-N-(4-morpholinophenyl)pyrimidin-2-amine | C | 7.0 | m/z 428.1/ 430.1 [M + H]+ | (300 MHz, d₆-DMSO) δ 8.86 (s, 1H), 7.61 (d, J = 5.1, 1H), 6.86 (d, J = 9.6, 2H), 6.82 (d, J = 8.4, 1H), 6.27 (d, J = 9.6, 2H), 6.23 (d, J = 6.0, 1H), 5.82 (d, J = 5.1, 1H), 5.35 (br s, 2H), 3.25-3.29 (m, 4H), 2.53-2.56 (m, 4H), 1.73 (s, 3H). |
| 161 | 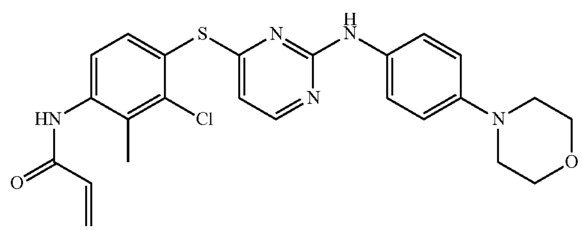 [SMILES: C=CC(=O)Nc1ccc(Sc2ccnc(Nc3ccc(N4CCOCC4)cc3)n2)c(Cl)c1C] | 481.13 | N-(3-chloro-2-methyl-4-(2-(4-morpholinophenylamino)pyrimidin-4-ylthio)phenyl)acrylamide | C | 6.8 | m/z 482.3/ 484.3 [M + H]+ | (300 MHz, CDCl₃) δ 9.87 (s, 1H), 8.14 (d, J = 5.7 Hz, 1H), 7.78 (d, J = 8.1 Hz, 1H), 7.66 (d, J = 8.4 Hz, 1H), 7.16 (d, J = 8.1 Hz, 2H), 6.62 (m, 3H), 6.53 (br s, 1H), 6.32 (dd J = 16.8, 1.8 Hz, 1H), 5.85 (dd J = 10.2, 1.8 Hz, 1H), 3.67 (m, 4H), 2.93 (m, 4H), 2.32 (s, 3H) |
| 162 | 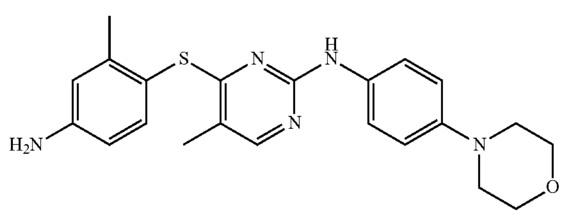 [SMILES: Cc1cc(N)ccc1Sc1nc(Nc2ccc(N3CCOCC3)cc2)ncc1C] | 407.18 | 4-(4-amino-2-methylphenylthio)-5-methyl-N-(4-morpholinophenyl)pyrimidin-2-amine | C | 7.0 | m/z 408.3 [M + H]+ | (300 MHz, CDCl₃) δ 7.85 (s, 1H), 7.33 (d, J = 8.0, 1H), 7.03 (d, J = 9.5, 2H), 6.74-6.70 (m, 3H), 6.60 (dd, J = 8.0, 1H), 3.86 (m, 4H), 3.08 (m, 4H) (s, 3H), 2.20 (s, 3H). |

TABLE 1-continued

| Compound number | Structure | Exact mass | Name | LCMS method | retention time (min) | Observed m/z | ¹H NMR |
|---|---|---|---|---|---|---|---|
| 163 | 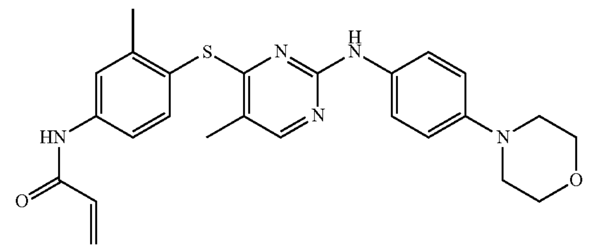 [SMILES: C=CC(=O)Nc1ccc(Sc2nc(Nc3ccc(N4CCOCC4)cc3)ncc2C)c(C)c1] | 461.19 | N-(3-methyl-4-(5-methyl-2-(4-morpholinophenyl-aminopyrimidin-4-ylthio)phenyl)acrylamide | C | 7.0 | m/z 462.3 [M + H]⁺ | (300 MHz, CDCl₃) δ 7.88 (s, 1H), 7.81 (d, J = 1.8 Hz, 1H), 7.55 (d, J = 8.4 Hz, 1H), 7.48 (dd, J = 8.4, 2.1 Hz, 1H), 7.36 (br.s., 1H), 6.94 (d, J = 8.7 Hz, 2H), 6.81 (br.s., 1H), 6.60 (d, J = 8.7 Hz, 2H), 6.52 (dd, J = 16.5, 1.5 Hz, 1H), 6.28 (dd, J = 16.8, 10.5 Hz, 1H), 5.85 (dd, J = 10.2, 1.2 Hz, 1H), 3.78 (m, 4H), 2.99 (m, 4H), 2.37 (s, 3H), 2.21 (s, 3H) |
| 164 | 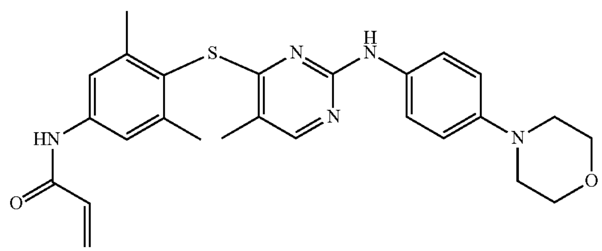 [SMILES: C=CC(=O)Nc1cc(C)c(Sc2nc(Nc3ccc(N4CCOCC4)cc3)ncc2C)c(C)c1] | 475.20 | N-(3,5-dimethyl-4-(5-methyl-2-(4-morpholinophenyl-aminopyrimidin-4-ylthio)phenyl)acrylamide | C | 7.2 | m/z 476.3 [M + H]⁺ | (300 MHz, CDCl₃) δ 7.87 (s, 1H), 7.55 (s, 1H), 7.31 (s, 1H), 6.93 (d, J = 9.3 Hz, 2H), 6.79, (br.s., 1H), 6.60 (d, J = 9.0 Hz, 2H), 6.50 (dd, J = 16.8, 1.2 Hz, 1H), 6.27 (dd, J = 16.8, 10.2 Hz, 1H), 5.84 (dd, J = 10.2, 1.5 Hz, 1H), 3.79 (m, 4H), 2.98 (m, 4H), 2.39 (s, 6H), 2.42 (s, 3H) |
| 165 | 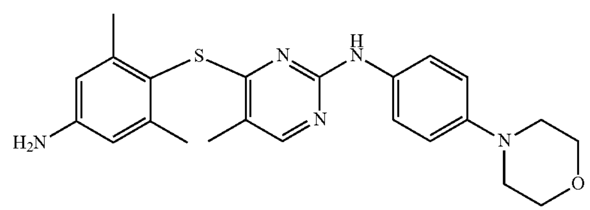 [SMILES: Cc1cnc(Nc2ccc(N3CCOCC3)cc2)nc1Sc1c(C)cc(N)cc1C] | 421.19 | 4- (4-amino-2,6-dimethylphenyl-thio)-5-methyl-N-(4-morpholinophenyl)pyrimidin-2-amine | C | 7.2 | m/z 422.4 [M + H]⁺ | (300 MHz, d₆-DMSO) δ 9.00 (br.s, 1H), 7.94 (s, 1H), 7.10 (d, J = 9.0, 2H), 6.64 (d, J = 9.0, 2H), 6.49 (s, 2H), 5.46 (s, 2H), 3.73-3.70 (m, 4H), 3.00-2.97 (m, 4H), 2.15 (s, 9H). |
| 166 | 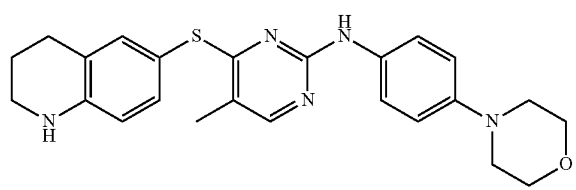 [SMILES: Cc1cnc(Nc2ccc(N3CCOCC3)cc2)nc1Sc1ccc2c(c1)CCCN2] | 433.19 | 5- methyl-N-(4-morpholinophenyl)-4-(1,2,3,4-tetrahydroquinolin-6-ylthio)pyrimidin-2-amine | C | 7.6 | m/z 434.4 [M + H]⁺ | (300 MHz, CDCl₃) δ 7.82 (s, 1H), 7.14 (m, 2H), 7.08 (d, J = 5.4 Hz, 2H), 6.88 (s, 1H), 6.73 (d, J = 5.7 Hz, 2H), 6.55 (d, J = 5.4 Hz, 1H), 3.86 (m, 4H), 3.40 (m, 2H), 3.07 (m, 4H), 2.76 (m, 2H), 2.16 (s, 3H), 1.97 (m, 3H) |

TABLE 1-continued

| Compound number | Structure | Exact mass | Name | LCMS method | retention time (min) | Observed m/z | 1H NMR |
|---|---|---|---|---|---|---|---|
| 167 | 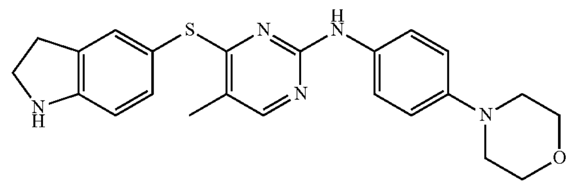 [SMILES: Cc1cnc(Nc2ccc(N3CCOCC3)cc2)nc1Sc1ccc2c(c1)CCN2] | 419.18 | 4-(indolin-5-ylthio)-5-methyl-N-(4-morpholinophenyl)pyrimidin-2-amine | C | 7.3 | m/z 420.4.4 [M + H]+ | |
| 168 | 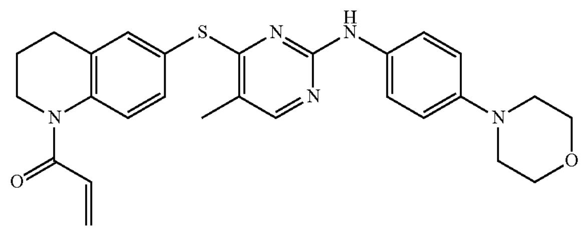 [SMILES: C=CC(=O)N1CCCc2cc(Sc3nc(Nc4ccc(N5CCOCC5)cc4)ncc3C)ccc21] | 487.20 | 1-(6-(5-methyl-2-(4-morpholinophenylaminopyrimidin-4-ylthio)-3,4-dihydroquinolin-1(2H)-yl)prop-2-en-1-one | C | 7.4 | m/z 488.4 [M + H]+ | |
| 169 | 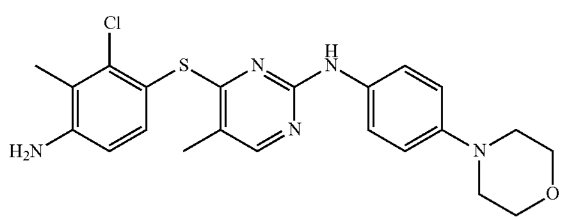 [SMILES: Cc1cnc(Nc2ccc(N3CCOCC3)cc2)nc1Sc1ccc(N)c(C)c1Cl] | 441.14 | 4-(4-amino-2-chloro-3-methylphenylthio)-5-methyl-N-(4-morpholinophenyl)pyrimidin-2-amine | C | 7.3 | m/z 442.3 [M + H]+ | |
| 170 | 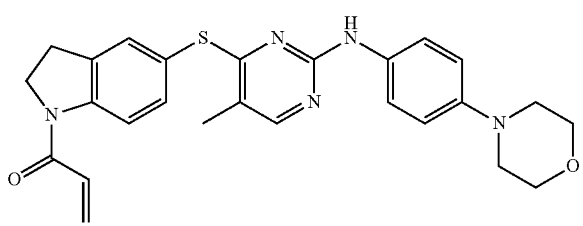 [SMILES: C=CC(=O)N1CCc2cc(Sc3nc(Nc4ccc(N5CCOCC5)cc4)ncc3C)ccc21] | 473.19 | 1-(5-(5-methyl-2-(4-morpholinophenylaminopyrimidin-4-ylthio)indolin-1-yl)prop-2-en-1-one 1(2H)-carbonitrile | C | 7.2 | m/z 474.3 [M + H]+ | |

TABLE 1-continued

| Compound number | Structure | Exact mass | Name | LCMS method | retention time (min) | Observed m/z | 1H NMR |
|---|---|---|---|---|---|---|---|
| 171 | 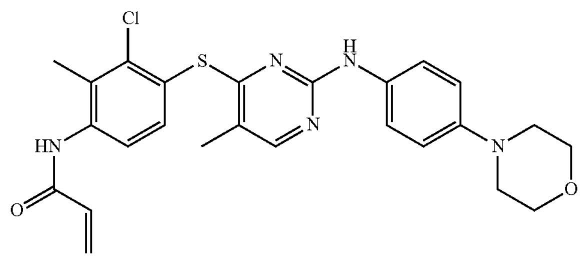 [SMILES: C=CC(=O)Nc1ccc(Sc2nc(Nc3ccc(N4CCOCC4)cc3)ncc2C)c(Cl)c1C] | 495.15 | N-(3-chloro-2-methyl-4-(5-methyl-2-(4-morpholinophenyl-amino)pyrimidin-4-ylthio)phenyl)acrylamide | C | 7.1 | m/z 496.3 [M + H]+ | |
| 172 | 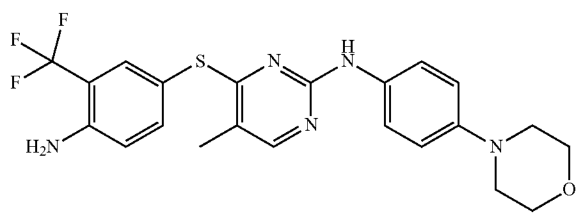 [SMILES: Cc1cnc(Nc2ccc(N3CCOCC3)cc2)nc1Sc1ccc(N)c(C(F)(F)F)c1] | 461.15 | 4-(4-amino-3-(trifluoromethyl)phenylthio)-5-methyl-N-(4-morpholinophenyl)pyrimidin-2-amine | C | 7.5 | m/z 462.3 [M + H]+ | |
| 173 | 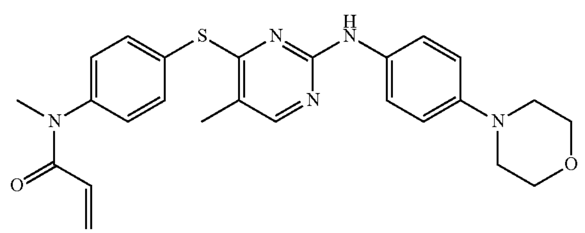 [SMILES: C=CC(=O)N(C)c1ccc(Sc2nc(Nc3ccc(N4CCOCC4)cc3)ncc2C)cc1] | 461.19 | N-methyl-N-(4-(5-methyl-2-(4-morpholinophenyl-amino)pyrimidin-4-ylthio)phenyl)acrylamide | C | 7.0 | m/z 462.3 [M + H]+ | |
| 174 | 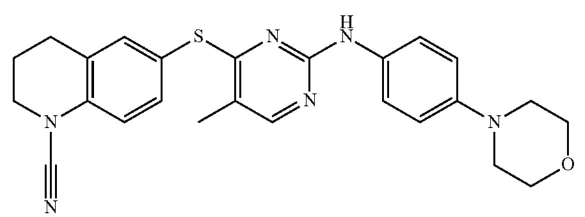 [SMILES: Cc1cnc(Nc2ccc(N3CCOCC3)cc2)nc1Sc1ccc2c(c1)CCCN2C#N] | 458.19 | 6-(5-methyl-2-(4-morpholinophenyl-amino)pyrimidin-4-ylthio)-3,4-dihydroquinoline-1(2H)-carbonitrile | C | 7.3 | m/z 459.4 [M + H]+ | |

TABLE 1-continued

| Compound number | Structure | Exact mass | Name | LCMS method | retention time (min) | Observed m/z | 1H NMR |
|---|---|---|---|---|---|---|---|
| 175 | 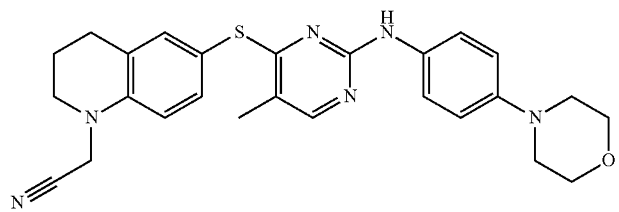 [SMILES: Cc1cnc(Nc2ccc(N3CCOCC3)cc2)nc1Sc1ccc2c(c1)CCCN2CC#N] | 472.20 | 2-(6-(5-methyl-2-(4-morpholinophenylaminopyrimidin-4-ylthio)-3,4-dihydroquinolin-1(2H)-yl)acetonitrile | C | 7.3 | m/z 473.4 [M + H]+ | |
| 176 | 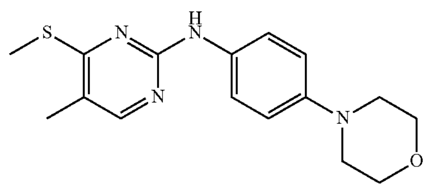 [SMILES: CSc1nc(Nc2ccc(N3CCOCC3)cc2)ncc1C] | 316.14 | 5-methyl-4-(methylthio)-N-(4-morpholinophenyl)pyrimidin-2-amine | C | 6.9 | m/z 317.3 [M + H]+ | (300 MHz, CDCl$_3$) δ 2.08 (s, 3H) 2.54 (s, 3H) 3.12 (m, 4H) 3.77-3.94 (m, 4H) 6.90 (m, 3H) 7.49 (d, J = 9.0 Hz, 2H) 7.84 (s, 1H) |
| 177 | 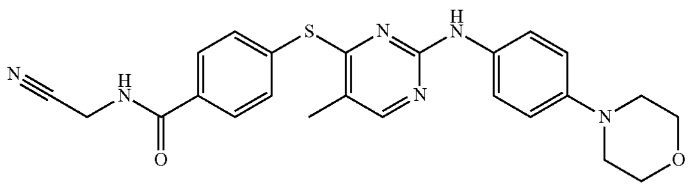 [SMILES: Cc1cnc(Nc2ccc(N3CCOCC3)cc2)nc1Sc1ccc(C(=O)NCC#N)cc1] | 460.17 | N-(cyanomethyl)-4-(5-methyl-2-(4-morpholinophenylaminopyrimidin-4-ylthio)benzamide | C | 6.4 | m/z 461.3 [M + H]+ | (300 MHz, CDCl$_3$) δ 2.20 (s, 3H) 3.06 (m, 4H) 3.87 (m, 4H) 4.42 (d, J = 5.94 Hz, 2H) 6.61 (d, J = 9.0 Hz, 2H) 6.71 (s, 1H) 6.97 (d, J = 9.0 Hz, 2H) 7.71 (d, J = 8.22 Hz, 2H) 7.86 (d, J = 8.22 Hz, 2H) 7.93 (s, 1H) |
| 178 | 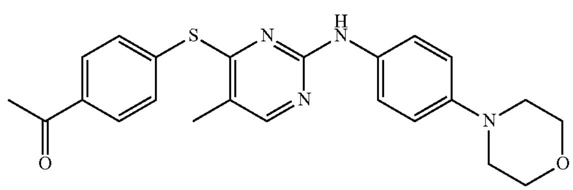 [SMILES: CC(=O)c1ccc(Sc2nc(Nc3ccc(N4CCOCC4)cc3)ncc2C)cc1] | 420.16 | 1-(4-(5-methyl-2-(4-morpholinophenylaminopyrimidin-4-ylthiophenyl)ethanone | C | 7.1 | m/z 421.4 [M + H]+ | (300 MHz, DMSO-d$_6$) δ 2.15 (s, 3H) 2.67 (s, 3H) 2.90 (m, 4H) 3.70 (m, 4H) 6.43 (d, J = 9.0 Hz, 2H) 6.99 (d, J = 9.0 Hz, 2H) 7.75 (d, J = 9.0 Hz, 2H) 8.07 (m, 3H) 9.14 (s, 1H) |

TABLE 1-continued

| Compound number | Structure | Exact mass | Name | LCMS method | retention time (min) | Observed m/z | ¹H NMR |
|---|---|---|---|---|---|---|---|
| 179 | 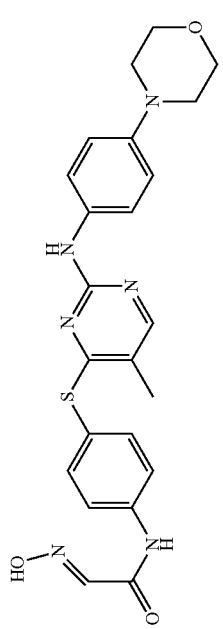 | 464.16 | (E)-2-(hydroxyio)-N-(4-(5-methyl-2-(4-morpholinophenyl-aminopyrimidin-4-ylthio)phenyl)acetamide | C | 6.5 | m/z 465.4 [M + H]⁺ | (300 MHz, DMSO-d₆) δ 2.13 (s, 3H) 2.84-2.87 (m, 4H) 3.64-3.67 (m, 4H) 6.46 (d, J = 9.0 Hz, 2H) 6.98 (d, J = 9.0 Hz, 2H) 7.56 (d, J = 9.0 Hz, 2H) 7.74 (s, 1H) 7.93 (d, J = 9.0 Hz, 2H) 8.01 (s, 1H) 9.11 (s, 1H) 10.57 (s, 1H) |
| 180 | 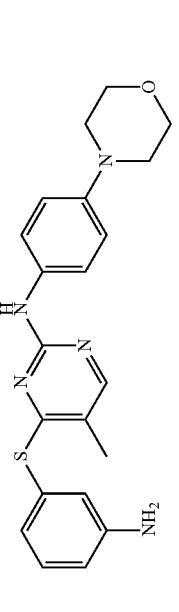 | 393.16 | 4-(3-aminophenyl-thio)-5-methyl-N-(4-morpholinophenyl)pyrimidin-2-amine | C | 6.6 | m/z 394.3 [M + H]⁺ | (300 MHz, DMSO-d₆) δ 2.11 (d, J = 0.6 Hz, 3H) 2.94-2.98 (m, 4H) 3.71-3.75 (m, 4H) 5.33 (bs, 2H), 6.62 (d, J = 9.0 Hz, 2H) 6.67-6.70 (m, 1H) 6.76-6.80 (m, 2H) 7.12-7.19 (m, 3H) 7.99 (s, 1H) 9.06 (s, 1H) |
| 181 | 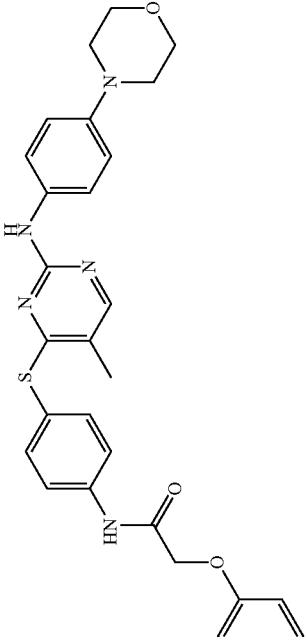 | 527.20 | N-(4-(5-methyl-2-(4-morpholinophenyl-aminopyrimidin-4-ylthio)phenyl)-2-phenoxyacetamide | C | 7.5 | m/z 528.3 [M + H]⁺ | (300 MHz, DMSO-d₆) δ 2.14 (s, 3 H) 2.87-2.93 (m, 4H) 3.61-3.64 (m, 4H) 4.73 (s, 1H) 6.52 (d, J = 9.0 Hz, 2H) 6.98 -7.07 (m, 5H) 7.56 (d, J = 9.0 Hz, 2H) 7.74 (s, 1H) 7.93 (d, J = 9.0 Hz, 2H) 8.01 (s, 1H) 9.11 (s, 1H) 10.57 (s, 1H) |

TABLE 1-continued

| Compound number | Exact mass | Name | Structure | LCMS method | retention time (min) | Observed m/z | ¹H NMR |
|---|---|---|---|---|---|---|---|
| 182 | 513.18 | N-(4-(2-(4-morpholinophenyl-amino)pyrimidin-4-ylthio)phenyl)-2-phenoxyacetamide | 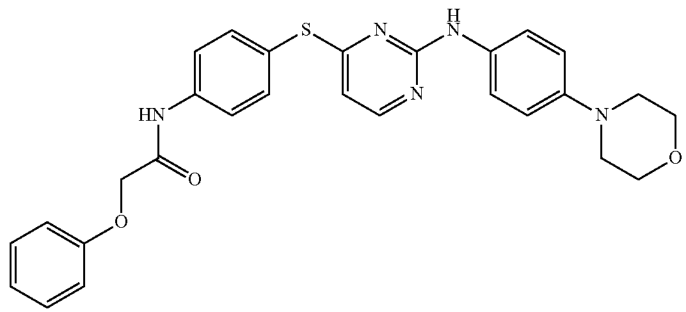 [SMILES: O=C(COc1ccccc1)Nc1ccc(Sc2ccnc(Nc3ccc(N4CCOCC4)cc3)n2)cc1] | C | 7.2 | m/z 514.3 [M + H]⁺ | (300 MHz, DMSO-d₆) δ 2.96-2.99 (m, 4H) 3.66-3.69 (m, 4H) 4.74 (s, 1H) 6.38 (d, J = 5.3 Hz, 1H) 6.70 (d, J = 9.0 Hz, 2H) 6.97-7.05 (m, 3H) 7.28-7.36 (m, 4 H) 7.59 (d, J = 9.0 Hz, 2H) 7.86 (d, J = 9.0 Hz, 2H) 8.10 (d, J = 5.3 Hz, 1H) 9.35 (s, 1H) 10.44 (s, 1H) |
| 183 | 481.16 | N-(3-(5-methyl-2-(4-morpholinophenyl-amino)pyrimidin-4-ylthio)phenyl)-2-(methylthio)acetamide | 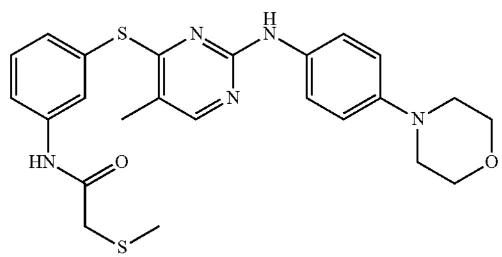 [SMILES: CSCC(=O)Nc1cccc(Sc2nc(Nc3ccc(N4CCOCC4)cc3)ncc2C)c1] | E | 9.7 | m/z 482.3 [M + H]⁺ | (300 MHz, DMSO-d₆) δ 2.10 (s, 3H) 2.14 (s, 3H), 2.93-2.96 (m, 4 H) 3.25 (s, 2H) 3.71-3.74 (m, 4H) 6.53 (d, J = 9.3 Hz, 2H) 7.01-7.04 (d, J = 9.3 Hz, 2H) 7.25-7.29 (m, 1H) 7.48 (t, J = 9.3 Hz, 1H), 7.84-7.85 (m, 4H), 7.91-7.94 (m, 4H) 8.04 (s, 1H) 9.10 (s, 1H) 10.25 (s, 1H) |
| 184 | 535.10 | N-(methylsulfonyl)-N-(3-(2-(4-morpholinophenyl-amino)pyrimidin-4-ylthio)phenyl)methanesulfonamide | 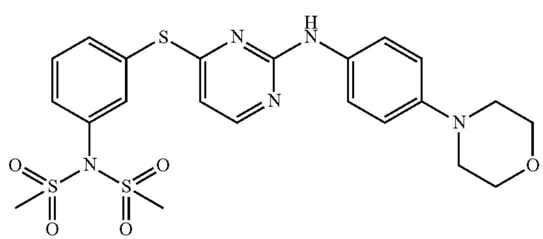 [SMILES: CS(=O)(=O)N(c1cccc(Sc2ccnc(Nc3ccc(N4CCOCC4)cc3)n2)c1)S(C)(=O)=O] | B | 8.7 | m/z 535.1 M+ | ¹H NMR (300 MHz, CDCl₃) δ 3.07-3.10 (m, 4H), 3.42 (s, 6H), 3.84-3.87 (m, 4H), 6.41 (d, J = 5.34 Hz, 1H), 6.83 (d, J = 9.02 Hz, 2H), 7.13 (br s, 1H), 7.36 (d, J = 8.98 Hz, 2H), 7.43-7.47 (m, 1H), 7.54 (t, J = 8.04 Hz, 1H), 7.68-7.72 (m, 2H) 8.08 (d, J = 5.35 Hz, 1H) |

TABLE 1-continued

| Compound number | Structure | Exact mass | Name | LCMS method | retention time (min) | Observed m/z | 1H NMR |
|---|---|---|---|---|---|---|---|
| 185 | 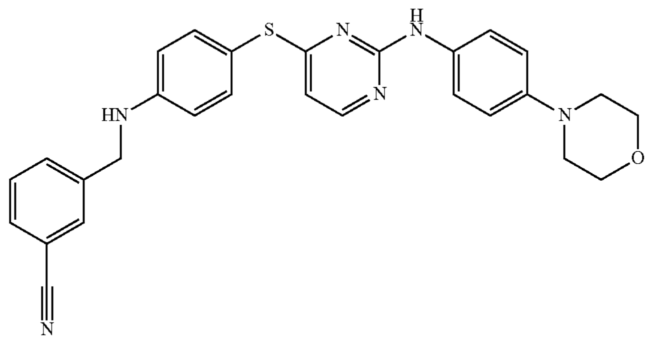 [SMILES: N#Cc1cccc(CNc2ccc(Sc3ccnc(Nc4ccc(N5CCOCC5)cc4)n3)cc2)c1] | 494.19 | 3-((4-(2-(4-morpholinophenyl-amino)pyrimidin-4-ylthio)phenylamino)methyl)benzonitrile | B | 9.7 | m/z 494.3 M+ | 1H NMR (300 MHz, d6-DMSO) δ 2.99-3.02 (m, 4H), 3.69-3.72 (m, 4H), 4.41 (d, J = 6.14 Hz, 2H), 6.19 (d, J = 5.34 Hz, 1H), 6.72 (d, J = 8.75 Hz, 2H), 6.77 (d, J = 9.12 Hz, 2H), 6.93 (t, J = 6.15 Hz, 1H), 7.28 (d, J = 8.64 Hz, 2H), 7.38 (d, J = 9.05 Hz, 2H), 7.56 (d, J = 7.86 Hz, 1H), 7.70-7.75 (m, 2H), 7.81-7.84 (m, 1H), 8.05 (d, J = 5.30 Hz, 1H), 9.32 (s, 1H) |
| 186 | 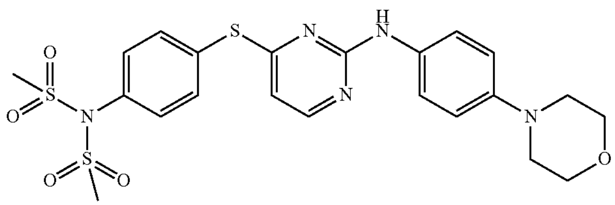 [SMILES: CS(=O)(=O)N(c1ccc(Sc2ccnc(Nc3ccc(N4CCOCC4)cc3)n2)cc1)S(C)(=O)=O] | 535.10 | N-(methylsulfonyl)-N-(4-(2-(4-morpholinophenyl-amino)pyrimidin-4-ylthio)phenyl)methanesulfonamide | B | 8.6 | m/z 535.6 M+ | 1H NMR (300 MHz, d6-DMSO) δ 2.99-3.03 (m, 4H), 3.57 (s, 6H), 3.70-3.73 (m, 4H), 6.35 (d, J = 5.31 Hz, 1H), 6.83 (d, J = 9.14 Hz, 2H), 7.45 (d, J = 9.03 Hz, 2H), 7.67 (d, J = 8.64 Hz, 2H), 7.77 (d, J = 8.64 Hz, 2H), 8.19 (d, J = 5.26 Hz, 1H), 9.47 (s, 1H) |
| 187 | 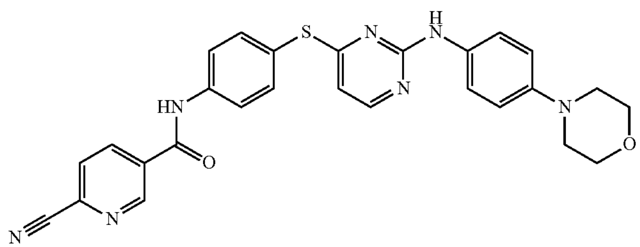 [SMILES: N#Cc1ccc(C(=O)Nc2ccc(Sc3ccnc(Nc4ccc(N5CCOCC5)cc4)n3)cc2)cn1] | 509.16 | 6-cyano-N-(4-(2-(4-morpholinophenyl-amino)pyrimidin-4-ylthio)phenyl)nicotinamide | B | 9.0 | m/z 509.5 M+ | 1H NMR (300 MHz, d6-DMSO) δ 2.88-2.92 (m, 4H), 3.54-3.56 (m, 4H), 6.45 (d, J = 5.08 Hz, 1H), 6.67 (d, J = 9.04 Hz, 2H), 7.26 (d, J = 8.63 Hz, 2H), 7.65 (d, J = 8.66 Hz, 2H), 7.98 (d, J = 8.70 Hz, 2H), 8.12 (d, J = 5.28 Hz, 1H), 8.29 (d, J = 8.10 Hz, 1H), 8.58 (dd, J = 2.20, 8.10 Hz, 1H), 9.25-9.32 (m, 1H), 9.36 (s, 1H), 10.93 (s, 1H) |

| Compound number | Structure | Exact mass | Name | LCMS method | retention time (min) | Observed m/z | ¹H NMR |
|---|---|---|---|---|---|---|---|
| 188 | 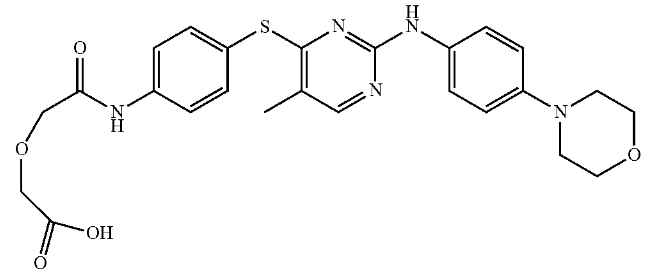 [SMILES: Cc1cnc(Nc2ccc(N3CCOCC3)cc2)nc1Sc1ccc(NC(=O)COCC(=O)O)cc1] | 509.17 | 2-(2-(4-(5-methyl-2-(4-morpholinophenylamino)pyrimidin-4-ylthio)phenylamino)-2-oxoethoxy)acetic acid | G | 6.0 | m/z 510.3 [M + H]+ | ¹H NMR (300 MHz, d₆-DMSO) δ 2.13 (d, J = 0.66 Hz, 3H), 2.88-2.92 (m, 4H), 3.69-3.72 (m, 4H), 4.23 (s, 2H), 4.26 (s, 2H), 6.49 (d, J = 9.11 Hz, 2H), 7.02 (d, J = 9.06 Hz, 2H), 7.54 (d, J = 8.71 Hz, 2H), 7.86 (d, J = 8.74 Hz, 2H), 8.00 (d, J = 0.68 Hz, 1H), 9.09 (s, 1H), 10.25 (s, 1H) |
| 189 | 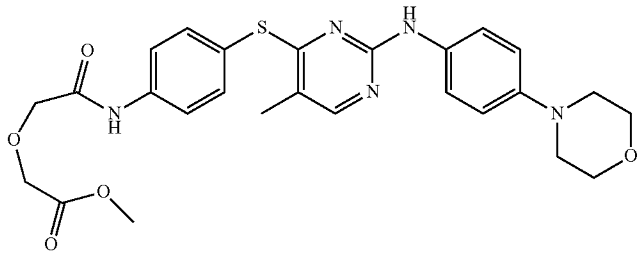 [SMILES: COC(=O)COCC(=O)Nc1ccc(Sc2nc(Nc3ccc(N4CCOCC4)cc3)ncc2C)cc1] | 523.19 | methyl 2-(2-(4-(5-methyl-2-(4-morpholinophenylamino)pyrimidin-4-ylthio)phenylamino)-2-oxoethoxy)acetate | C | 6.6 | m/z 524.3 [M + H]+ | ¹H NMR (300 MHz, CDCl₃) δ 2.18 (s, 3H), 3.00-3.03 (m, 4H), 3.78-3.82 (m, 4H), 3.81 (s, 4H), 4.23 (s, 2H), 4.30 (s, 2H), 6.63 (d, J = 9.02 Hz, 2H), 6.75 (br s, 1H), 7.02 (d, J = 9.03 Hz, 2H), 7.57 (d, J = 8.64 Hz, 2H), 7.78 (d, J = 8.66 Hz, 2H), 7.87 (s, 1H), 9.24 (br s, 1H) |
| 190 | 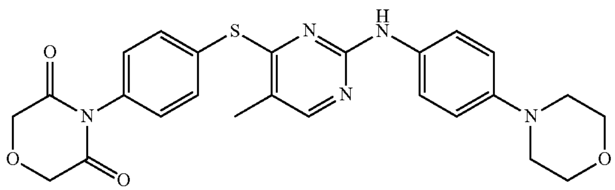 [SMILES: Cc1cnc(Nc2ccc(N3CCOCC3)cc2)nc1Sc1ccc(N2C(=O)COCC2=O)cc1] | 491.16 | 4-(4-(5-methyl-2-(4-morpholinophenylaminopyrimidin-4-ylthiophenyl)morpholine-3,5-dione | C | 6.6 | m/z 492.3 [M + H]+ | ¹H NMR (300 MHz, CDCl₃) δ 2.19 (s, 3H), 3.04-3.07 (m, 4H), 3.82-3.85 (m, 4H), 4.54 (s, 4H), 6.77 (d, J = 9.04 Hz, 2H), 6.86 (brs, 1H), 7.18 (d, J = 8.97 Hz, 2H), 7.26 (d, J = 8.54 Hz, 2H), 7.72 (d, J = 8.54 Hz, 2H), 7.79 (s, 1H) |
| 191 | 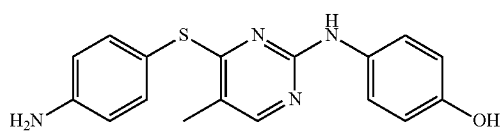 [SMILES: Cc1cnc(Nc2ccc(O)cc2)nc1Sc1ccc(N)cc1] | 324.10 | 4-(4-(4-aminophenylthio)-5-methylpyrimidin-2-ylamino)phenol | C | 6.2 | m/z 325.3 [M + H]+ | ¹H NMR (300 MHz, d₆-DMSO) δ 2.09 (d, J = 0.61 Hz, 3H), 6.46 (d, J = 8.65 Hz, 2H), 6.68 (d, J = 8.63 Hz, 2H), 7.08 (d, J = 8.97 Hz, 2H), 7.17 (d, J = 8.56 Hz, 2H), 7.93 (d, J = 0.68 Hz, 1H), 8.71 9s, 1H), 8.92 (s, 1H) |

TABLE 1-continued

| Compound number | Structure | Exact mass | Name | LCMS method | retention time (min) | Observed m/z | ¹H NMR |
|---|---|---|---|---|---|---|---|
| 192 | 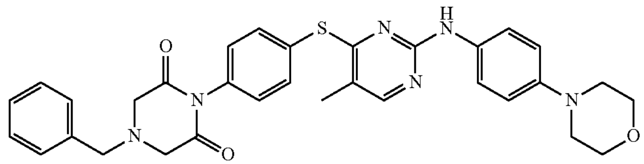 [SMILES: Cc1cnc(Nc2ccc(N3CCOCC3)cc2)nc1Sc1ccc(N2C(=O)CN(Cc3ccccc3)CC2=O)cc1] | 580.23 | 4-benzyl-1-(4-(5-methyl-2-(4-morpholinophenyl-aminopyrimidin-4-ylthio)phenyl)piperazine-2,6-dione | C | 7.3 | m/z 581.3 [M + H]+ | ¹H NMR (300 MHz, CDCl₃) δ 2.18 (d, J = 0.47 Hz, 3H), 3.03-3.06 (m, 4H), 3.57 (s, 4H), 3.73 (s, 2H), 3.77-3.80 (m, 4H), 6.78 (d, J = 9.07 Hz, 2H), 6.89 (brs, 1H), 7.18 (d, J = 8.88 Hz, 2H), 7.22 (d, J = 8.61 Hz, 2H), 7.31-7.45 (m, 5H), 7.68 (d, J = 8.64 Hz, 2H), 7.91 (brs, 1H |
| 193 | 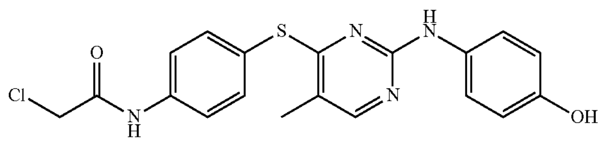 [SMILES: Cc1cnc(Nc2ccc(O)cc2)nc1Sc1ccc(NC(=O)CCl)cc1] | 400.08 | 2-chloro-N-(4-(4-hydroxyphenyl-amino)-5-methyl-pyrimidin-4-ylthio)phenyl)acetamide | C | 6.5 | m/z 401.2/ 403.2 [M + H]+ | ¹H NMR (300 MHz, d₆-DMSO) δ 2.12 (d, J = 0.49 Hz, 3H), 4.34 (s, 2H), 6.36 (d, J = 8.97 Hz, 2H), 6.99 (d, J = 9.16 Hz, 2H), 7.54 (d, J = 8.68 Hz, 2H), 7.76 (d, J = 8.74 Hz, 2H), 8.00 (d, J = 0.68 Hz, 1H), 8.75 (s, 1H), 8.97 (s, 1H), 10.58 (s, 1H) |
| 194 | 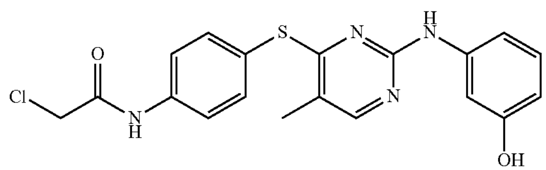 [SMILES: Cc1cnc(Nc2cccc(O)c2)nc1Sc1ccc(NC(=O)CCl)cc1] | 400.08 | 2-chloro-N-(4-(2-(3-hydroxyphenyl-amino)-5-methyl-pyrimidin-4-ylthio)phenyl)acetamide | C | 6.5 | m/z 401.2/ 403.2 [M + H]+ | ¹H NMR (300 MHz, d₆-DMSO) δ 2.15 (d, J = 0.67 Hz, 3H), 4.33 (s, 2H), 6.24 (ddd, J = 1.17, 2.42, 7.93 Hz, 1H), 6.58-6.65 (m, 2H), 6.67-6.74 (m, 1H), 7.55 (d, J = 8.71 Hz, 2H), 7.77 (d, J = 8.83 Hz, 2H), 8.07 (d, J = 0.74 Hz, 1H), 9.45 (s, 1H), 10.67 (s, 1H) |
| 195 | 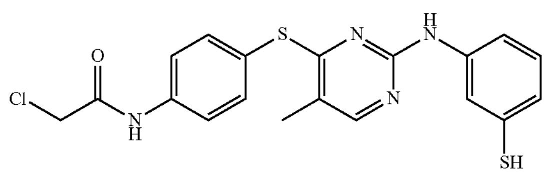 [SMILES: Cc1cnc(Nc2cccc(S)c2)nc1Sc1ccc(NC(=O)CCl)cc1] | 416.05 | 2-chloro-N-(4-(2-(3-mercaptophenyl-amino)-5-methyl-pyrimidin-4-ylthio)phenyl)acetamide | C | 7.2 | m/z 417.2/ 419.2 [M + H]+ | ¹H NMR (300 MHz, d₆-DMSO) δ 2.16 (d, J = 0.65 Hz, 3H), 4.32 (s, 2H), 5.02 (s, 1H), 6.66-6.72 (m, 2H), 6.69-7.05 (m, 1H), 7.07-7.13 (m, 1H), 7.55 (d, J = 8.77 Hz, 2H), 7.76 (d, J = 8.77 Hz, 2H), 8.09 (d, J = 0.73 Hz, 1H), 9.40 (s, 1H), 10.66 (s, 1H) |
| 196 | 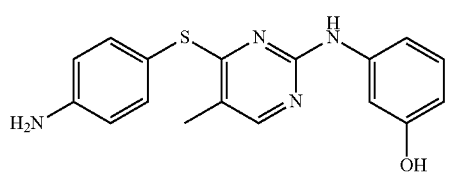 [SMILES: Cc1cnc(Nc2cccc(O)c2)nc1Sc1ccc(N)cc1] | 324.10 | 3-(4-(4-aminophenylthio)-5-methylpyrimidin-2-ylamino)phenol | C | 6.4 | m/z 325.3 [M + H]+ | ¹H NMR (300 MHz, CDCl₃) δ 2.19 (d, J = 0.65 Hz, 3H), 4.10 (br s, 2H), 6.37-6.48 (m, 2H), 6.81 (d, J = 8.65 Hz, 2H), 6.95 (brs, 1H), 6.96-7.03 (m, 2H), 7.43 (d, J = 8.65 Hz, 2H), 7.88 (d, J = 0.66 Hz, 1H) |

TABLE 1-continued

| Compound number | Structure | Exact mass | Name | LCMS method | retention time (min) | Observed m/z | ¹H NMR |
|---|---|---|---|---|---|---|---|
| 197 | 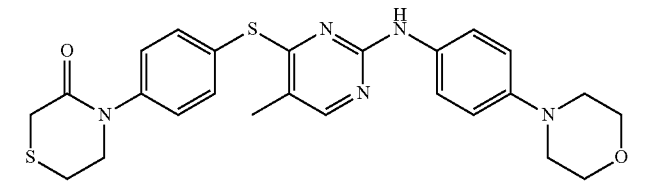 [SMILES: Cc1cnc(Nc2ccc(N3CCOCC3)cc2)nc1Sc1ccc(N2CCSCC2=O)cc1] | 493.16 | 4-(4-(5-methyl-2-(4-morpholinophenylamino)pyrimidin-4-ylthio)phenyl)thiomorpholin-3-one | C | 7.1 | m/z 494.2 [M+H]+ | ¹H NMR (300 MHz, d₆-DMSO) δ 2.14 (d, J = 0.56 Hz, 3H), 2.92-2.95 (m, 4H), 3.07-3.11 (m, 2H), 3.47 (s, 2H), 3.69-3.72 (m, 4H), 4.06-4.10 (m, 2H), 6.59 (d, J = 9.14 Hz, 2H), 7.12 (d, J = 9.05 Hz, 2H), 7.51 (d, J = 8.76 Hz, 2H), 7.60 (d, J = 8.76 Hz, 2H), 8.04 (d, J = 0.69 Hz, 1H), 9.12 (s, 1H) |
| 198 | 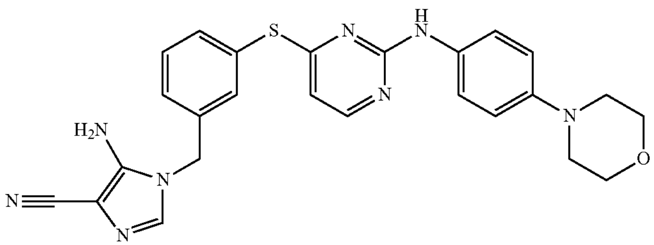 [SMILES: N#Cc1ncn(Cc2cccc(Sc3ccnc(Nc4ccc(N5CCOCC5)cc4)n3)c2)c1N] | 484.18 | 5-amino-1-(3-(4-morpholinophenylamino)pyrimidin-4-ylthio)benzyl)-1H-imidazole-4-carbonitrile | C | 6.2 | m/z 485.2 [M+H]+ | ¹H NMR (300 MHz, d₆-DMSO) δ 2.98-3.01 (m, 4H), 3.72-3.75 (m, 4H), 5.13 (s, 2H), 6.27-6.29 (m, 3H), 6.73 (d, J = 9.02 Hz, 2H), 7.30 (s, 1H), 7.34 (d, J = 8.83 Hz, 2H), 7.36-7.42 (m, 1H), 7.50-7.59 (m, 3H), 8.11 (d, J = 5.29 Hz, 1H), 9.39 (s, 1H) |
| 199 | 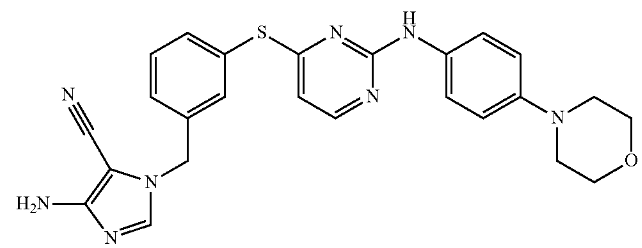 [SMILES: N#Cc1c(N)ncn1Cc1cccc(Sc2ccnc(Nc3ccc(N4CCOCC4)cc3)n2)c1] | 484.18 | 4-amino-1-(3-(2-(4-morpholinophenyl-aminopyrimidin-4-ylthio)benzyl)-1H-imidazole-5-carbonitrile | C | 6.2 | m/z 485.2 [M+H]+ | ¹H NMR (300 MHz, d₆-DMSO) δ 2.99-3.02 (m, 4H), 3.71-3.75 (m, 4H), 5.16 (s, 2H), 5.89 (s, 2H), 6.26 (d, J = 5.20 Hz, 1H), 6.75 (d, J = 9.00 Hz, 2H), 7.35 (d, J = 9.26 Hz, 2H), 7.39-7.45 (m, 1H), 7.49-7.62 (m, 3H), 7.67 (s, 1H), 8.10 (d, J = 5.29 Hz, 1H), 9.38 (s, 1H) |
| 200 | 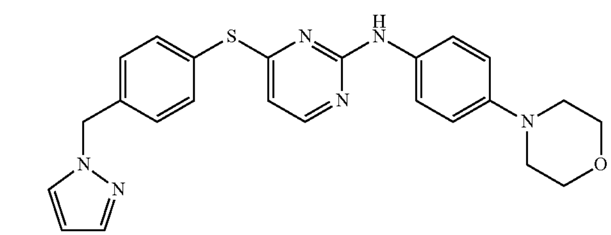 [SMILES: c1cnn(Cc2ccc(Sc3ccnc(Nc4ccc(N5CCOCC5)cc4)n3)cc2)c1] | 444.17 | 4-(4-((1H-pyrazol-1-yl)methyl)phenyl-thio)-N-(4-morpholinophenyl)pyrimidin-2-amine | C | 6.8 | m/z 445.2 [M+H]+ | ¹H NMR (300 MHz, d₆-DMSO) δ 3.01-3.04 (m, 4H), 3.72-3.75 (m, 4H), 5.46 (s, 2H), 6.26 (d, J = 5.08 Hz, 1H), 6.31 (dd, J = 1.92, 2.33 Hz, 1H), 6.77 (d, J = 9.13 Hz, 2H), 7.30 (d, J = 8.47 Hz, 2H), 7.37 (d, J = 8.95 Hz, 2H), 7.51 (dd, J = 0.68, 1.86 Hz, 1H), 7.61 (d, J = 8.33 Hz, 2H), 7.88 (dd, J = 0.68, 2.25 Hz, 1H), 8.10 (d, J = 5.31 Hz, 1H), 9.38 (s, 1H) |

TABLE 1-continued

| Compound number | Structure | Exact mass | Name | LCMS method | retention time (min) | Observed m/z | ¹H NMR |
|---|---|---|---|---|---|---|---|
| 201 | 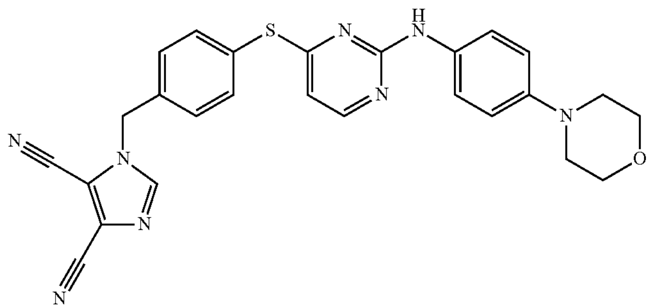 [SMILES: N#Cc1ncn(Cc2ccc(Sc3ccnc(Nc4ccc(N5CCOCC5)cc4)n3)cc2)c1C#N] | 494.16 | 1-(4-(2-(4-morpholinophenyl-aminopyrimidin-4-ylthio)benzyl)-1H-imidazole-4,5-dicarbonitrile | C | 7.0 | m/z 495.2 [M + H]+ | ¹H NMR (300 MHz, d₆-DMSO) δ 3.01-3.03 (m, 4H), 3.72-3.75 (m, 4H), 5.58 (s, 2H), 6.24 (d, J = 5.36 Hz, 1H), 6.77 (d, J = 9.08 Hz, 2H), 7.39 (d, J = 9.01 Hz, 2H), 7.50 (d, J = 8.47 Hz, 2H), 7.70 (d, J = 8.34 Hz, 2H), 8.11 (d, J = 5.28 Hz, 1H), 8.51 (s, 1H), 9.39 (s, 1H) |
| 202 | 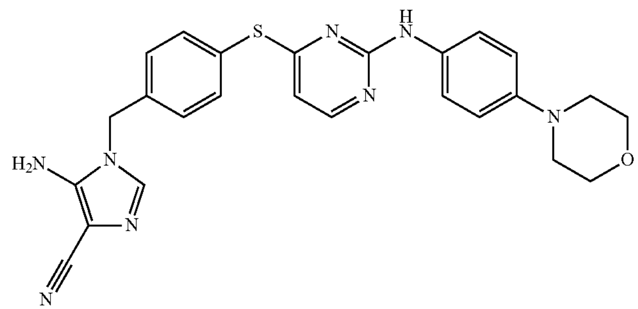 [SMILES: N#Cc1ncn(Cc2ccc(Sc3ccnc(Nc4ccc(N5CCOCC5)cc4)n3)cc2)c1N] | 484.18 | 5-amino-1-(4-(2-(4-morpholino-phenylamino)pyrimidin-4-ylthio)benzyl)-1H-imidazole-4-carbonitrile | C | 6.2 | m/z 485.3 [M + H]+ | ¹H NMR (300 MHz, d₆-DMSO) δ 3.00-3.04 (m, 4H) 3.72-3.76 (m, 4H), 5.18 (s, 2H), 6.18 (d, J = 5.23 Hz, 1H), 6.31 (brs, 1H), 7.36 (d, J = 9.07 Hz, 2H), 7.34 (s, 1H), 6.78 (d, J = 8.37 Hz, 2H), 7.42 (d, J = 8.87 Hz, 2H), 7.65 (d, J = 8.30 Hz, 2H), 8.11 (d, J = 5.29 Hz, 1H), 9.40 (s, 1H) |
| 203 | 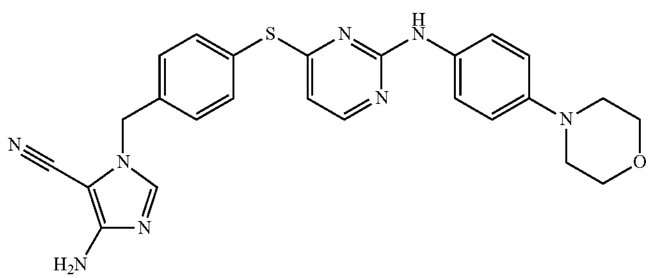 [SMILES: N#Cc1c(N)ncn1Cc1ccc(Sc2ccnc(Nc3ccc(N4CCOCC4)cc3)n2)cc1] | 484.18 | 4-amino-1-(4-(2-(4-morpholinophenyl-aminopyrimidin-4-ylthio)benzyl)-1H-imidazole-5-carbonitrile | C | 6.2 | m/z 485.3 [M + H]+ | ¹H NMR (300 MHz, d₆-DMSO) δ 3.00-3.03 (m, 4H), 3.72-3.75 (m, 4H), 5.21 (s, 2H), 5.91 (s, 2H), 6.21 (d, J = 5.23 Hz, 1H), 6.78 (d, J = 9.10 Hz, 2H), 7.38 (d, J = 8.33 Hz, 2H), 7.41 (d, J = 8.84 Hz, 2H), 7.67 (d, J = 8.35 Hz, 2H), 7.70 (s, 1H), 8.11 (d, J = 5.30 Hz, 1H), 9.39 (s, 1H) |

| Compound number | Structure | Exact mass | Name | LCMS method | retention time (min) | Observed m/z | 1H NMR |
|---|---|---|---|---|---|---|---|
| 204 | 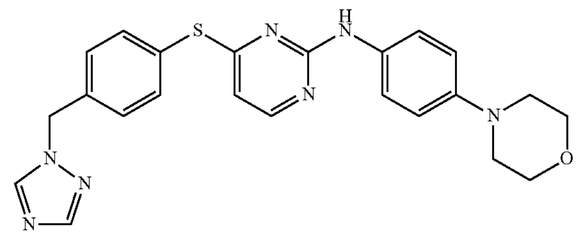 [SMILES: c1cc(Sc2ccc(Cn3cncn3)cc2)nc(Nc2ccc(N3CCOCC3)cc2)n1] | 445.17 | 4-(4-((1H-1,2,4-triazol-1-yl)methyl)phenyl-thio)-N-(4-morpholinophenyl)pyrimidin-2-amine | C | 6.2 | m/z 446.2 [M + H]+ | 1H NMR (300 MHz, d6-DMSO) δ 3.01-3.04 (m, 4H), 3.72-3.75 (m, 4H), 5.54 (s, 2H), 6.26 (d, J = 5.17 Hz, 1H), 6.77 (d, J = 9.10 Hz, 2H), 7.36 (d, J = 8.54 Hz, 2H), 7.40 (d, J = 8.43 Hz, 2H), 7.64 (d, J = 8.35 Hz, 2H), 8.03 (s, 1H), 8.11 (d, J = 5.28 Hz, 1H), 8.70 (s, 1H), 9.39 (s, 1H) |
| 205 | 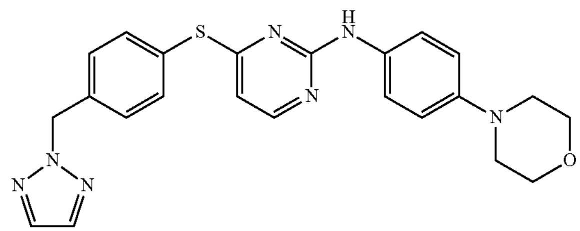 [SMILES: c1cc(Sc2ccc(Cn3nccn3)cc2)nc(Nc2ccc(N3CCOCC3)cc2)n1] | 445.17 | 4-(4-((2H-1,2,3-triazol-2-yl)methyl)phenyl-thio)-N-(4-morpholinophenyl)pyrimidin-2-amine | C | 6.9 | m/z 446.3 [M + H]+ | 1H NMR (300 MHz, d6-DMSO) δ 3.01-3.05 (m, 4H), 3.72-3.75 (m, 4H), 5.79 (s, 2H), 6.29 (d, J = 4.93 Hz, 1H), 6.76 (d, J = 9.07 Hz, 2H), 7.33 (d, J = 8.44 Hz, 2H), 7.34 (d, J = 9.01 Hz, 2H), 7.62 (d, J = 8.33 Hz, 2H), 7.87 (s, 2H), 8.11 (d, J = 5.10 Hz, 1H), 9.38 (s, 1H) |
| 206 | 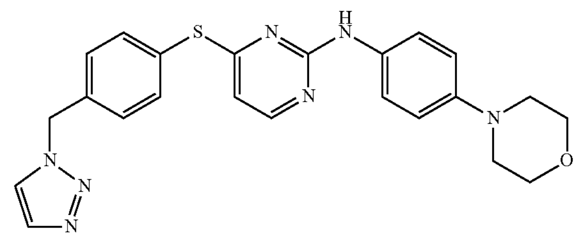 | 445.17 | 4-(4-((1H-1,2,3-triazol-1-yl)methyl)phenylthio)-N-(4-morpholinophenyl)pyrimidin-2-amine | C | 6.4 | m/z 446.3 [M + H]+ | 1H NMR (300 MHz, d6-DMSO) δ 3.01-3.04 (m, 4H), 3.72-3.75 (m, 4H), 5.74 (s, 2H), 6.26 (d, J = 5.16 Hz, 1H), 6.76 (d, J = 9.11 Hz, 2H), 7.37 (d, J = 9.00 Hz, 2H), 7.40 (d, J = 8.02 Hz, 2H), 7.65 (d, J = 8.39 Hz, 2H), 7.78 (d, J = 1.02 Hz, 1H), 8.11 (d, J = 5.28 Hz, 1H), 8.24 (d, J = 1.02 Hz, 1H), 9.39 (s, 1H) |
| 207 | 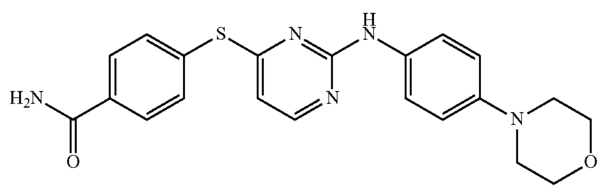 [SMILES: NC(=O)c1ccc(Sc2ccnc(Nc3ccc(N4CCOCC4)cc3)n2)cc1] | 407.14 | 4-(2-(4-morpholinophenyl-amino)pyrimidin-4-ylthio)benzamide | C | 5.8 | m/z 408.3 [M + H]+ | 1H NMR (300 MHz, d6-DMSO) δ 2.96-2.99 (m, 4H), 3.70-3.74 (m, 4H), 6.52 (d, J = 4.71 Hz, 1H), 6.62 (d, J = 8.91 Hz, 2H), 7.16 (d, J = 8.28 Hz, 2H), 7.57 (br s, 1H), 7.71 (d, J = 8.51 Hz, 2H), 8.02 (d, J = 8.53 Hz, 2H), 8.13 (d, J = 5.24 Hz, 1H), 9.37 (s, 1H) |

TABLE 1-continued

| Compound number | Structure | Exact mass | Name | LCMS method | retention time (min) | Observed m/z | ¹H NMR |
|---|---|---|---|---|---|---|---|
| 208 | 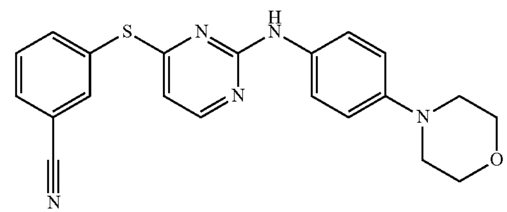 [SMILES: N#Cc1cccc(Sc2ccnc(Nc3ccc(N4CCOCC4)cc3)n2)c1] | 389.13 | 3-(2-(4-morpholinophenylamino)pyrimidin-4-ylthio)benzonitrile | C | 6.9 | m/z 390.2 [M − H]+ | ¹H NMR (300 MHz, CDCl₃) δ 3.08-3.12 (m, 4H), 3.85-3.88 (m, 4H), 6.40 (d, J = 5.31 Hz, 1H), 6.77 (d, J = 9.02 Hz, 2H), 6.97 (br s, 1H), 7.19 (d, J = 8.82 Hz, 2H), 7.55 (dt, J = 0.57, 7.85 Hz, 1H), 7.73-7.77 (m, 1H), 7.82 (ddd, J = 1.19, 1.81, 7.85 Hz, 1H), 7.91-92 (m, 1H), 8.08 (d, J = 5.31 Hz, 1H) |
| 209 | 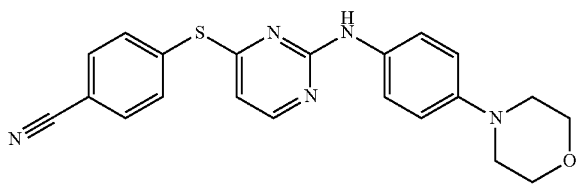 [SMILES: N#Cc1ccc(Sc2ccnc(Nc3ccc(N4CCOCC4)cc3)n2)cc1] | 389.13 | 4-(2-(4-morpholinophenylamino)pyrimidin-4-ylthio)benzonitrile | C | 7.0 | m/z 390.2 [M + H]+ | ¹H NMR (300 MHz, CDCl₃) δ 3.10-3.13 (m, 4H), 3.85-3.87 (m, 4H), 6.47 (d, J = 5.28 Hz, 1H), 6.74 (d, J = 8.94 Hz, 2H), 6.91 (br s, 1H), 7.13 (d, J = 8.80 Hz, 2H), 7.71 (s, 4H), 8.09 (d, J = 5.31 Hz, 1H) |
| 210 | 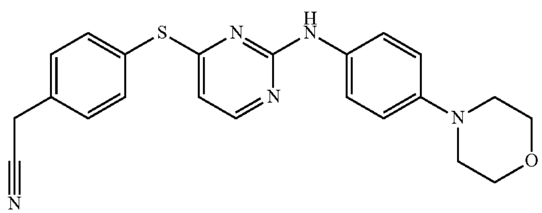 [SMILES: N#CCc1ccc(Sc2ccnc(Nc3ccc(N4CCOCC4)cc3)n2)cc1] | 403.15 | 2-(4-(2-(4-morpholinophenylamino)pyrimidin-4-ylthio)phenyl)acetonitrile | C | 6.9 | m/z 404.3 [M + H]+ | ¹H NMR (300 MHz, d₆-DMSO) δ 2.99-3.02 (m, 4H), 3.70-3.74 (m, 4H), 4.18 (s, 2H), 6.34 (d, J = 5.10 Hz, 1H), 6.72 (d, J = 9.07 Hz, 2H), 7.32 (d, J = 9.08 Hz, 2H), 7.52 (d, J = 8.50 Hz, 2H), 7.67 (d, J = 8.36 Hz, 2H), 8.12 (d, J = 5.27 Hz, 1H), 9.38 (s, 1H) |
| 211 | 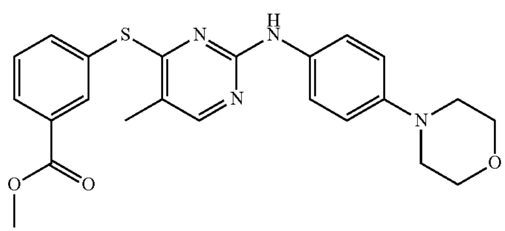 [SMILES: COC(=O)c1cccc(Sc2nc(Nc3ccc(N4CCOCC4)cc3)ncc2C)c1] | 436.16 | methyl 3-(5-methyl-2-(4-morpholinophenylamino)pyrimidin-4-ylthio)benzoate | C | 7.5 | m/z 437.3 [M + H]+ | ¹H NMR (300 MHz, CDCl₃) δ 2.03 (d, J = 0.68 Hz, 3H), 3.02-3.05 (m, 4H), 3.85-3.88 (m, 4H), 3.89 (s, 3H), 6.57 (d, J = 9.03 Hz, 2H), 6.70 (br s, 1H), 6.92 (d, J = 8.98 Hz, 2H), 7.53 (dt, J = 0.51, 7.76 Hz, 1H), 7.77 (ddd, J = 1.26, 1.82, 7.73 Hz, 1H), 7.91 (d, J = 0.71 Hz, 1H), 8.19 (ddd, J = 1.20, 1.69, 7.79 Hz, 1H), 8.26-8.27 (m, 1H) |

| Compound number | Structure | Exact mass | Name | LCMS method | retention time (min) | Observed m/z | 1H NMR |
|---|---|---|---|---|---|---|---|
| 212 | 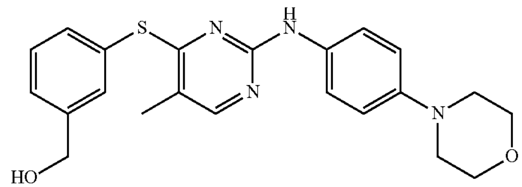 [SMILES: Cc1cnc(Nc2ccc(N3CCOCC3)cc2)nc1Sc1cccc(CO)c1] | 408.16 | (3-(5-methyl-2-(4-morpholinophenyl-aminopyrimidin-4-ylthio)phenyl) methanol | C | 6.6 | m/z 409.4 [M + H]+ | 1H NMR (300 MHz, d6-DMSO) δ 2.13 (d, J = 0.59 Hz, 3H), 2.93-2.96 (m, 4H), 3.71-3.75 (m, 4H), 4.55 (d, J = 5.55 Hz, 2H), 5.31 (t, J = 5.59 Hz, 1H), 6.52 (d, J = 9.13 Hz, 2H), 7.01 (d, J = 9.05 Hz, 2H), 7.40-7.61 (m, 4H), 8.02 (s, 1H), 9.07 (s, 1H) |
| 213 | 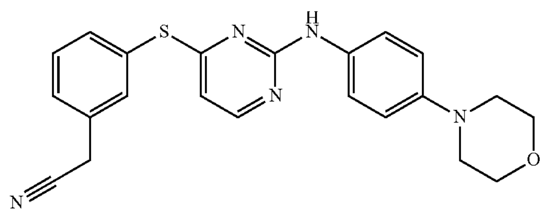 [SMILES: N#CCc1cccc(Sc2ccnc(Nc3ccc(N4CCOCC4)cc3)n2)c1] | 403.15 | 2-(3-(2-(4-morpholinophenyl-aminopyrimidin-4-ylthio)phenyl) acetonitrile | C | 6.8 | m/z 404.3 [M + H]+ | 1H NMR (300 MHz, d6-DMSO) δ 2.99-3.01 (m, 4H), 3.71-3.73 (m, 4H), 4.14 (s, 2H), 6.32-6.38 (br s, 1H), 6.72 (d, J = 8.84 Hz, 2H), 7.30 (d, J = 7.76 Hz, 2H), 7.58-7.63 (m, 4H), 8.13 (d, J = 5.24 Hz, 1H), 9.38 (s, 1H) |
| 214 | 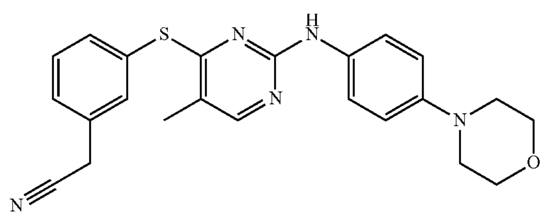 [SMILES: Cc1cnc(Nc2ccc(N3CCOCC3)cc2)nc1Sc1cccc(CC#N)c1] | 417.16 | 2-(3-(5-methyl-2-(4-morpholino-phenylamino)pyrimidin-4-ylthio)phenyl) acetonitrile | C | 7.1 | m/z 418.3 [M + H]+ | 1H NMR (300 MHz, d6-DMSO) δ 2.15 (d, J = 0.62 Hz, 3H), 2.96-2.98 (m, 4H), 3.72-3.74 (m, 4H), 4.10 (s, 2H), 6.52 (d, J = 8.97 Hz, 2H), 7.01 (d, J = 8.94 Hz, 2H), 7.55-7.65 (m, 4H), 8.05 (d, J = 0.73, 1H), 9.10 (s, 1H) |
| 215 | 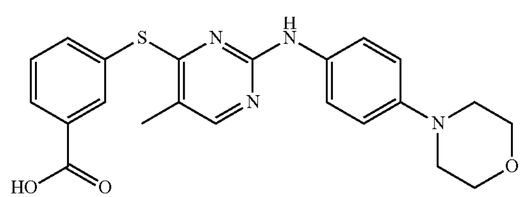 [SMILES: Cc1cnc(Nc2ccc(N3CCOCC3)cc2)nc1Sc1cccc(C(=O)O)c1] | 422.14 | 3-(5-methyl-2-(4-morpholinophenyl-aminopyrimidin-4-ylthio)benzoic acid | C | 6.5 | m/z 423.3 [M + H]+ | 1H NMR (300 MHz, d6-DMSO) δ 2.14 (d, J = 0.61 Hz, 3H), 2.93-2.95 (m, 4H), 3.71-3.72 (m, 4H), 6.52 (d, J = 9.08 Hz, 2H), 6.97 (d, J = 8.87 Hz, 2H), 7.42 (t, J = 7.35 Hz, 1H), 7.49-7.51 (m, 1H), 8.01 (d, J = 0.73 Hz, 1H), 8.04-8.06 (m, 1H), 8.07-8.09 (m, 1H), 9.02 (s, 1H) |

TABLE 1-continued

| Compound number | Structure | Exact mass | Name | LCMS method | retention time (min) | Observed m/z | $^1$H NMR |
|---|---|---|---|---|---|---|---|
| 216 | 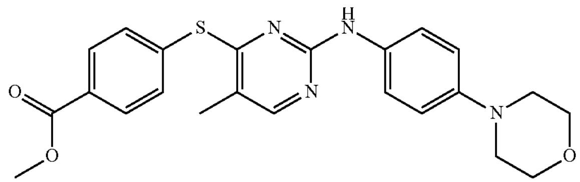 [SMILES: COC(=O)c1ccc(Sc2nc(Nc3ccc(N4CCOCC4)cc3)ncc2C)cc1] | 436.16 | methyl 4-(5-methyl-2-(4-morpholino-phenylamino)pyrimidin-4-ylthio)benzoate | C | 7.6 | m/z 437.3 [M + H]+ | $^1$H NMR (300 MHz, d$_6$-DMSO) δ 2.15 (s, 3H), 2.87-2.90 (m, 4H), 3.71-3.74 (m, 4H), 3.91 (s, 3H), 6.43 (d, J = 9.22 Hz, 2H), 6.95 (d, J = 8.84 Hz, 2H), 7.76 (d, J = 8.28 Hz, 2H), 8.06-8.09 (m, 3H), 9.15 (s, 1H) |
| 217 | 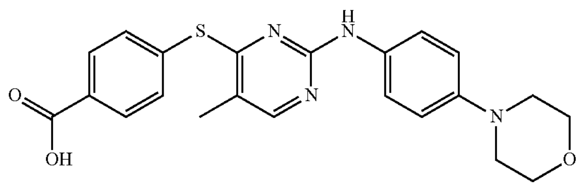 [SMILES: Cc1cnc(Nc2ccc(N3CCOCC3)cc2)nc1Sc1ccc(C(=O)O)cc1] | 422.14 | 4-(5-methyl-2-(4-morpholino-phenylamino)pyrimidin-4-ylthio)benzoic acid | C | 0.9 | m/z 423.3 [M + H]+ | $^1$H NMR (300 MHz, d$_6$-DMSO) δ 2.15 (s, 3H), 2.89-2.92 (m, 4H), 3.70-3.73 (m, 4H), 6.44 (d, J = 9.10 Hz, 2H), 7.73 (d, J = 8.57 Hz, 2H), 8.06 (d, J = 8.55 Hz, 1H), 8.06 (d, J = 0.68 Hz, 1H), 9.16 (s, 1H) |
| 218 | 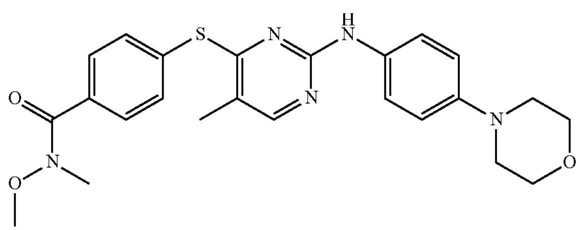 [SMILES: CON(C)C(=O)c1ccc(Sc2nc(Nc3ccc(N4CCOCC4)cc3)ncc2C)cc1] | 465.18 | N-methoxy-N-methyl-4-(5-methyl-2-(4-morpholino-phenylamino)pyrimidin-4-ylthio)benzamide | C | 7.0 | m/z 466.4 [M + H]+ | $^1$H NMR (300 MHz, d$_6$-DMSO) δ 2.15 (s, 3H), 2.93-2.96 (m, 4H), 3.29 (s, 3H), 3.58 (s, 3H), 3.69-3.72 (m, 4H), 6.56 (d, J = 9.00 Hz, 2H), 6.97 (d, J = 8.96 Hz, 2H), 7.68 (d, J = 8.58 Hz, 2H), 7.75 (d, J = 8.57 Hz, 2H), 8.05 (d, J = 0.65 Hz, 1H), 9.15 (s, 1H) |
| 219 | 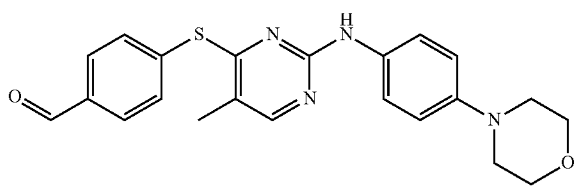 [SMILES: Cc1cnc(Nc2ccc(N3CCOCC3)cc2)nc1Sc1ccc(C=O)cc1] | 406.15 | 4-(5-methyl-2-(4-morpholinophenyl-aminopyrimidin-4-ylthio)benzaldehyde | C | 7.2 | m/z 407.4 [M + H]+ | $^1$H NMR (300 MHz, d$_6$-DMSO) δ 2.15 (d, J = 0.57 Hz, 3H), 2.87-2.90 (m, 4H), 3.69-3.72 (m, 4H), 6.43 (d, J = 9.01 Hz, 2H), 6.97 (d, J = 8.78 Hz, 2H), 7.83 (d, J = 8.07 Hz, 2H), 8.04 (d, J = 8.47 Hz, 2H), 8.08 (d, J = 0.65 Hz, 1H), 9.16 (s, 1H), 10.18 (s, 1H) |
| 220 | 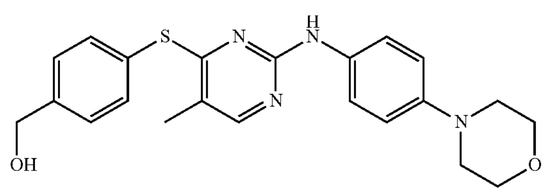 [SMILES: Cc1cnc(Nc2ccc(N3CCOCC3)cc2)nc1Sc1ccc(CO)cc1] | 408.16 | (4-(5-methyl-2-(4-morpholinophenyl-aminopyrimidin-4-ylthio)phenyl)methanol | C | 6.6 | m/z 409.3 [M + H]+ | $^1$H NMR (300 MHz, d$_6$-DMSO) δ 2.13 (d, J = 0.59 Hz, 3H), 2.94-2.97 (m, 4H), 3.69-3.73 (m, 4H), 4.66 (d, J = 5.19 Hz, 2H), 5.45 (t, J = 5.34 Hz, 1H), 6.52 (d, J = 9.14 Hz, 2H), 6.99 (d, J = 9.07 Hz, 2H), 7.49 (d, J = 8.51 Hz, 2H), 7.55 (d, J = 8.37 Hz, 2H), 8.01 (d, J = 0.68 Hz, 1H), 9.09 (s, 1H) |

TABLE 1-continued

| Compound number | Structure | Exact mass | Name | LCMS method | retention time (min) | Observed m/z | ¹H NMR |
|---|---|---|---|---|---|---|---|
| 221 | 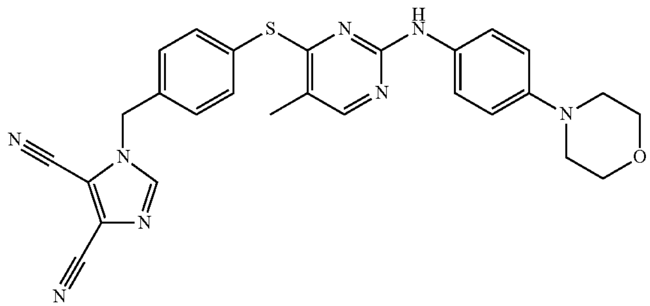 [SMILES: Cc1cnc(Nc2ccc(N3CCOCC3)cc2)nc1Sc1ccc(Cn2cnc(C#N)c2C#N)cc1] | 508.18 | 1-(4-(5-methyl-2-(4-morpholinophenylamino)pyrimidin-4-ylthio)benzyl)-1H-imidazole-4,5-dicarbonitrile | C | 7.3 | m/z 509.4 [M + H]+ | ¹H NMR (300 MHz, d₆-DMSO) δ 2.13 (d, J = 0.60 Hz, 3H), 2.96-2.99 (m, 4H), 3.72-3.75 (m, 4H), 5.60 (s, 2H), 6.52 (d, J = 9.08 Hz, 2H), 7.09 (d, J = 9.10 Hz, 2H), 7.53 (d, J = 8.46 Hz, 2H), 7.65 (d, J = 8.39 Hz, 2H), 8.04 (d, J = 0.68 Hz, 1H), 8.50 (s, 1H), 9.09 (s, 1H) |
| 222 | 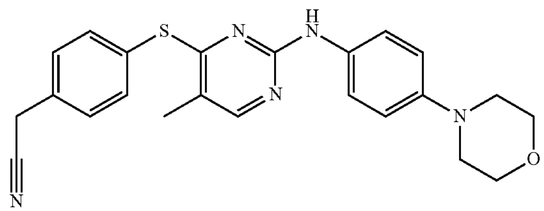 [SMILES: Cc1cnc(Nc2ccc(N3CCOCC3)cc2)nc1Sc1ccc(CC#N)cc1] | 417.16 | 2-(4-(5-methyl-2-(4-morpholinophenylamino)pyrimidin-4-ylthio)phenyl)acetonitrile | C | 7.1 | m/z 418.4 [M + H]+ | ¹H NMR (300 MHz, d₆-DMSO) δ 2.13 (s, 3H), 2.94-2.98 (m, 4H), 3.69-3.72 (m, 4H), 4.21 (s, 2H), 6.50 (d, J = 9.10 Hz, 2H), 7.04 (d, J = 8.87 Hz, 2H), 7.52 (d, J = 8.39 Hz, 2H), 7.63 (d, J = 8.26 Hz, 2H), 8.03 (s, 1H), 9.13 9s, 1H) |
| 223 | 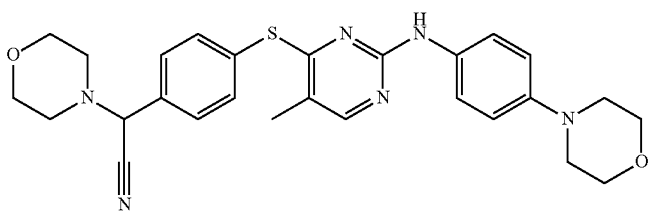 [SMILES: Cc1cnc(Nc2ccc(N3CCOCC3)cc2)nc1Sc1ccc(C(C#N)N2CCOCC2)cc1] | 502.22 | 2-(4-(5-methyl-2-(4-morpholinophenylamino)pyrimidin-4-ylthio)phenyl)-2-morpholinoacetonitrile | C | 7.4 | m/z 503.4 [M + H]+ | ¹H NMR (300 MHz, d₆-DMSO) δ 2.13 (s, 3H), 2.35-2.44 (m, 2H), 2.53-2.64 (m, 2H), 2.96-2.99 (m, 4H), 3.57-3.60 (m, 4H), 3.69-3.72 (m, 4H), 5.55 (s, 1H), 6.54 (d, J = 9.04 Hz, 2H), 7.07 (d, J = 8.93 Hz, 2H), 7.60 (d, J = 8.24 Hz, 2H), 7.70 (d, J = 8.33 Hz, 2H), 8.05 (s, 1H), 9.12 (s, 1H) |
| 224 | 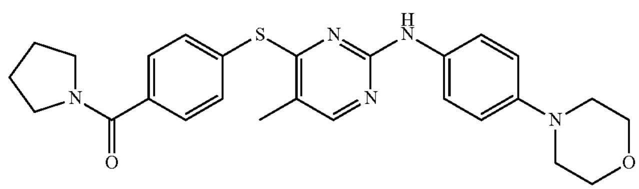 [SMILES: Cc1cnc(Nc2ccc(N3CCOCC3)cc2)nc1Sc1ccc(C(=O)N2CCCC2)cc1] | 475.20 | (4-(5-methyl-2-(4-morpholinophenylaminopyrimidin-4-ylthio)phenyl)(pyrrolidin-1-yl)methanone | C | 6.8 | m/z 476.4 [M + H]+ | ¹H NMR (300 MHz, CDCl₃) δ 1.88-2.01 (m, 4H), 2.20 (d, J = 0.68 Hz, 3H), 3.08-3.11 (m, 4H), 3.44-3.48 (m, 2H), 3.64-3.69 (m, 2H), 3.84-3.88 (m, 4H), 6.71 (d, J = 9.07 Hz, 2H), 6.79 (br s, 1H), 7.01 (d, J = 9.08 Hz, 2H), 7.64 (s, 4H), 7.91 (d, J = 0.70 Hz, 1H) |

TABLE 1-continued

| Compound number | Structure | Exact mass | Name | LCMS method | retention time (min) | Observed m/z | ¹H NMR |
|---|---|---|---|---|---|---|---|
| 225 | 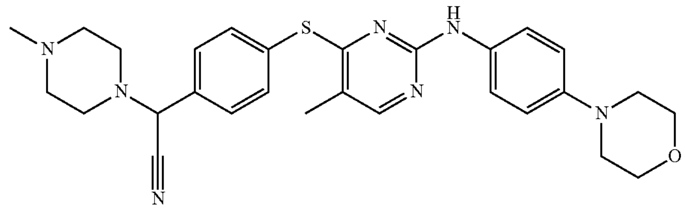 [SMILES: Cc1cnc(Nc2ccc(N3CCOCC3)cc2)nc1Sc1ccc(C(C#N)N2CCN(C)CC2)cc1] | 515.25 | 2-(4-(5-methyl-2-(4-morpholinophenylaminopyrimidin-4-ylthio)phenyl)-2-(4-methylpiperazin-1-yl)acetonitrile | D | 5.6 | m/z 489.0 [M − CN]+ | ¹H NMR (300 MHz, CDCl$_3$) δ 2.20 (d, J = 0.66 Hz, 3H), 2.30 (s, 3H), 2.43-2.52 (m, 4H), 2.62-2.69 (m, 4H), 3.06-3.10 (m, 4H), 3.85-3.88 (m, 4H), 4.92 (s, 1H), 6.67 (d, J = 9.05 Hz, 2H), 6.69 (s, 1H), 7.07 (d, J = 9.01 Hz, 2H), 7.64 (s, 4H), 7.92 (d, J = 0.71 Hz, 1H) |
| 226 | 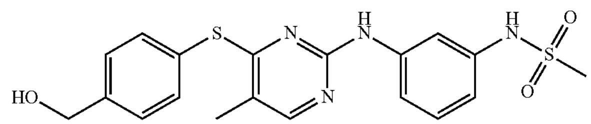 [SMILES: Cc1cnc(Nc2cccc(NS(C)(=O)=O)c2)nc1Sc1ccc(CO)cc1] | 416.10 | N-(3-(4-(hydroxymethyl)phenylthio)-5-methylpyrimidin-2-ylamino)phenyl)methanesulfonamide | E | 9.4 | m/z 417.3 [M + H]+ | ¹H NMR (300 MHz, d$_6$-DMSO) δ 2.14 (d, J = 0.58, 3H), 2.85 (s, 3H), 4.70 (d, J = 5.41 Hz, 2H), 5.29 (t, J = 5.73 Hz, 1H), 6.76 (d, J = 8.99 Hz, 2H), 7.10 (d, J = 9.02 Hz, 2H), 7.46 (d, J = 8.48 Hz, 2H), 7.55 (d, J = 8.29 Hz, 2H), 8.05 (d, J = 0.68 Hz, 1H), 9.24 (s, 1H), 9.31 (s, 1H) |
| 227 | 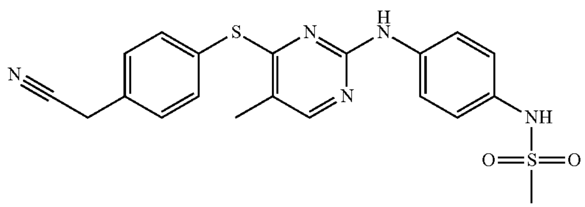 [SMILES: Cc1cnc(Nc2ccc(NS(C)(=O)=O)cc2)nc1Sc1ccc(CC#N)cc1] | 425.10 | N-(4-(4-(cyanomethyl)phenylthio)-5-methylpyrimidin-2-ylamino)phenyl)methanesulfonamide | C | 6.7 | m/z 426.3 [M + H]+ | ¹H NMR (300 MHz, d$_6$-DMSO) δ 2.17 (s, 3H), 2.87 (s, 3H), 4.24 (s, 2H), 6.76 (d, J = 8.84 Hz, 2H), 7.09 (d, J = 8.74 Hz, 2H), 7.52 (d, J = 8.25 Hz, 2H), 7.65 (d, J = 8.13 Hz, 2H), 8.08 (s, 1H), 9.31 (s, 1H), 9.38 (s, 1H) |
| 228 | 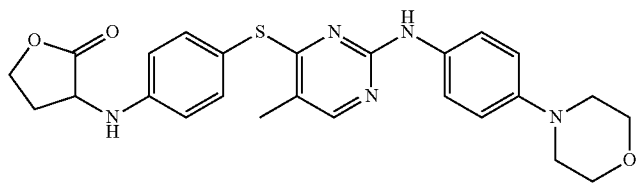 [SMILES: Cc1cnc(Nc2ccc(N3CCOCC3)cc2)nc1Sc1ccc(NC2CCOC2=O)cc1] | 477.18 | 3-(4-(5-methyl-2-(4-morpholinophenylaminopyrimidin-4-ylthio)phenylamino)dihydrofuran-2(3H)-one | C | 6.8 | m/z 478.4 [M + H]+ | ¹H NMR (300 MHz, d$_6$-DMSO) δ 2.12 (d, J = 0.60 Hz, 3H), 2.57-2.75 (m, 1H), 2.88-2.97 (m, 4H), 3.68-3.71 (m, 4H), 4.23-4.32 (m, 1H), 4.38-4.45 (m, 1H), 4.58-4.69 (m, 1H), 6.56-6.59 (m, 1H), 6.57 (d, J = 9.16 Hz, 2H), 6.84 (d, J = 8.77 Hz, 2H), 7.09 (d, J = 9.11 Hz, 2H), 7.28 (d, J = 8.67 Hz, 2H), 7.95 (d, J = 0.67 Hz, 1H), 9.07 (s, 1H) |
| 229 | 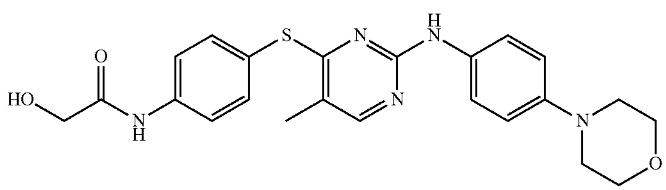 [SMILES: Cc1cnc(Nc2ccc(N3CCOCC3)cc2)nc1Sc1ccc(NC(=O)CO)cc1] | 451.17 | 2-hydroxy-N-(4-(5-methyl-2-(4-morpholinophenylaminopyrimidin-4-ylthio)phenyl)acetamide | C | 6.1 | m/z 452.3 [M + H]+ | ¹H NMR (300 MHz, d$_6$-DMSO) δ 2.12 (d, J = 0.44 Hz, 3H), 3.64-3.68 (m, 4H), 4.04 (s, 2H), 6.48 (d, J = 9.08 Hz, 2H), 7.01 (d, J = 8.88 Hz, 2H), 7.52 (d, J = 8.61 Hz, 2H), 7.93 (d, J = 8.66 Hz, 2H), 8.00 (d, J = 0.69 Hz, 2H), 9.08 (s, 1H), 10.13 (s, 1H) |

TABLE 1-continued

| Compound number | Structure | Exact mass | Name | LCMS method | retention time (min) | Observed m/z | 1H NMR |
|---|---|---|---|---|---|---|---|
| 230 | 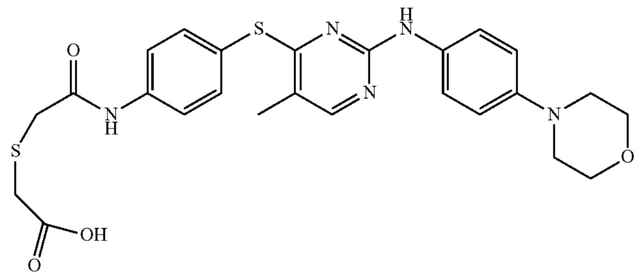 [SMILES: Cc1cnc(Nc2ccc(N3CCOCC3)cc2)nc1Sc1ccc(NC(=O)CSCC(=O)O)cc1] | 525.15 | 2-(2-(4-(5-methyl-2-(4-morpholinophenylamino)pyrimidin-4-ylthio)phenyl-amino)-2-oxoethylthio)acetic acid | D | 4.70 | m/z 526.3 [M + H]+ | 1H NMR (300 MHz, d6-DMSO) δ 2.13 (d, J = 0.47 Hz, 3H), 2.90-2.93 (m, 4H), 3.48 (s, 2H), 3.50 (s, 2H), 3.71-3.74 (m, 4H), 6.50 (d, J = 9.06 Hz, 2H), 7.03 (d, J = 9.01 Hz, 2H), 7.54 (d, J = 8.68 Hz, 2H), 7.76 (d, J = 8.75 Hz, 2H), 8.00 (d, J = 0.64 Hz, 1H), 9.08 (s, 1H), 10.47 (s, 1H) |
| 231 | 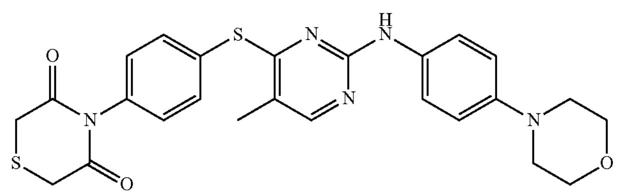 [SMILES: Cc1cnc(Nc2ccc(N3CCOCC3)cc2)nc1Sc1ccc(N2C(=O)CSCC2=O)cc1] | 507.14 | 4-(4-(5-methyl-2-(4-morpholinophenylamino)pyrimidin-4-ylthio)phenyl)thiomorpholine-3,5-dione | I | 10.3 | m/z 508.3 [M + H]+ | 1H NMR (300 MHz, d6-DMSO) δ 2.16 (d, J = 0.49 Hz, 3H), 2.94-2.97 (m, 4H), 3.70-3.74 (m, 4H), 3.87 (s, 4H), 6.65 (d, J = 9.21 Hz, 2H), 7.24 (d, J = 9.06 Hz, 2H), 7.27 (d, J = 8.54 Hz, 2H), 7.69 (d, J = 8.56 Hz, 2H), 8.07 (d, J = 0.65 Hz, 1H), 9.14 (s, 1H) |
| 232 | 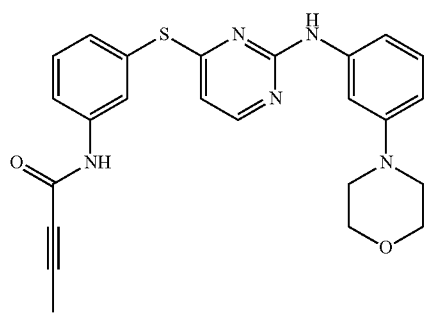 [SMILES: CC#CC(=O)Nc1cccc(Sc2ccnc(Nc3cccc(N4CCOCC4)c3)n2)c1] | 445.16 | N-(3-(2-(3-morpholinophenylamino)pyrimidin-4-ylthio)phenyl)but-2-ynamide | C | 6.90 | m/z 446.2 [M + H]+ | 1H NMR (300 MHz, CDCl3) δ ppm 8.48 (d, 1H, J = 5.7 Hz), 7.83 (br s, 1H), 7.76 (d, 1H, J = 7.5 Hz), 7.69 (m, 1H), 7.41 (dd, 1H, J = 7.8, 7.8 Hz), 7.36 (d, 1H, J = 7.2 Hz), 7.29 (s, 1H), 7.13 (m, 1H), 7.09 (d, 1H, J = 8.4 Hz), 6.94 (dd, 1H, J = 7.5, 1.2 Hz), 6.56 (dd, 1H, J = 8.1, 1.8 Hz), 6.31 (d, 1H, J = 5.4 Hz), 3.84 (dd, 4H, J = 5.0, 4.8 Hz), 3.13 (dd, 4H, J = 5.1, 4.8 Hz), 1.98 (s, 3H). |

| Compound number | Structure | Exact mass | Name | LCMS method | retention time (min) | Observed m/z | 1H NMR |
|---|---|---|---|---|---|---|---|
| 233 | 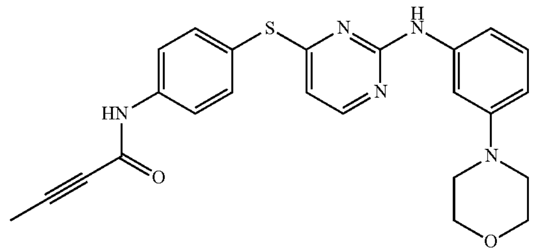 [SMILES: CC#CC(=O)Nc1ccc(Sc2ccnc(Nc3cccc(N4CCOCC4)c3)n2)cc1] | 445.16 | N-(4-(2-(3-morpholinophenyl-amino)pyrimidin-4-ylthio)phenyl)but-2-ynamide | C | 6.91 | m/z 446.3 [M + H]+ | 1H NMR (300 MHz, d-Acetone) δ ppm 9.71 (br s, 1H), 8.29 (br s, 1H), 7.99 (d, J = 3.0 Hz, 1H), 7.71 (d, J = 5.4 Hz, 2H), 7.46 (d, J = 4.8 Hz, 2H), 7.21 (m, 1H), 7.06 (dd, J = 4.8, 0.9 Hz, 1H), 6.92 (dd, J = 5.0, 4.8 Hz, 1H), 6.43 (dd, J = 4.8, 1.5 Hz, 1H), 6.19 (d, J = 3.0 Hz, 1H), 3.63 (dd, J = 2.9, 2.7 Hz, 4H), 2.97 (dd, J = 3.0, 2.9 Hz, 4H), 1.88 (s, 3H). |
| 234 | 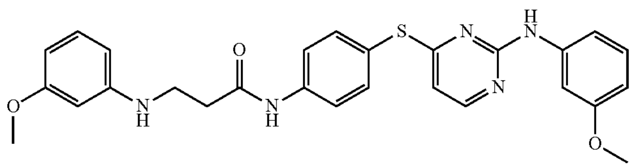 [SMILES: COc1cccc(NCCC(=O)Nc2ccc(Sc3ccnc(Nc4cccc(OC)c4)n3)cc2)c1] | 501.18 | 3-(3-methoxyphenyl-amino)-N-(4-(2-(3-methoxyphenyl-amino)pyrimidin-4-ylthio)phenyl)propanamide | C | 7.45 | m/z 502.3 [M + H]+ | 1H NMR (300 MHz, d-Acetone) δ ppm 9.51 (br s, 1H), 8.53 (br s, 1H), 8.12 (d, J = 5.4 Hz, 1H), 7.83 (d, J = 5.1 Hz, 2H), 7.56 (d, J = 8.7 Hz, 2H), 7.41 (m, 1H), 7.24 (m, 1H), 7.09 (t, J = 8.4 Hz, 1H), 7.00 (t, J = 7.5 Hz, 1H), 6.50 (m, 1H), 6.32 (d, J = 5.4 Hz, 1H), 6.22 (m, 3H), 5.04 (m, 1H), 3.75 (s, 3H), 3.72 (s, 3H), 3.52 (q, J = 6.4 Hz, 2H), 2.73 (t, J = 6.4 Hz, 2H). |
| 235 | 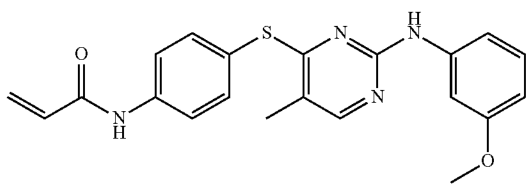 [SMILES: C=CC(=O)Nc1ccc(Sc2nc(Nc3cccc(OC)c3)ncc2C)cc1] | 392.13 | N-(4-(2-(3-methoxyphenyl-amino)-5-methylpyrimidin-4-ylthio)phenyl)acrylamide | C | 7.07 | m/z 393.3 [M + H]+ | 1H NMR (300 MHz, d-Acetone) δ ppm 9.62 (br s, 1H), 8.27 (br s, 1H), 8.01 (s, 1H), 7.89 (dd, J = 6.3, 1.5 Hz, 2H), 7.54 (dd, J = 6.9, 1.8 Hz, 2H), 7.02 (m, 1H), 6.95 (dd, J = 2.4, 2.1 Hz, 1H), 6.89 (dd, J = 8.0, 7.8 Hz, 1H), 6.49 (d, J = 10.2 Hz, 1H), 6.43 (d, J = 2.4 Hz, 1H), 6.37 (m, 1H), 5.77 (dd, J = 10.2, 2.7 Hz, 1H), 3.67 (s, 3H), 2.19 (s, 3H). |
| 236 | 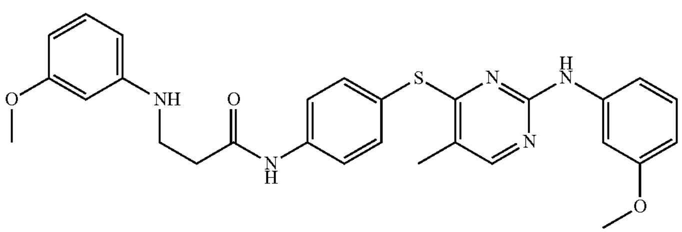 [SMILES: COc1cccc(NCCC(=O)Nc2ccc(Sc3nc(Nc4cccc(OC)c4)ncc3C)cc2)c1] | 515.20 | 3-(3-methoxy-phenylamino)-N-(4-(2-(3-methoxy-phenylamino)-5-methylpyrimidin-4-ylthio)phenyl)propanamide | C | 7.53 | m/z 516.5 [M + H]+ | 1H NMR (300 MHz, d-Acetone) δ ppm 9.52 (br s, 1H), 8.26 (br s, 1H), 7.99 (s, 1H), 7.82 (d, J = 8.7 Hz, 2H), 7.51 (d, J = 8.7 Hz, 2H), 7.01 (dd, J = 7.8, 7.8 Hz, 2H), 6.90 (m, 2H), 6.28 (m, 4H), 5.05 (bt, 1H), 3.72 (s, 3H), 3.66 (s, 3H), 3.54 (m, 2H), 2.76 (m, 2H), 2.18 (s, 3H). |

TABLE 1-continued

| Compound number | Structure | Exact mass | Name | LCMS method | retention time (min) | Observed m/z | ¹H NMR |
|---|---|---|---|---|---|---|---|
| 237 | 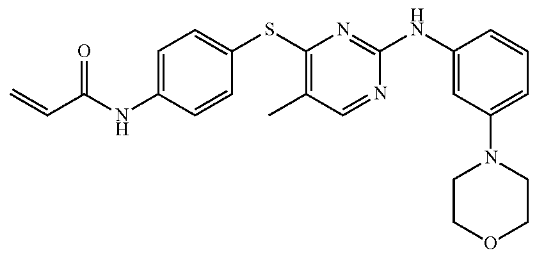 [SMILES: C=CC(=O)Nc1ccc(Sc2nc(Nc3cccc(N4CCOCC4)c3)ncc2C)cc1] | 447.17 | N-(4-(5-methyl-2-(3-morpholinophenyl-amino)pyrimidin-4-ylthio)phenyl)acrylamide | C | 6.98 | m/z 448.3 [M + H]+ | ¹H NMR (300 MHz, d-Acetone) δ ppm 9.62 (br s, 1H), 8.13 (br s, 1H), 7.99 (d, J = 0.9 Hz, 1H), 7.89 (d, J = 8.7 Hz, 2H), 7.54 (d, J = 8.7 Hz, 2H), 6.99 (m, 1H), 6.85 (m, 2H), 6.47 (m, 3H), 5.78 (dd, J = 9.6, 2.7 Hz, 1H), 3.72 (m, 4H), 3.02 (m, 4H), 2.18 (s, 3H). |
| 238 | 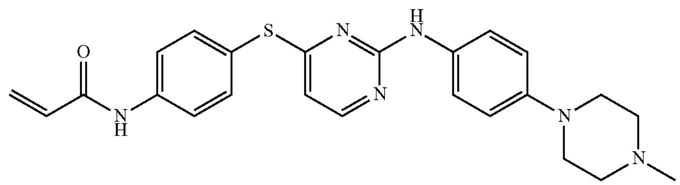 [SMILES: C=CC(=O)Nc1ccc(Sc2ccnc(Nc3ccc(N4CCN(C)CC4)cc3)n2)cc1] | 446.19 | N-(4-(2-(4-(4-methylpiperazin-1-yl)phenylamino)pyrimidin-4-ylthio)phenyl)acrylamide | C | 5.89 | m/z 447.4 [M + H]+ | ¹H NMR (300 MHz, d-Acetone) δ ppm 9.53 (br s, 1H), 8.33 (br s, 1H), 8.05 (m, 3H), 7.50 (m, 1H), 7.41 (d, J = 8.7 Hz, 2H), 7.34 (m, 1H), 6.78 (d, J = 9.3 Hz, 2H), 6.41 (m, 2H), 5.74 (dd, J = 9.0, 2.7 Hz, 1H), 3.07 (m, 4H), 2.47 (m, 4H), 2.25 (s, 3H). |
| 239 | 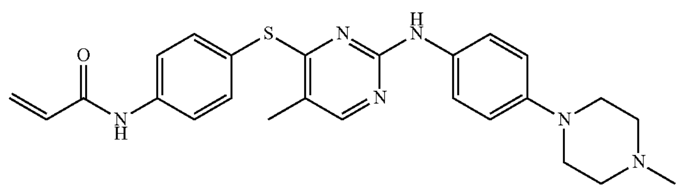 | 460.20 | N-(4-(5-methyl-2-(4-(4-methylpiperazin-1-yl)phenylamino)pyrimidin-4-ylthio)phenyl)acrylamide | C | 5.28 | m/z 461.4 [M + H]+ | ¹H NMR (300 MHz, CDCl₃) δ ppm 7.87 (s, 1H), 7.75 (d, J = 8.4 Hz, 2H), 7.56 (m, 3H), 6.96 (d, J = 9.3 Hz, 2H), 6.69 (br s, 1H), 6.63 (d, J = 9.3 Hz, 2H), 6.53 (dd, J = 17.1, 1.4 Hz, 1H), 6.32 (m, 1H), 5.86 (dd, J = 10.2, 1.4 Hz, 1H), 3.05 (m, 4H), 2.53 (m, 4H), 2.33 (s, 3H), 2.19 (s, 3H). |
| 240 | 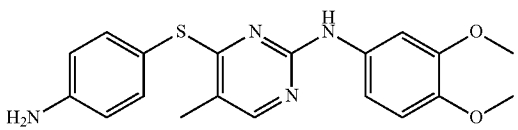 | 368.13 | 4-(4-aminophenyl-thio)-N-(3,4-dimethoxyphenyl)-5-methyl-pyrimidin-2-amine | C | 10.13 | m/z 369.3 [M + H]+ | ¹H NMR (300 MHz, CDCl₃) δ ppm 7.86 (s, 1H), 7.33 (d, J = 8.4 Hz, 2H), 6.88 (dd, J = 8.7, 2.7 Hz, 1H), 6.80 (br s, 1H), 6.75 (d, J = 8.7 Hz, 2H), 6.67 (d, J = 8.7 Hz, 2H), 6.62 (m, 1H), 3.85 (s, 3H), 3.78 (s, 3H), 2.18 (s, 3H). |
| 241 | 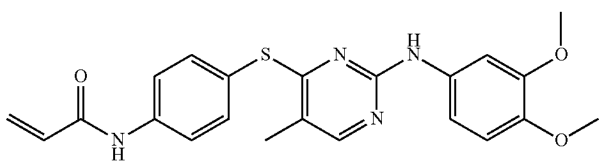 [SMILES: C=CC(=O)Nc1ccc(Sc2nc(Nc3ccc(OC)c(OC)c3)ncc2C)cc1] | 422.14 | N-(4-(2-(3,4-dimethoxyphenyl-amino)-5-methylpyrimidin-4-ylthio)phenyl)acrylamide | C | 6.92 | m/z 423.3 [M + H]+ | ¹H NMR (300 MHz, CDCl₃ + CD₃OD) δ ppm 7.70 (d, J = 0.9 Hz, 1H), 7.65 (d, J = 8.7 Hz, 2H), 7.39 (d, J = 8.7 Hz, 2H), 6.64 (dd, J = 8.7, 2.7 Hz, 1H), 6.49 (d, J = 2.1 Hz, 1H), 6.35 (d, J = 9.0 Hz, 1H), 6.29 (m, 2H), 5.65 (dd, J = 7.8, 4.1 Hz, 1H), 3.60 (s, 3H), 3.59 (s, 3H), 2.06 (s, 3H). |

TABLE 1-continued

| Compound number | Structure | Exact mass | Name | LCMS method | retention time (min) | Observed m/z | 1H NMR |
|---|---|---|---|---|---|---|---|
| 242 | 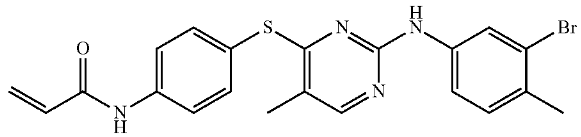 [SMILES: C=CC(=O)Nc1ccc(Sc2nc(Nc3ccc(C)c(Br)c3)ncc2C)cc1] | 454.05 | N-(4-(2-(3-bromo-4-methylphenyl-amino)-5-methyl-pyrimidin-4-ylthio)phenyl)acrylamide | C | 7.78 | m/z 455.3/ 457.3 [M + H]+ | 1H NMR (300 MHz, d-MeOH + DMSO) δ ppm 8.02 (s, 1H), 7.87 (d, J = 8.4 Hz, 2H), 7.57 (d, J = 8.4 Hz, 2H), 7.38 (d, J = 2.4 Hz, 1H), 7.17 (dd, J = 8.4, 2.7 Hz, 1H), 6.82 (d, J = 8.7 Hz, 1H), 6.53 (d, J = 9.6 Hz, 1H), 6.48 (d, J = 2.1 Hz, 1H), 5.87 (dd, J = 9.6, 2.4 Hz, 1H), 2.23 (s, 3H), 2.21 (s, 3H). |
| 243 | 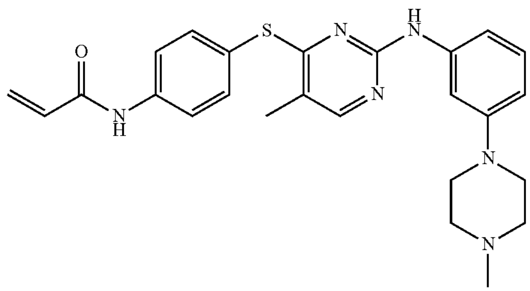 [SMILES: C=CC(=O)Nc1ccc(Sc2nc(Nc3cccc(N4CCN(C)CC4)c3)ncc2C)cc1] | 460.20 | N-(4-(5-methyl-2-(3-(4-methyl-piperazin-1-yl)phenylamino)pyrimidin-4-ylthio)phenyl)acrylamide | C | 5.35 | m/z 461.4 [M + H]+ | 1H NMR (300 MHz, CDCl3) δ ppm 7.92 (s, 1H), 7.68 (m, 2H), 7.54 (m, 3H), 6.88 (m, 2H), 6.77 (br s, 1H), 6.63 (br s, 1H), 6.50 (m, 2H), 6.30 (m, 1H), 5.84 (dd, J = 9.9, 1.4 Hz, 1H), 3.10 (m, 4H), 2.53 (m, 4H), 2.33 (s, 3H), 2.19 (s, 3H). |
| 244 | 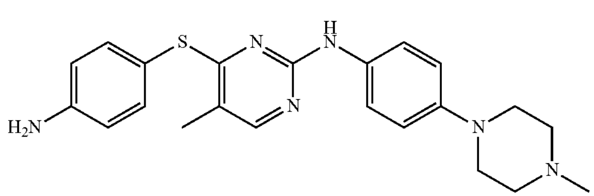 [SMILES: Cc1cnc(Nc2ccc(N3CCN(C)CC3)cc2)nc1Sc1ccc(N)cc1] | 406.19 | 4-(4-aminophenyl-thio)-5- methyl-N-(4-(4-methyl-piperazin-1-yl)phenyl)pyrimidin-2-amine | D | 4.46 | m/z 407.4 [M + H]+ | 1H NMR (300 MHz, d-MeOH + DMSO) δ ppm 7.86 (s, 1H), 7.25 (d, J = 8.4 Hz, 2H), 7.12 (d, J = 9.0 Hz, 2H), 6.78 (m, 4H), 3.13 (m, 4H), 2.62 (m, 4H), 2.36 (s, 3H), 2.16 (s, 3H). |
| 245 | 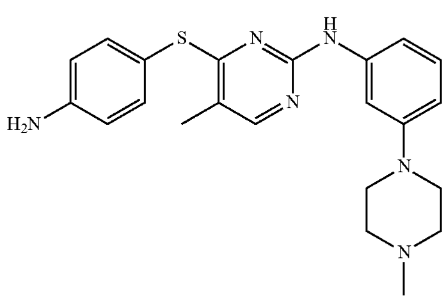 [SMILES: Cc1cnc(Nc2cccc(N3CCN(C)CC3)c2)nc1Sc1ccc(N)cc1] | 406.19 | 4- (4-aminophenyl-thio)-5-methyl-N-(3-(4-methyl-piperazin-1-yl)phenyl)pyrimidin-2-amine | D | 5.31 | m/z 407.4 [M + H]+ | 1H NMR (300 MHz, d-DMSO) δ ppm 8.95 (s, 1H), 7.98 (s, 1H), 7.16 (d, J = 8.7 Hz, 2H), 6.98 (d, J = 9.6 Hz, 1H), 6.83 (dd, J = 8.4, 8.3 Hz, 1H), 6.72 (m, 1H), 6.67 (d, J = 9.0 Hz, 2H), 6.38 (dd, J = 8.1, 1.8 Hz, 1H), 5.59 (br s, 2H), 3.01 (m, 4H), 2.41 (m, 4H), 2.20 (s, 3H), 2.11 (s, 3H). |

TABLE 1-continued

| Compound number | Structure | Exact mass | Name | LCMS method | retention time (min) | Observed m/z | ¹H NMR |
|---|---|---|---|---|---|---|---|
| 246 | 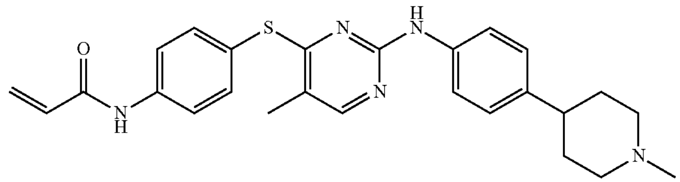 [SMILES: C=CC(=O)Nc1ccc(Sc2nc(Nc3ccc(C4CCN(C)CC4)cc3)ncc2C)cc1] | 459.21 | N-(4-(5-methyl-2-(4-(1-methyl-piperidin-4-yl)phenylamino)pyrimidin-4-ylthio)phenyl)acrylamide | D | 4.54 | m/z 460.3 [M+H]+ | ¹H NMR (300 MHz, CDCl₃ + CD₃OD) δ ppm 7.86 (m, 3H), 7.54 (d, J = 8.1 Hz, 2H), 6.97 (d, J = 8.1 Hz, 2H), 6.85 (d, J = 8.7 Hz, 2H), 6.53 (m, 2H), 5.77 (dd, J = 9.3, 2.7 Hz, 1H), 2.96 (d, J = 10.5 Hz, 2H), 2.38 (s, 3H), 2.20 (s, 3H), 1.7 (m, 6H). |
| 247 | 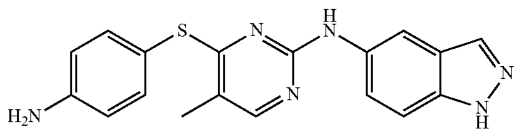 [SMILES: Cc1cnc(Nc2ccc3[nH]ncc3c2)nc1Sc1ccc(N)cc1] | 348.12 | N-(4-(4-aminophenylthio)-5-methyl-pyrimidin-2-yl)-1H-indazol-5-amine | C | 6.30 | m/z 349.3 [M+H]+ | ¹H NMR (300 MHz, d-DMSO) δ ppm 7.96 (s, 1H), 7.89 (s, 1H), 7.72 (dd, J = 1.8, 0.9 Hz, 1H), 7.31 (d, J = 8.7 Hz, 2H), 7.23 (m, 2H), 6.81 (d, J = 8.7 Hz, 2H), 2.19 (s, 3H). |
| 248 | 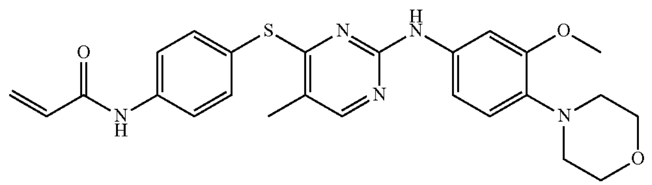 [SMILES: C=CC(=O)Nc1ccc(Sc2nc(Nc3ccc(N4CCOCC4)c(OC)c3)ncc2C)cc1] | 477.18 | N-(4-(2-(3-methoxy-4-morpholino-phenylamino)-5-methylpyrimidin-4-ylthio)phenyl)acrylamide | C | 6.68 | m/z 478.4 [M+H]+ | ¹H NMR (300 MHz, d-DMSO) δ ppm 10.49 (br s, 1H), 9.07 (br s, 1H), 8.02 (s, 1H), 7.88 (d, J = 8.7 Hz, 2H), 7.54 (d, J = 8.7 Hz, 2H), 6.70 (m, 2H), 6.51 (dd, J = 16.9, 10.1 Hz, 1H), 6.33 (dd, J = 17.1, 1.8 Hz, 1H), 6.20 (d, J = 8.7 Hz, 1H), 5.85 (dd, J = 9.9, 2.1 Hz, 1H), 3.63 (m, 3H), 3.62 (m, 4H), 2.73 (m, 4H), 2.14 (s, 3H). |
| 249 | 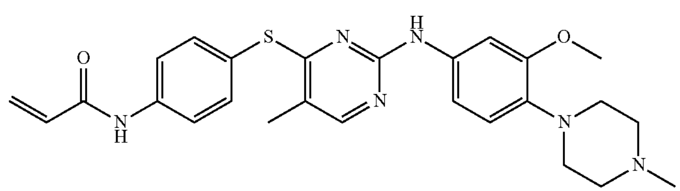 [SMILES: C=CC(=O)Nc1ccc(Sc2nc(Nc3ccc(N4CCN(C)CC4)c(OC)c3)ncc2C)cc1] | 490.22 | N-(4-(2-(3-methoxy-4-(4-methylpiperazin-1-yl)phenyl-amino)-5-methylpyrimidin-4-ylthio)phenyl)acrylamide | D | 4.53 | m/z 491.4 [M+H]+ | ¹H NMR (300 MHz, d-DMSO) δ ppm 10.47 (br s, 1H), 9.04 (br s, 1H), 8.02 (s, 1H), 7.88 (d, J = 8.7 Hz, 2H), 7.53 (d, J = 8.7 Hz, 2H), 6.69 (m, 2H), 6.50 (dd, J = 17.1, 10.2 Hz, 1H), 6.32 (dd, J = 17.1, 2.7 Hz, 1H), 6.21 (d, J = 8.4 Hz, 1H), 5.84 (dd, J = 10.2, 2.1 Hz, 1H), 4.01 (d, J = 0.9 Hz, 3H), 3.63 (s, 3H), 2.73 (br s, 4H), 2.37 (br s, 4H), 2.19 (s, 3H). |
| 250 | 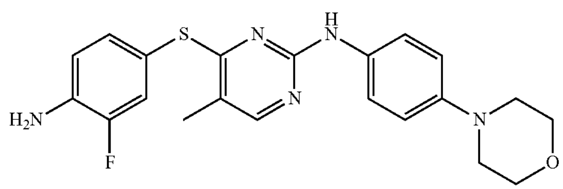 [SMILES: Cc1cnc(Nc2ccc(N3CCOCC3)cc2)nc1Sc1ccc(N)c(F)c1] | 411.15 | 4-(4-amino-3-fluorophenylthio)-5-methyl-N-(4-morpholinophenyl)pyrimidin-2-amine | C | 6.93 | m/z 412.3 [M+H]+ | ¹H NMR (300 MHz, d-DMSO) δ ppm 9.11 (s, 1H), 7.97 (s, 1H), 7.18 (dd, J = 11.4, 2.1 Hz, 1H), 7.07 (m, 3H), 6.88 (dd, J = 9.9, 9.0 Hz, 1H) 6.62 (d, J = 9.3 Hz, 2H), 5.80 (br s, 2H), 3.73 (m, 4H), 2.99 (m, 4H), 2.10 (s, 3H). |

TABLE 1-continued

| Compound number | Structure | Exact mass | Name | LCMS method | retention time (min) | Observed m/z | ¹H NMR |
|---|---|---|---|---|---|---|---|
| 251 | 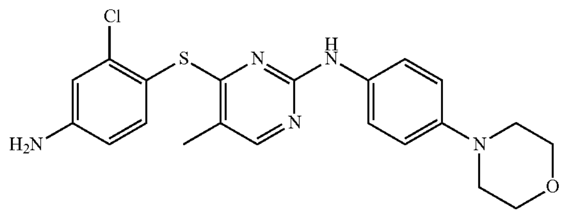 [SMILES: Cc1cnc(Nc2ccc(N3CCOCC3)cc2)nc1Sc1ccc(N)cc1Cl] | 427.12 | 4-(4-amino-2-chlorophenylthio)-5-methyl-N-(4-morpholinophenyl)pyrimidin-2-amine | C | 6.93 | m/z 428.3/ 430.3 [M + H]+ | ¹H NMR (300 MHz, DMSO-d) δ ppm 9.11 (s, 1H) 7.98 (s, 1H) 7.30 (d, J = 8.7 Hz, 1H) 7.12 (d, J = 9.0 Hz, 2H) 6.87 (d, J = 2.4 Hz, 1H) 6.63 (m, 3H) 6.02 (s, 2H) 3.72 (m, 4H), 2.99 (m, 4H) 2.12 (s, 3H). |
| 252 | 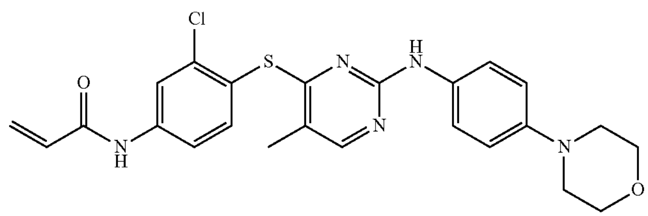 [SMILES: C=CC(=O)Nc1ccc(Sc2nc(Nc3ccc(N4CCOCC4)cc3)ncc2C)c(Cl)c1] | 481.13 | N-(3-chloro-4-(5-methyl-2-(4-morpholinophenylaminopyrimidin-4-ylthio)phenyl)acrylamide | C | 7.00 | m/z 482.3/ 484.3 [M + H]+ | ¹H NMR (300 MHz, DMSO-d) δ ppm 10.69 (s, 1H) 9.19 (s, 1H) 8.24 (d, J = 1.8 Hz, 1H) 8.04 (s, 1H) 7.71 (m, 2H) 6.98 (d, J = 9.0 Hz, 2H) 6.38 (m, 2H) 5.90 (dd, J = 9.0, 2.1 Hz, 1H) 3.64 (m, 4H) 2.84 (m, 4H) 2.16 (s, 3H). |
| 253 | 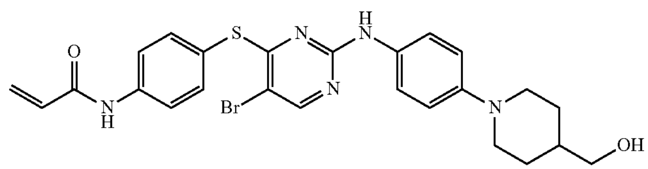 [SMILES: C=CC(=O)Nc1ccc(Sc2nc(Nc3ccc(N4CCC(CO)CC4)cc3)ncc2Br)cc1] | 539.10 | N-(4-(5-bromo-2-(4-(4-(hydroxymethyl)piperidin-1-yl)phenylamino)pyrimidin-4-ylthio)phenyl)acrylamide | C | 6.78 | m/z 540.2/ 542.2 [M + H]+ | ¹H NMR (300 MHz, d6-acetone) δ ppm 9.76 (br s, 1H), 8.42 (br s, 1H), 8.15 (s, 1H), 7.98 (d, J = 8.7 Hz, 2H), 7.58 (d, J = 8.7 Hz, 2H), 7.05 (d, J = 9.3 Hz, 2H), 6.62 (m, 2H), 6.59 (m, 1H), 6.45 (dd, J = 17.1, 2.7 Hz, 1H), 5.82 (dd, J = 9.6, 2.4 Hz, 1H), 3.51 (m, 2=3H), 3.42 (m, 2H), 1.78 (m, 2H), 0.87 (m, 2H). |
| 254 | 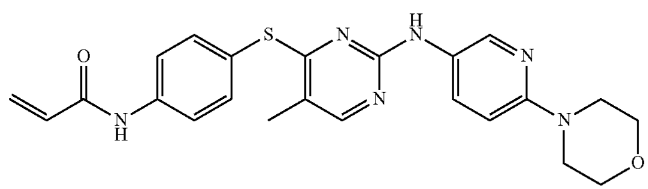 | 448.17 | N-(4-(5-methyl-2-(6-morpholinopyridin-3-ylamino)pyrimidin-4-ylthio)phenyl)acrylamide | C | 6.51 | m/z 449.3 [M + H]+ | ¹H NMR (300 MHz, d-DMSO) δ ppm 10.50 (br s, 1H), 9.23 (br s, 1H), 8.03 (br s, 1H), 7.93 (d, J = 2.4 Hz, 1H), 7.86 (d, J = 9.0 Hz, 2H), 7.54 (d, J = 8.7 Hz, 2H), 7.30 (dd, J = 9.6, 2.7 Hz, 1H), 6.49 (dd, J= 17.1, 10.2 Hz, 2H), 6.33 (d, J = 17.1, 2.4 Hz, 1H), 6.19 (d, J = 9.0 Hz, 1H) 5.86 (dd, J = 10.2, 2.1 Hz, 1H), 3.62 (m, 4H), 3.15 (m, 4H), 2.14 (s, 3H). |
| 255 | 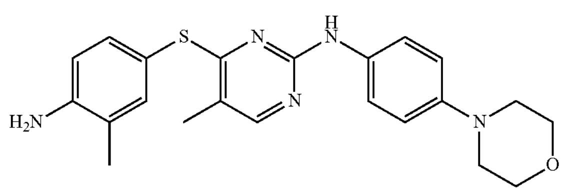 | 407.18 | 4-(4-amino-3-methylphenyl-thio)-5-methyl-N-(4-morpholinophenyl)pyrimidin-2-amine | C | 6.84 | m/z 408.3 [M + H]+ | ¹H NMR (300 MHz, d-acetone) δ ppm 8.01 (br s, 1H), 7.88 (s, 1H), 7.16 (m, 4H), 6.84 (d, J = 8.4 Hz, 1H), 6.69 (d, J = 9.0 Hz, 2H), 5.05 (br s, 2H), 3.74 (m, 4H), 3.05 (m, 4H), 2.18 (s, 3H), 2.14 (s, 3H). |

TABLE 1-continued

| Compound number | Structure | Exact mass | Name | LCMS method | retention time (min) | Observed m/z | ¹H NMR |
|---|---|---|---|---|---|---|---|
| 256 | 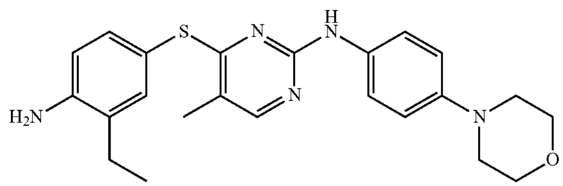 [SMILES: CCc1cc(Sc2nc(Nc3ccc(N4CCOCC4)cc3)ncc2C)ccc1N] | 421.19 | 4-(4-amino-3-ethylphenylthio)-5-methyl-N-(4-morpholinophenyl)pyrimidin-2-amine | C | 7.10 | m/z 422.4 [M + H]+ | ¹H NMR (300 MHz, d-acetone) δ ppm 8.01 (br s, 1H), 7.88 (s, 1H), 7.16 (m, 4H), 6.85 (d, J = 8.4Hz, 1H), 6.70 (d, J = 9.0 Hz, 2H), 5.07 (br s, 2H), 3.74 (m, 4H), 3.05 (m, 4H), 2.54 (q, J = 7.6 Hz, 2H), 2.14 (s, 3H), 1.17 (t, J = 7.5 Hz, 3H). |
| 257 | 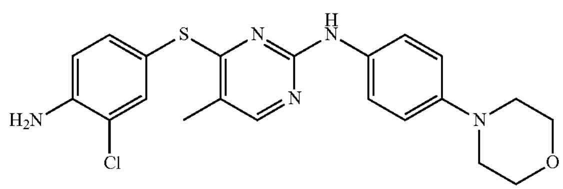 | 427.12 | 4-(4-amino-3-chlorophenylthio)-5-methyl-N-(4-morpholinophenyl)pyrimidin-2-amine | C | 7.17 | m/z 428.2/ 430.2 [M + H]+ | ¹H NMR (300 MHz, d-DMSO) δ ppm 9.08 (s, 1H), 7.97 (d, J = 0.9 Hz, 1H), 7.37 (d, J = 2.1 Hz, 1H), 7.19 (dd, J = 8.4, 2.1 Hz, 1H), 7.10 (d, J = 9.0 Hz, 2H), 6.91 (d, J = 8.4 Hz, 1H), 6.61 (d, J = 9.3 Hz, 2H), 5.97 (br s, 2H), 3.73 (m, 4H), 2.99 (m, 4H), 2.10 (d, J = 0.3 Hz, 3H). |
| 258 | 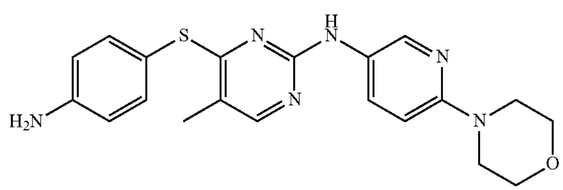 [SMILES: Cc1cnc(Nc2ccc(N3CCOCC3)nc2)nc1Sc1ccc(N)cc1] | 394.16 | 4-(4-aminophenylthio)-5-methyl-N-(6-morpholinopyridin-3-yl)pyrimidin-2-amine | C | 6.45 | m/z 395.3 [M + H]+ | ¹H NMR (300 MHz, d-MeOH) δ ppm 7.88 (d, J = 3.0 Hz, 1H), 7.84 (d, J = 0.9 Hz, 1H), 7.60 (dd, J = 9.0, 3.0 Hz, 1H), 7.22 (d, J = 8.7 Hz, 2H), 6.76 (d, J = 8.7 Hz, 2H), 6.58 (d, J = 9.3 Hz, 1H), 3.80 (m, 4H), 3.36 (m, 4H), 2.16 (d, J = 0.6 Hz, 3H). |
| 259 | 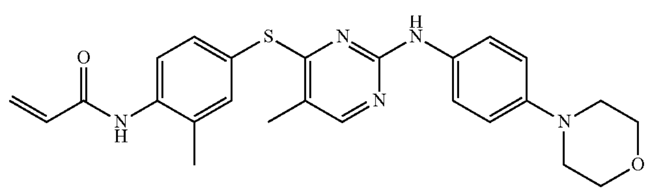 [SMILES: C=CC(=O)Nc1ccc(Sc2nc(Nc3ccc(N4CCOCC4)cc3)ncc2C)cc1C] | 461.19 | N-(2-methyl-4-(5-methyl-2-(4-morpholinophenylaminopyrimidin-4-ylthio)phenyl) acrylamide | C | 6.72 | m/z 462.3 [M + H]+ | ¹H NMR (300 MHz, d-DMSO) δ ppm 9.56 (s, 1H), 9.11 (s, 1H), 8.01 (m, 2H), 7.44 (m, 2H), 7.01 (d, J = 5.4 Hz, 2H), 6.71 (dd, J = 9.9, 6.3 Hz, 1H), 6.50 (d, J = 5.1 Hz, 2H), 6.32 (d, J = 9.9 Hz, 1H), 5.85 (d, J = 6.3 Hz, 1H), 3.66 (m, 4H), 2.88 (m, 4H), 2.27 (s, 3H), 2.13 (s, 3H). |
| 260 | 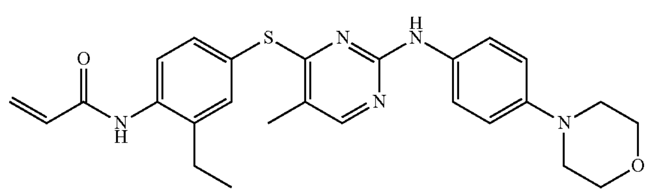 [SMILES: C=CC(=O)Nc1ccc(Sc2nc(Nc3ccc(N4CCOCC4)cc3)ncc2C)cc1CC] | 475.20 | N-(2-ethyl-4-(5-methyl-2-(4-morpholinophenylaminopyrimidin-4-ylthio)phenyl) acrylamide | C | 7.02 | m/z 476.3 [M + H]+ | ¹H NMR (300 MHz, d-DMSO) δ ppm 9.55 (s, 1H), 9.10 (s, 1H), 8.03 (s, 1H), 7.97 (d, J = 5.1 Hz, 1H), 7.44 (m, 2H), 7.01 (d, J = 5.4 Hz, 2H), 6.72 (dd, J = 10.2, 5.7 Hz, 2H), 6.51 (d, J = 5.4 Hz, 2H), 6.33 (d, J = 10.2 Hz, 1H), 5.84 (d, J = 5.7 Hz, 1H), 3.66 (m, 4H), 2.89 (m, 4H), 2.69 (q, J = 4.5 Hz, 2H), 2.15 (s, 3H), 1.05 (t, J = 4.5 Hz, 3H). |

| Compound number | Structure | Exact mass | Name | LCMS method | retention time (min) | Observed m/z | 1H NMR |
|---|---|---|---|---|---|---|---|
| 261 | 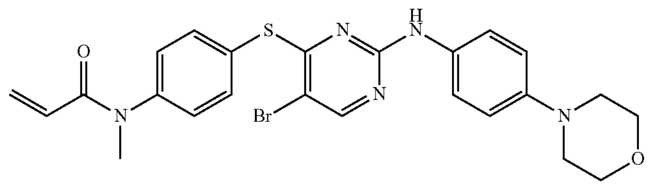 [SMILES: C=CC(=O)N(C)c1ccc(Sc2nc(Nc3ccc(N4CCOCC4)cc3)ncc2Br)cc1] | 525.08 | N-(4-(5-bromo-2-(4-morpholinophenylamino)pyrimidin-4-ylthio)phenyl)-N-methylacrylamide | C | 7.26 | m/z 526.2/528.2 [M+H]+ | 1H NMR (300 MHz, d-DMSO) δ ppm 7.35 (s, 1H), 6.86 (d, J = 8.7 Hz, 2H), 6.57 (d, J = 8.7 Hz, 2H), 6.32 (d, J = 9.3 Hz, 2H), 6.15 (s, 1H), 5.89 (d, J = 9.0 Hz, 2H), 5.48 (d, J = 17.1 Hz, 2H), 4.98 (dd, J = 6.9, 10.8 Hz, 1H), 2.99 (m, 4H), 2.61 (s, 3H), 2.19 (m, 4H). |
| 262 | 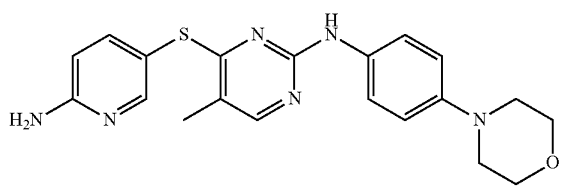 [SMILES: Cc1cnc(Nc2ccc(N3CCOCC3)cc2)nc1Sc1ccc(N)nc1] | 394.16 | 4-(6-aminopyridin-3-ylthio)-5-methyl-N-(4-morpholinophenyl)pyrimidin-2-amine | C | 5.89 | m/z 395.3 [M+H]+ | 1H NMR (300 MHz, d-DMSO) δ ppm 9.08 (br s, 1H), 7.99 (m, 2H), 7.46 (dd, J = 8.7, 2.4 Hz, 1H), 7.15 (d, J = 9.3 Hz, 2H), 6.67 (d, J = 9.0 Hz, 2H), 6.59 (dd, J = 8.7, 0.6 Hz, 2H), 6.55 (br s, 1H), 3.73 (m, 4H), 3.00 (m, 4H), 2.12 (s, 3H). |
| 263 | 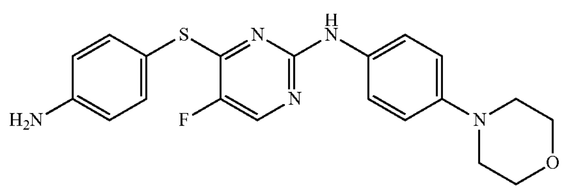 [SMILES: Nc1ccc(Sc2nc(Nc3ccc(N4CCOCC4)cc3)ncc2F)cc1] | 397.14 | 4-(4-aminophenylthio)-5-fluoro-N-(4-morpholinophenyl)pyrimidin-2-amine | E | 10.1 | m/z 398.3 [M+H]+ | 1H NMR (DMSO-d6, 300 MHz) δ 9.31 (s, 1H), 8.19 (d, J = 2.3, 1H), 7.21 (d, J = 8.2 Hz, 2H), 7.10 (d, J = 8.7 Hz, 2H), 6.75-6.62 (m, 4H), 5.78 (s, 2H), 3.73 (m, 4H), 3.00 (m, 4H) |
| 264 | 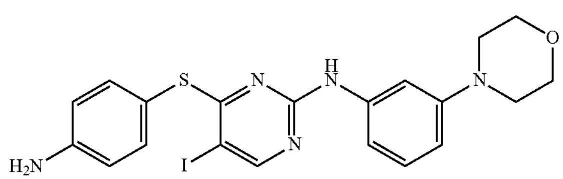 [SMILES: Nc1ccc(Sc2nc(Nc3cccc(N4CCOCC4)c3)ncc2I)cc1] | 505.04 | 4-(4-aminophenylthio)-5-iodo-N-(3-morpholinophenyl)pyrimidin-2-amine | E | 10.9 | m/z 506.2 [M+H]+ | 1H NMR (CDCl3, 300 MHz) δ 8.26 (s, 1H), 7.34 (d, J = 8.7 Hz, 2H), 7.00 (t, J = 8.5 Hz, 1H), 6.95-6.82 (m, 2H), 6.75 (d, J = 8.7 Hz, 2H), 6.52 (d, J = 6.9 Hz, 2H), 3.97 (s, 2H), 3.84 (t, J = 4.6 Hz, 4H), 3.09 (t, J = 5.0 Hz, 4H). |

TABLE 1-continued

| Compound number | Structure | Exact mass | Name | LCMS method | retention time (min) | Observed m/z | ¹H NMR |
|---|---|---|---|---|---|---|---|
| 265 | 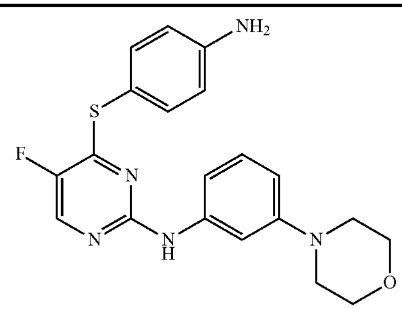 | 397.14 | 4-(4-aminophenyl-thio)-5-fluoro-N-(3-morpholino-phenyl)pyrimidin-2-amine | C | 6.9 | m/z 398.3 [M + H]+ | ¹H NMR (DMSO-d₆, 300 MHz) δ 9.27 (s, 1H), 8.23 (d, J = 1.8 Hz, 1H), 7.21 (d, J = 8.2 Hz, 2H), 7.00-6.93 (m, 1H), 6.88 (t, J = 8.0 Hz, 1H), 6.77 (s, 1H), 6.68 (d, J = 8.7 Hz, 2H), 6.44 (d, J = 7.8 Hz, 1H), 5.67 (s, 2H), 3.71 (m, 4H), 2.98 (m, 4H) |
| 266 | 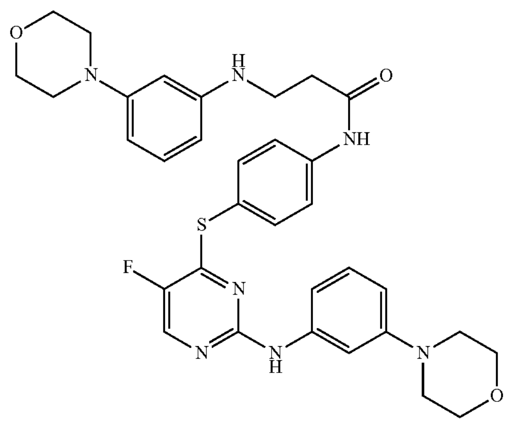 [SMILES: O=C(CCNc1cccc(N2CCOCC2)c1)Nc1ccc(Sc2nc(Nc3cccc(N4CCOCC4)c3)ncc2F)cc1] | 629.26 | N-(4-(5-fluoro-2-(3-morpholino-phenylamino)pyrimidin-4-ylthio)phenyl)-3-(3-morpholino-phenylamino)propanamide | C | 7.1 | m/z 630.4 [M + H]+ | ¹H NMR (CDCl₃, 300 MHz) δ 7.98 (d, J = 1.8 Hz, 1H), 7.89 (s, 1H), 7.63-7.55 (m, 2H), 7.55-7.49 (m, 2H), 7.12 (t, J = 8.0 Hz, 1H), 6.95 (t, J = 8.2 Hz, 1H), 6.89 (s, 1H), 6.83 (d, J = 8.7 Hz, 2H), 6.70 (s, 1H), 6.47 (dd, J = 8.2, 1.8 Hz, 1H), 6.37 (dd, J = 8.2, 1.8 Hz, 1H), 6.30-6.20 (m, 2H), 3.88-3.75 (m, 8H), 3.60 (t, J = 5.7 Hz, 2H), 3.11 (m, 4H), 3.05 (m, 4H), 2.71 (t, J = 5.7 Hz, 2H) |
| 267 | 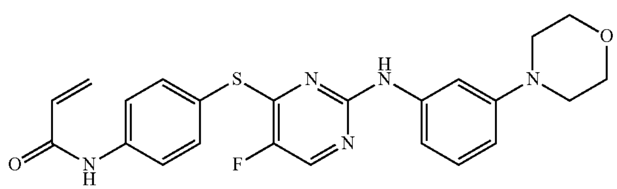 [SMILES: C=CC(=O)Nc1ccc(Sc2nc(Nc3cccc(N4CCOCC4)c3)ncc2F)cc1] | 451.15 | N-(4-(5-fluoro-2-(3-morpholino-phenylamino)pyrimidin-4-ylthio)phenyl)acrylamide | C | 6.9 | m/z 452.3 [M + H]+ | ¹H NMR (DMSO-d₆, 300 MHz) δ 10.44 (s, 1H), 9.32 (s, 1H), 8.31 (d, J = 1.8 Hz, 1H), 7.85 (d, J = 8.7 Hz, 2H), 7.59 (d, J = 8.7 Hz, 2H), 6.83-6.74 (m, 2H), 6.70 (t, J = 8.45 Hz, 1H), 6.50 (dd, J = 16.9, 10.0 Hz, 1H), 6.41 (d, J = 8.7 Hz, 1H), 6.33 (dd, J = 16.9, 1.8), 5.83 (dd, J = 10.0, 1.8 Hz, 1H), 3.69 (m, 4H), 2.96 (m, 4H) |

TABLE 1-continued

| Compound number | Structure | Exact mass | Name | LCMS method | retention time (min) | Observed m/z | ¹H NMR |
|---|---|---|---|---|---|---|---|
| 268 | 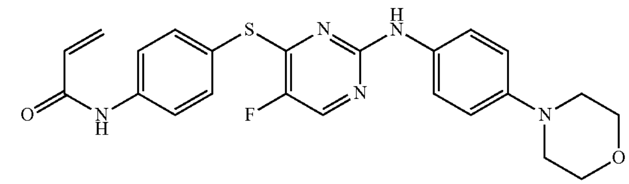 [SMILES: C=CC(=O)Nc1ccc(Sc2nc(Nc3ccc(N4CCOCC4)cc3)ncc2F)cc1] | 451.15 | N-(4-(5-fluoro-2-(4-morpholinophenylamino)pyrimidin-4-ylthio)phenyl)acrylamide | C | 6.9 | m/z 452.3 [M + H]+ | ¹H NMR (DMSO-d₆, 300 MHz) δ 10.54 (s, 1H), 9.37 (s, 1H), 8.26 (d, J = 1.8 Hz, 1H), 7.91 (d, J = 8.7 Hz, 2H), 7.60 (d, J = 8.2 Hz, 2H), 6.98 (d, J = 9.1 Hz, 2H), 6.59-6.42 (m, 3H), 6.34 (dd, J = 16.9, 1.8 Hz, 1H), 5.87 (dd, J = 10.0, 1.8, 1H), 3.65 (m, 4H), 2.86 (m, 4H) |
| 269 | 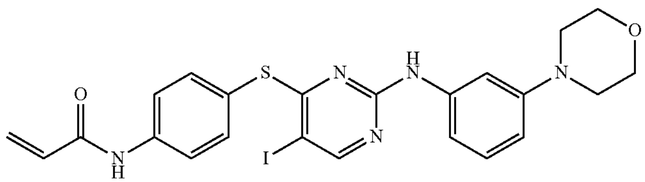 [SMILES: C=CC(=O)Nc1ccc(Sc2nc(Nc3cccc(N4CCOCC4)c3)ncc2I)cc1] | 559.05 | N-(4-(5-iodo-2-(3-morpholinophenylamino)pyrimidin-4-ylthio)phenyl)acrylamide | E | 10.9 | m/z 560.2 [M + H]+ | ¹H NMR (DMSO-d₆, 300 MHz) δ 10.44 (s, 1H), 9.35 (s, 1H), 8.39 (s, 1H), 7.83 (d, J = 8.7 Hz, 2H), 7.55 (d, J = 8.7 Hz, 2H), 6.76-6.58 (m, 3H), 6.51 (dd, J = 16.9, 10.0 Hz, 1H), 6.40 (m, 1H), 6.33 (dd, J = 16.9, 1.8 Hz, 1H), 5.83 (dd, J = 10.0, 1.8 Hz, 1H), 3.68 (m, 4H), 2.95 (m, 4H) |
| 270 | 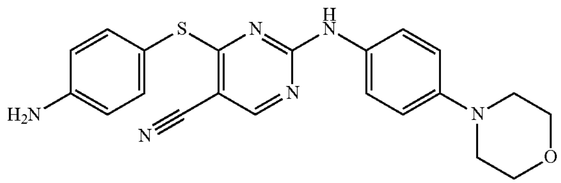 [SMILES: N#Cc1cnc(Nc2ccc(N3CCOCC3)cc2)nc1Sc1ccc(N)cc1] | 404.14 | 4-(4-aminophenylthio)-2-(4-morpholinophenylamino)pyrimidine-5-carbonitrile | C | 6.6 | m/z 405.3 [M + H]+ | ¹H NMR (DMSO-d₆, 300 MHz) δ 10.12 (s, 1H), 8.52 (s, 1H), 7.21 (d, J = 8.2 Hz, 2H), 7.12 (d, J = 8.7 Hz, 2H), 6.70 (m, 4H), 5.83 (br. s., 2H), 3.73 (m, 4H), 3.04 (m, 4H) |
| 271 | 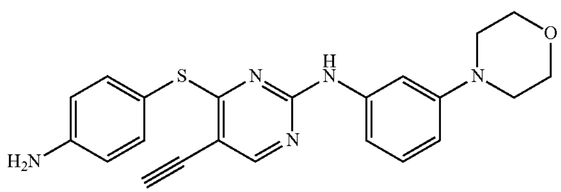 [SMILES: C#Cc1cnc(Nc2cccc(N3CCOCC3)c2)nc1Sc1ccc(N)cc1] | 403.15 | 4-(4-aminophenylthio)-5-ethynyl-N-(3-morpholinophenyl)pyrimidin-2-amine | C | 6.8 | m/z 404.3 [M + H]+ | ¹H NMR (CD₃OD, 300 MHz) δ 809.24 (s, 1H), 8.51 (d, J = 8.6 Hz, 2H), 8.10 (m, 5H), 7.78 (m, 1H), 5.09 (s, 1H), 4.91 (m, 4H), 4.26 (m, 4H) |
| 272 | 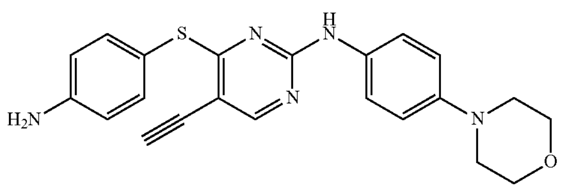 [SMILES: C#Cc1cnc(Nc2ccc(N3CCOCC3)cc2)nc1Sc1ccc(N)cc1] | 403.15 | 4-(4-aminophenylthio)-5-ethynyl-N-(4-morpholinophenyl)pyrimidin-2-amine | C | 6.7 | m/z 404.3 [M + H]+ | ¹H NMR (DMSO-d₆, 300 MHz) δ 9.56 (s, 1H), 8.21 (s, 1H), 7.17 (d, J = 8.6 Hz, 2H), 7.13 (m, 2H), 6.68 (m, 4H), 5.72 (br.s., 2H), 4.65 (s, 1H), 3.73 (m, 4H), 3.01 (m, 4H) |

| Compound number | Structure | Exact mass | Name | LCMS method | retention time (min) | Observed m/z | ¹H NMR |
|---|---|---|---|---|---|---|---|
| 273 | 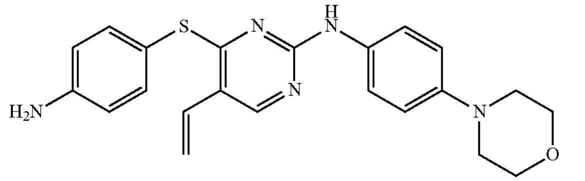 [SMILES: C=Cc1cnc(Nc2ccc(N3CCOCC3)cc2)nc1Sc1ccc(N)cc1] | 405.16 | 4-(4-aminophenyl-thio)-N-(4-morpholinophenyl)-5-vinylpyrimidin-2-amine | E | 10.0 | m/z 406.3 [M + H]+ | ¹H NMR (CDCl₃, 300 MHz) δ 8.19 (s, 1H), 7.35 (d, J = 8.7 Hz, 2H), 7.05 (d, J = 8.9 Hz, 2H), 6.92 (br.s., 1H), 6.75 (m, 5H), 5.64 (dd, J = 17.3, 0.9 Hz, 1H), 5.30 (dd, J = 11.1, 0.9 Hz, 1H), 3.95 (br.s., 2H), 3.86 (m, 4H), 3.09 (m, 4H) |
| 274 | 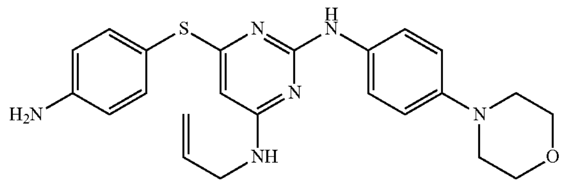 [SMILES: C=CCNc1cc(Sc2ccc(N)cc2)nc(Nc2ccc(N3CCOCC3)cc2)n1] | 434.19 | N4-allyl-6-(4-aminophenylthio)-N2-(4-morpholino-phenyl)pyrimidine-2,4-diamine | C | 4.3 | m/z 435.3 [M + H]+ | ¹H NMR (CDCl₃, 300 MHz) δ 7.33 (d, J = 6.7 Hz, 2H), 7.26 (s, 1H), 7.12 (d, J = 8.8 Hz, 2H), 6.80 (d, J = 7.6 Hz, 2H), 6.67 (d, J = 8.8 Hz, 2H), 6.20 (br.s., 1H), 5.92 (m, 1H), 5.25 (d, J = 17.2 Hz, 1H), 5.10 (d, J = 10.0 Hz, 1H), 4.00 (m, 2H), 3.85 (m, 6H), 3.10 (m, 4H) |
| 275 | 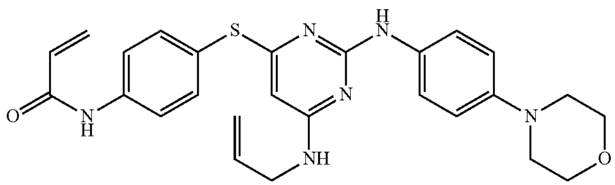 [SMILES: C=CCNc1cc(Sc2ccc(NC(=O)C=C)cc2)nc(Nc2ccc(N3CCOCC3)cc2)n1] | 488.20 | N-(4-(6-(allyl-amino)-2-(4-morpholino-aminophenyl-4-ylthio)phenyl) acrylamide | C | 6.7 | m/z 489.3 [M + H]+ | ¹H NMR (CDCl₃, 300 MHz) δ 7.61 (d, J = 8.7 Hz, 2H), 7.52 (d, J = 8.6 Hz, 2H), 7.47 (br.s., 1H), 7.09 (d, J = 8.8 Hz, 2H), 6.79 (d, J = 8.9 Hz, 2H), 6.46 (dd, J = 16.7, 1.2 Hz, 1H), 6.26 (dd, J = 16.7, 10.2 Hz, 1H), 5.90-5.74 (m, 2H), 5.39 (s, 1H), 5.21 (m, 1H), 5.10 (m, 1H), 4.99 (m, 1H), 4.92 (m, 1H), 3.99 (m, 2H), 3.82 (m, 4H), 3.07 (m, 4H) |
| 276 | 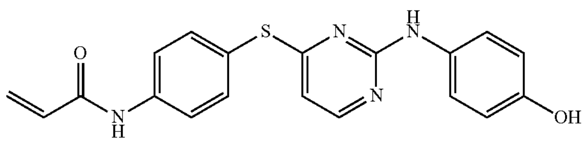 [SMILES: C=CC(=O)Nc1ccc(Sc2ccnc(Nc3ccc(O)cc3)n2)cc1] | 364.10 | N-(4-(2-(4-hydroxyphenyl-aminopyrimidin-4-ylthio)phenyl) acrylamide | C | 6.3 | m/z 365.3 [M + H]+ | (d₆-Acetone, 300 MHz) δ 9.62 (br s, 1H), 8.29 (br s, 1H), 8.06 (d, J = 5.5, 1H), 7.91 (dd, J = 7.0, 2.0, 2H), 7.58 (2H, m, J = 7.0, 2.0), 7.43 (dd, J = 7.0, 2.0, 2H), 7.70 (dd, J = 7.0, 2.0, 2H), 6.50 (dd, J = 17.0, 9.5, 1H), 6.39 (dd, J = 17.0, 2.5, 1H), 6.29 (d, J = 5.5, 1H), 5.77 (dd, J = 9.5, 2.5, 1H). |
| 277 | 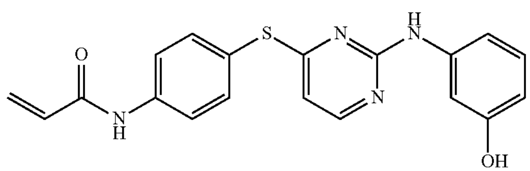 [SMILES: C=CC(=O)Nc1ccc(Sc2ccnc(Nc3cccc(O)c3)n2)cc1] | 364.10 | N-(4-(2-(3-hydroxyphenyl-aminopyrimidin-4-ylthio)phenyl) acrylamide | C | 6.3 | m/z 365.2 [M + H]+ | (d₆-Acetone, 300 MHz) δ 9.64 (br s, 1H), 8.46 (br s, 1H), 8.19 (br s, 1H), 8.11 (d, J = 5.5, 1H), 7.92 (d, J = 9.0, 2H), 7.59 (d, J = 9.0, 2H), 7.32 (ap t, J = 2.5, 1H), 7.16 (ddd, J = 8.5, 2.0, 1.0, 1H), 7.01 (ap t, J = 8.0, 1H), 6.50 (dd, J = 17.0, 9.5, 1H), 6.44 (ddd, J = 8.0, 2.5, 1.0, 1H), 6.39 (dd, J = 17.0, 2.5, 1H), 6.30 (d, J = 5.0, 1H), 5.77 (dd, J = 9.5, 2.5, 1H). |

TABLE 1-continued

| Compound number | Structure | Exact mass | Name | LCMS method | retention time (min) | Observed m/z | ¹H NMR |
|---|---|---|---|---|---|---|---|
| 278 | 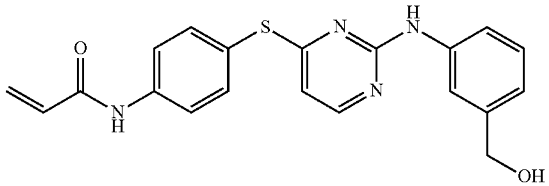 [SMILES: C=CC(=O)Nc1ccc(Sc2ccnc(Nc3cccc(CO)c3)n2)cc1] | 378.12 | N-(4-(2-(3-(hydroxymethyl)phenylamino)pyrimidin-4-ylthio)phenyl)acrylamide | C | 6.2 | m/z 379.3 [M + H]+ | (d₆-Acetone, 300 MHz) δ 9.66 (br s, 1H), 8.52 (br s, 1H), 8.12 (d, J = 5.0, 1H), 7.91 (d, J = 8.5, 2H), 7.59 (d, J = 8.5, 2H), 7.59 (m, 2H), 7.14 (dd, J = 8.5, 8.0, 1H), 6.94 (m, 1H), 6.50 (dd, J = 17.0, 9.5, 1H), 6.39 (dd, J = 17.0, 2.5, 1H), 6.36 (d, J = 5.0, 1H), 5.77 (dd, J = 9.5, 2.5, 1H), 4.56 (d, J = 6.0, 2H), 4.11 (t, J = 6.0, 1H). |
| 279 | 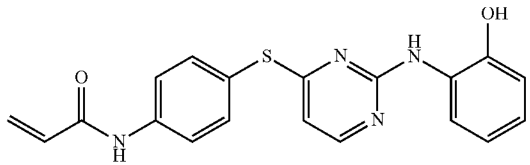 [SMILES: C=CC(=O)Nc1ccc(Sc2ccnc(Nc3ccccc3O)n2)cc1] | 364.10 | N-(4-(2-(2-hydroxyphenylamino)pyrimidin-4-ylthio)phenyl)acrylamide | C | 6.6 | m/z 365.3 [M + H]+ | (d₆-Acetone, 300 MHz) δ 9.64 (br s, 1H), 9.24 (br s, 1H), 8.14 (d, J = 5.5, 1H), 7.99 (br s, 1H), 7.93 (d, J = 8.5, 2H), 7.73 (dd, J = 8.0, 1.5, 1H), 7.60 (d, J = 8.5, 2H), 6.90-9.82 (m, 2H), 6.72 (ddd, J = 8.0, 6.5, 2.5, 1H), 6.50 (dd, J = 17.0, 9.5, 1H), 6.40 (d, J = 5.5, 1H), 6.40 (dd, J = 17.0, 2.5, 1H), 5.77 (dd, J = 9.5, 2.5, 1H), |
| 280 | 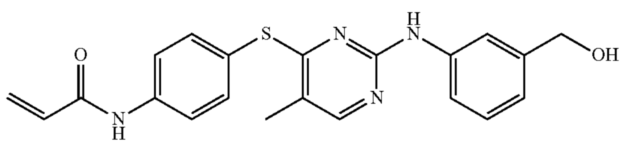 [SMILES: C=CC(=O)Nc1ccc(Sc2nc(Nc3cccc(CO)c3)ncc2C)cc1] | 392.13 | N-(4-(2-(3-(hydroxymethyl)phenylamino)-5-methylpyrimidin-4-ylthio)phenyl)acrylamide | C | 6.4 | m/z 394.3 [M + H]+ | (d₆-Acetone, 300 MHz) δ 9.62 (br s, 1H), 8.25 (br s, 1H), 8.00 (d, J = 0.5, 1H), 7.90 (d, J = 9.0, 2H), 7.56 (d, J = 9.0, 2H), 7.34-7.30 (m, 1H), 7.24-7.23 (m, 1H), 6.93 (dd, J = 8.0, 7.5, 1H), 6.82-6.78 (m, 1H), 6.52 (dd, J = 17.0, 9.5, 1H), 6.41 (dd, J = 17.0, 2.5, 1H), 5.78 (dd, J = 9.5, 2.5, 1H), 4.47 (d, J = 5.5, 2H), 3.95 (t, J = 5.5, 1H), 2.19 (d, J = 0.5, 3H). |
| 281 | 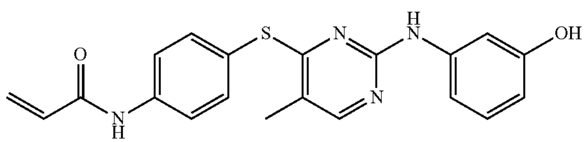 [SMILES: C=CC(=O)Nc1ccc(Sc2nc(Nc3cccc(O)c3)ncc2C)cc1] | 378.12 | N-(4-(2-(3-hydroxyphenylamino)-5-methylpyrimidin-4-ylthio)phenyl)acrylamide | C | 6.5 | m/z 379.3 [M + H]+ | (d₆-Acetone, 300 MHz) δ 9.61 (br s, 1H), 8.20 (br s, 1H), 7.99 (d, J = 1.0, 1H), 7.96 (br s, 1H), 7.89 (d, J = 8.5, 2H), 7.54 (d, J = 8.5, 2H), 6.94 (ddd, J = 8.5, 2.0, 1.0, 1H), 6.86 (ap t, J = 2.0, 1H), 6.79 (ap t, J = 8.0, 1H), 6.52 (dd, J = 17.0, 9.5, 1H), 6.40 (dd, J = 17.0, 2.5, 1H), 6.30 (ddd, J = 8.0, 2.0, 1.0, 1H), 5.77 (dd, J = 10.0, 2.5, 1H), 2.18 (d, J = 0.5, 3H). |
| 282 | 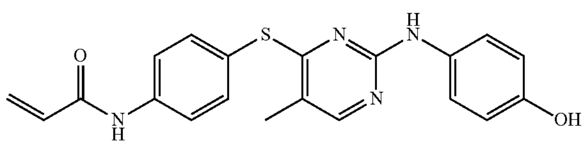 [SMILES: C=CC(=O)Nc1ccc(Sc2nc(Nc3ccc(O)cc3)ncc2C)cc1] | 378.12 | N-(4-(2-(4-hydroxyphenylamino)-5-methylpyrimidin-4-ylthio)phenyl)acrylamide | C | 6.5 | m/z 379.4 [M + H]+ | (d₆-Acetone, 300 MHz) δ 9.65 (br s, 1H), 8.05 (br s, 1H), 7.94 (s, 1H), 7.90 (d, J = 8.5, 2H), 7.77 (br s, 1H), 7.54 (d, J = 8.5, 2H), 7.15 (d, J = 9.0m 2H), 6.57-6.52 (m, 3H), 6.40 (dd, 17.0, 2.5, 1H), 5.77 (dd, J = 10.0, 2.5, 1H), 2.16 (s, 3H). |

TABLE 1-continued

| Compound number | Structure | Exact mass | Name | LCMS method | retention time (min) | Observed m/z | 1H NMR |
|---|---|---|---|---|---|---|---|
| 283 | 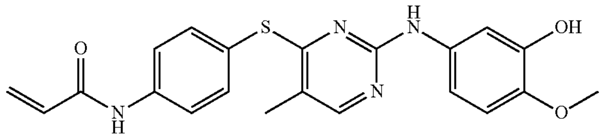 [SMILES: C=CC(=O)Nc1ccc(Sc2nc(Nc3ccc(OC)c(O)c3)ncc2C)cc1] | 408.13 | N-(4-(2-(3-hydroxy-4-methoxyphenyl-amino)-5-methyl-pyrimidin-4-ylthio)phenyl)acrylamide | C | 6.6 | m/z 409.4 [M + H]+ | (d$_6$-Acetone, 300 MHz) δ 9.66 (br s, 1H), 8.05 (br s, 1H), 7.95 (d, J = 0.5, 1H), 7.92 (d, J = 8.5, 2H), 7.55 (d, J = 8.5, 2H), 7.22 (br s, 1H), 6.83 (dd, J = 9.0, 2.5, 1H), 6.53 (dd, J = 17.0, 10.0, 1H), 6.50 (d, J = 8.0, 1H), 6.40 (dd, J = 17.0, 2.0, 1H), 5.77 (dd, J = 10.0, 2.0, 1H), 3.68 (s, 3H), 2.17 (d, J = 0.5, 3H). |
| 284 | 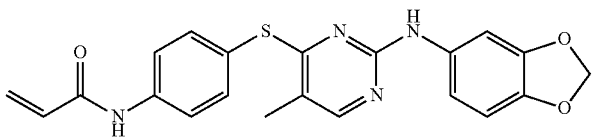 [SMILES: C=CC(=O)Nc1ccc(Sc2nc(Nc3ccc4c(c3)OCO4)ncc2C)cc1] | 406.11 | N-(4-(2-(benzo[d][1,3]dioxol-5-ylamino)-5-methylpyrimidin-4-ylthio)phenyl)acrylamide | C | 7.0 | m/z 407.4 [M + H]+ | (d$_6$-Acetone, 300 MHz) δ 9.58 (br s, 1H), 8.21 (br s, 1H), 7.96 (s, 1H), 7.90 (d, J = 8.5, 2H), 7.53 (d, J = 8.5, 2H), 6.96 (d, J = 2.0, 1H), 6.77 (dd, J = 8.5, 2.0, 1H), 6.53 (dd, J = 17.0, 9.5, 1H), 6.50 (d, J = 8.5, 1H), 6.41 (dd, J = 17.0, 2.0, 1H), 5.81 (s, 2H), 5.77 (dd, J = 9.5, 2.0, 1H), 2.17 (d, J = 0.5, 3H). |
| 285 | 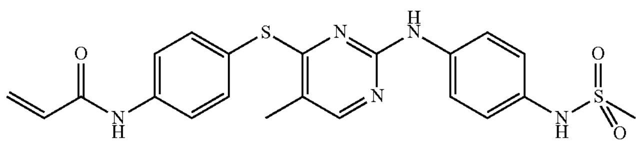 [SMILES: C=CC(=O)Nc1ccc(Sc2nc(Nc3ccc(NS(C)(=O)=O)cc3)ncc2C)cc1] | 455.11 | N-(4-(5-methyl-2-(4-(methylsulfon-amido)phenyl-amino)pyrimidin-4-ylthio)phenyl)acrylamide | C | 6.5 | m/z 456.3 [M + H]+ | (d$_6$-DMSO, 300 MHz) δ 10.37 (br s, 1H), 9.31 (br s, 1H), 9.19 (br s, 1H), 8.06 (d, J = 0.5, 1H), 7.85 (d, J = 8.5, 2H), 7.55 (d, J = 8.5, 2H), 7.17 (d, J = 9.0, 2H), 6.79 (d, J = 9.0, 2H), 6.49 (dd, J = 17.0, 10.0, 1H), 6.29 (dd, J = 17.0, 2.0, 1H), 5.80 (dd, J = 10.0, 2.0, 1H), 2.80 (s, 3H), 2.15 (s, 3H). |
| 286 | 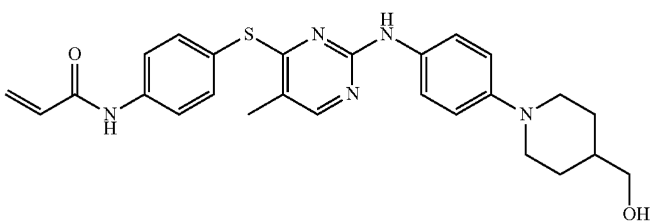 [SMILES: C=CC(=O)Nc1ccc(Sc2nc(Nc3ccc(N4CCC(CO)CC4)cc3)ncc2C)cc1] | 475.20 | N-(4-(2-(4-(4-(hydroxymethyl)piperidin-1-yl)phenylamino)-5-methylpyrimidin-4-ylthio)phenyl)acrylamide | C | 6.4 | m/z 476.3 [M + H]+ | (d-Chloroform, 300 MHz) δ 7.83 (s, 1H) 7.82 (d, J = 7.5, 2H), 7.54 (d, J = 8.5, 2H), 6.94 (d, J = 9.0, 2H), 6.65 (d, J = 9.0, 2H), 6.50 (dd, J = 17.0, 3.0, 1H), 6.42 (dd, J = 17.0, 8.5, 1H), 5.81 (dd, J = 8.5, 3.0, 1H), 3.48 (d, J = 6.5, 2H), 3.44 (br d, J = 12.5, 2H), 2.57 (d ap t, J = 12.0, 3.0, 2H), 2.20 (s, 3H), 1.79 (br d, J = 12.5, 2H), 1.58 (br s, 1H), 1.39 (ddd, J = 12.5, 3.5, 0.5, 1H), 1.29 (ddd, J = 12.5, 4.0, 1.0, 1H). |
| 287 | 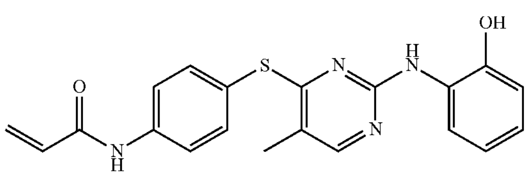 [SMILES: C=CC(=O)Nc1ccc(Sc2nc(Nc3ccccc3O)ncc2C)cc1] | 378.12 | N-(4-(2-(2-hydroxyphenyl-amino)-5-methyl-pyrimidin-4-ylthio)phenyl)acrylamide | E | 10.1 | m/z 379.3 [M + H]+ | (d$_6$-Acetone, 300 MHz) δ 9.64 (br s, 1H), 8.01 (d, J = 1.0, 1H), 7.92 (d, J = 9.0, 2H), 7.66 (br s, 1H), 7.56 (d, J = 9.0, 2H), 7.43 (dd, J = 8.0, 1.5, 1H), 6.78 (dd, J = 8.0, 2.0, 1H), 6.67 (ddd, J = 8.0, 8.0, 1.5, 1H), 6.52 (dd, J = 17.0, 9.5, 1H), 6.54-6.48 (m, 1H), 6.41 (dd, J = 17.0, 2.5, 1H), 5.77 (dd, J = 9.0, 2.5, 1H), 2.20 (d, J = 1.0, 3H). |

TABLE 1-continued

| Compound number | Structure | Exact mass | Name | LCMS method | retention time (min) | Observed m/z | ¹H NMR |
|---|---|---|---|---|---|---|---|
| 288 | 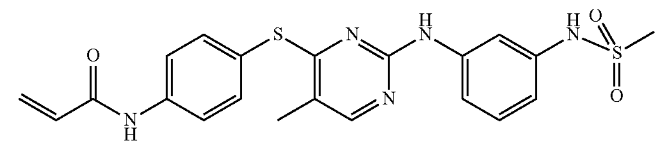 [SMILES: C=CC(=O)Nc1ccc(Sc2nc(Nc3cccc(NS(C)(=O)=O)c3)ncc2C)cc1] | 455.11 | N-(4-(5-methyl-2-(3-(methylsulfonamido phenyl-amino)pyrimidin-4-ylthio)phenyl) acrylamide | C | 6.6 | m/z 456.3 [M + H]+ | (d-Chloroform, 300 MHz) δ 7.72 (s, 1H), 7.62 (d, J = 8.5, 2H), 7.36 (d, J = 8.5, 2H), 6.91 (ddd, J = 8.0, 2.0, 1.0, 1H), 6.81 (ap t, J = 2.0, 1H), 6.76, (ap t, J = 8.0, 1H), 6.56 (ddd, J = 8.0, 2.0, 1.0, 1H), 6.27 (d, J = 4.5, 1H), 6.26 (d, J = 7.5, 1H), 5.62 (dd, J = 7.5, 4.5, 1H), 2.74 (s, 3H), 2.03 (d, J = 0.5, 3H). |
| 289 | 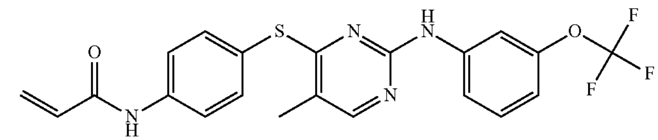 [SMILES: C=CC(=O)Nc1ccc(Sc2nc(Nc3cccc(OC(F)(F)F)c3)ncc2C)cc1] | 446.10 | N-(4-(5-methyl-2-(3-(trifluoromethoxy) phenylamino) pyrimidin-4-ylthio) phenyl)acrylamide | C | 7.7 | m/z 447.3 [M + H]+ | (d₆-Acetone, 300 MHz) δ 9.64 (br s, 1H), 8.05 (d, J = 0.5, 1H), 7.91 (d, J = 8.5, 2H), 7.65 (d, J = 8.5, 2H), 7.44 (ddd, J = 8.0, 2.0, 1.0, 1H), 7.36 (br s, 1H), 7.07 (ap t, J = 8.0, 1H), 6.71 (ddd, J = 8.0, 2.0, 1.0, 1H), 6.52 (dd, J = 17.0, 10.0, 1H), 6.41 (dd, J = 17.0, 2.5, 1H), 5.78 (dd, J = 9.5, 2.5, 1H) 2.20 (d, J = 0.5, 3H). |
| 290 | 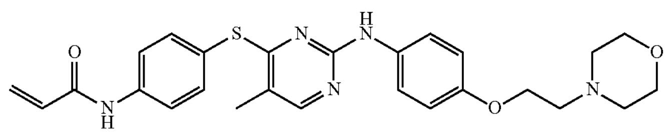 [SMILES: C=CC(=O)Nc1ccc(Sc2nc(Nc3ccc(OCCN4CCOCC4)cc3)ncc2C)cc1] | 491.20 | N-(4-(5-methyl-2-(4-(2-morpholinoethoxy)phenylamino) pyrimidin-4-ylthio)phenyl)acrylamide | D | 4.5 | m/z 492.4 [M + H]+ | (d₆-Acetone, 300 MHz) δ 9.72 (br s, 1H), 7.95 (d, J = 0.5, 1H), 7.94 (d, J = 9.0, 2H), 7.56 (d, J = 9.0, 2H), 7.17 (d, J = 9.0, 2H), 6.59 (d, J = 9.0, 2H), 6.56 (dd, J = 17.0, 9.5, 1H), 6.45 (dd, J = 17.0, 2.5, 1H), 5.83 (dd, J = 9.5, 2.5, 1H), 3.96 (t, J = 5.5, 2H), 3.61 (m, 4H), 2.65 (t, J = 5.5, 2H), 2.49 (m, 4H). |
| 291 | 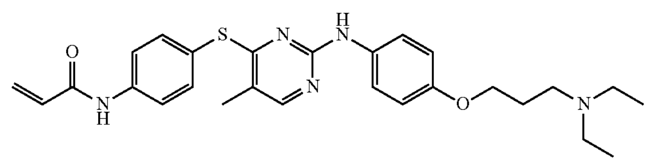 [SMILES: C=CC(=O)Nc1ccc(Sc2nc(Nc3ccc(OCCCN(CC)CC)cc3)ncc2C)cc1] | 491.24 | N-(4-(2-(4-(3-(diethyl-amino)propoxy) phenylamino)-5-methylpyrimidin-4-ylthio)phenyl) acrylamide | D | 4.6 | m/z 492.4 [M + H]+ | (d₆-Acetone, 300 MHz) δ 9.83 (br s, 1H), 8.14 (br s, 1H), 7.95 (d, J = 9.0, 2H), 7.94 (d, J = 1.0, 1H), 7.56 (d, J = 9.0, 2H), 7.17 (d, J = 9.0, 2H) 6.59 (d, J = 9.0, 2H), 6.56 (dd, J = 17.0, 9.5, 1H) 6.45 (dd, J = 17.0, 2.5, 1H), 5.83 (dd, J = 9.5, 2.5, 1H), 3.96 (t, J = 5.5, 2H), 3.61 (m, 4H), 2.65 (t, J = 5.5, 2H), 2.49 (m, 4H). |
| 292 | 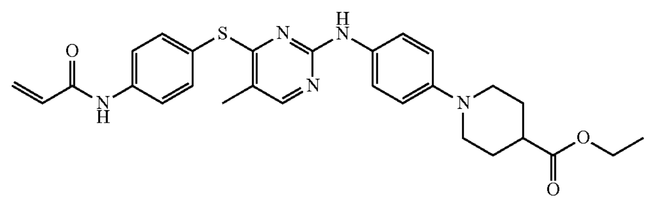 [SMILES: C=CC(=O)Nc1ccc(Sc2nc(Nc3ccc(N4CCC(C(=O)OCC)CC4)cc3)ncc2C)cc1] | 517.21 | ethyl 1-(4-(4-(4-acrylamidophenyl-thio)-5-methyl-pyrimidin-2-ylamino) phenyl)piperidine-4-carboxylate | C | 7.4 | m/z 518.4 [M + H]+ | (d₆-Acetone, 300 MHz) δ 9.80 (br s, 1H), 8.04 (br s, 1H), 7.95 (d, J = 8.5, 2H), 7.92 (s, 1H), 7.54 (d, J = 8.5, 2H), 7.08 (d, J = 9.0, 2H), 6.61 (d, J = 9.0, 2H), 6.57 (dd, J = 17.0, 9.5, 1H), 6.46 (dd, J = 17.0, 2.5, 1H), 5.81 (dd, J = 9.5, 2.5, 1H), 4.12 (q, J = 7.0, 2H), 3.44 (d t, J = 13.0, 3.5, 2H), 2.59 (d t, J = 12.0, 2.5, 2H), 2.35 (t t, J = 11.5, 4.0, 1H), 2.17 (s, 3H), 1.92 (br dd, J = 13.5, 3.5, 2H), 1.73 (br ddd, J = 24.0, 11.5, 3.5, 2H), 1.25 (t, J = 7.0, 3H). |

TABLE 1-continued

| Compound number | Structure | Exact mass | Name | LCMS method | retention time (min) | Observed m/z | ¹H NMR |
|---|---|---|---|---|---|---|---|
| 293 | 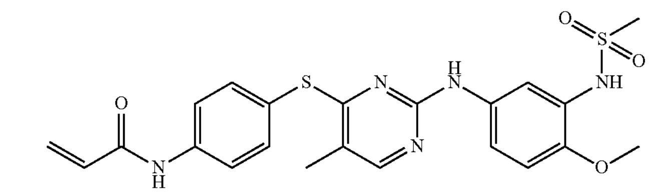 [SMILES: C=CC(=O)Nc1ccc(Sc2nc(Nc3ccc(OC)c(NS(C)(=O)=O)c3)ncc2C)cc1] | 485.12 | N-(4-(2-(4-methoxy-3-(methylsulfon-amidophenylamino)-5-methylpyrimidin-4-ylthio)phenyl)acrylamide | C | 6.7 | m/z 486.3 [M + H]+ | (d₆-Acetone, 300 MHz) δ 9.72 (br s, 1H), 8.38 (br s, 1H), 7.97 (d, J = 0.5, 1H), 7.93 (d, J = 9.0, 2H), 7.57 (dd, J = 9.0, 2H), 7.22 (d, J = 2.5, 1H), 7.22 (dd, J = 9.5, 2.5, 1H), 6.59 (d, J = 9.5, 1H), 6.54 (dd, J = 17.0, 9.5, 1H), 6.41 (dd, J = 17.0, 2.0, 1H), 5.78 (dd, J = 9.5, 2.0, 1H), 3.74 (s, 3H), 2.92 (s, 3H), 2.18 (d, J = 0.5, 3H). |
| 294 | 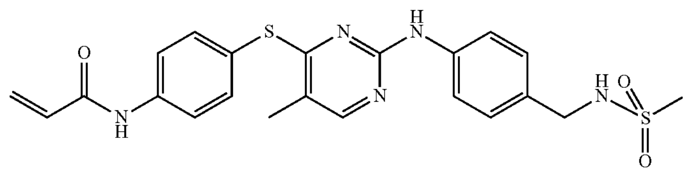 [SMILES: C=CC(=O)Nc1ccc(Sc2nc(Nc3ccc(CNS(C)(=O)=O)cc3)ncc2C)cc1] | 469.12 | N-(4-(5-methyl-2-(4-(methylsulfon-amidomethyl)phenyl-aminopyrimidin-4-ylthio)phenyl)acrylamide | C | 6.6 | m/z 470.3 [M + H]+ | (d-Chloroform & d₄-Methanol, 300 MHz) δ 7.87 (d, J = 0.5, 1H), 7.77 (d, J = 8.5, 2H), 7.55 (d, J = 8.5, 2H), 7.09 (d, J = 9.0, 2H), 7.01 (d, J = 9.0, 2H), 6.51 (s, 1H), 6.49 (d, J = 4.0, 1H), 5.84 (dd, J = 8.0, 4.0, 1H), 4.11 (s, 2H), 2.72 (s, 3H), 2.22 (d, J = 0.5, 3H). |
| 295 | 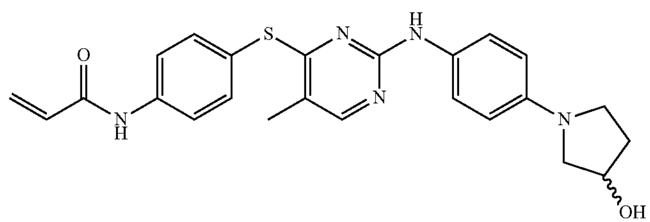 [SMILES: C=CC(=O)Nc1ccc(Sc2nc(Nc3ccc(N4CCC(O)C4)cc3)ncc2C)cc1] | 447.17 | N-(4-(2-(4-(3-hydroxypyrrolidin-1-yl)phenylamino)-5-methylpyrimidin-4-ylthio)phenyl)acrylamide | C | 6.5 | m/z 448.3 [M + H]+ | (d₆-DMSO, 300 MHz) δ 10.51 (br s, 1H), 8.95 (br s, 1H), 7.97 (d, J = 0.5, 1H), 7.89 (d, J = 8.5, 2H), 7.54 (d, J = 8.5, 2H), 6.93 (d, J = 8.5, 2H), 6.51 (dd, J = 17.0, 10.0, 1H), 6.32 (dd, J = 17.0, 2.0, 1H), 5.82 (dd, J = 10.0, 2.0, 1H), 4.84 (br s, 1H), 4.30 (br s, 1H), 3.23 (dd, J = 10.5, 5.5, 1H), 3.12 (br d, J = 5.0, 1H), 3.04 (dd, J = 8.5, 4.0, 1H), 2.89 (br d, J = 10.5, 1H), 2.12 (s, 3H), 1.96-1.90 (m, 1H), 1.81-1.74 (m, 1H). |
| 296 | 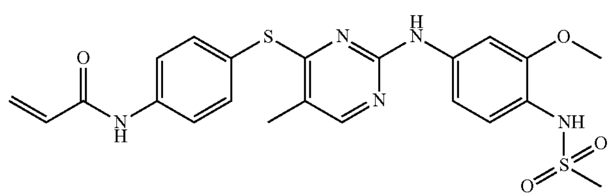 [SMILES: C=CC(=O)Nc1ccc(Sc2nc(Nc3ccc(NS(C)(=O)=O)c(OC)c3)ncc2C)cc1] | 485.12 | N-(4-(2-(3-methoxy-4-(methylsulfon-amidophenyl)amino)-5-methyl-pyrimidin-4-ylthio)phenyl)acrylamide | C | 6.6 | m/z 486.2 [M + H]+ | (d₆-Acetone & d6-DMSO, 300 MHz) δ 9.95 (br s, 1H), 8.73 (br s, 1H), 8.03 (d, J = 1.0, 1H), 7.90 (d, J = 8.5, 2H), 7.71 (s, 1H), 7.53 (d, J = 8.5, 2H), 7.10 (d, J = 2.0, 1H), 7.04 (dd, J = 8.5, 2.5 1H), 6.96 (d, J = 8.5, 1H), 6.55 (dd, J = 17.0, 10.0, 1H), 6.37 (dd, J = 17.0, 2.5, 1H), 5.74 (dd, J = 10.0, 2.0, 1H), 3.72 (s, 3H), 2.85 (s, 3H), 2.19 (d, J = 1.0, 3H). |

TABLE 1-continued

| Compound number | Structure | Exact mass | Name | LCMS method | retention time (min) | Observed m/z | ¹H NMR |
|---|---|---|---|---|---|---|---|
| 297 | 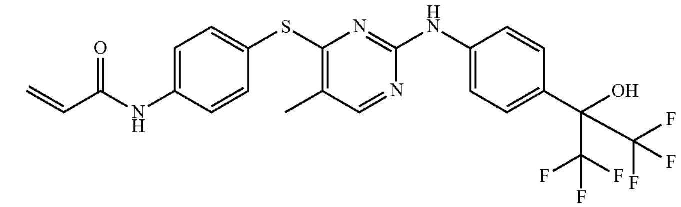 [SMILES: C=CC(=O)Nc1ccc(Sc2nc(Nc3ccc(C(O)(C(F)(F)F)C(F)(F)F)cc3)ncc2C)cc1] | 528.11 | N-(4-(2-(4-(1,1,1,3,3,3-hexafluoro-2-hydroxypropan-2-yl)phenylamino)-5-methylpyrimidin-4-ylthio)phenyl)acrylamide | C | 7.2 | m/z 529.2 [M + H]+ | (d₆-Acetone, 300 MHz) δ 9.69 (br s, 1H), 8.58 (br s, 1H), 8.04 (d, J = 0.5, 1H), 7.93 (d, J = 8.5, 2H), 7.60 (d, J = 9.0, 2H), 7.43 (s, 4H), 7.08 (br s, 1H), 6.52 (dd, J = 17.0, 10.0, 1H), 6.41 (dd, J = 17.0, 2.5, 1H), 5.78 (dd, J = 9.5, 2.5, 1H), 2.21 (d, J = 0.5, 3H). |
| 298 | 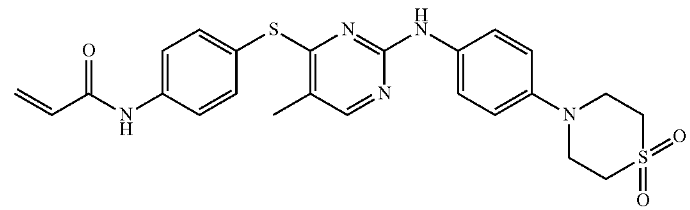 [SMILES: C=CC(=O)Nc1ccc(Sc2nc(Nc3ccc(N4CCS(=O)(=O)CC4)cc3)ncc2C)cc1] | 495.14 | N-{4-[(2-{[4-(1,1-dioxo-1λ⁶,4-thiomorpholin-4-yl)phenyl]amino}-5-methylpyrimidin-4-yl)sulfanyl]phenyl}prop-2-enamide | C | 6.6 | m/z 496.3 [M + H]+ | (d₆-DMSO, 300 MHz) δ 10.52 (br, s, 1H), 9.16 (br s, 1H), 7.87 (d, J = 8.5, 2H), 7.56 (d, J = 8.5, 2H), 7.03 (d, J = 9.0, 2H), 6.56 (d, J = 9.0, 2H), 6.53 (dd, J = 17.0, 9.5, 1H), 6.37 (dd, J = 17.0, 2.5, 1H), 5.88 (dd, J = 9.5, 2.5, 1H), 3.51-3.48 (m, 4H), 3.05-3.01 (m, 4H), 2.14 (s, 3H). |
| 299 | 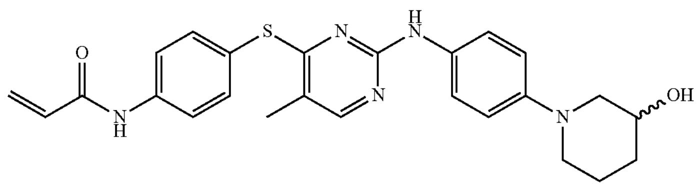 [SMILES: C=CC(=O)Nc1ccc(Sc2nc(Nc3ccc(N4CCCC(O)C4)cc3)ncc2C)cc1] | 461.19 | N-(4-(2-(4-(3-hydroxypiperidin-1-yl)phenylamino)-5-methylpyrimidin-4-ylthio)phenyl)acrylamide | C | 6.5 | m/z 462.3 [M + H]+ | (d₆-Acetone, 300 MHz) δ 9.74 (br s, 1H), 8.04 (br s, 1H), 7.95 (d, J = 9.0, 2H), 7.93 (d, J = 0.5, 1H), 7.55, (d, J = 9.0, 2H), 7.10 (d, J = 9.0, 2H), 6.62 (d, J = 9.0, 2H), 6.57 (dd, J = 17.0, 9.5, 1H), 6.45 (dd, J = 17.0, 2.5, 1H), 5.80 (dd, J = 9.5, 2.5, 1H), 3.72-3.70 (m, 1H), 3.45-3.39 (m, 1H), 3.22-3.15 (m, 1H), 2.66-2.49 (m, 2H), 2.18 (d, J = 0.5, 3H), 1.95-1.75 (m, 2H), 1.64-1.52 (m, 1H), 0.90-0.86 (m, 1H). |
| 300 | 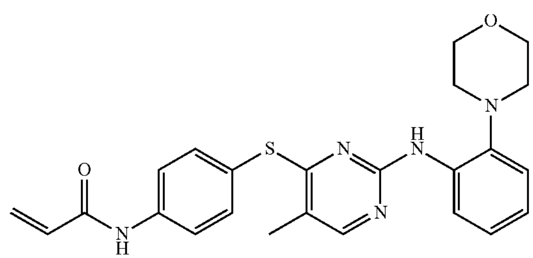 [SMILES: C=CC(=O)Nc1ccc(Sc2nc(Nc3ccccc3N3CCOCC3)ncc2C)cc1] | 447.17 | N-(4-(5-methyl-2-(2-morpholinophenylamino)pyrimidin-4-ylthio)phenyl)acrylamide | C | 7.4 | m/z 448.3 [M + H]+ | (d₆-Acetone, 300 MHz) δ 9.71 (br s, 1H), 8.23 (br s, 1H0, 8.04 (d, J = 0.5, 1H), 7.96 (d, J = 8.5, 2H), 7.66-7.63 (m, 1H), 7.57 (d, J = 9.0, 2H), 7.13-7.09 (m, 1H), 6.81-6.76 (m, 2H), 6.53 (dd, J = 17.0, 10.0, 1H), 6.41 (dd, J = 17.0, 2.5, 1H), 5.77 (dd, J = 10.0, 2.5, 1H), 3.80-3.77 (m, 4H), 2.80-2.77 (m, 4H), 2.21 (d, J = 0.5, 3H). |

TABLE 1-continued

| Compound number | Structure | Exact mass | Name | LCMS method | retention time (min) | Observed m/z | ¹H NMR |
|---|---|---|---|---|---|---|---|
| 301 | 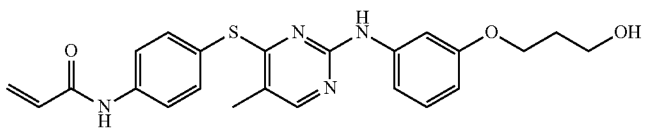 [SMILES: C=CC(=O)Nc1ccc(Sc2nc(Nc3cccc(OCCCO)c3)ncc2C)cc1] | 436.16 | N-(4-(2-(3-hydroxypropoxy)phenylamino)-5-methylpyrimidin-4-ylthio)phenyl)acrylamide | C | 6.6 | m/z 437.3 [M + H]+ | (d₆-Acetone, 300 MHz) δ 9.62 (br s, 1 H), 8.24 (br s, 1H), 8.01 (d, J = 0.5, 1H), 7.89 (d, J = 9.0, 2H), 7.54 (d, J = 9.0, 2H), 7.33 (ddd, J = 8.0, 2.0, 1.0, 1H), 6.95 (ap t, J = 2.0, 1H), 6.87 (ap t, J = 8.0, 1H), 6.52 (dd, J = 17.0, 9.5, 1H), 6.41 (dd, J = 17.0, 2.5, 1H), 6.39 (ddd, J = 8.0, 2.5, 1.0, 1H), 4.00 (t, J = 6.5, 2H), 3.70 (ddd, J = 11.5, 6.0, 5.0, 2H), 3.59 (dd, J = 5.5, 5.0, 1H), 2.19 (d, J = 0.5, 3H), 1.92 (quin, J = 6.5, 2H). |
| 302 | 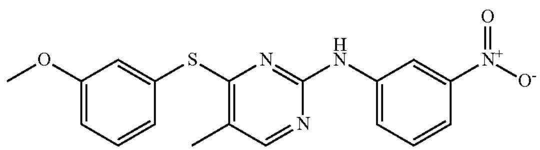 [SMILES: COc1cccc(Sc2nc(Nc3cccc([N+](=O)[O-])c3)ncc2C)c1] | 368.09 | 4-(3-methoxyphenylthio)-5-methyl-N-(3-nitrophenyl)pyrimidin-2-amine | C | 7.9 | m/z 369.2 [M + H]+ | (d₆-DMSO, 300 MHz) δ 9.92 (br s, 1H), 8.18 (d, J = 1.0, 1H), 8.11 (ap t, J = 2.0, 1H), 7.69 (ddd, J = 8.0, 2.0, 0.5, 1H), 7.63 (ddd, J = 8.0, 2.0, 1.0, 1H), 7.46-7.40 (m, 1H), 7.20-7.14 (m, 3H), 7.09 (ap t, J = 8.5, 1H), 3.73 (s, 3H), 2.18 (d, J = 0.5, 3H). |
| 303 | 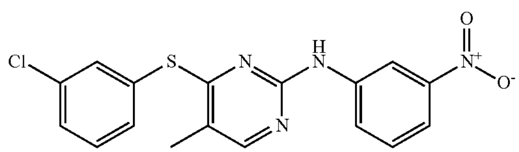 [SMILES: Cc1cnc(Nc2cccc([N+](=O)[O-])c2)nc1Sc1cccc(Cl)c1] | 372.04 | 4-(3-chlorophenylthio)-5-methyl-N-(3-nitrophenyl)pyrimidin-2-amine | C | 8.3 | m/z 373.2/ 375.2 [M + H]+ | (d₆-DMSO, 300 MHz) δ 9.90 (br s, 1H), 8.20 (d, J = 1.0, 1H), 8.14 (ap t, J = 2.5, 1H), 7.71-7.51 (m, 6H), 7.14 (ap t, J = 8.5, 1H), 2.19 (d, J = 0.5, 3H). |
| 304 | 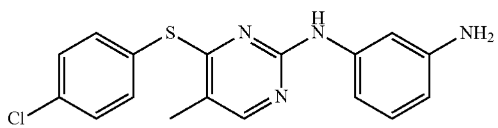 [SMILES: Cc1cnc(Nc2cccc(N)c2)nc1Sc1ccc(Cl)cc1] | 342.07 | N1-(4-(4-chlorophenylthio)-5-methylpyrimidin-2-yl)benzene-1,3-diamine | I | 11.5 | m/z 343.2/ 345.2 [M + H]+ | (d₆-Acetone, 300 MHz) δ 8.05 (br s, 1H), 8.00 (d, J = 0.5, 1H), 7.62 (d, J = 8.5, 2H), 7.54 (d, J = 8.5, 2H), 6.73 (ap t, J = 8.0, 1H), 6.64 (ap t, J = 2.0, 2H), 6.60 (ddd, J = 8.0, 2.0, 1.0, 1H), 6.22 (ddd, J = 8.0, 2.0, 1.0, 1H), 2.17 (d, J = 0.5, 3H). |
| 306 | 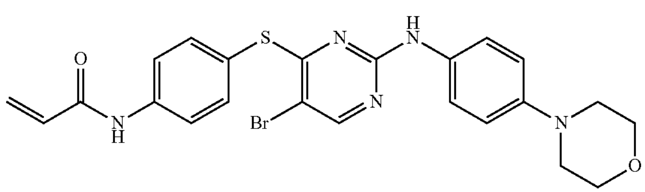 [SMILES: C=CC(=O)Nc1ccc(Sc2nc(Nc3ccc(N4CCOCC4)cc3)ncc2Br)cc1] | 511.07 | N-(4-(5-bromo-2-(4-morpholinophenylamino)pyrimidin-4-ylthio)phenyl)acrylamide | C | 7.24 | m/z 511.2/ 513.2 [M + H]+ | ¹H-NMR (300 MHz, CDCl₃) δ 10.53 (s, 1H), 9.50 (s, 1H), 7.89 (d, J = 8.7 Hz, 2H), 7.57 (d, J = 8.7 Hz, 2H), 6.94 (bd, J = 8.8 Hz, 2H), 6.54-6.45 (m, 3H), 6.33 (dd, J = 16.9, 2.1 Hz, 1H), 5.86 (dd, J = 9.9, 2.1 Hz, 1H), 3.64 (m, 4H), 2.85 (m, 4H) |

TABLE 1-continued

| Compound number | Structure | Exact mass | Name | LCMS method | retention time (min) | Observed m/z | $^1$H NMR |
|---|---|---|---|---|---|---|---|
| 307 | 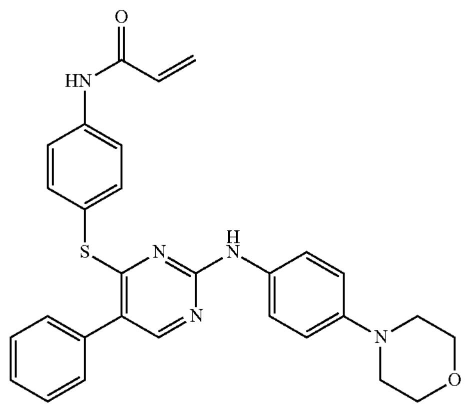 [SMILES: C=CC(=O)Nc1ccc(Sc2nc(Nc3ccc(N4CCOCC4)cc3)ncc2-c2ccccc2)cc1] | 509.19 | N-(4-(2-(4-morpholinophenyl-amino)-5-phenyl-pyrimidin-4-ylthio)phenyl)acrylamide | C | 7.41 | m/z 510.3 [M + H]+ | $^1$H-NMR (300 MHz, D$_6$-DMSO) δ 9.43 (s, 1H), 8.13 (s, 1H), 7.91 (d, J = 8.7 Hz, 2H), 7.59-7.53 (m, 6H), 7.47 (m, 1H), 7.05 (bd, J = 8.7 Hz, 2H), 6.56-6.51 (m, 3H), 6.38 (dd, J = 16.9, 1.9 Hz, 1H), 5.90 (dd, J = 10.0, 1.9 Hz, 1H), 3.69 (m, 4H), 2.91 (m, 4H) |
| 308 | 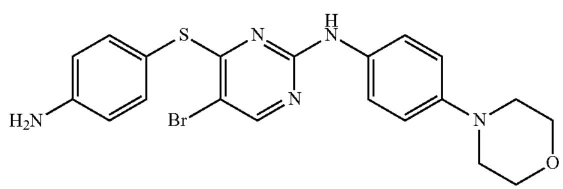 | 457.06 | 4-(4-aminophenyl-thio)-5-bromo-N-(4-morpholino-phenyl)pyrimidin-2-amine | C | 7.24 | m/z 458.3/ 460.3 [M + H]+ | $^1$H-NMR (300MHz, D$_6$-DMSO) δ 7.94 (bs, 1H), 7.14 (d, J = 8.5 Hz, 2H), 7.01 (d, J = 9.0 Hz, 2H), 6.65 (d, J = 8.5 Hz, 2H), 6.57 (d, J = 9.0 Hz, 2H), 3.71 (m, 4H), 2.90 (m, 4H) |
| 309 | 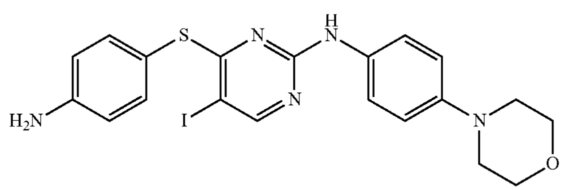 [SMILES: Nc1ccc(Sc2nc(Nc3ccc(N4CCOCC4)cc3)ncc2I)cc1] | 505.04 | 4-(4-aminophenyl-thio)-5-iodo-N-(4-morpholino-phenyl)pyrimidin-2-amine | C | 7.23 | m/z 506.2 [M + H]+ | $^1$H-NMR (300 MHz, D$_6$-DMSO) δ 9.36 (s, 1H), 8.27 (s, 1H), 7.17 (d, J = 8.5 Hz, 2H), 7.06 (d, J = 9.0 Hz, 2H), 6.68 (d, J = 8.5 Hz, 2H), 6.65 (d, J = 9.0 Hz, 2H), 5.73 (bs, 2H), 3.72 (m, 4H), 3.00 (m, 4H) |

| Compound number | Structure | Exact mass | Name | LCMS method | retention time (min) | Observed m/z | 1H NMR |
|---|---|---|---|---|---|---|---|
| 310 | 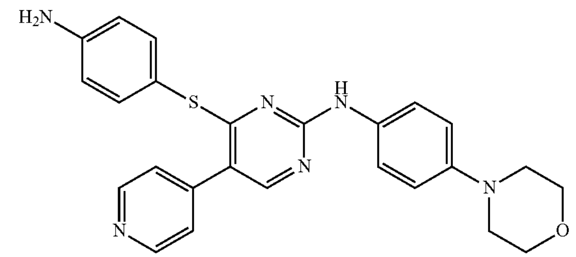 [SMILES: Nc1ccc(Sc2nc(Nc3ccc(N4CCOCC4)cc3)ncc2-c2ccncc2)cc1] | 456.17 | 4-(4-aminophenyl-thio)-N-(4-morpholinophenyl)-5-(pyridin-4-yl)pyrimidin-2-amine | C | 6.29 | m/z 457.3 [M + H]+ | 1H-NMR (300 MHz, D6-DMSO) δ 9.50 (s, 1H), 8.66 (d, J = 6.0 Hz, 2H), 8.14 (s, 1H), 7.60 (d, J = 6.0 Hz, 2H), 7.17 (d, J = 8.5 Hz, 2H), 7.13 (d, J = 9.2 Hz, 2H), 6.68 (d, J = 8.5 Hz, 2H), 6.67 (d, J = 9.2 Hz, 2H), 3.71 (m, 4H), 3.01 (m, 4H) |
| 311 | 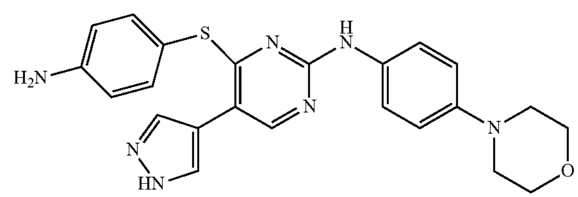 [SMILES: Nc1ccc(Sc2nc(Nc3ccc(N4CCOCC4)cc3)ncc2-c2cn[nH]c2)cc1] | 445.17 | 4-(4-aminophenyl-thio)-N-(4-morpholinophenyl)-5-(1H-pyrazol-4-yl)pyrimidin-2-amine | F | 5.73 | m/z 446.3 [M + H]+ | 1H-NMR (300 MHz, D6-acetone) δ 12.57 (b, 1H), 8.53 (bs, 1H), 8.14 (s, 1H), 7.92 (bs, 2H), 7.25 (d, J = 8.6 Hz, 4H), 6.86-6.75 (m, 4H), 5.34 (bs, 2H), 3.75 (m, 4H), 3.07 (m, 4H) |
| 312 | 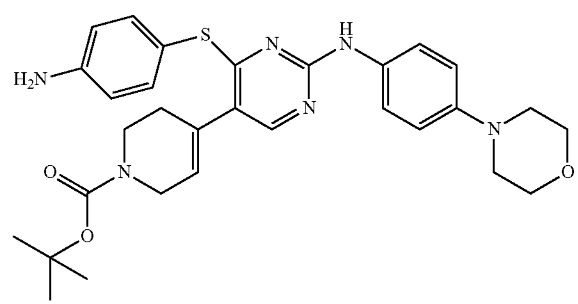 [SMILES: CC(C)(C)OC(=O)N1CC=C(c2cnc(Nc3ccc(N4CCOCC4)cc3)nc2Sc2ccc(N)cc2)CC1] | 560.26 | tert-butyl 4-(4-(4-aminophenylthio)-2-(4-morpholino-phenylamino)pyrimidin-5-yl)-5,6-dihydropyridine-1(2H)-carboxylate | F | 7.45 | m/z 561.4 [M + H]+ | 1H-NMR (300 MHz, D6-acetone) δ 8.21 (bs, 1H), 7.87 (s, 1H), 7.24 (d, J = 8.6 Hz, 2H), 7.23 (d, J = 9.0 Hz, 2H), 6.81 (d, J = 8.6 Hz, 2H), 6.77 (d, J = 9.0 Hz, 2H), 5.86 (m, 1H), 5.24 (bs, 2H), 4.07 (m, 2H), 3.74 (m, 4H), 3.64 (t, J = 5.6 Hz, 2H), 3.07 (m, 4H), 2.46 (m, 2H), 1.49 (s, 9H) |
| 313 | 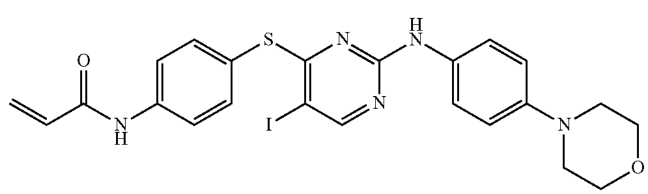 [SMILES: C=CC(=O)Nc1ccc(Sc2nc(Nc3ccc(N4CCOCC4)cc3)ncc2I)cc1] | 559.05 | N-(4-(5-iodo-2-(4-morpholinophenyl-aminopyrimidin-4-ylthio)phenyl)acrylamide | C | 7.15 | m/z 560.2 [M + H]+ | 1H-NMR (300 MHz, D6-DMSO) δ 10.54 (s, 1H), 9.45 (s, 1H), 8.33 (s, 1H), 7.88 (d, J = 8.7 Hz, 2H), 7.56 (d, J = 8.7 Hz, 2H), 6.92 (bd, J = 9.0 Hz, 2H), 6.54-6.43 (m, 3H), 6.33 (dd, J = 16.9, 2.0 Hz, 1H), 5.86 (dd, J = 9.9, 2.0 Hz, 1H), 3.63 (m, 4H), 2.85 (m, 4H) |

TABLE 1-continued

| Compound number | Structure | Exact mass | Name | LCMS method | retention time (min) | Observed m/z | ¹H NMR |
|---|---|---|---|---|---|---|---|
| 314 | 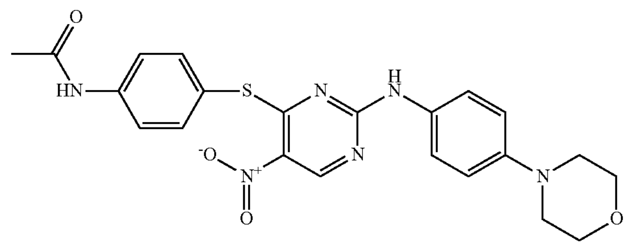 | 466.14 | N-(4-(2-(4-morpholinophenyl-amino)-5-nitro-pyrimidin-4-ylthio)phenyl)acetamide | C | 6.45 | m/z 467.3 [M + H]+ | ¹H-NMR (300 MHz, D₆-acetone) δ 10.4 (bs, 1H), 10.24 (bs, 1H), 9.03 (s, 1H), 7.86 (d, J = 8.7 Hz, 2H), 7.50 (d, J = 8.7 Hz, 2H), 7.05 (d, J = 9.2 Hz, 2H), 6.54 (d, J = 9.2 Hz, 2H), 3.75 (m, 4H), 2.97 (m, 4H), 2.12 (s, 3H) |
| 315 | 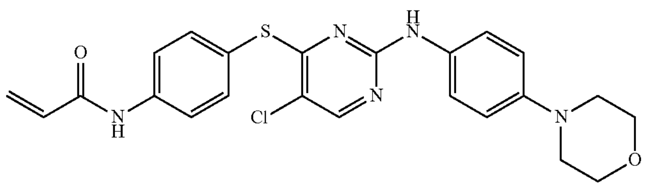 [SMILES: C=CC(=O)Nc1ccc(Sc2nc(Nc3ccc(N4CCOCC4)cc3)ncc2Cl)cc1] | 467.12 | N-(4-(5-chloro-2-(4-morpholino-phenylamino)pyrimidin-4-ylthio)phenyl)acrylamide | C | 7.01 | m/z 468.3/ 470.3 [M + H]+ | ¹H-NMR (300 MHz, D₆-DMSO) δ 10.56 (bs, 1H), 9.53 (bs, 1H), 8.23 (s, 1H), 7.90 (d, J = 6.8 Hz, 2H), 7.58 (d, J = 8.6 Hz, 2H), 6.94 (bd, J = 9.0 Hz, 2H), 6.54-6.44 (m, 3H), 6.33 (dd, J = 16.9, 2.1 Hz, 1H), 5.87 (dd, J = 10.0, 2.1 Hz, 1H), 3.62 (m, 4H), 2.85 (m, 4H) |
| 316 | 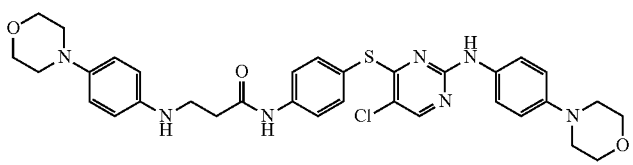 [SMILES: O=C(CCNc1ccc(N2CCOCC2)cc1)Nc1ccc(Sc2nc(Nc3ccc(N4CCOCC4)cc3)ncc2Cl)cc1] | 645.23 | N-(4-(5-chloro-2-(4-morpholino-phenylamino)pyrimidin-4-ylthio)phenyl)-3-(4-morpholino-phenylamino)propanamide | C | 7.14 | m/z 646.3/ 648.3 [M + H]+ | ¹H-NMR (300 MHz, D₆-DMSO) δ 10.36 (bs, 1H), 9.52 (bs, 1H), 8.23 (s, 1H), 7.81 (d, J = 8.7 Hz, 2H), 7.55 (d, J = 8.7 Hz, 2H), 6.98 (d, J = 8.9 Hz, 2H), 6.77 (d, J = 8.9 Hz, 2H), 6.57 (d, J = 8.9 Hz, 2H), 6.51 (d, J = 8.7 Hz, 2H), 5.22 (m, 1H), 3.65 (m, 4H), 3.45-3.25 (m, 12H), 2.86 (m, 4H) |
| 317 | 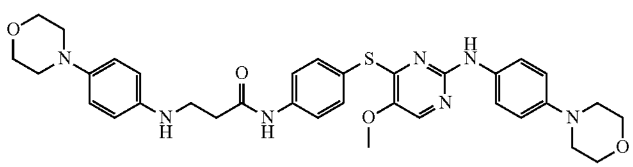 [SMILES: COc1cnc(Nc2ccc(N3CCOCC3)cc2)nc1Sc1ccc(NC(=O)CCNc2ccc(N3CCOCC3)cc2)cc1] | 641.28 | N-(4-(5-methoxy-2-(4-morpholino-phenylamino)pyrimidin-4-ylthio)phenyl)-3-(4-morpholino-phenylamino)propanamide | C | 6.59 | m/z 642.4 [M + H]+ | ¹H-NMR (300 MHz, D₆-DMSO) δ 10.32 (bs, 1H), 9.02 (bs, 1H), 8.02 (s, 1H), 7.79 (d, J = 8.7 Hz, 2H), 7.50 (d, J = 8.9 Hz, 2H), 6.99 (d, J = 9.2 Hz, 2H), 6.77 (d, J = 8.9 Hz, 2H), 6.57 (d, J = 8.7 Hz, 2H), 6.50 (d, J = 9.2 Hz, 2H), 5.20 (m, 1H), 3.87 (s, 3H), 3.70 (m, 4H), 3.47-3.27 (m, 12H), 2.87 (m, 4H) |
| 318 | 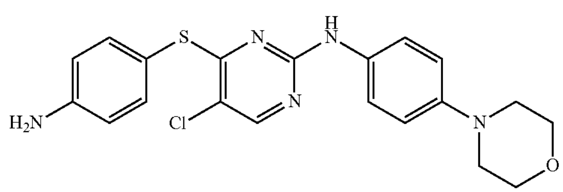 [SMILES: Nc1ccc(Sc2nc(Nc3ccc(N4CCOCC4)cc3)ncc2Cl)cc1] | 413.11 | 4-(4-aminophenyl-thio)-5-chloro-N-(4-morpholino-phenyl)pyrimidin-2-amine | C | 7.05 | m/z 414.2/ 416.3 [M + H]+ | ¹H-NMR (300 MHz, D₆-acetone) δ 8.46 (bs, 1H), 8.05 (s, 1H), 7.26 (d, J = 8.5 Hz, 2H), 7.20 (d, J = 9.0 Hz, 2H), 6.84 (d, J = 8.5 Hz, 2H), 6.78 (d, J = 9.0 Hz, 2H), 5.37 (bs, 2H), 3.73 (m, 4H), 3.05 (m, 4H), |

TABLE 1-continued

| Compound number | Structure | Exact mass | Name | LCMS method | retention time (min) | Observed m/z | ¹H NMR |
|---|---|---|---|---|---|---|---|
| 319 | 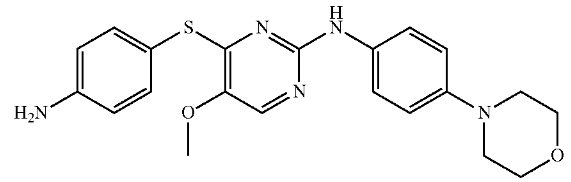 [SMILES: COc1cnc(Nc2ccc(N3CCOCC3)cc2)nc1Sc1ccc(N)cc1] | 409.16 | 4-(4-aminophenylthio)-5-methoxy-N-(4-morpholinophenyl)pyrimidin-2-amine | C | 6.41 | m/z 410.3 [M + H]+ | ¹H-NMR (300 MHz, D₆-acetone) δ 8.00 (bs, 1H), 7.88 (s, 1H), 7.23 (d, J = 8.3 Hz, 2H), 7.22 (d, J = 9.0 Hz, 2H), 6.82 (d, J = 8.3 Hz, 2H), 6.76 (d, J = 9.0 Hz, 2H), 5.26 (bs, 2H), 3.91 (s, 3H), 3.74 (m, 4H), 3.04 (m, 4H) |
| 320 | 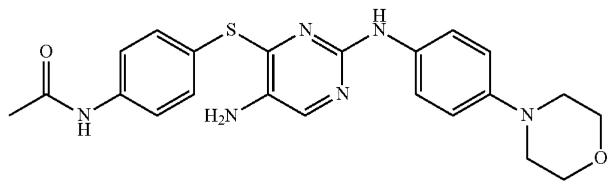 [SMILES: CC(=O)Nc1ccc(Sc2nc(Nc3ccc(N4CCOCC4)cc3)ncc2N)cc1] | 436.17 | N-(4-(5-amino-2-(4-morpholinophenylamino)pyrimidin-4-ylthio)phenyl)acetamide | C | 5.21 | m/z 437.3 [M + H]+ | ¹H-NMR (300 MHz, D₆-DMSO) δ 10.28 (bs, 1H), 8.66 (bs, 1H), 7.77 (d, J = 8.7 Hz, 2H), 7.77 (s, 1H), 7.50 (d, J = 8.7 Hz, 2H), 6.97 (d, J = 9.1 Hz, 2H), 6.48 (d, J = 9.1 Hz, 2H), 4.47 (bs, 2H), 3.73 (m, 4H), 3.24 (m, 4H), 2.10 (s, 3H) |
| 321 | 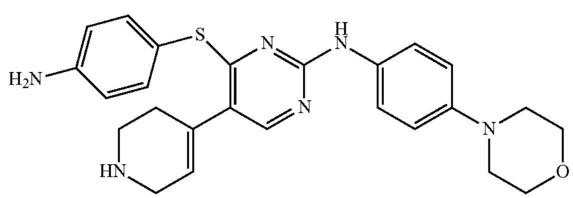 [SMILES: Nc1ccc(Sc2nc(Nc3ccc(N4CCOCC4)cc3)ncc2C2=CCNCC2)cc1] | 460.20 | 4-(4-aminophenylthio)-N-(4-morpholinophenyl)-5-(1,2,3,6-tetrahydropyridin-4-yl)pyrimidin-2-amine | C | 0.89 | m/z 461.3 [M + H]+ | ¹H-NMR (300 MHz, CDCl₃) δ 7.87 (s, 1H), 7.35 (d, J = 8.6 Hz, 2H), 7.06 (d, J = 9.0 Hz, 2H), 6.84 (bs, 1H), 6.78 (d, J = 8.6 Hz, 2H), 6.75 (m, 2H), 5.92 (m, 1H), 3.97 (bs, 2H), 3.90 (m, 4H), 3.58 (m, 2H), 3.16 (t, J = 5.6 Hz, 2H), 3.12 (m, 4H), 2.44 (m, 2H) |
| 322 | 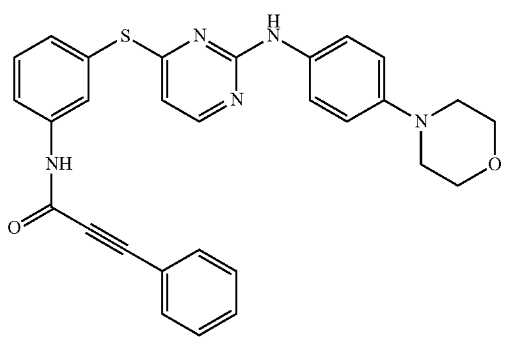 [SMILES: O=C(C#Cc1ccccc1)Nc1cccc(Sc2ccnc(Nc3ccc(N4CCOCC4)cc3)n2)c1] | 507.17 | N-(3-(2-(4-morpholinophenylaminopyrimidin-4-ylthio)phenyl)-3-phenylpropiolamide | C | 7.5 | m/z 508.2 [M + H]+ | ¹H-NMR (300 MHz, CD₃OD) δ 8.06-7.92 (m, 2H), 7.86 (t, J = 1.8, 1H), 7.68-7.57 (m, 2H), 7.55-7.32 (m, 5H), 7.27-7.14 (m, 2H), 6.75 (d, J = 9.0, 2H), 6.49 (d, J = 5.4, 1H), 3.88-3.73 (m, 4H), 3.13-2.96 (m, 4H) |

TABLE 1-continued

| Compound number | Structure | Exact mass | Name | LCMS method | retention time (min) | Observed m/z | ¹H NMR |
|---|---|---|---|---|---|---|---|
| 323 | 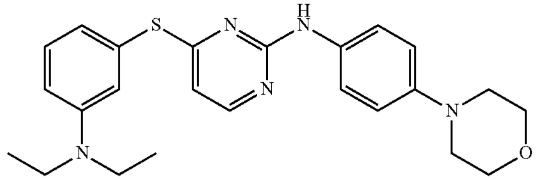 [SMILES: CCN(CC)c1cccc(Sc2ccnc(Nc3ccc(N4CCOCC4)cc3)n2)c1] | 435.21 | 4-(3-(diethylamino)phenylthio)-N-(4-morpholinophenyl)pyrimidin-2-amine | C | 8.0 | m/z 436.3 [M + H]+ | ¹H-NMR (300 MHz, DMSO) δ 9.36 (s, 1H), 8.09 (d, J = 5.3, 1H), 7.42 (d, J = 9.0, 2H), 7.29 (dd, J = 7.4, 8.8, 1H), 6.93-6.64 (m, 4H), 6.25 (d, J = 5.4, 1H), 3.82-3.62 (m, 4H), 3.06-2.89 (m, 4H), 1.06 (t, J = 7.0, 6H). |
| 324 | 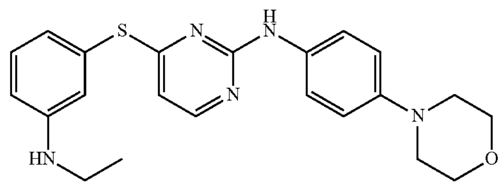 [SMILES: CCNc1cccc(Sc2ccnc(Nc3ccc(N4CCOCC4)cc3)n2)c1] | 407.18 | 4-(3-(ethylamino)phenylthio)-N-(4-morpholinophenyl)pyrimidin-2-amine | C | 7.3 | m/z 408.3 [M + H]+ | ¹H-NMR (300 MHz, DMSO) δ 9.36 (s, 1H), 8.09 (d, J = 5.3, 1H), 7.42 (d, J = 9.0, 2H), 7.21 (t, J = 7.8, 1H), 6.81-6.70 (m, 5H), 6.25 (d, J = 5.3, 1H), 5.87 (t, J = 5.3, 1H), 3.83-3.64 (m, 4H), 3.08-2.96 (m, 6H), 1.14 (t, J = 7.1, 3H). |
| 325 | 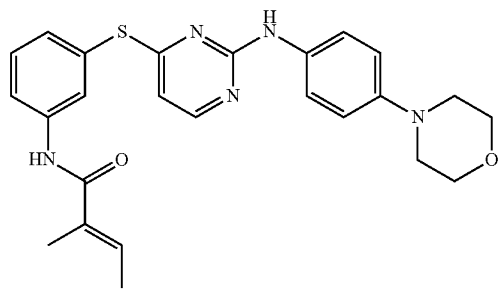 [SMILES: C/C=C(\C)C(=O)Nc1cccc(Sc2ccnc(Nc3ccc(N4CCOCC4)cc3)n2)c1] | 461.19 | (E)-2-methyl-N-(3-(2-(4-morpholinophenylamino)pyrimidin-4-ylthio)phenyl)but-2-enamide | C | 7.0 | m/z 462.3 [M + H]+ | ¹H-NMR (300 MHz, DMSO) δ 9.83 (s, 1H), 9.37 (s, 1H), 8.12 (d, J = 5.3, 1H), 7.99-7.94 (m, 2H), 7.46 (t, J = 8.2, 1H), 7.38-7.22 (m, 3H), 6.71 (d, J = 9.0, 2H), 6.44 (dd, J = 1.5, 6.9, 1H), 6.37 (d, J = 5.2, 1H), 3.79-3.64 (m, 4H), 3.04-2.90 (m, 4H), 1.83-1.79 (m, 3H), 1.79-1.72 (m, 3H). |
| 326 | 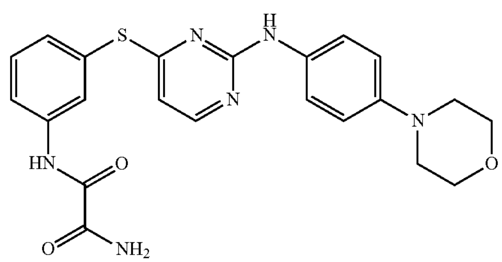 | 450.15 | N1-(3-(2-(4-morpholinophenylamino)pyrimidin-4-ylthio)phenyl)oxalamide | C | 6.2 | m/z 451.3 [M + H]+ | ¹H-NMR (300 MHz, DMSO) δ 10.82 (s, 1H), 9.37 (s, 1H), 8.29 (s, 1H), 8.17 (t, J = 1.8, 1H), 8.14-8.06 (m, 2H), 7.99 (s, 1H), 7.50 (t, J = 7.9, 1H), 7.43-7.33 (m, 1H), 7.29 (d, J = 8.8, 2H), 6.69 (d, J = 9.0, 2H), 6.40 (d, J = 5.2, 1H), 3.82-3.62 (m, 4H), 3.05-2.88 (m, 4H). |

TABLE 1-continued

| Compound number | Structure | Exact mass | Name | LCMS method | retention time (min) | Observed m/z | ¹H NMR |
|---|---|---|---|---|---|---|---|
| 327 | 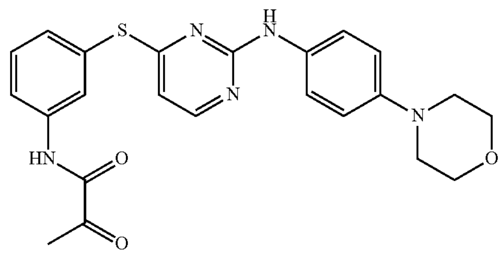 [SMILES: CC(=O)C(=O)Nc1cccc(Sc2ccnc(Nc3ccc(N4CCOCC4)cc3)n2)c1] | 449.15 | N-(3-(2-(4-morpholino-phenylamino)pyrimidin-4-ylthio)phenyl)-2-oxopropanamide | C | 6.8 | m/z 450.2 [M + H]+ | |
| 328 | 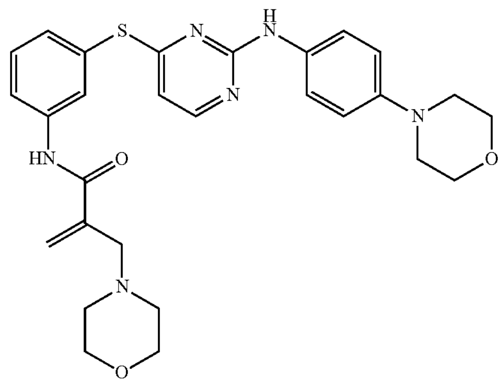 [SMILES: C=C(CN1CCOCC1)C(=O)Nc1cccc(Sc2ccnc(Nc3ccc(N4CCOCC4)cc3)n2)c1] | 532.23 | 2-(morpholino-methyl)-N-(3-(2-(4-morpholino-phenylamino)pyrimidin-4-ylthio)phenyl)acrylamide | C | 6.9 | m/z 533.3 [M + H]+ | ¹H-NMR (500 MHz, DMSO) δ 11.11 (s, 1H), 9.39 (d, J =12.9, 1H), 8.14 (d, J = 5.3, 1H), 7.96-7.92 (m, 2H), 7.52 (t, J = 8.1, 1H), 7.40-7.26 (m, 3H), 6.72 (d, J = 8.7, 2H), 6.43 (br s, 1H), 6.06 (d, J = 1.5, 1H), 5.64 (d, J = 1.2, 1H), 3.73 (t, J = 4.8, 4H), 3.56 (t, J = 4.3, 4H), 3.29 (t, J = 4.8, 4H), 2.99 (m, 4H), 2.42 (s, 3H). |
| 329 | 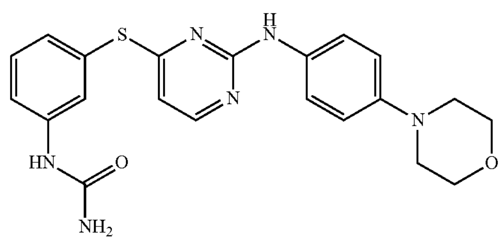 [SMILES: NC(=O)Nc1cccc(Sc2ccnc(Nc3ccc(N4CCOCC4)cc3)n2)c1] | 422.15 | 1-(3-(2-(4-morpholino-phenylamino)pyrimidin-4-ylthio)phenyl)urea | C | 6.0 | m/z 423.3 [M + H]+ | ¹H-NMR (500 MHz, DMSO) δ 9.38 (s, 1H), 8.83 (s, 1H), 8.12 (d, J = 5.3, 1H), 7.76 (t, J = 1.8, 1H), 7.60 (d, J = 8.1, 1H), 7.42-7.32 (m, 3H), 7.18-7.12 (m, 1H), 6.76 (d, J = 9.0, 2H), 6.35 (br s, 1H), 5.94 (s, 2H), 3.80-3.69 (m, 4H), 3.08-2.95 (m, 4H). |

| Compound number | Structure | Exact mass | Name | LCMS method | retention time (min) | Observed m/z | ¹H NMR |
|---|---|---|---|---|---|---|---|
| 330 | 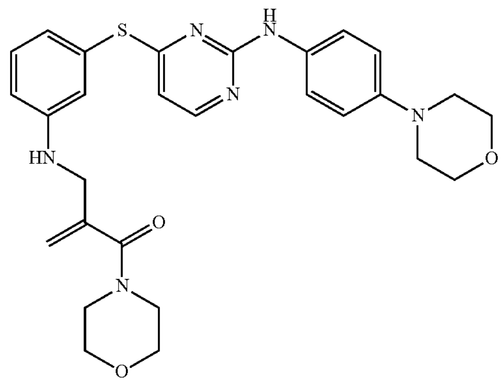 [SMILES: C=C(CNc1cccc(Sc2ccnc(Nc3ccc(N4CCOCC4)cc3)n2)c1)C(=O)N1CCOCC1] | 532.23 | 1-morpholino-2-((3-(2-(4-morpholinophenylamino)pyrimidin-4-ylthio)phenylamino)methyl)prop-2-en-1-one | C | 6.5 | m/z 533.4 [M + H]+ | ¹H-NMR (500 MHz, DMSO) δ 9.38 (s, 1H), 8.10 (d, J = 5.3, 1H), 7.43 (d, J = 8.9, 2H), 7.25 (t, J = 7.8, 1H), 6.90-6.68 (m, 5H), 6.41 (t, J = 6.4, 1H), 6.23 (d, J = 4.9, 1H), 5.38 (s, 1H), 5.10 (s, 1H), 3.90 (d, J = 6.3, 2H), 3.78-3.69 (m, 4H), 3.56-3.38 (m, 4H), 3.06-2.97 (m, 4H). |
| 331 | 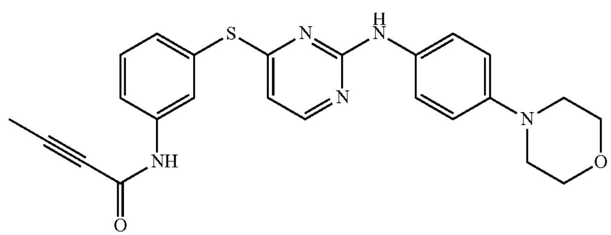 [SMILES: CC#CC(=O)Nc1cccc(Sc2ccnc(Nc3ccc(N4CCOCC4)cc3)n2)c1] | 445.16 | N-(3-(2-(4-morpholinophenylaminopyrimidin-4-ylthio)phenyl)but-2-ynamide | C | 6.7 | m/z 446.4 [M + H]+ | ¹H-NMR (300 MHz, DMSO) δ 10.81 (s, 1H), 9.37 (s, 1H), 8.12 (d, J = 5.3, 1H), 7.88 (s, 1H), 7.83 (d, J = 7.9, 1H), 7.47 (t, J = 7.9, 1H), 7.38-7.21 (m, 3H), 6.70 (d, J = 9.0, 2H), 6.39 (d, J = 5.1, 1H), 3.79-3.67 (m, 4H), 3.07-2.92 (m, 4H), 2.03 (s, 3H). |
| 332 | 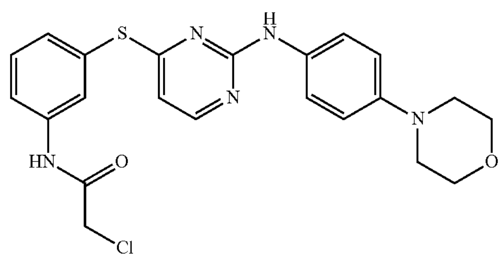 [SMILES: O=C(CCl)Nc1cccc(Sc2ccnc(Nc3ccc(N4CCOCC4)cc3)n2)c1] | 455.12 | 2-chloro-N-(3-(2-(4-morpholinophenylamino)pyrimidin-4-ylthio)phenyl)acetamide | C | 6.7 | m/z 457.3/459.3 [M + H]+ | ¹H-NMR (300 MHz, DMSO) δ 10.53 (s, 1H), 9.40 (s, 1H), 8.12 (d, J = 5.3, 1H), 7.92-7.77 (m, 2H), 7.51 (t, J = 8.0, 1H), 7.37-7.28 (m, 3H), 6.71 (d, J = 8.9, 2H), 6.37 (d, J = 4.8, 1H), 4.25 (s, 2H), 3.72 (t, J = 4.8, 4H), 2.98 (t, J = 4.8, 4H). |

TABLE 1-continued

| Compound number | Structure | Exact mass | Name | LCMS method | retention time (min) | Observed m/z | ¹H NMR |
|---|---|---|---|---|---|---|---|
| 333 | 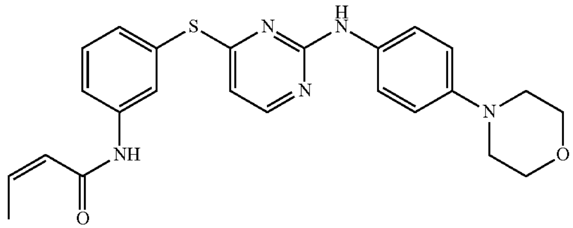 [SMILES: C/C=C\C(=O)Nc1cccc(Sc2ccnc(Nc3ccc(N4CCOCC4)cc3)n2)c1] | 447.17 | (Z)-N-(3-(2-(4-morpholinophenylamino)pyrimidin-4-ylthio)phenyl)but-2-enamide | C | 6.8 | m/z 448.4 [M + H]+ | δ 10.17 (s, 1H), 9.37 (s, 1H), 8.12 (d, J = 5.3, 1H), 7.91 (m, 2H), 7.47 (t, J = 8.1, 1H), 7.29 (m, 3H), 6.70 (d, J = 8.9, 2H), 6.41 (d, J = 4.8, 1H), 6.24 (dd, J = 7.2, 11.4, 1H), 5.98 (dd, J = 1.8, 11.4, 1H), 3.72 (t, J = 4.8, 4H), 2.98 (t, J = 4.8, 4H), 2.11 (dd, J = 1.6, 7.2, 3H). |
| 334 | 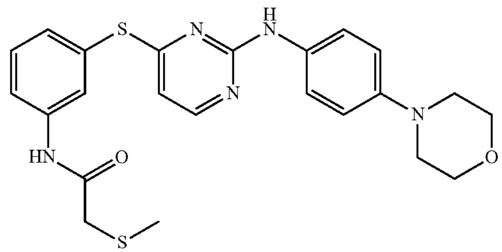 [SMILES: CSCC(=O)Nc1cccc(Sc2ccnc(Nc3ccc(N4CCOCC4)cc3)n2)c1] | 467.14 | 2-(methylthio)-N-(3-(2-(4-morpholinophenylamino)pyrimidin-4-ylthio)phenyl)acetamide | C | 6.5 | m/z 468.3 [M + H]+ | ¹H-NMR (500 MHz, DMSO) δ 10.28 (s, 1H), 9.39 (s, 1H), 8.13 (d, J = 5.2, 1H), 7.91 (s, 1H), 7.83 (d, J = 8.1, 1H), 7.49 (t, J = 8.0, 1H), 7.32 (d, J = 7.5, 3H), 6.73 (d, J = 8.4, 2H), 6.39 (s, 1H), 3.81-3.66 (m, 4H), 3.27 (s, 2H), 3.09-2.95 (m, 4H), 2.14 (s, 3H). |
| 335 | 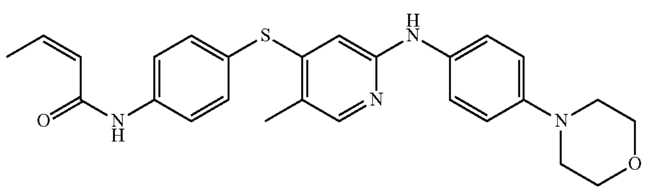 [SMILES: C/C=C\C(=O)Nc1ccc(Sc2cc(Nc3ccc(N4CCOCC4)cc3)ncc2C)cc1] | 461.19 | (Z)-N-(4-(5-methyl-2-(4-morpholinophenylamino)pyrimidin-4-ylthio)phenyl)but-2-enamide | C | 7.1 | m/z 462.3 [M + H]+ | ¹H-NMR (300 MHz, DMSO) δ 10.35 (s, 1H), 9.12 (s, 1H), 8.00 (s, 1H), 7.85 (d, J = 8.7, 2H), 7.51 (d, J = 8.6, 2H), 6.98 (d, J = 9.0, 2H), 6.47 (d, J = 9.1, 2H), 6.33 (dd, J = 7.2, 11.4, 1H), 6.06 (dd, J = 1.7, 11.5, 1H), 3.65 (t, J = 4.5, 4), 2.87 (t, J = 4.5, 4H), 2.17 (dd, J = 1.5, 7.2, 3H), 2.12 (s, 3H). |
| 336 | 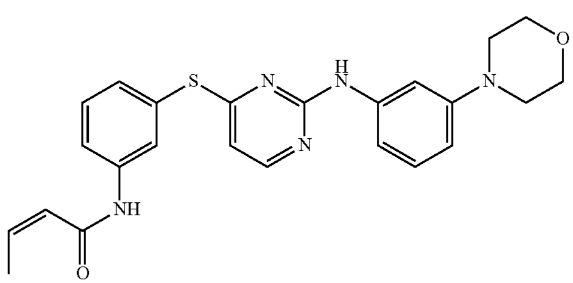 [SMILES: C/C=C\C(=O)Nc1cccc(Sc2ccnc(Nc3cccc(N4CCOCC4)c3)n2)c1] | 447.17 | (Z)-N-(3-(2-(3-morpholinophenylaminopyrimidin-4-ylthiophenyl)but-2-enamide | C | 7.0 | m/z 448.3 [M + H]+ | ¹H-NMR (300 MHz, DMSO) δ 10.18 (s, 1H), 9.48 (s, 1H), 8.17 (d, J = 5.3, 1H), 7.99 (s, 1H), 7.78 (d, J = 7.1, 1H), 7.47 (t, J = 7.9, 1H), 7.31 (d, J = 7.8, 1H), 7.20 (s, 1H), 7.08 (d, J = 9.3, 1H), 6.97 (t, J = 8.1, 1H), 6.51 (dd, J = 1.5, 8.3, 1H), 6.32 (d, J = 5.3, 1H), 6.24 (dd, J = 7.2, 11.4, 1H), 5.99 (dd, J = 1.7, 11.4, 1H), 3.79-3.65 (m, 4H), 3.11-2.95 (m, 4H), 2.10 (dd, J = 1.5, 7.2, 3H). |

TABLE 1-continued

| Compound number | Structure | Exact mass | Name | LCMS method | retention time (min) | Observed m/z | 1H NMR |
|---|---|---|---|---|---|---|---|
| 337 | 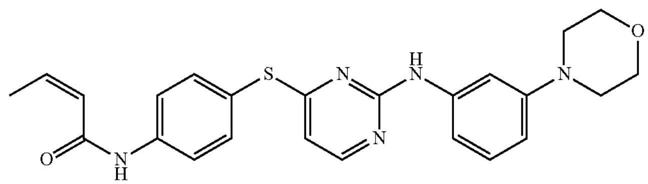 [SMILES: C/C=C\C(=O)Nc1ccc(Sc2ccnc(Nc3cccc(N4CCOCC4)c3)n2)cc1] | 447.17 | (Z)-N-(4-(2-(3-morpholinophenyl-amino)pyrimidin-4-ylthio)phenyl)but-2-enamide | C | 7.0 | m/z 448.3 [M + H]+ | 1H-NMR (300 MHz, DMSO) δ 10.26 (s, 1H), 9.46 (s, 1H), 8.14 (d, J = 5.3, 1H), 7.80 (d, J = 8.7, 2H), 7.56 (d, J = 8.6, 2H), 7.21 (s, 1H), 7.09 (d, J = 7.7, 1H), 7.04-6.91 (m, 1H), 6.51 (dd, J = 1.8, 8.3, 1H), 6.35-6.20 (m, 2H), 6.04 (dd, J = 1.7, 11.5, 1H), 3.83-3.64 (m, 4H), 3.09-2.94 (m, 4H), 2.13 (dd, J = 1.5, 7.2, 3H). |
| 338 | 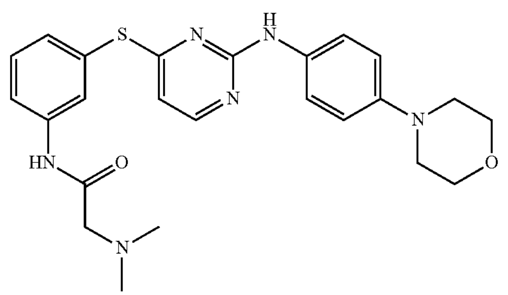 [SMILES: CN(C)CC(=O)Nc1cccc(Sc2ccnc(Nc3ccc(N4CCOCC4)cc3)n2)c1] | 464.20 | 2-(dimethylamino)-N-(3-(2-(4-morpholinophenyl-amino)pyrimidin-4-ylthio)phenyl)acetamide | D | 7.7 | m/z 465.4 [M + H]+ | 1H-NMR (300 MHz, DMSO) δ 9.94 (s, 1H), 9.37 (s, 1H), 8.12 (d, J = 5.3, 1H), 7.98 (d, J = 1.7, 1H), 7.92 (d, J = 8.3, 1H), 7.46 (t, J = 7.9, 1H), 7.38-7.22 (m, 3H), 6.71 (d, J = 9.0, 2H), 6.36 (d, J = 4.9, 1H), 3.78-3.67 (m, 4H), 3.06 (s, 2H), 3.03-2.92 (m, 4H), 2.24 (s, 6H). |
| 339 | 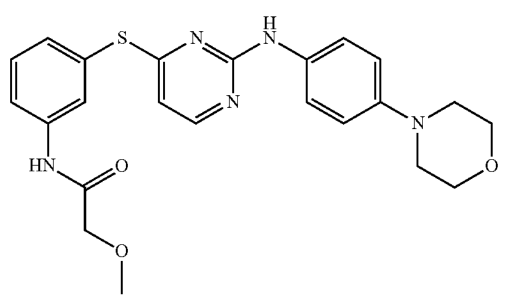 [SMILES: COCC(=O)Nc1cccc(Sc2ccnc(Nc3ccc(N4CCOCC4)cc3)n2)c1] | 451.17 | 2-methoxy-N-(3-(2-(4-morpholino-phenylamino)pyrimidin-4-ylthio)phenyl)acetamide | C | 6.4 | m/z 452.3 [M + H]+ | 1H-NMR (300 MHz, DMSO) δ 9.98 (s, 1H), 9.37 (s, 1H), 8.12 (d, J = 5.3, 1H), 7.99 (t, J = 1.7, 1H), 7.93 (d, J = 7.9, 1H), 7.47 (t, J = 7.9, 1H), 7.31 (d, J = 8.9, 3H), 6.72 (d, J = 9.0, 2H), 6.36 (d, J = 4.9, 1H), 3.99 (s, 2H), 3.78-3.66 (m, 4H), 3.35 (s, 3H), 3.07-2.93 (m, 4H). |

| Compound number | Structure | Exact mass | Name | LCMS method | retention time (min) | Observed m/z | ¹H NMR |
|---|---|---|---|---|---|---|---|
| 340 | 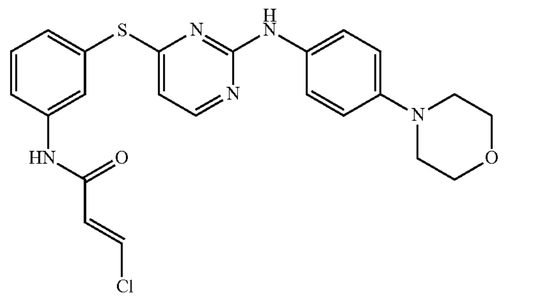 [SMILES: O=C(/C=C/Cl)Nc1cccc(Sc2ccnc(Nc3ccc(N4CCOCC4)cc3)n2)c1] | 467.12 | (E)-3-chloro-N-(3-(2-(4-morpholinophenylamino)pyrimidin-4-ylthio)phenyl)acrylamide | C | 6.9 | m/z 468.3/470.3 [M + H]+ | ¹H-NMR (300 MHz, DMSO) δ 10.42 (s, 1H), 9.38 (s, 1H), 8.12 (d, J = 5.3, 1H), 7.95-7.81 (m, 2H), 7.50 (t, J = 7.9, 1H), 7.43 (d, J = 13.2, 1H), 7.37-7.24 (m, 3H), 6.70 (d, J = 9.0, 2H), 6.60 (d, J = 13.2, 1H), 6.40 (d, J = 4.3, 1H), 3.72 (t, J = 4.8, 4H), 2.97 (t, J = 4.8, 4H). |
| 341 | 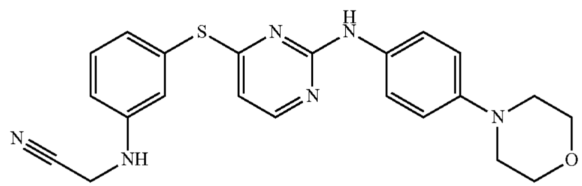 [SMILES: N#CCNc1cccc(Sc2ccnc(Nc3ccc(N4CCOCC4)cc3)n2)c1] | 418.16 | 2-(3-(2-(4-morpholinophenylaminopyrimidin-4-ylthio)phenylamino)acetonitrile | C | 6.5 | m/z 419.3 [M + H]+ | ¹H-NMR (300 MHz, DMSO) δ 9.37 (s, 1H), 8.10 (d, J = 5.3, 1H), 7.41 (d, J = 9.0, 2H), 7.34 (t, J = 7.9, 1H), 7.06-6.86 (m, 3H), 6.78 (d, J = 9.1, 2H), 6.56 (t, J = 6.6, 1H), 6.26 (d, J = 5.2, 1H), 4.31 (d, J = 6.8, 2H), 3.86-3.62 (m, 4H), 3.10-2.89 (m, 4H). |
| 342 | 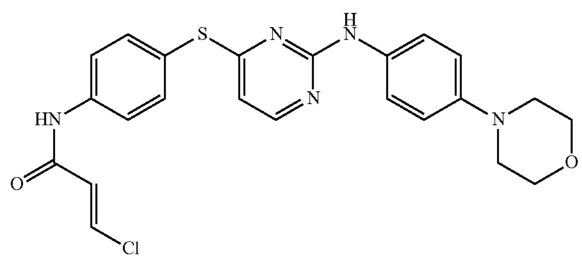 [SMILES: O=C(/C=C/Cl)Nc1ccc(Sc2ccnc(Nc3ccc(N4CCOCC4)cc3)n2)cc1] | 467.12 | (E)-3-chloro-N-(4-(2-(4-morpholinophenylamino)pyrimidin-4-ylthio)phenyl)acrylamide | C | 6.9 | m/z 468.3 [M + H]+ | ¹H-NMR (300 MHz, DMSO) δ 10.56 (s, 1H), 9.36 (s, 1H), 8.10 (d, J = 5.2, 1H), 7.82 (d, J = 8.6, 2H), 7.58 (d, J = 8.5, 2H), 7.51 (d, J = 13.1, 1H), 7.16 (d, J = 8.0, 2H), 6.67 (d, J = 13.2, 1H), 6.59 (d, J = 8.7, 2H), 6.55-6.44 (m, 1H), 3.81-3.57 (m, 4H), 3.00-2.82 (m, 4H). |
| 343 | 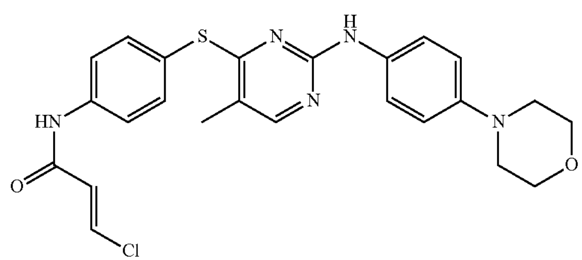 [SMILES: Cc1cnc(Nc2ccc(N3CCOCC3)cc2)nc1Sc1ccc(NC(=O)/C=C/Cl)cc1] | 481.13 | (E)-3-chloro-N-(4-(5-methyl-2-(4-morpholinophenyl-aminopyrimidin-4-ylthio)phenyl)acrylamide | C | 7.2 | m/z 482.3 [M + H]+ | ¹H-NMR (300 MHz, DMSO) δ 10.59 (s, 1H), 9.13 (s, 1H), 8.00 (s, 1H), 7.84 (d, J = 8.6, 2H), 7.61-7.48 (m, 3H), 6.96 (d, J = 8.9, 2H), 6.69 (d, J = 13.2, 1H), 6.44 (d, J = 9.0, 2H), 3.76-3.57 (m, 4H), 2.92-2.78 (m, 4H), 2.12 (s, 3H). |

TABLE 1-continued

| Compound number | Structure | Exact mass | Name | LCMS method | retention time (min) | Observed m/z | 1H NMR |
|---|---|---|---|---|---|---|---|
| 344 | 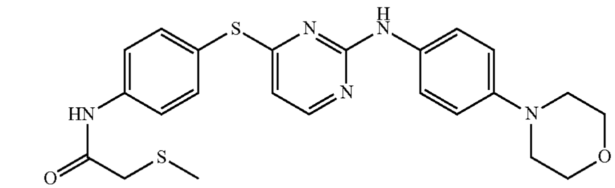 [SMILES: CSCC(=O)Nc1ccc(Sc2ccnc(Nc3ccc(N4CCOCC4)cc3)n2)cc1] | 467.14 | 2-(methylthio)-N-(4-(2-(4-morpholino-phenylamino)pyrimidin-4-ylthio)phenyl)acetamide | C | 6.6 | m/z 468.3 [M + H]+ | 1H-NMR (300 MHz, DMSO) δ 10.36 (s, 1H), 9.35 (s, 1H), 8.10 (d, J = 5.3, 1H), 7.84-7.70 (m, 2H), 7.63-7.50 (m, 2H), 7.29 (d, J = 8.8, 2H), 6.70 (d, J = 9.0, 2H), 6.37 (d, J = 5.2, 1H), 3.82-3.61 (m, 4H), 3.32 (s, 2H), 3.10-2.89 (m, 4H). |
| 345 | 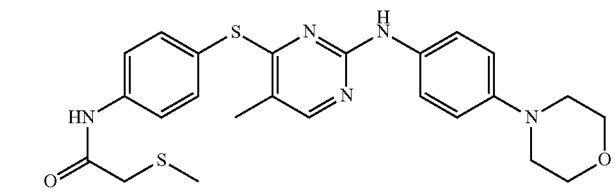 [SMILES: CSCC(=O)Nc1ccc(Sc2nc(Nc3ccc(N4CCOCC4)cc3)ncc2C)cc1] | 481.16 | N-(4-(5-methyl-2-(4-morpholino-phenylamino)pyrimidin-4-ylthio)phenyl)-2-(methyl-thio)acetamide | C | 6.9 | m/z 482.2 [M + H]+ | 1H-NMR (300 MHz, DMSO) δ 10.39 (s, 1H), 9.09 (s, 1H), 8.01 (d, J = 0.6, 1H), 7.78 (d, J = 8.7, 2H), 7.54 (d, J = 8.7, 2H), 7.04 (d, J = 9.0, 2H), 6.51 (d, J = 9.1, 2H), 3.81-3.64 (m, 4H), 3.33 (s, 2H), 2.94-2.89 (m, 4H), 2.22 (s, 3H), 2.13 (s, 3H). |
| 346 | 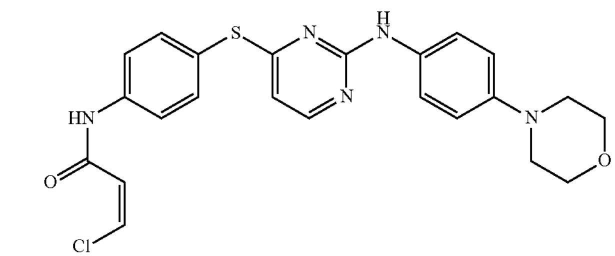 [SMILES: O=C(/C=C\Cl)Nc1ccc(Sc2ccnc(Nc3ccc(N4CCOCC4)cc3)n2)cc1] | 467.12 | (Z)-3-chloro-N-(4-(2-(4-morpholino-phenylamino)pyrimidin-4-ylthio)phenyl)acrylamide | C | 6.6 | m/z 468.3/ 470.3 [M + H]+ | 1H-NMR (300 MHz, DMSO) δ 10.50 (s, 1H), 9.34 (s, 1H), 8.10 (d, J = 5.3, 1H), 7.82 (d, J = 8.7, 2H), 7.57 (d, J = 8.7, 2H), 7.21 (d, J = 8.6, 2H), 7.01 (d, J = 8.0, 1H), 6.63 (d, J = 9.0, 2H), 6.57 (d, J = 8.0, 1H), 6.51-6.42 (m, 1H), 3.69 (t, J = 4.8, 4H), 2.94 (t, J = 4.8, 4H). |
| 347 | 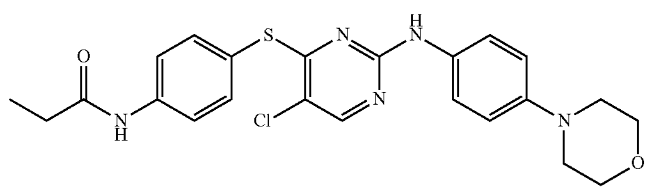 [SMILES: CCC(=O)Nc1ccc(Sc2nc(Nc3ccc(N4CCOCC4)cc3)ncc2Cl)cc1] | 469.13 | N-(4-(5-chloro-2-(4-morpholino-phenylamino)pyrimidin-4-ylthio)phenyl)propionamide | C | 7.1 | m/z 470.2/ 472.2 [M + H]+ | 1H-NMR (300 MHz, DMSO) δ 10.29 (s, 1H), 9.49 (s, 1H), 8.23 (s, 1H), 7.82 (d, J = 8.7, 2H), 7.54 (d, J = 8.6, 2H), 6.99 (d, J = 8.9, 2H), 6.51 (d, J = 9.1, 2H), 3.71 (t, J = 4.8, 4H), 2.93 (t, J = 4.8, 4H), 2.39 (q, J = 7.5, 2H), 1.12 (t, J = 7.5, 3H). |

TABLE 1-continued

| Compound number | Structure | Exact mass | Name | LCMS method | retention time (min) | Observed m/z | 1H NMR |
|---|---|---|---|---|---|---|---|
| 348 | 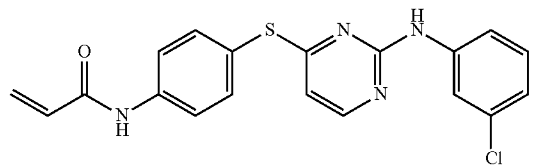 [SMILES: C=CC(=O)Nc1ccc(Sc2ccnc(Nc3cccc(Cl)c3)n2)cc1] | 382.07 | N-(4-(2-(3-chlorophenylamino)pyrimidin-4-ylthio)phenyl)acrylamide | C | 7.4 | m/z 383.2 [M+H]+ | 1H NMR (300 MHz, Acetone) δ 9.63 (br s, 1H), 8.76 (br s, 1H), 8.17 (d, J = 5.5, 1H), 7.90 (m, 3H), 7.58 (m, 3H), 7.20 (m, 1H), 6.93 (m, 3H), 6.54-6.36 (m, 3H), 5.77 (dd, J = 9.4, 2.5, 1H) |
| 349 | 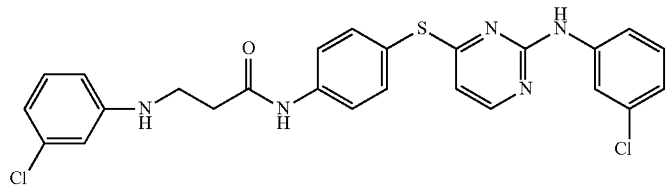 [SMILES: O=C(CCNc1cccc(Cl)c1)Nc1ccc(Sc2ccnc(Nc3cccc(Cl)c3)n2)cc1] | 509.08 | 3-(3-chlorophenylamino)-N-(4-(2-(3-chlorophenylamino)pyrimidin-4-ylthio)phenyl)propanamide | C | 8.1 | m/z 511.2/ 513.2 [M+H]+ | 1H NMR (300 MHz, Acetone) δ 9.54 (br s, 1H), 8.75 (br s, 1H), 8.16 (d, J = 5.4, 1H), 7.84 (d, J = 8.7, 3H), 7.57 (d, J = 8.7, 3H), 7.14 (dt, J = 8.1, 27.9, 2H), 6.92 (dd, J = 1.1, 7.9, 1H), 6.74-6.54 (m, 3H), 6.41 (d, J = 5.3, 1H), 5.38 (m, 1H), 3.55 (q, J = 6.4, 2H), 2.78-2.69 (m, 2H) |
| 350 | 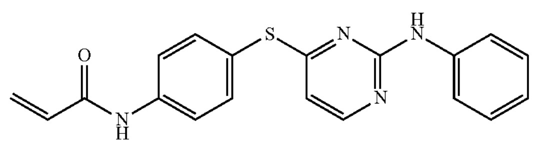 [SMILES: C=CC(=O)Nc1ccc(Sc2ccnc(Nc3ccccc3)n2)cc1] | 348.10 | N-(4-(2-(phenylamino)pyrimidin-4-ylthio)phenyl)acrylamide | C | 6.9 | m/z 349.2 [M+H]+ | 1H NMR (300 MHz, Acetone) δ 9.66 (br s, 1H), 8.57 (br s, 1H), 8.13 (d, J = 5.3, 1H), 7.93 (d, J = 8.7, 2H), 7.60 (m, 4H), 7.25-7.14 (m, 2H), 6.89 (t, J = 7.4, 1H), 6.59-6.32 (m, 3H), 5.78 (dd, J = 2.5, 9.5, 1H). |
| 351 | 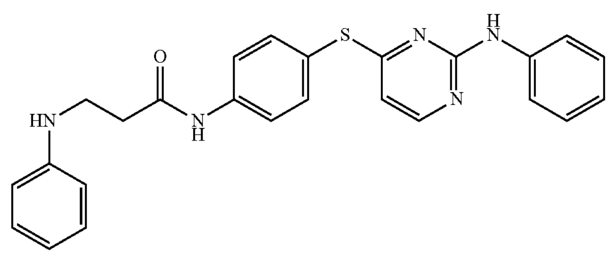 [SMILES: O=C(CCNc1ccccc1)Nc1ccc(Sc2ccnc(Nc3ccccc3)n2)cc1] | 441.16 | 3-(phenylamino)-N-(4-(2-(phenylamino)pyrimidin-4-ylthio)phenyl)propanamide | C | 7.5 | m/z 442.3 [M+H]+ | 1H NMR (300 MHz, Acetone) δ 9.56 (br s, 1H), 8.56 (br s, 1H), 8.12 (d, J = 5.5, 1H), 7.85 (d, J = 8.7, 2H), 7.58 (m, 4H), 7.22-7.08 (m, 4H), 6.89 (m, 1H), 6.68 (m, 2H), 6.60 (m, 1H), 5.04 (br s, 1H), 3.53 (m, 2H), 2.75 (m, 2H) |
| 352 | 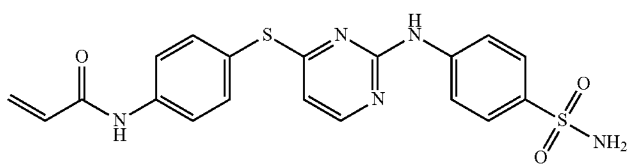 [SMILES: C=CC(=O)Nc1ccc(Sc2ccnc(Nc3ccc(S(N)(=O)=O)cc3)n2)cc1] | 427.08 | N-(4-(2-(4-sulfamoylphenylamino)pyrimidin-4-ylthio)phenyl)acrylamide | C | 6.2 | m/z 428.2 [M+H]+ | 1H NMR (300 MHz, DMSO) δ 10.46 (s, 1H), 10.03 (s, 1H), 8.24 (d, J = 5.0, 1H), 7.87 (d, J = 8.7, 2H), 7.70-7.56 (m, 6H), 7.08 (s, 2H), 6.53-6.27 (m, 3H), 5.82 (dd, J = 10.0, 1.8, 1H) |

TABLE 1-continued

| Compound number | Structure | Exact mass | Name | LCMS method | retention time (min) | Observed m/z | 1H NMR |
|---|---|---|---|---|---|---|---|
| 353 | 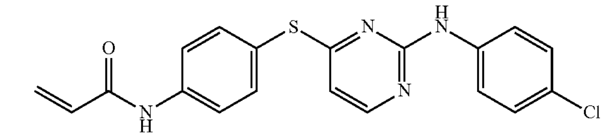 [SMILES: C=CC(=O)Nc1ccc(Sc2ccnc(Nc3ccc(Cl)cc3)n2)cc1] | 382.07 | N-(4-(2-(4-chlorophenylamino)pyrimidin-4-ylthio)phenyl)acrylamide | C | 7.3 | m/z 383.2/385.2 [M + H]+ | 1H NMR (300 MHz, Acetone) δ 9.65 (s, 1H), 8.68 (s, 1H), 8.14 (d, J = 5.3, 1H), 7.93 (d, J = 8.8, 2H), 7.60 (m, 4H), 7.16 (d, J = 9.2, 2H), 6.53-6.39 (m, 3H), 5.78 (dd, J = 9.9, 1.9, 1H) |
| 354 | 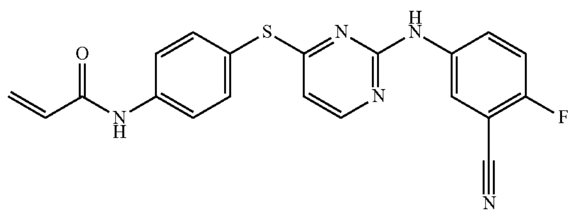 [SMILES: C=CC(=O)Nc1ccc(Sc2ccnc(Nc3ccc(F)c(C#N)c3)n2)cc1] | 391.09 | N-(4-(2-(3-cyano-4-fluorophenylamino)pyrimidin-4-ylthio)phenyl)acrylamide | C | 7.0 | m/z 392.2 [M + H]+ | 1H NMR (300 MHz, DMSO) δ 10.42 (s, 1H), 9.99 (s, 1H), 8.22 (d, J = 5.3, 1H), 8.00 (b s, 1H), 7.84 (d, J = 8.8, 3H), 7.60 (d, J = 8.8, 2H), 7.27 (m, 1H), 6.50-6.30 (m, 3H), 5.82 (dd, J = 9.9, 1.9, 1H) |
| 355 | 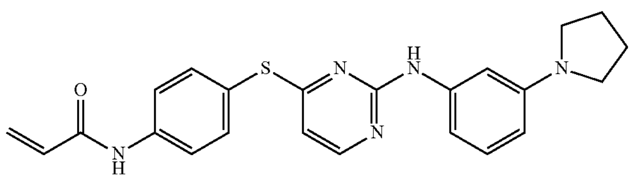 [SMILES: C=CC(=O)Nc1ccc(Sc2ccnc(Nc3cccc(N4CCCC4)c3)n2)cc1] | 417.16 | N-(4-(2-(3-(pyrrolidin-1-yl)phenylamino)pyrimidin-4-ylthio)phenyl)acrylamide | C | 7.5 | m/z 418.3 [M + H]+ | |
| 356 | 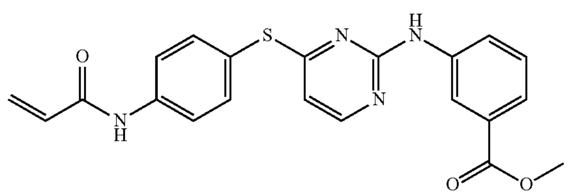 [SMILES: C=CC(=O)Nc1ccc(Sc2ccnc(Nc3cccc(C(=O)OC)c3)n2)cc1] | 406.11 | methyl 3-(4-(4-acrylamidophenylthio)pyrimidin-2-ylamino)benzoate | C | 7.0 | m/z 407.2 [M + H]+ | 1H NMR (300 MHz, Acetone) δ 9.64 (br s, 1H), 8.82 (br s, 1H), 8.29 (br s, 1H), 8.17 (d, J = 5.5, 1H), 7.99-7.85 (m, 3H), 7.58 (m, 3H), 7.30 (m, 1H), 6.54-6.37 (m, 3H), 5.78 (dd, J = 9.2, 2.8, 1H), 3.87 (s, 3H) |
| 357 | 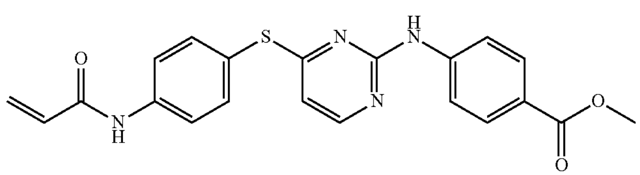 [SMILES: C=CC(=O)Nc1ccc(Sc2ccnc(Nc3ccc(C(=O)OC)cc3)n2)cc1] | 406.11 | methyl 4-(4-acrylamidophenylthio)pyrimidin-2-ylamino)benzoate | C | 6.9 | m/z 407.2 [M + H]+ | 1H NMR (300 MHz, Acetone) δ 9.68 (br s, 1H), 8.94 (br s, 1H), 8.19 (d, J = 5.2, 1H), 7.96 (m, 2H), 7.81 (m, 2H), 7.69-7.58 (m, 4H), 6.60-6.38 (m, 3H), 5.80 (dd, J = 9.6, 2.5, 1H), 3.81 (s, 3H) |

TABLE 1-continued

| Compound number | Structure | Exact mass | Name | LCMS method | retention time (min) | Observed m/z | 1H NMR |
|---|---|---|---|---|---|---|---|
| 358 | 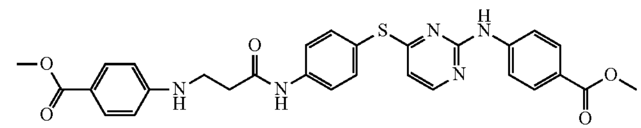 | 557.17 | methyl 4-(4-(4-(3-(4-(methoxycarbonyl)phenylamino)propanamido)phenylthio)pyrimidin-2-ylamino)benzoate | C | 7.4 | m/z 558.3 [M + H]+ | |
| 359 | 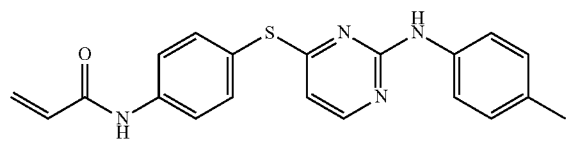 [SMILES: C=CC(=O)Nc1ccc(Sc2ccnc(Nc3ccc(C)cc3)n2)cc1] | 362.12 | N-(4-(2-(p-tolylamino)pyrimidin-4-ylthio)phenyl)acrylamide | C | 7.2 | m/z 363.4 [M + H]+ | 1H NMR (500 MHz, Acetone) δ 9.67 (s, 1H), 8.43 (s, 1H), 8.10 (d, J = 5.3, 1H), 7.92 (d, J = 8.7, 2H), 7.58 (d, J = 8.7, 2H), 7.45 (d, J = 8.3, 2H), 6.99 (d, J = 8.3, 2H), 6.59-6.35 (m, 3H), 5.78 (dd, J = 2.1, 10.0, 1H), 2.22 (s, 3H). |
| 360 | 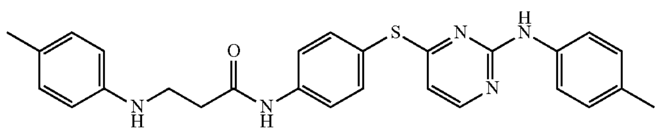 | 469.19 | 3-(p-tolylamino)-N-(4-(2-(p-tolylamino)pyrimidin-4-ylthio)phenyl)propanamide | C | 7.9 | m/z 470.4 [M + H]+ | |
| 361 | 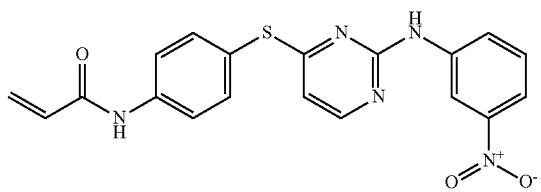 [SMILES: C=CC(=O)Nc1ccc(Sc2ccnc(Nc3cccc([N+](=O)[O-])c3)n2)cc1] | 393.09 | N-(4-(2-(3-nitrophenylamino)pyrimidin-4-ylthio)phenyl)acrylamide | C | 7.0 | m/z 394.2 [M + H]+ | |
| 362 | 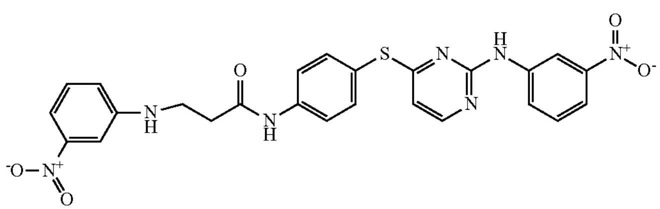 | 531.13 | 3-(3-nitrophenylamino)-N-(4-(2-(3-nitrophenylamino)pyrimidin-4-ylthio)phenyl)propanamide | C | 7.6 | m/z 532.3 [M + H]+ | |

TABLE 1-continued

| Compound number | Structure | Exact mass | Name | LCMS method | retention time (min) | Observed m/z | ¹H NMR |
|---|---|---|---|---|---|---|---|
| 363 | 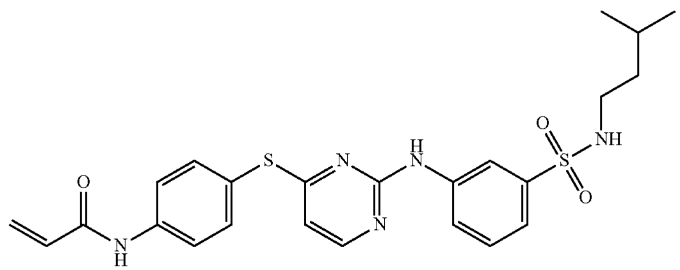 [SMILES: C=CC(=O)Nc1ccc(Sc2ccnc(Nc3cccc(S(=O)(=O)NCCC(C)C)c3)n2)cc1] | 497.16 | N-(4-(2-(3-(N-isopentyl-sulfamoyl)phenyl-aminopyrimidin-4-ylthio)phenyl)acrylamide | C | 7.4 | m/z 498.4 [M + H]+ | ¹H NMR (300 MHz, Acetone) δ 9.68 (s, 1H), 8.92 (s, 1H), 8.27-8.12 (m, 2H), 7.93 (m, 3H), 7.61 (d, J = 8.7, 2H), 7.37 (m, 2H), 6.59-6.22 (m, 4H), 5.78 (dd, J = 2.5, 9.6, 1H), 3.02-2.91 (m, 2H), 1.64 (m, 1H), 1.40 (m, 2H), 0.83 (d, J = 6.6, 6H). |
| 364 | 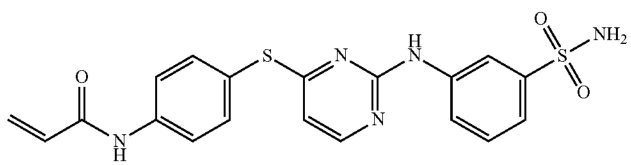 [SMILES: C=CC(=O)Nc1ccc(Sc2ccnc(Nc3cccc(S(N)(=O)=O)c3)n2)cc1] | 427.08 | N-(4-(2-(3-sulfamoylphenyl-aminopyrimidin-4-ylthio)phenyl)acrylamide | C | 6.1 | m/z 428.3 [M + H]+ | |
| 365 | 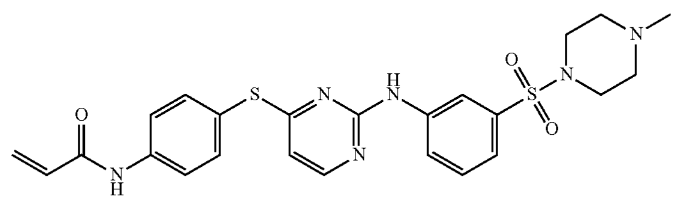 [SMILES: C=CC(=O)Nc1ccc(Sc2ccnc(Nc3cccc(S(=O)(=O)N4CCN(C)CC4)c3)n2)cc1] | 510.15 | N-(4-(2-(3-(4-methylpiperazin-1-ylsulfonyl)phenyl-aminopyrimidin-4-ylthio)phenyl)acrylamide | C | 6.6 | m/z 511.3 [M + H]+ | |
| 366 | 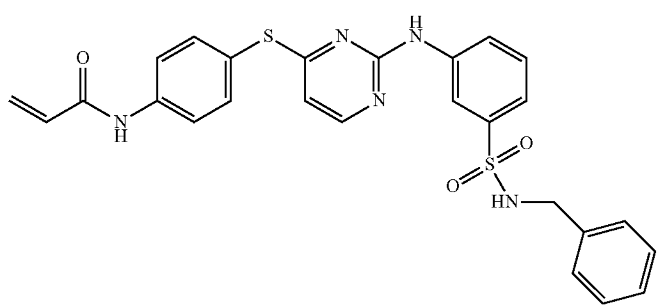 [SMILES: C=CC(=O)Nc1ccc(Sc2ccnc(Nc3cccc(S(=O)(=O)NCc4ccccc4)c3)n2)cc1] | 517.12 | N-(4-(2-(3-(N-benzyl(sulfamoyl)phenylamino)pyrimidin-4-ylthio)phenyl)acrylamide | C | 7.1 | m/z 518.4 [M + H]+ | |

TABLE 1-continued

| Compound number | Structure | Exact mass | Name | LCMS method | retention time (min) | Observed m/z | 1H NMR |
|---|---|---|---|---|---|---|---|
| 367 | 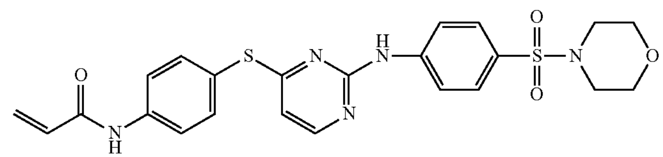 [SMILES: C=CC(=O)Nc1ccc(Sc2ccnc(Nc3ccc(S(=O)(=O)N4CCOCC4)cc3)n2)cc1] | 497.12 | N-(4-(2-(4-(morpholinosulfonyl)phenylaminopyrimidin-4-ylthio)phenyl)acrylamide | C | 6.7 | m/z 498.3 [M + H]+ | |
| 368 | 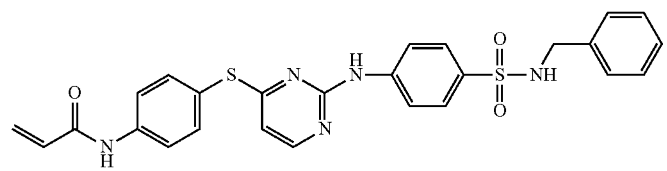 [SMILES: C=CC(=O)Nc1ccc(Sc2ccnc(Nc3ccc(S(=O)(=O)NCc4ccccc4)cc3)n2)cc1] | 517.12 | N-(4-(2-(4-(N-benzylsulfamoyl)phenylamino)pyrimidin-4-ylthio)phenyl)acrylamide | C | 7.2 | m/z 518.3 [M + H]+ | |
| 369 | 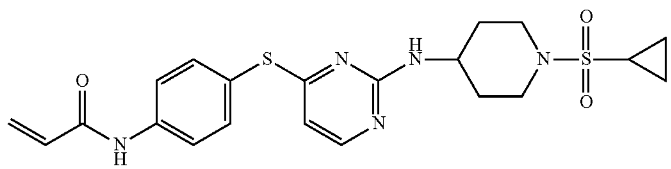 [SMILES: C=CC(=O)Nc1ccc(Sc2ccnc(NC3CCN(S(=O)(=O)C4CC4)CC3)n2)cc1] | 459.14 | N-(4-(2-(1-(cyclopropylsulfonyl)piperidin-4-ylaminopyrimidin-4-ylthio)phenyl)acrylamide | C | 6.5 | m/z 460.3 [M + H]+ | |
| 370 | 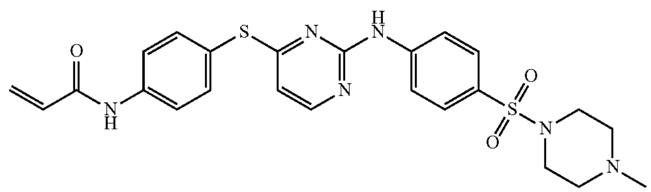 [SMILES: C=CC(=O)Nc1ccc(Sc2ccnc(Nc3ccc(S(=O)(=O)N4CCN(C)CC4)cc3)n2)cc1] | 510.15 | N-(4-(2-(4-(4-methylpiperazin-1-ylsulfonyl)phenylaminopyrimidin-4-ylthio)phenyl)acrylamide | C | 6.4 | m/z 511.3 [M + H]+ | |
| 371 | 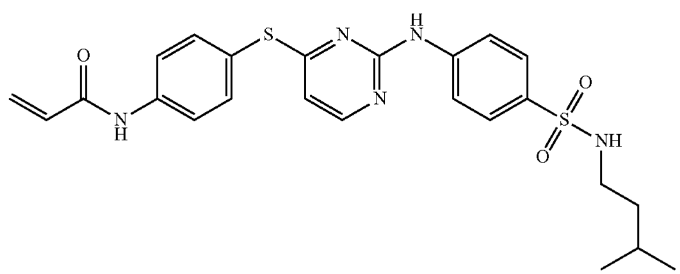 [SMILES: C=CC(=O)Nc1ccc(Sc2ccnc(Nc3ccc(S(=O)(=O)NCCC(C)C)cc3)n2)cc1] | 497.16 | N-(4-(2-(4-(N-isopentylsulfamoyl)phenylaminopyrimidin-4-ylthiophenyl)acrylamide | C | 7.3 | m/z 498.2 [M + H]+ | |

TABLE 1-continued

| Compound number | Structure | Exact mass | Name | LCMS method | retention time (min) | Observed m/z | 1H NMR |
|---|---|---|---|---|---|---|---|
| 372 | 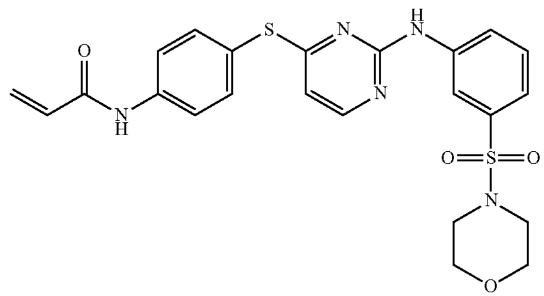 [SMILES: C=CC(=O)Nc1ccc(Sc2ccnc(Nc3cccc(S(=O)(=O)N4CCOCC4)c3)n2)cc1] | 497.12 | N-(4-(2-(3-(morpholinosulfonyl)phenylaminopyrimidin-4-ylthio)phenyl)acrylamide | C | 9.7 | m/z 498.2 [M + H]+ | |
| 373 | 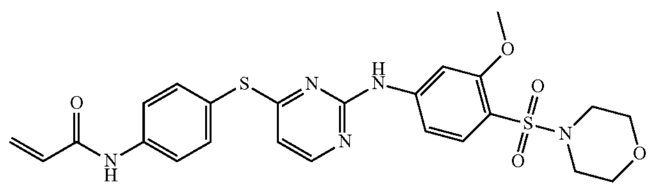 [SMILES: C=CC(=O)Nc1ccc(Sc2ccnc(Nc3ccc(S(=O)(=O)N4CCOCC4)c(OC)c3)n2)cc1] | 527.13 | N-(4-(2-(3-methoxy-4-(morpholinosulfonyl)phenylaminopyrimidin-4-ylthio)phenyl)acrylamide | E | 9.43 | m/z 528.3 [M + H]+ | 1H NMR (300 MHz, DMSO) δ 10.46 (s, 1H), 9.99 (s, 1H), 8.26 (d, J = 5.4, 1H), 7.88 (d, J = 8.7, 2H), 7.70-7.43 (m, 4H), 7.27 (dd, J = 1.9, 8.7, 1H), 6.84 (s, 2H), 6.58-6.24 (m, 3H), 5.88-5.72 (m, 1H), 3.83 (s, 3H). |
| 374 | 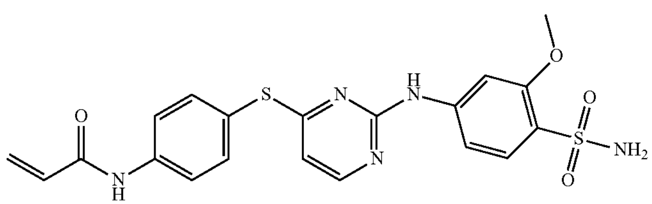 [SMILES: C=CC(=O)Nc1ccc(Sc2ccnc(Nc3ccc(S(N)(=O)=O)c(OC)c3)n2)cc1] | 457.09 | N-(4-(2-(3-methoxy-4-sulfamoylphenylaminopyrimidin-4-ylthio)phenyl)acrylamide | C | 6.1 | m/z 458.2 [M + H]+ | |
| 375 | 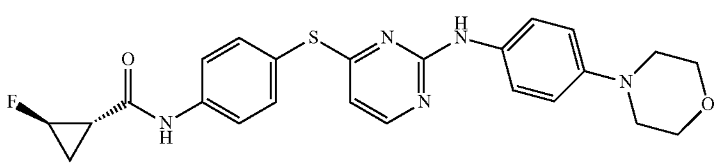 [SMILES: O=C(Nc1ccc(Sc2ccnc(Nc3ccc(N4CCOCC4)cc3)n2)cc1)[C@@H]1C[C@H]1F] | 465.16 | (1S,2R)-2-fluoro-N-(4-(2-(4-morpholinophenylaminopyrimidin-4-ylthio)phenyl)cyclopropanecarboxamide | C | 6.8 | m/z 466.3 [M + H]+ | |

TABLE 1-continued

| Compound number | Structure | Exact mass | Name | LCMS method | retention time (min) | Observed m/z | 1H NMR |
|---|---|---|---|---|---|---|---|
| 376 | 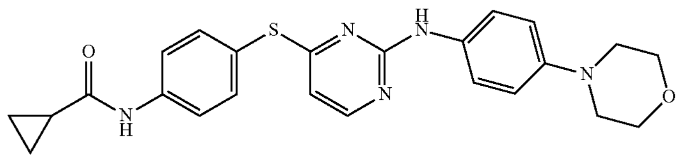 [SMILES: O=C(Nc1ccc(Sc2ccnc(Nc3ccc(N4CCOCC4)cc3)n2)cc1)C1CC1] | 447.17 | N-(4-(2-(4-morpholinophenyl-aminopyrimidin-4-ylthio)phenyl)cyclopropane-carboxamide | C | 6.7 | m/z 448.3 [M + H]+ | |
| 377 | 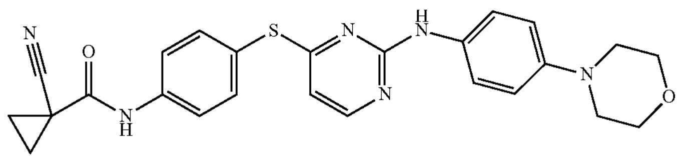 [SMILES: N#CC1(C(=O)Nc2ccc(Sc3ccnc(Nc4ccc(N5CCOCC5)cc4)n3)cc2)CC1] | 472.17 | 1-cyano-N-(4-(2-(4-morpholino phenylamino) pyrimidin-4-ylthio) phenyl)cyclopropanecarboxamide | C | 6.8 | m/z 473.3 [M + H]+ | |
| 378 | 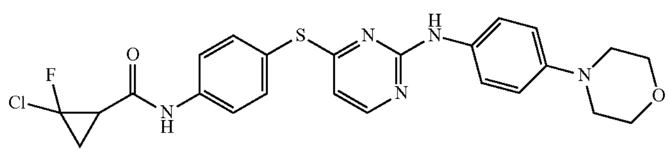 [SMILES: O=C(Nc1ccc(Sc2ccnc(Nc3ccc(N4CCOCC4)cc3)n2)cc1)C1CC1(F)Cl] | 499.12 | 2-chloro-2-fluoro-N-(4-(2-(4-morpholinoylamino) pyrimidin-4-ylthio) phenyl)cyclopropanecarboxamide | C | 7.1 | m/z 500.3 [M + H]+ | |
| 379 | 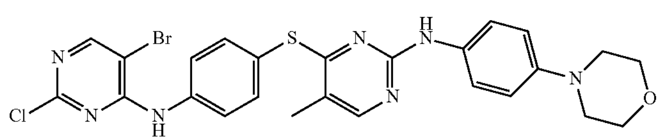 [SMILES: Cc1cnc(Nc2ccc(N3CCOCC3)cc2)nc1Sc1ccc(Nc2nc(Cl)ncc2Br)cc1] | 583.06 | 4-(4-(5-bromo-2-chloropyrimidin-4-ylaminophenyl-thio)-5-methyl-N-(4-morpholino-phenyl)pyrimidin-2-amine | E | 10.9 | m/z 584.2/ 586.2/ 588.2 [M + H]+ | 1H NMR (300 MHz, DMSO) δ 9.51 (s, 1H), 8.62 (s, 1H), 8.02 (s, 1H), 7.95 (d, J = 8.7, 2H), 7.60 (d, J = 8.7, 2H), 7.01 (d, J = 9.1, 2H), 6.46 (d, J = 9.1, 2H), 3.57 (m, 4H), 2.72 (m, 4H), 2.14 (s, 3H) |
| 380 | 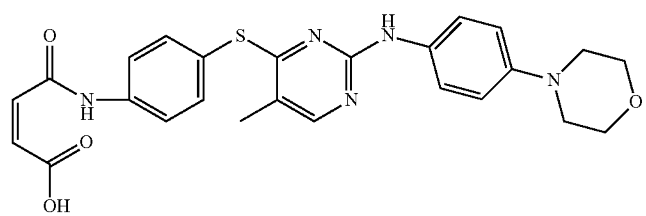 [SMILES: Cc1cnc(Nc2ccc(N3CCOCC3)cc2)nc1Sc1ccc(NC(=O)/C=C\C(=O)O)cc1] | 491.16 | (Z)-4-(4-(5-methyl-2-(4-morpholino-phenylamino) pyrimidin-4-ylthio) phenylamino)-4-oxobut-2-enoic acid | G | 6.1 | m/z 492.3 [M + H]+ | 1H NMR (300 MHz, DMSO) δ 11.04 (br s, 1H), 9.13 (s, 1H), 8.01 (s, 1H), 7.83 (d, J = 8.7, 2H), 7.55 (d, J = 8.7, 2H), 6.98 (d, J = 9.1, 2H), 6.48-6.36 (m, 4H), 3.68 (m, 4H), 2.88 (m, 4H), 2.13 (s, 3H) |

TABLE 1-continued

| Compound number | Structure | Exact mass | Name | LCMS method | retention time (min) | Observed m/z | ¹H NMR |
|---|---|---|---|---|---|---|---|
| 381 | 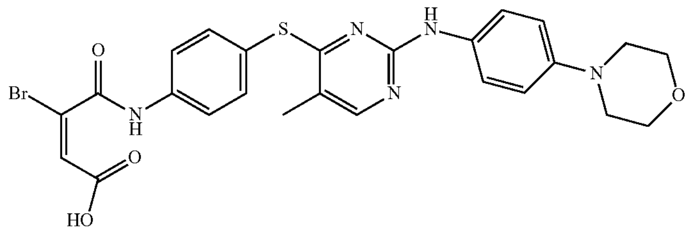 [SMILES: Cc1cnc(Nc2ccc(N3CCOCC3)cc2)nc1Sc1ccc(NC(=O)/C(Br)=C\C(=O)O)cc1] | 569.07 | (E)-3-bromo-4-(4-(5-methyl-2-(4-morpholinophenyl-amino)pyrimidin-4-ylthio)phenyl-amino)-4-oxobut-2-enoic acid | G | 6.2 | m/z 570.2/ 572.2 [M + H]+ | 1H NMR (300 MHz, DMSO) δ 9.14 (s, 1H), 8.02 (s, 1H), 7.80 (d, J = 8.7, 2H), 7.54 (d, J = 8.7, 2H), 6.96 (d, J = 9.1, 2H), 6.74 (s, 1H), 6.46 (d, J = 9.1, 2H), 3.70 (m, 4H), 2.89 (m, 4H), 2.13 (s, 3H) |
| 382 | 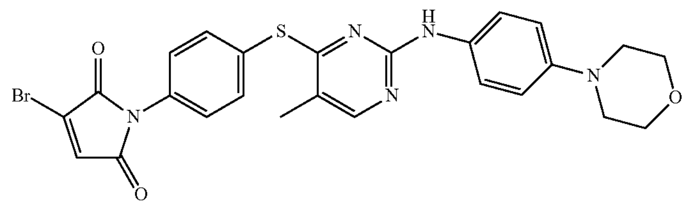 [SMILES: Cc1cnc(Nc2ccc(N3CCOCC3)cc2)nc1Sc1ccc(N2C(=O)C=C(Br)C2=O)cc1] | 551.06 | 3-bromo-1-(4-(5-methyl-2-(4-morpholinophenyl-amino)pyrimidin-4-ylthiophenyl)-1H-pyrrole-2,5-dione | C | 7.3 | m/z 552.2/ 554.2 [M + H]+ | 1H NMR (300 MHz, Acetone) δ 8.01 (s, 1H), 7.76 (d, J = 8.4, 2H), 7.62 (d, J = 8.4, 2H), 7.48 (s, 1H), 7.21 (d, J = 8.8, 2H), 6.69 (d, J = 9.2, 2H), 3.74 (m, 4H), 2.98 (m, 4H), 2.08 (s, 3H) |
| 383 | 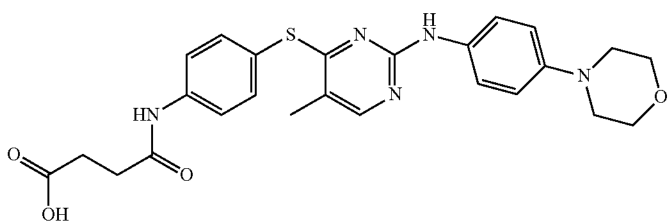 [SMILES: Cc1cnc(Nc2ccc(N3CCOCC3)cc2)nc1Sc1ccc(NC(=O)CCC(=O)O)cc1] | 493.18 | 4-(4-(5-methyl-2-(4-morpholino-phenylamino)pyrimidin-4-ylthio)phenylamino)-4-oxobutanoic acid | D | 4.6 | m/z 494.3 [M + H]+ | 1H NMR (300 MHz, DMSO) δ 12.15 (br s, 1H), 10.32 (s, 1H), 9.09 (s, 1H), 8.00 (s, 1H), 7.77 (d, J = 8.7, 2H), 7.51 (d, J = 8.7, 2H), 7.02 (d, J = 9.0, 2H), 6.50 (d, J = 9.0, 2H), 3.72 (m, 4H), 2.92 (m, 4H), 2.59 (m, 4H), 2.13 (s, 3H) |
| 384 | 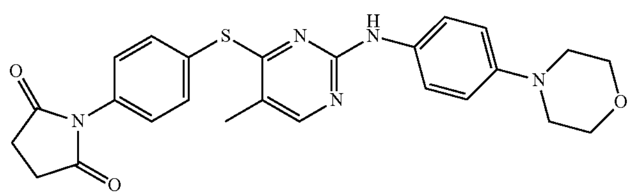 [SMILES: Cc1cnc(Nc2ccc(N3CCOCC3)cc2)nc1Sc1ccc(N2C(=O)CCC2=O)cc1] | 475.17 | 1-(4-(5-methyl-2-(4-morpholino-phenylamino)pyrimidin-4-ylthio)phenyl)pyrrolidine-2,5-dione | E | 9.1 | m/z 476.3 [M + H]+ | 1H NMR (300 MHz, DMSO) δ 9.14 (s, 1H), 8.07 (s, 1H), 7.73 (d, J = 8.7, 2H), 7.46 (d, J = 8.7, 2H), 7.13 (d, J = 9.1, 2H), 6.61 (d, J = 9.1, 2H), 3.70 (m, 4H), 2.93 (m, 4H), 2.83 (s, 4H), 2.16 (s, 3H) |

| Compound number | Exact mass | Name | Structure | LCMS method | retention time (min) | Observed m/z | 1H NMR |
|---|---|---|---|---|---|---|---|
| 385 | 519.19 | (E)-ethyl 4-(4-(5-methyl-2-(4-morpholinophenylaminopyrimidin-4-ylthio)phenyl-amino)-4-oxobut-2-enoate | 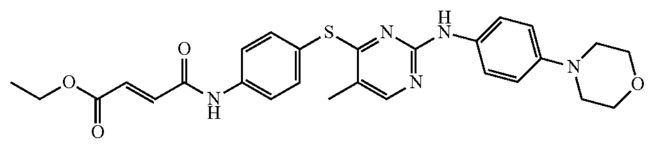 [SMILES: CCOC(=O)/C=C/C(=O)Nc1ccc(Sc2nc(Nc3ccc(N4CCOCC4)cc3)ncc2C)cc1] | C | 7.2 | m/z 520.3 [M+H]+ | 1H NMR (300 MHz, DMSO) δ 10.93 (s, 1H), 9.12 (s, 1H), 8.01 (s, 1H), 7.89 (d, J = 8.8, 2H), 7.58 (d, J = 8.8, 2H), 7.28 (d, J = 15.4, 1H), 6.97 (d, J = 9.2, 2H), 6.79 (d, J = 15.4, 1H), 6.45 (d, J = 9.2, 2H), 4.26 (q, J = 7.1, 2H), 3.62 (m, 4H), 2.84 (m, 4H), 2.14 (s, 3H), 1.28 (t, J = 7.1, 3H) |
| 386 | 506.21 | N1-methyl-N4-(4-(5-methyl-2-(4-morpholinophenylaminopyrimidin-4-ylthio)phenyl) succinamide | 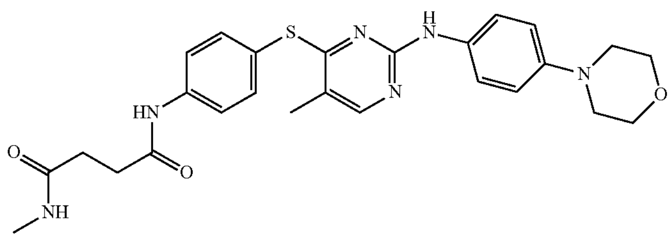 [SMILES: CNC(=O)CCC(=O)Nc1ccc(Sc2nc(Nc3ccc(N4CCOCC4)cc3)ncc2C)cc1] | C | 6.0 | m/z 507.3 [M+H]+ | 1H NMR (300 MHz, DMSO) d 10.31 (s, 1H), 9.09 (s, 1H), 8.00 (s, 1H), 7.77 (d, J = 9.2, 2H), 7.51 (d, J = 8.3, 2H), 7.02 (d, J = 8.3, 2H), 6.49 (d, J = 9.2, 2H), 3.72 (br s, 4H), 2.92 (br s, 4H), 2.59 (m, 4H), 2.44 (d, J = 7.5, 2H), 2.13 (s, 3H) |
| 387 | 491.16 | (E)-4-(4-(5-methyl-2-(4-morpholinophenylamino)pyrimidin-4-ylthio)phenylamino)-4-oxobut-2-enoic acid | 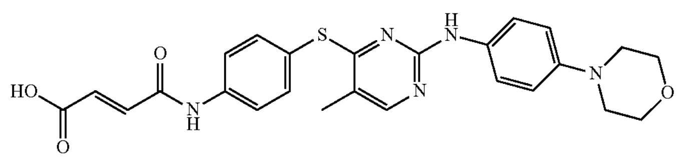 [SMILES: Cc1cnc(Nc2ccc(N3CCOCC3)cc2)nc1Sc1ccc(NC(=O)/C=C/C(=O)O)cc1] | D | 4.8 | m/z 492.3 [M+H]+ | 1H NMR (300 MHz, DMSO) δ 10.53 (s, 1H), 9.09 (s, 1H), 8.00 (s, 1H), 7.90 (d, J = 8.8, 2H), 7.52 (d, J = 8.8, 2H), 6.96 (d, J = 9.2, 2H), 6.69 (d, J = 3.6, 2H), 6.45 (d, J = 9.2, 2H), 3.65 (m, 4H), 2.84 (m, 4H), 2.13 (s, 3H) |
| 388 | 519.19 | (Z)-ethyl 4-(4-(5-methyl-2-(4-morpholinophenylaminopyrimidin-4-ylthio)phenyl-amino)-4-oxobut-2-enoate | 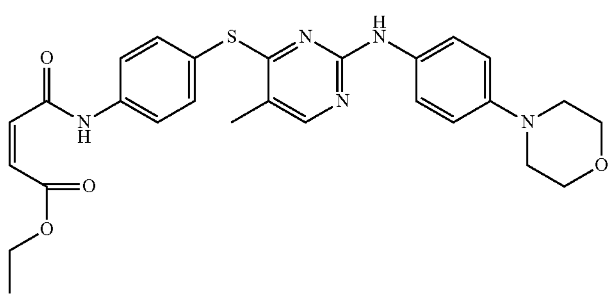 [SMILES: CCOC(=O)/C=C\C(=O)Nc1ccc(Sc2nc(Nc3ccc(N4CCOCC4)cc3)ncc2C)cc1] | C | 7.0 | m/z 520.3 [M+H]+ | 1H NMR (300 MHz, DMSO) δ 10.65 (s, 1H), 9.10 (s, 1H), 8.00 (s, 1H), 7.82 (d, J = 8.7, 2H), 7.55 (d, J = 8.7, 2H), 6.98 (d, J = 9.1, 2H), 6.58-6.33 (m, 4H), 4.16 (m, 2H), 3.69 (m, 4H), 2.88 (m, 4H), 2.13 (s, 3H), 1.19 (t, 3H) |

TABLE 1-continued

| Compound number | Structure | Exact mass | Name | LCMS method | retention time (min) | Observed m/z | 1H NMR |
|---|---|---|---|---|---|---|---|
| 389 | 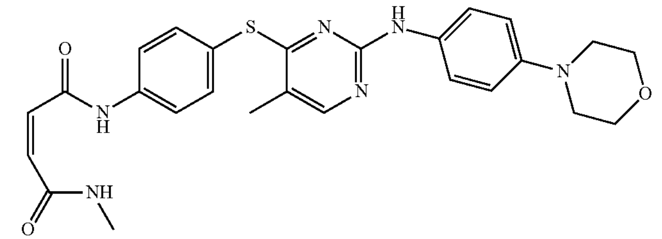 [SMILES: CNC(=O)/C=C\C(=O)Nc1ccc(Sc2nc(Nc3ccc(N4CCOCC4)cc3)ncc2C)cc1] | 504.19 | N1-methyl-N4-(4-(5-methyl-2-(4-morpholinophenylaminopyrimidin-4-ylthio)phenyl)maleamide | C | 6.5 | m/z 505.3 [M + H]+ | 1H NMR (300 MHz, DMSO) d 12.31 (s, 1H), 9.10 (s, 1H), 8.79 (m, 1H), 8.01 (s, 1H), 7.82 (d, J = 8.7, 2H), 7.55 (d, J = 8.7, 2H), 6.99 (d, J = 9.2, 2H), 6.46 (d, J = 9.2, 2H), 6.38 (d, J = 12.8, 1H), 6.28 (d, J = 12.8, 1H), 3.66 (m, 4H), 2.86 (m, 4H), 2.72 (d, J = 5.0, 3H), 2.14 (s, 3H) |
| 390 | 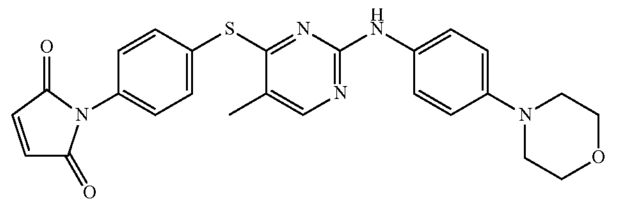 [SMILES: Cc1cnc(Nc2ccc(N3CCOCC3)cc2)nc1Sc1ccc(N2C(=O)C=CC2=O)cc1] | 473.15 | 1-(4-(5-methyl-2-(4-morpholinophenylamino)pyrimidin-4-ylthio)phenyl)-1H-pyrrole-2,5-dione | C | 6.9 | m/z 474.3 [M + H]+ | 1H NMR (300 MHz, DMSO) δ 9.18 (s, 1H), 8.06 (s, 1H), 7.73 (d, 2H), 7.56 (d, 2H), 7.29 (s, 2H), 7.08 (d, 2H), 6.53 (d, 2H), 3.67 (m, 4H), 2.87 (m, 4H), 2.16 (m, 3H) |
| 391 | 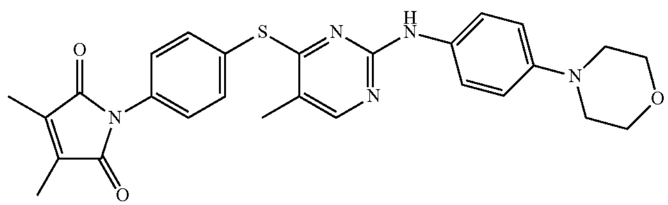 [SMILES: CC1=C(C)C(=O)N(c2ccc(Sc3nc(Nc4ccc(N5CCOCC5)cc4)ncc3C)cc2)C1=O] | 501.18 | 3,4-dimethyl-1-(4-(5-methyl-2-(4-morpholinophenylaminopyrimidin-4-ylthio)phenyl)-1H-pyrrole-2,5-dione | C | 7.6 | m/z 502.3 [M + H]+ | 1H NMR (300 MHz, DMSO) δ 9.14 (s, 1H), 8.05 (s, 1H), 7.71 (m, 2H), 7.55 (m, 2H), 7.08 (d, J = 9.1, 2H), 6.56 (d, J = 9.1, 2H), 3.67 (m, 4H), 2.88 (m, 4H), 2.16 (s, 3H), 2.02 (s, 6H) |
| 392 | 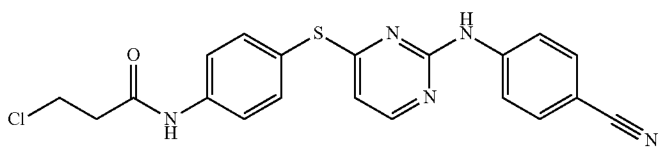 [SMILES: N#Cc1ccc(Nc2nccc(Sc3ccc(NC(=O)CCCl)cc3)n2)cc1] | 409.08 | 3-chloro-N-(4-(2-(4-cyanophenyl-aminopyrimidin-4-ylthiophenyl)propanamide | C | 7.0 | m/z 410.1/412.1 [M + H]+ | |

TABLE 1-continued

| Compound number | Structure | Exact mass | Name | LCMS method | retention time (min) | Observed m/z | 1H NMR |
|---|---|---|---|---|---|---|---|
| 393 | 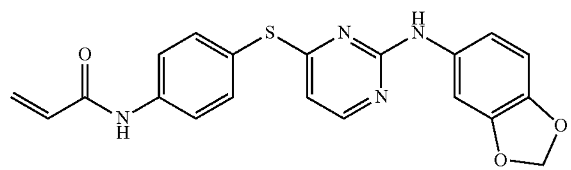 [SMILES: C=CC(=O)Nc1ccc(Sc2ccnc(Nc3ccc4c(c3)OCO4)n2)cc1] | 392.09 | N-(4-(2-(benzo[d][1,3]dioxol-5-ylamino)pyrimidin-4-ylthio)phenyl)acrylamide | E and H | 8.3 | m/z 392.3 M+ | 1H NMR (300 MHz, d6-DMSO) δ 10.46 (br s, 1H), 9.47 (s, 1H), 8.12 (d, J = 5.2, 1H), 7.84 (d, J = 8.7, 2H), 7.57 (d, J = 8.7, 2H), 7.16-7.15 (m, 1H), 6.92 (dd, J = 8.5, 2.2, 1H), 6.66 (d, J = 8.2, 1H), 6.50 (dd, J = 10.0, 6.9, 1H), 6.33 (s, 1H), 6.31-6.27 (m, 1H), 5.88 (s, 2H), 5.80 (dd, J = 10.1, 1.9, 1H |
| 394 | 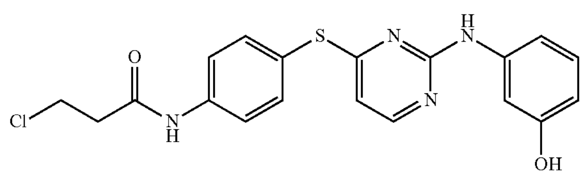 [SMILES: O=C(CCCl)Nc1ccc(Sc2ccnc(Nc3cccc(O)c3)n2)cc1] | 400.08 | 3-chloro-N-(4-(2-(3-hydroxyphenyl)aminopyrimidin-4-ylthio)phenyl)propanamide | C | 6.4 | m/z 401.3/403.3 [M + H]+ | |

The term "$C_{1-6}$alkyl" refers to straight chain or branched chain hydrocarbon groups having from 1 to 6 carbon atoms. Examples include ethyl, propyl, isopropyl, butyl, isobutyl, sec-butyl, tert-butyl, pentyl, neopentyl and hexyl.

The term "$C_{1-6}$alkylene" is the divalent equivalent of "$C_{1-6}$alkyl".

The term "$C_{2-6}$alkenyl" refers to straight chain or branched chain hydrocarbon groups having at least one double bond of either E or Z stereochemistry where applicable and 2 to 6 carbon atoms. Examples include vinyl, 1-propenyl, 1- and 2-butenyl and 2-methyl-2-propenyl.

The term "$C_{2-6}$alkynyl" refers to straight chain or branched chain hydrocarbon groups having at least one triple bond and 2 to 4 carbon atoms. Examples include ethynyl, 1- or 2-propynyl, 1-, 2- or 3-butynyl and methyl-2-propynyl.

The term "$C_{3-8}$cycloalkyl" refers to non-aromatic cyclic hydrocarbon groups having from 3 to 8 carbon atoms. Examples include cyclopropyl, cyclobutyl, cyclopentyl and cyclohexyl.

The term "aryl" refers to single, polynuclear, conjugated or fused residues of aromatic hydrocarbons. Examples include phenyl, biphenyl, terphenyl, quaterphenyl, naphthyl, tetrahydronaphthyl, anthracenyl, dihydroanthracenyl, benzanthracenyl, dibenxanthracenyl and phenanthrenyl. 5 to 7 membered monocyclic aromatic ring systems such as phenyl are preferred.

The term "heterocyclyl" refers to saturated or unsaturated, monocyclic or polycyclic hydrocarbon groups containing at least one heteroatom atom selected from the group consisting of consisting of N, O, S and $SO_2$.

Suitable heterocyclyls include N-containing heterocyclic groups, such as, unsaturated 3 to 6-membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

Preferred heterocyclyls are 5 to 7 membered saturated or unsaturated heterocyclyls having 1 to 4 heteroatoms independently selected from N, O, S and $SO_2$ such as morpholino, piperidinyl, piperazinyl, pyrrolidinyl and 1,3-thiazolidine 1,1-dioxide or 8 to 10 membered bicyclic ring systems having 1 to 5 heteroatoms independently selected from N, O, S and $SO_2$.

The term "halogen" refers to fluorine, chlorine, bromine and iodine.

The term "substituted or unsubstituted" refers to a group that may or may not be further substituted with one or more groups selected from $C_{1-6}$ alkyl, $C_{3-6}$ cycloalkyl, $C_{2-6}$ alkenyl, $C_{2-6}$ alkynyl, $C_{1-6}$ alkylaryl, aryl, heterocyclyl, halo, halo$C_{1-6}$alkyl, halo$C_{3-6}$cycloalkyl, halo$C_{2-6}$alkenyl, halo$C_{2-6}$alkynyl, haloaryl, haloheterocyclyl, hydroxy, $C_{1-6}$ alkoxy, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, nitro, nitro$C_{1-6}$alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclylamino acyl, $C_{1-6}$alkylacyl, $C_{2-6}$alkenylacyl, $C_{2-6}$alkynylacyl, arylacyl, heterocycylylacyl, acylamino, acyloxy, aldehydro, $C_{1-6}$alkylsulphonyl, arylsulphonyl, $C_{1-6}$alkylsulphonylamino, arylsulphonylamino, $C_{1-6}$alkylsulphonyloxy, arylsulphonyloxy, $C_{1-6}$alkylsulphenyl, $C_{2-6}$alklysulphenyl, arylsulphenyl, carboalkoxy, carboaryloxy, mercapto, $C_{1-6}$alkylthio, arylthio, acylthio, cyano and the like. Preferred substituents are selected from the group consisting of $C_{1-4}$ alkyl, $C_{3-6}$ cycloalkyl, $C_{2-6}$ alkenyl, $C_{2-6}$ alkynyl, $C_{1-6}$ alkylaryl, aryl, heterocyclyl, halo, haloaryl, haloheterocyclyl, hydroxy, $C_{1-4}$ alkoxy, aryloxy, carboxy, amino, $C_{1-6}$alkylacyl, arylacyl, heterocyclylacyl, acylamino, acyloxy, $C_{1-6}$alkylsulphenyl, arylsulphonyl and cyano.

The compounds of the invention may also be prepared as salts which are pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Where a compound possesses a chiral center the compound can be used as a purified enantiomer or diastereomer, or as a mixture of any ratio of stereoisomers. It is however preferred that the mixture comprises at least 70%, 80%, 90%, 95%, 97.5% or 99% of the preferred isomer, where the preferred isomer gives the desired level of potency and selectivity.

This invention also encompasses prodrugs of the compounds of formula I. The invention also encompasses methods of treating disorders that can be treated by the inhibition of protein kinases, such as JAK comprising administering drugs or prodrugs of compounds of the invention. For example, compounds of formula I having free amino, amido, hydroxy or carboxylic acid groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of compounds of the present invention through the carbonyl carbon prodrug sidechain. Prodrugs also include phosphate derivatives of compounds (such as acids, salts of acids, or esters) joined through a phosphorus-oxygen bond to a free hydroxyl of compounds of formula I. Prodrugs may also include N-oxides, and S-oxides of appropriate nitrogen and sulfur atoms in formula I.

This invention also encompasses methods of treating or preventing disorders that can be treated or prevented by the inhibition of protein kinases, such as JAK kinases comprising administering drugs or prodrugs of compounds of the invention.

Process of Making Compounds

Compounds are generally prepared in a 3-step process starting from a dihaloheterocycle.

The first step is a nucleophilic aromatic substitution to generate a monothio-monohalo intermediate.

The nucleophilic aromatic substitution is typically carried out by addition of a thiol to the di-halogenated heterocycle in a solvent such as water, methanol, ethanol, isopropanol, tert-butanol, dioxane, THF, DMF, ethoxyethanol, toluene or xylene or a solvent mixture comprising 2-3 solvents selected from those listed above. The reaction is typically performed at room temperature to elevated temperature in the presence of excess amine or a non-nucleophilic base such as triethylamine or diisopropylethylamine, or an inorganic base such as potassium hydroxide, potassium carbonate or sodium hydroxide or sodium carbonate. Alternatively the thiol may be introduced through in situ generation of a thiolate from a protected thiol species or from reduction of a thiocyanate. Protected thiol species may be, for example, thiosilicones, which may be deprotected with a fluoride anion.

The thiols employed in the first step of the synthesis of these compounds are obtained commercially or are prepared using methods well known to those skilled in the art. Thus for example, an aromatic or heteroaromatic bromide or iodide can be converted to the corresponding thiol by a palladium catalysed reaction between triisopropylsilylthiol and the halide following the method of Soderquist (Soderquist, 1994), or related methods.

The second step is a nucleophilic aromatic substitution to generate the required monoamino-monothio product.

The nucleophilic aromatic substitution is typically carried out by addition of a primary or secondary amine to the mono-halogenated heterocycle in a solvent such as ethanol, isopropanol, tert-butanol, dioxane, THF, DMF, ethoxyethanol, toluene or xylene. The reaction is typically performed at elevated temperature in the presence of excess amine or a non-nucleophilic base such as triethylamine or diisopropylethylamine, or an inorganic base such as potassium carbonate or sodium carbonate. The reaction may also be performed under acidic conditions in solvents such as dioxane, ethanol or isopropanol, with acids such as p-toluenesulfonic acid and HCl. With either acidic or basic conditions, the reactions may be performed under pressure using for example microwave heating.

Alternatively, the amino substituent may be introduced through a transition metal catalysed amination reaction. Typical catalysts for such transformations include $Pd(OAc)_2/P(t-Bu)_3$, $Pd_2(dba)_3$/BINAP and $Pd(OAc)_2$/BINAP. These reactions are typically carried out in solvents such as toluene or dioxane, in the presence of bases such as caesium carbonate or sodium or potassium tert-butoxide at temperatures ranging from room temperature to reflux.

The products formed from either reaction step may be further derivatised using techniques known to those skilled in the art. Alternatively, derivatisation of the mono-halo intermediate may be undertaken prior to reaction of the second halo substituent. Those skilled in the art will appreciate that the order of the reactions described for the syntheses above may be changed in certain circumstances and that certain functionalities may need to be derivatised (i.e. protected) in certain instances for the reactions described above to proceed with reasonable yield and efficiency. The types of protecting functionality are well-known to those skilled in the art and are described for example in Greene (Greene, T., Wuts, P. (1999) *Protective Groups in Organic Synthesis*. Wiley-Interscience; 3rd edition.).

The leaving group may be any suitable known type such as those disclosed in J. March, "Advanced Organic Chemistry: Reactions, Mechanisms and Structure" $4^{th}$ Edition, pp 352-357, John Wiley & Sons, New York, 1992 which is incorporated herein by reference. Preferably, the leaving group is halogen, more preferably chlorine.

JAK Inhibition

The compounds of formula I have activity against protein kinases, particularly the JAK kinases and most particularly selective activity against JAK1, JAK2 or JAK3 kinases or combinations thereof. A JAK2 inhibitor is any compound that selectively inhibits the activity of JAK2. A JAK3 inhibitor is any compound that selectively inhibits the activity of JAK3. A JAK1/JAK2 selective inhibitor is any compound that selectively inhibits both JAK1 and JAK2. One activity of both JAK2 and JAK3 is to phosphorylate a STAT protein. Therefore an example of an effect of a JAK2 or JAK3 inhibitor is to decrease the phosphorylation of one or more STAT proteins. The inhibitor may inhibit the phosphorylated form of JAK2 or JAK3 or the non-phosphorylated form of JAK2 or JAK3.

Selective and Irreversible Inhibition of JAK3

A PTK catalyses the transfer of a phosphate group from a molecule of ATP to a tyrosine residue located on a protein substrate. The inhibitors known in the art are usually competitive with either the ATP or the protein substrate of the kinase (Levitzki 2000). Since the concentration of ATP in a cell is normally very high (millimolar), compounds that are competitive with ATP may lack in vivo activity since it is unlikely that said compounds can reach the concentrations within the cell that are necessary to displace the ATP from its binding site.

An alternative approach which has been attempted in relation to EGFR is to design or select compounds which bind to EGFR TK in an irreversible manner. Such compounds are disclosed in Fry 1998; Discafani 1999; Smaill 1999; Smaill 2000; Tsou 2001; Smaill 2001; Wissner 2003. These compounds function as irreversible inhibitors by virtue of the fact that they can form covalent bonds to amino acid residues located at the active site of the enzyme which results in enhanced potency of the compounds in vitro and in the inhibition of growth of human tumors in in vivo models of cancer. A further benefit of such irreversible inhibitors when compared to reversible inhibitors, is that irreversible inhibitors can be used in prolonged suppression of the tyrosine kinase, limited only by the normal rate of receptor turnover.

Alignment of the four members of the JAK family of protein tyrosine kinases reveals that within the amino acids that comprise the ATP-binding pocket of these kinases there are very few amino acid differences that could be used to target potential inhibitors towards one family member or another. Interestingly, JAK3 alone amongst this sub-family of kinases possesses a Cysteine residue close to the front lip of the ATP-binding cavity (Cys 963). By targeting this Cysteine with a functionality bearing an alkylating group such as a Michael acceptor, or other such group that can react reversibly or irreversibly with the thiol moiety of this Cysteine residue, highly selective JAK3 inhibition can be achieved.

Pharmaceutical Compositions

The present invention provides pharmaceutical compositions comprising at least one of the compounds of the formula I and a pharmaceutically acceptable carrier. The carrier must be "pharmaceutically acceptable" means that it is compatible with the other ingredients of the composition and is not deleterious to a subject. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: The Science and Practice of Pharmacy, 21st Ed., 2005, Lippincott Williams & Wilkins).

The compounds of the invention may be administered by any suitable means, for example, orally, such as in the form of tablets, capsules, granules or powders; sublingually; buccally; parenterally, such as by subcutaneous, intravenous, intramuscular, intra(trans)dermal, or intracisternal injection or infusion techniques (e.g., as sterile injectable aqueous or non-aqueous solutions or suspensions); nasally such as by inhalation spray or insufflation; topically, such as in the form of a cream or ointment ocularly I the form of a solution or suspension; vaginally in the form of pessaries, tampons or creams; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

The pharmaceutical compositions for the administration of the compounds of the invention may conveniently be presented in dosage unit form and may be prepared by any of the methods well known in the art of pharmacy. These methods generally include the step of bringing the compound of formula I into association with the carrier which constitutes one or more accessory ingredients. In general, the pharmaceutical compositions are prepared by uniformly and intimately bringing the compound of formula I into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the compound of formula I may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents such as sweetening agents, flavouring agents, colouring agents and preserving agents, e.g. to provide pharmaceutically stable and palatable preparations. Tablets contain the compound of formula I in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the compound of formula I is mixed with an inert solid diluent, for example, calcium carbonate, calcium phosphate or kaolin, or as soft gelatin capsules wherein the compound of formula I is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the compound of formula I in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compound of formula I in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

For administration to the respiratory tract, including intranasal administration, the active compound may be administered by any of the methods and formulations employed in the art for administration to the respiratory tract.

Thus in general the active compound may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose and carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the subject administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of active compound may be controlled by provision of a metered valve.

Alternatively the active compound may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler.

In formulations intended for administration to the respiratory tract, including intranasal formulations, the active compound will generally have a small particle size, for example of the order of 5 microns or less. Such a particle size may be obtained by means known in the art, for example by micronisation.

When desired, formulations adapted to give sustained release of the active compound may be employed.

The active compound may be administered by oral inhalation as a free-flow powder via a "Diskhaler" (trade mark of Glaxo Group Ltd) or a meter dose aerosol inhaler.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions suitable for vaginal administration may be presented as pessaries, tampons, creams, gels, pastes, foams or sprays containing in addition to the active ingredient such carriers as are known in the art to be appropriate.

For topical use, creams, ointments, jellies, solutions or suspensions, etc., containing the compounds of the present invention are employed. (For purposes of this application, topical application shall include mouthwashes and gargles.)

For application to the eye, the active compound may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride, or chlorhexidine and thickening agents such as hypromellose may also be included.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

Efficacy of this class of compounds may be applicable to drug eluting stents. Potential applications of drug eluting stents with these compounds include pulmonary artery stenosis, pulmonary vein stenosis, as well as coronary artery stenosis. Drug eluting stents may also be used in saphenous vein grafts or arterial grafts or conduits. Drug eluting stents that release this class of compounds may also be applicable for treating stenoses of the aorta or peripheral arteries, such as the iliac artery, the femoral artery or the popliteal artery. The compound may be bound to the drug eluting stent by any of various methods known in the field. Examples of such methods include polymers, phosphoryl choline, and ceramics. The compound may also be impregnated into a bioabsorbable stent.

The active compounds may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) rectally or intravaginally, e.g. as a pessary, cream or foam.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following: endothelin receptor antagonists (eg ambrisentan, bosentan, sitaxsentan), PDE-V inhibitors (eg sildenafil, tadalafil, vardenafil), Calcium channel blockers (eg amlodipine, felodipine, varepamil, diltiazem, menthol), prostacyclin, treprostinil, iloprost, beraprost, nitric oxide, oxygen, heparin, warfarin, diuretics, digoxin, cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABA's such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

Methods of Treatment

The compounds of formula I may be used in the treatment of kinase associated diseases including JAK kinase associated diseases such immunological and inflammatory diseases including organ transplants; hyperproliferative diseases including cancer and myeloproliferative diseases; viral diseases; metabolic diseases; and vascular diseases.

Generally, the term "treatment" means affecting a subject, tissue or cell to obtain a desired pharmacological and/or physiological effect and include: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The term "subject" refers to any animal having a disease which requires treatment with the compound of formula I.

In addition to primates, such as humans, a variety of other mammals can be treated using the compounds, compositions and methods of the present invention. For instance, mammals including, but not limited to, cows, sheep, goats, horses, dogs, cats, guinea pigs, rats or other bovine, ovine, equine, canine, feline, rodent or murine species can be treated. However, the invention can also be practiced in other species, such as avian species (e.g., chickens).

The term "administering" should be understood to mean providing a compound of the invention to a subject in need of treatment.

The term "kinase associated diseases" refers to a disorder or disorders that directly or indirectly result from or are aggravated by aberrant kinase activity, in particular JAK kinase activity and/or which are alleviated by inhibition of one or more of these kinase enzymes.

In a preferred embodiment the kinase associated disease state involves one or more of the JAK kinases, JAK1, JAK2, JAK3 or TYK2. In a particularly preferred embodiment, the disease involves JAK2 or JAK3 kinase. Such diseases include, but are not limited to, those listed in the Table below.

| | | | | |
|---|---|---|---|---|
| Activation of the JAK/STAT pathway in various pathologies | | | | |
| Disease Type | Cell Types Involved | Cytokines involved | JAK Kinase Involved | Characteristics |
| Atopy | | | | |
| Allergic Asthma, Atopic Dermatitis (Eczema), Allergic Rhinitis, | Mast Cells, Eosinophils, T-Cells, B-Cells, | IL-4, IL-5, IL-6, IL-7, IL-13 | JAK1, JAK2, JAK3, Tyk2 | T-cell activation of B-cells followed by IgE mediated activation of resident Mast cells and Eosinophils |
| CMH | | | | |
| Allergic Contact Dermatitis, hypersensitivity pneumonitis AutoImmune Diseases | T-cells, B-cells, macrophages, neutrophils | IL-2, IL-4, IL-5, IL-6, IL-10, IFNγ, TNF, IL-7, IL-13, | JAK1, JAK2, JAK3, Tyk2 | B cell and/or $T_{DH}$ cell activation Macrophage/granulocyte activation |
| Multiple sclerosis, Glomerulonephritis Systemic Lupus Erythematosus (SLE), Rheumatoid Arthritis, Juvenile Arthritis, Sjögren's Syndrome, Scleroderma Polymyositis, Ankylosing Spondylitis, Psoriatic Arthritis Transplantation | B-Cells, T cells, monocytes, Macrophages, Neutrophils, Mast Cells, Eosinophils, | IL-2, IL-4, IL-5, IL-6, IL-7, Il-10, IL-13, IFNγ, TNF, GM-CSF; G-CSF, | JAK1, JAK2, JAK3, Tyk2 | Cytokine Production (e.g. TNFα/β, IL-1, CSF-1, GM-CSF), T-cell Activation, B cell activation, JAK/STAT activation |
| Allograft Rejection GvHD | T cells, B cells, macrophages | IL-2, IL-4, IL-5, IL-7, IL-13, TNF | JAK1, JAK2, JAK3, | Macrophage/T cell mediated necrosis, Tc cell mediated apoptosis, and B cell/Ig mediated opsonization/necrosis of foreign graft |
| Viral Diseases | | | | |
| Epstein Barr Virus (EBV) Hepatitis B Hepatitis C HIV HTLV 1 Varicella-Zoster Virus (VZV) Human Papilloma Virus (HPV) Hyperproliferative diseases-cancer | Lymphocytes Hepatocytes Hepatocytes Lymphocytes Lymphocytes Fibroblasts Epithelial cells | Viral Cytokines, IL-2, | JAK1, JAK2, JAK3 | JAK/STAT Mediation |
| Leukemia Lymphoma Multiple Myeloma prostate cancer breast cancer hodgkins lympohoma B-cell chronic lymphocytic leukemia lung cancer hepatoma metastatic myeloma glioma Myeloproliferative Diseases | Leucocytes Lymphocytes various various various various various various various various various | Various Autocrine cytokines, Intrinsic Activation | JAK1, JAK2, JAK3 | Cytokine production, JAK/STAT Activation |
| Polycythemia rubra vera, primary myelofibrosis, thrombocythemia, essential | Hematopoietic | Interleukin-3, erythropoietin, thrombopoietin | JAK2 mutation | JAK/STAT activation |

-continued

| Activation of the JAK/STAT pathway in various pathologies | | | | |
|---|---|---|---|---|
| Disease Type | Cell Types Involved | Cytokines involved | JAK Kinase Involved | Characteristics |
| thrombocythemia, idiopathic myelofibrosis, chronic myelogenous leukemia | | | | |
| Vascular Disease | | | | |
| Hypertension, Hypertrophy, Heart Failure, Ischemia, Pulmonary arterial hypertension | Endothelial cells, smooth muscle cells including pulmonary artery smooth muscle cells, cardiac myocytes, fibroblasts, endothelial cells | IL6, angiotensin II, LIF, TNFalpha, serotonin, caveolin1 | JAK1, JAK2, TYK2 | JAK/STAT activation |
| Metabolic disease | | | | |
| Obesity, metabolic syndrome | Adipocytes, pituitary cells, neurons, monocytes | Leptin | JAK2 | JAK/STAT activation |

The term "immunological and inflammatory disease" refers to an immunological, inflammatory or autoimmune disease, including but not limited to rheumatoid arthritis, polyarthritis, rheumatoid spondylitis, osteoarthritis, gout, asthma, bronchitis, allergic rhinitis, chronic obstructive pulmonary disease, cystic fibrosis, inflammatory bowel disease, irritable bowel syndrome, mucous colitis, ulcerative colitis, diabrotic colitis, Crohn's disease, autoimmune thyroid disorders, gastritis, esophagitis, hepatitis, pancreatitis, nephritis, psoriasis, eczema, acne vulgaris, dermatitis, hives, multiple sclerosis, Alzheimer's disease, Lou Gehrig's disease, Paget's disease, sepsis, conjunctivitis, neranl catarrh, chronic arthrorheumatism, systemic inflammatory response syndrome (SIRS), polymyositis, dermatomyositis (DM), *Polaritis nodoa* (PN), mixed connective tissue disorder (MCTD), Sjoegren's syndrome, Crouzon syndrome, achondroplasia, systemic lupus erythematosus, scleroderma, vasculitis, thanatophoric dysplasia, insulin resistance, Type I diabetes and complications from diabetes and metabolic syndrome.

The term "hyperproliferative diseases" includes cancer and myeloproliferative disease states such as cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostrate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfrorna (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma]), fallopian tubes (carcinoma); Hematologic: blood (myeloid leukemia [acute and chronic], acute lymphoblastic leukemia, chronic lymphocytic leukemia, multiple myeloma, myelodysplastic syndrome), Hodgkin's disease, non-Hodgkin's lymphoma [malignant lymphomaj; çji: malignant melanoma, basal cell carcinoma, squamous cell carcinoma, Karposi's sarcoma, moles dysplastic nevi, lipoma, angioma, dermatofibroma, keloids, psoriasis; Adrenal glands: neuroblastoma; and Myeloproliferative diseases such as polycythemia rubra vera, primary myelofibrosis, thrombocythemia, essential thrombocythemia (ET), agnoneic myeloid metaplasia (AMM), also referred to as idiopathic myelofibrosis (IMF), and chronic myelogenous leukemia (CML).

The term "vascular diseases" refers to diseases including but not limited to cardiovascular diseases, hypertension, hypertrophy, hypercholesterolemia, hyperlipidemia, thrombotic disorders, stroke, Raynaud's phenomenon, POEMS syndrome, angina, ischemia, migraine, peripheral arterial disease, heart failure, restenosis, atherosclerosis, left ventricular hypertrophy, myocardial infarction, ischemic diseases of heart, kidney, liver and brain, and pulmonary arterial hypertension.

Preferred diseases for JAK2 selective inhibitors include immunological and inflammatory diseases such as auto-immune diseases for example atopic dermatitis, asthma, allergic rhinitis, rheumatoid arthritis, juvenile arthritis, Sjögren's syndrome, scleroderma, polymyositis, ankylosing spondylitis, psoriatic arthritis, cell mediated hypersensitivity for example allergic contact dermatitis and hypersensitivity pneumonitis, Crohn's disease, psoriasis, Crouzon syndrome, achondroplasia, systemic lupus erythematosus, scleroderma, mixed connective tissue disease, vasculitis, thanatophoric dysplasia and diabetes; hyperproliferative disorders such as cancer for example prostate cancer, colon cancer, breast cancer, liver cancer such as hepatoma, lung cancer, head and neck cancer such as glioma, skin cancer such as metastatic melanoma, leukemia, lymphoma, multiple myeloma and myeloproliferative diseases such as polycythemia rubra vera, myelofibrosis, thrombocythemia, essential thrombocythemia (ET), agnoneic myeloid metaplasia (AMM), also referred to as idiopathic myelofibrosis (IMF), and chronic myelogenous leukemia (CML); and vascular diseases such as hypertension, hypertrophy, stroke, Raynaud's phenomenon, POEMS syndrome, angina, ischemia, migraine, peripheral arterial disease, heart failure, restenosis, atherosclerosis and pulmonary arterial hypertension.

Preferred diseases for compounds which selectively inhibit both JAK1 and JAK2 are hyperproliferative diseases such as cancer for example prostate cancer, colon cancer, breast cancer, liver cancer such as hepatoma, lung cancer, head and neck cancer such as glioma, skin cancer such as metastatic melanoma, leukemia, lymphoma and multiple myeloma.

Preferred diseases for selective inhibitors of JAK3 are immunological and inflammatory diseases including autoimmune diseases such as systemic lupus erythematosus, mixed connective tissue disease, scleroderma, multiple sclerosis, autoimmune neuritis, rheumatoid arthritis, psoriasis, insulin resistance, Type I diabetes and complications from diabetes, metabolic syndrome, asthma, atopic dermatitis, autoimmune thyroid disorders, ulcerative colitis, Crohn's disease, Alzheimer's disease, and other indications where immunosuppression may be desirable such as organ transplants and graft vs host disease. Furthermore specific inhibitors of JAK3 may find application for therapeutic treatments for hyperproliferative diseases such as leukaemia and lymphoma where JAK3 is hyperactivated.

The compounds of formula may also be used in a method of suppressing the immune system of a subject. In one embodiment, the method of suppressing the immune system is to modify the immune system response to a transplant into the subject. More preferably, the transplant is an organ transplant or tissue transplant.

Preferably, the method of suppressing the immune system is for the treatment of disease states selected from Atopy, such as Allergic Asthma, Atopic Dermatitis (Eczema), and Allergic Rhinitis; Cell Mediated Hypersensitivity, such as Allergic Contact Dermatitis and Hypersensitivity Pneumonitis; AutoImmune Diseases, such as Multiple sclerosis, Glomerulonephritis, Systemic Lupus Erythematosus (SLE), Rheumatoid Arthritis, Juvenile Arthritis, Sjögren's Syndrome, Scleroderma Polymyositis, Ankylosing Spondylitis, Psoriatic Arthritis, Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis, Ulcerative Colitis, Crohn's disease; Other autoimmune diseases such as Type I diabetes, autoimmune thyroid disorders, and Alzheimer's disease; Transplantation related diseases, such as Allographt Rejection, and graft vs host disease; Viral Diseases, such as Epstein Barr Virus (EBV), Hepatitis B, Hepatitis C, HIV, HTLV 1, Varicella-Zoster Virus (VZV), Human Papilloma Virus (HPV), Cancer, such as Leukemia, Lymphoma and Prostate Cancer.

Dosages

The term "therapeutically effective amount" refers to the amount of the compound of formula I that will elicit the biological or medical response of a tissue, system, animal or human that is being sought by the researcher, veterinarian, medical doctor or other clinician.

In the treatment or prevention of conditions which require kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The dosage may be selected, for example to any dose within any of these ranges, for therapeutic efficacy and/or symptomatic adjustment of the dosage to the patient to be treated. The compounds will preferably be administered on a regimen of 1 to 4 times per day, preferably once or twice per day.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order to exemplify the nature of the present invention such that it may be more clearly understood, the following non-limiting examples are provided.

EXAMPLES

Compound Synthesis

The compounds of the invention may be prepared by methods well known to those skilled in the art, and as described in the synthetic and experimental procedures shown below for selected compounds.

Definitions

PyBOP benzotriazole-1-yloxytripyrrolidinophosphonium hexafluorophosphate

DMF N,N-dimethylformamide

DMAP 4-Dimethylaminopyridine

DCM dichloromethone

NMP 1-methyl-2-pyrrolidinone
n-PrOH n-propanol
ACN acetonitrile
EDC.HCl 1-ethyl-3-(dimethylaminopropyl)carbodiimide hydrochloride
HOBT N-hydroxybenzotriazole
TEA triethylamine
DIPEA diisopropylethylamine
p-TsOH p-toluene sulfonic acid
HATU o-(7-azabenzotriazol-1-yl)-N,N,N',N'-tetramethyluronium hexafluorophosphate
THF tetrahydrofuran General Examples Synthesis of Thiocyanates from Anilines and Subsequent Reduction and Reaction with Dichloropyrimidine

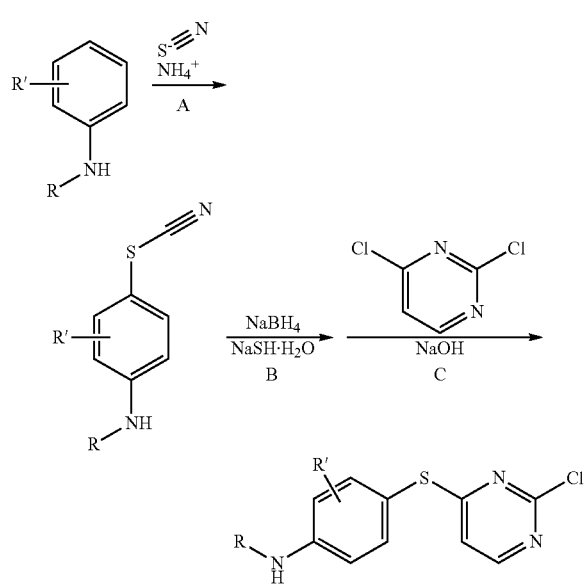

Step A 4-amino-2-chloro-3-methylphenyl thiocyanate (J. S. Yadav, B. V. Subba Reddy, U. V. Subba Reddy and A. D. Krishna "Iodine/MeOH as a novel and versatile reagent system for the synthesis of α-ketothiocyanates" *Tetrahedron Letters*, Volume 48, Issue 30, 23 Jul. 2007, Pages 5243-5246)

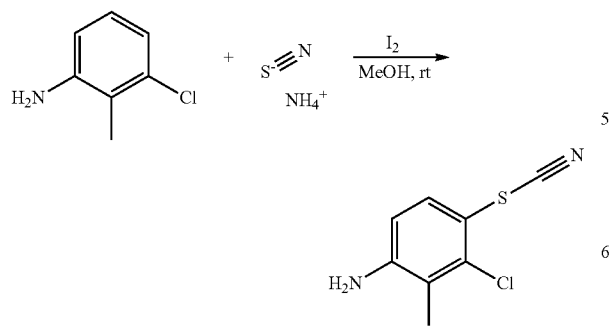

To a stirred solution of ammonium thiocyanate (1.61 g, 0.02 mol) and iodine (1.79 g, 7.1 mmol) in methanol was added 3-chloro-2-methylaniline (0.84 mL, 7.1 mmol) dropwise. The mixture was allowed to stir at room temperature for 2 days after which time water (50 mL) was added and the mixture was extracted with dichloromethane (4×50 mL). The extracts were washed with a 15% aqueous solution of sodium thiosulfate (100 mL) then dried ($Na_2SO_4$) and the solvent removed in vacuo to afford 4-amino-2-chloro-3-methylphenyl thiocyanate as a brown solid (1.26 g, 90%). Material was used crude in subsequent steps.

Step B,C 3-chloro-4-[(2-chloropyrimidin-4-yl)thio]-2-methylaniline

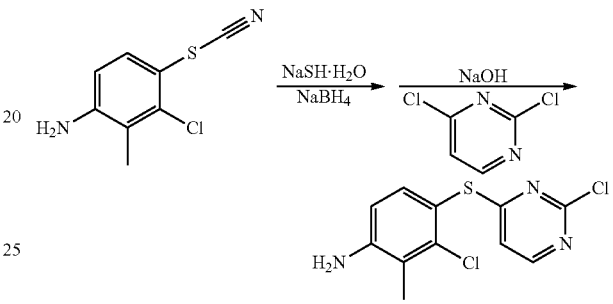

Crude 4-amino-2-chloro-3-methylphenyl thiocyanate (600 mg, 3.0 mmol) was dissolved in a mixture of methanol:water (2:1, 22 mL) and cooled to 0° C. Sodium hydrosulfide monohydrate (338 mg, 4.6 mmol) and sodium borohydride (447 mg, 11.8 mmol) were added then the mixture was allowed to warm to room temperature and stir overnight. After this time sodium hydroxide (96 mg, 2 4 mmol) was added followed by 2,4-dichloropyrimidine (360 mg, 2 4 mmol) and the mixture allowed to stir for a further 24h. The methanol was removed in vacuo and then the mixture was extracted with ethyl acetate. The extracts were dried ($Na_2SO_4$) and evaporated then the residue was purified by flash chromatography to afford 3-chloro-4-[(2-chloropyrimidin-4-yl)thio]-2-methylaniline (353 mg, 41%).

Synthesis of Thiols from Aryl Halides and Subsequent Reaction with Dichloropyrimidine

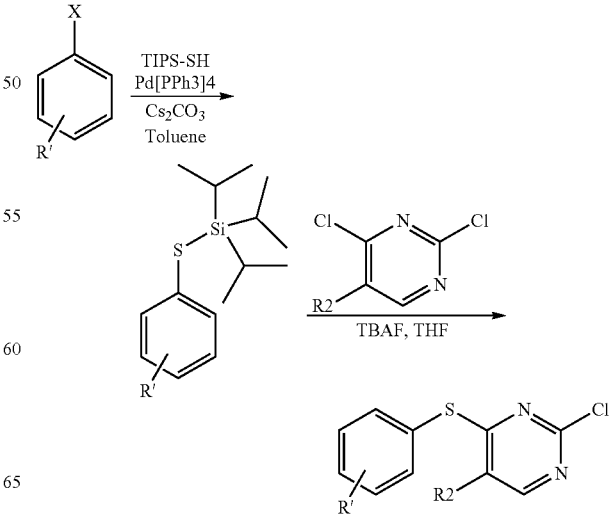

Example I

4-[(2-chloro-5-methylpyrimidin-4-yl)thio]-2-(trifluoromethyl)aniline

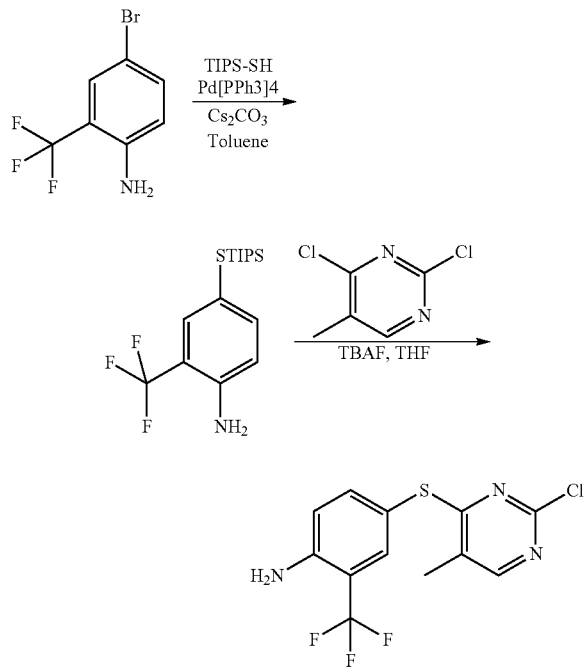

A mixture of Pd[PPh₃]₄ (75 mg, 0.065 mmol) and Cs₂CO₃ (550 mg, 1.69 mmol) was evacuated and purged with nitrogen. Toluene (12 mL) was then added followed by 4-bromo-2-(trifluoromethyl)aniline (187 µL, 1.33 mmol) and Triisopropylsilanethiol (TIPS-SH) (363 µL, 1.69 mmol). The mixture was heated at 100° C. for 24 h then cooled to room temperature. Saturated aqueous NH₄Cl (5 mL) was added then diluted with water and extracted twice with EtOAc. The combined extracts were washed with water, brine then dried (Na₂SO₄). The solvent was removed under reduced pressure to give the crude TIPS thiophenol as a dark red oil (675 mg). This oil was dissolved in THF (13 mL), 2,4-dichloro-5-methylpyrimidine (190 µL, 1.62 mmol) was added and the solution was cooled to 0° C. Tetrabutyl ammonium fluoride (TBAF) (1.0 M in THF, 2.6 mL, 2.6 mmol) was added dropwise and the mixture was allowed to warm to room temperature and stirred for 3 h. Water was added and the mixture was extracted three times with EtOAc. The combined extracts were washed with water, brine then dried (Na₂SO₄). Solvent removal under reduced pressure and the resulting residue was purified by silica gel chromatography with 30% EtOAc/Petrol as eluent to give 4-[(2-chloro-5-methylpyrimidin-4-yl)thio]-2-(trifluoromethyl)aniline (410 mg, 95%). ¹H NMR (CDCl₃, 300 MHz) δ 8.07 (d, J=0.9 Hz, 1 H), 7.58 (d, J=2.4 Hz, 1 H), 7.43 (dd, J=8.7, 2.4 Hz, 1 H), 6.81 (d, J=8.4 Hz, 1 H), 4.43 (br s, 2 H), 2.25 (d, J=0.6 Hz, 3 H); LRMS (ESI): m/z calcd for [M+H]⁺ 320.0, found 320.2.

Example II

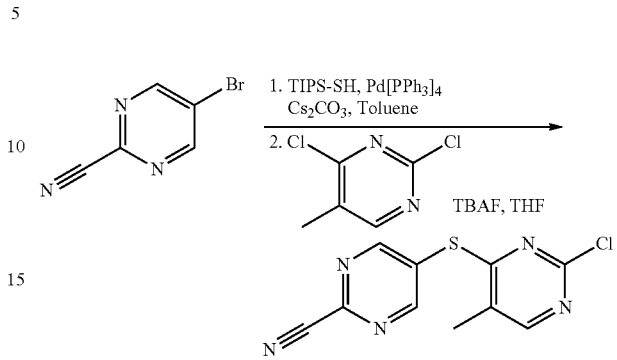

A mixture of 4-bromo-2-cyanopyrimidine (280 mg, 1.52 mmol), Pd[PPh₃]₄ (86 mg, 0.074 mmol) and Cs₂CO₃ (628 mg, 1.93 mmol) was evacuated and purged with nitrogen. Toluene (15 mL) was then added followed by TIPS-SH (413 µL, 1.92 mmol). The mixture was heated at 100° C. for 22 h and the resulting orange suspension was then cooled to 0° C. 2,4-Dichloro-5-methylpyrimidine (267 µL, 2.28 mmol) was then added followed by tetrabutyl ammonium fluoride (1.0 M in THF, 3.8 mL, 3.8 mmol) dropwise. The mixture was stirred at 0° C. for 30 min then allowed to warm to room temperature and stirred for 6 h. The reaction was quenched with saturated aqueous NH₄Cl and the mixture was extracted three times with EtOAc. The combined extracts were washed with water, brine then dried (Na₂SO₄). Solvent removal under reduced pressure and purification by silica gel chromatography with 100% dichloromethane then 1% EtOAc/dichloromethane as eluent gave 5-(2-chloro-5-methylpyrimidin-4-ylthio)pyrimidine-2-carbonitrile (327 mg, 82%) as a pale yellow solid: ¹H NMR (300 MHz, CDCl₃): δ 8.97 (s, 2H), 8.25 (s, 1H), 2.35 (s, 3H); Std LC-MS; rt 6.30 min; m/z 264.1 [M+H]+; purity 96% at 254 nm.

Example 1

2-Chloro-4-(phenylthio)pyrimidine

To a stirred solution of 2,4-dichloropyrimidine (1.00 g, 6.71 mmol) in absolute ethanol (10 mL), was added sodium salt of benzenethiol (0.89 g, 6.73 mmol) in small portions. The mixture was stirred at room temperature for 2 hours, then at 40° C. for 16 hours. It was diluted with ethyl acetate (20 mL), and filtered. The filtrate was concentrated in vacuo, and the residue was flash chromatographed on silica gel using ethyl acetate:petroleum ether (1:99→25:75) as eluant to give the desired product (498 mg, 36%).

1H-n.m.r. (CDCl₃): δ 6.62 (d, 1H, J=5.4 Hz, pyrimidine-H), 7.47-7.54 (m, 3H, Ar—H), 7.59-7.62 (m, 2H, Ar—H), 8.18 (d, 1H, J=5.4 Hz, pyrimidine-H).

The minor-isomer, 4-chloro-2-(phenylthio)pyrimidine was also obtained (274 mg, 20%). 1H-n.m.r. (CDCl₃): δ 7.58-7.63 (m, 2H, Ar—H), 7.69-7.73 (m, 1H, Ar—H), 8.03 (d, 1H, J=4.8 Hz, pyrimidine-H), 8.06-8.09 (m, 2H, Ar—H), 8.92 (d, 1H, J=4.8 Hz, pyrimdine-H).

Example 2

Methyl 4-(2-chloropyrimidin-4-ylthio)benzoate

To a sodium hydroxide (2.38 g, 59 mmol) solution in methanol (50 mL) and water (5 mL), was added dropwise a solution of methyl 4-mercaptobenzoate (9.00 g, 54 mmol) in methanol (100 mL). The mixture was stirred at room temperature for 1 hour, to this was added methanol solution (100 mL) of 2,4-dichloropyrimidine (8.77 g, 59 mmol) over 5 minutes. The whole was stirred at room temperature for 16 hours. Methanol was removed in vacuo, and the residue was partitioned between ethyl acetate (200 mL) and water (100 mL). The organic layer was separated and dried ($Na_2SO_4$). Removal of the solvent in vacuo yielded the product (14.60 g, 97%).

Example 3a 4-(2-Chloropyrimidin-4-ylthio)benzenamine

To a suspension of sodium hydride (60% dispensed in mineral oil, 0.97 g, 24 mmol) in anhydrous tetrahydrofuran (80 mL), was added 4-aminobenzenethiol (2.77 g, 22 mmol) dissolved in tetrahydrofuran (20 mL) over 5 minutes. The mixture was stirred at room temperature for 30 minutes, to this was added a solution of 2,4-dichloropyrimidine (3.00 g, 20 mmol) dissolved in tetrahydrofuran (20 mL) over 5 minutes. The resulting mixture was stirred at room temperature for 64 hours, diluted with ethyl acetate (100 mL), washed with water and brine. After being dried ($Na_2SO_4$), the organic solution was concentrated in vacuo. The residue was flash chromatographed on silica gel using 5% of acetone in dichloromethane as eluant to give the product (3.60 g, 75%).

Example 3b

4-[(2-chloro-5-methylpyrimidin-4-yl)thio]aniline

Sodium hydroxide (2.38 g, 5.9 mmol) was dissolved in water (10 mL), 4-aminothiophenol (6.77 g, 5 4 mmol) was added as a solution in methanol (25 mL) and the reaction was stirred at room temperature for 30 minutes. 2,4-Dichloro-5-methylpyrimidine (7.05 g, 4 3 mmol) was slowly added as a solution in methanol (25 mL) and the reaction was stirred at room temperature for a further 1 hour during which time a precipitate formed. This precipitate was isolated by filtration, washed with minimum ice cold diethyl ether and dried under vacuum to give 4-[(2-chloro-5-methylpyrimidin-4-yl)thio]aniline (8.49 g, 92%).

Example 4

3-(2-Chloropyrimidin-4-ylthio)benzenamine

In a procedure analogous to Example 3, reaction of 4-aminobenzenethiol (4.62 g, 37 mmol) and 2,4-dichloropyrimidine (5.00 g, 34 mmol) furnished the product (7.98 g, 100%).

Example 5

2-Chloro-4-(pyrimidin-2-ylthio)pyrimidine

In a procedure analogous to Example 3, reaction of pyrimidine-2-thiol (415 mg, 3.70 mmol) and 2,4-dichloropyrimidine (500 mg, 3.36 mmol) furnished the product (705 mg, 93%).

Example 6

N1-(4-(phenylthio)pyrimidin-2-yl)benzene-1,3-diamine

To a stirred mixture of 2-chloro-4-(phenylthio)pyrimidine (300 mg, 1.35 mmol) and diisopropylethylamine (0.35 mL, 2.02 mmol) in 2-ethoxyethanol (2 mL), was added 1,3-phenylenediamine (291 mg, 2.70 mmol) in one portion. The whole was heated under reflux for 20 hours. The mixture was cooled to room temperature, diluted with ethyl acetate (20 mL), washed with water and brine. The organic solution was dried ($Na_2SO_4$), concentrated in vacuo. The residue was flash chromatographed on silica gel using ethyl acetate:petroleum ether (20:80→50:50) as eluant to give the product (167 mg, 42%).

Example 7

N1-(4-(pyridin-2-ylthio)pyrimidin-2-yl)benzene-1,3-diamine

In a procedure analogous to Example 6, reaction of 2-chloro-4-(pyridin-2-ylthio)pyrimidine (100 mg, 0.45 mmol) and 1,3-phenylenediamine (193 mg, 1.78 mmol) furnished the product (40 mg, 30%).

Example 8

Methyl 4-(2-(4-morpholinophenylamino)pyrimidin-4-ylthio)benzoate (Compound 66)

To a stirred mixture of methyl 4-(2-chloropyrimidin-4-ylthio)benzoate (3.80 g, 14 mmol) and 4-morpholinoaniline (2.89 g, 16 mmol) in 1,4-dioxane (100 mL), was added p-toluensulfonic acid monohydrate (2.57 g, 14 mmol) in one portion. The whole was heated at 100° C. for 16 hours, cooled to room temperature, and poured into water (200 mL). The precipitate was collected by filtration, washed repeatedly with 2% aqueous citric acid, water, and ethyl acetate. It was then dried under high vacuum to afford the product (2.90 g, 51%).

Example 9

N-(4-(2-(4-morpholinophenylamino)pyrimidin-4-ylthio)phenyl)acrylamide (Compound 25)

In a procedure analogous to Example 8, reaction of N-(4-(2-chloropyrimidin-4-ylthio)phenyl)acrylamide (540 mg, 1.85 mmol) and 4-morpholinoaniline (400 mg, 2.24 mmol) furnished the product (430 mg, 54%).

Example 10

N-(3-(2-(4-morpholinophenylamino)pyrimidin-4-ylthio)phenyl)acrylamide (Compound 23)

In a procedure analogous to Example 8, reaction of N-(3-(2-chloropyrimidin-4-ylthio)phenyl)acrylamide (1.10 g, 3.77 mmol) and 4-morpholinoaniline (806 mg, 4.52 mmol) furnished the product (690 mg, 43%).
1H-n.m.r. ($CDCl_3$): δ P84, book 155

Example 11

N-(3-(2-(3,4,5-trimethoxyphenylamino)pyrimidin-4-ylthio)phenyl)acrylamide (Compound 51)

In a procedure analogous to Example 8, reaction of N-(3-(2-chloropyrimidin-4-ylthio)phenyl)acrylamide (100 mg, 0.34 mmol) and 3,4,5-trimethoxyaniline (75 mg, 0.41 mmol) furnished the product (20 mg, 14%).

Example 12

(E)-N-(3-(2-(4-morpholinophenylamino)pyrimidin-4-ylthio)phenyl)but-2-enamide (Compound 54)

In a procedure analogous to Example 8, reaction of (E)-N-(3-(2-chloropyrimidin-4-ylthio)phenyl)but-2-enamide (103 mg, 0.26 mmol) and 4-morpholinoaniline (47 mg, 0.26 mmol) furnished the product (81 mg, 69%).

Example 13

Methyl 3-(2-(4-morpholinophenylamino)pyrimidin-4-ylthio)benzoate (Compound 48)

In a procedure analogous to Example 8, reaction of methyl 3-(2-chloropyrimidin-4-ylthio)benzoate (310 mg, 1.84 mmol) and 4-morpholinoaniline (394 mg, 2.21 mmol) furnished the product (410 mg, 87%).

Example 14

4-(4-(1H-tetrazol-1-yl)phenylthio)-N-(4-morpholinophenyl)pyrimidin-2-amine (Compound 80)

In a procedure analogous to Example 8, reaction of 4-(4-(1H-tetrazol-1-yl)phenylthio)-2-chloropyrimidine (100 mg, 0.34 mmol) and 4-morpholinoaniline (75 mg, 0.41 mmol) furnished the product (56 mg, 38%).

Example 15

N-(3-(4-(phenylthio)pyrimidin-2-ylamino)phenyl)acrylamide (Compound 16)

To a stirred solution of N1-(4-(phenylthio)pyrimidin-2-yl)benzene-1,3-diamine (80 mg, 0.27 mmol) and acrylic acid (37 µL, 0.54 mmol) in anhydrous dichloromethane (2 mL), was added 1-[3-(dimethylamino)propyl]-3-ethylcarbodiimide hydrochloride salt (78 mg, 0.41 mmol), triethylamine (114 µL, 0.82 mmol) and 4-pyrrolidinopyridine (5 mg). The resulting mixture was stirred at room temperature under nitrogen atmosphere for 16 hours. It was diluted with dichloromethane (20 mL), washed with water, 2.0 M aqueous sodium carbonate solution, and dried (Na$_2$SO$_4$). After removal of the solvent in vacuo, the residue was flash chromatographed on silica gel using ethyl acetate:petroleum ether (50:50→100:0) as eluant to give the desired product (31 mg, 33%).

Example 16

N-(3-(4-(phenylthio)pyrimidin-2-ylamino)phenyl)-2-cyanoacetamide (Compound 17)

In a procedure analogous to Example 15, reaction of N1-(4-(phenylthio)pyrimidin-2-yl)benzene-1,3-diamine (80 mg, 0.27 mmol) and cyanoacetic acid (46 mg, 0.54 mmol) furnished the product (46 mg, 47%).

Example 17

N-(3-(4-(pyridin-2-ylthio)pyrimidin-2-ylamino)phenyl)acrylamide (Compound 2)

In a procedure analogous to Example 15, reaction of N1-(4-(pyridin-2-ylthio)pyrimidin-2-yl)benzene-1,3-diamine (35 mg, 0.12 mmol) and acrylic acid (16 µL, 0.24 mmol) furnished the product (18 mg, 43%).

Example 18

N-(3-(2-(4-morpholinophenylamino)pyrimidin-4-ylthio)phenyl)-2-cyanoacetamide (Compound 24)

In a procedure analogous to Example 15, reaction of 4-(3-aminophenylthio)-N-(4-morpholinophenyl)pyrimidin-2-amine (50 mg, 0.13 mmol) and cyanoacetic acid (23 mg, 0.26 mmol) furnished the product (38 mg, 64%).

Example 19

N-(4-(2-(4-morpholinophenylamino)pyrimidin-4-ylthio)phenyl)-2-cyanoacetamide (Compound 26)

In a procedure analogous to Example 15, reaction of 4-(4-aminophenylthio)-N-(4-morpholinophenyl)pyrimidin-2-amine (60 mg, 0.16 mmol) and cyanoacetic acid (46 mg, 0.32 mmol) furnished the product (48 mg, 68%).

Example 20

N-(3-(2-chloropyrimidin-4-ylthio)phenyl)acrylamide

In a procedure analogous to Example 15, reaction of 3-(2-chloropyrimidin-4-ylthio)benzenamine (300 mg, 1.26 mmol) and acrylic acid (173 µL, 2.52 mmol) furnished the product (250 mg, 68%).

Example 21

N-(4-(2-chloropyrimidin-4-ylthio)phenyl)acrylamide

In a procedure analogous to Example 15, reaction of 4-(2-chloropyrimidin-4-ylthio)benzenamine 2-chloro-4-(4'-aminothiophenyl)pyrimidine (800 mg, 3.37 mmol) and acrylic acid (463 µL, 6.74 mmol) furnished the product (550 mg, 56%).

Example 22

N-(4-(4-(4-methoxyphenylthio)pyrimidin-2-ylamino)phenyl)acrylamide (Compound 39)

In a procedure analogous to Example 15, reaction of N1-(4-(4-methoxyphenylthio)pyrimidin-2-yl)benzene-1,4-diamine (80 mg, 0.23 mmol) and acrylic acid (24 µL, 0.46 mmol) furnished the product (48 mg, 55%).

Example 23

N-(4-(4-(4-methoxyphenylthio)pyrimidin-2-ylamino)phenyl)methacrylamide (Compound 41)

In a procedure analogous to Example 15, reaction of N1-(4-(4-methoxyphenylthio)pyrimidin-2-yl)benzene-1,4-diamine (80 mg, 0.23 mmol) and methacrylic acid (50 mg, 0.46 mmol) furnished the product (42 mg, 47%).

Example 24

N-(4-(2-(4-morpholinophenylamino)pyrimidin-4-ylthio)benzyl)acrylamide (Compound 111)

In a procedure analogous to Example 15, reaction of 4-(4-(aminomethyl)phenylthio)-N-(4-morpholinophenyl)pyrimidin-2-amine (70 mg, 0.18 mmol) and acrylic acid (19 mg, 0.27 mmol) furnished the product (22 mg, 27%).

Example 25

4-(2-(4-Morpholinophenylamino)pyrimidin-4-ylthio)-N-(cyanomethyl)benzamide (Compound 72)

In a procedure analogous to Example 15, reaction of 4-(4-(aminomethyl)phenylthio)-N-(4-morpholinophenyl)pyrimidin-2-amine (70 mg, 0.18 mmol) and cyanoacetic acid (23 mg, 0.27 mmol) furnished the product (5 mg, 6%).

Example 26

N-(3-(2-(4-morpholinophenylamino)pyrimidin-4-ylthio)benzyl)acrylamide (Compound 112)

In a procedure analogous to Example 15, reaction of 4-(3-(aminomethyl)phenylthio)-N-(4-morpholinophenyl)pyrimidin-2-amine (60 mg, 0.15 mmol) and acrylic acid (16 mg, 0.23 mmol) furnished the product (21 mg, 31%).

Example 27

(3-(2-(4-Morpholinophenylamino)pyrimidin-4-ylthio)phenyl)methanol (Compound 62)

To a stirred mixture of methyl 3-(2-(4-morpholinophenylamino)pyrimidin-4-ylthio)benzoate (4.00 g, 9.46 mmol) in anhydrous tetrahydrofuran, was added lithium aluminum hydride (360 mg, 9.46 mmol) in small portions while the mixture was gently warmed to 40° C. The mixture was stirred at this temperature for about 4 hours. It was then cooled on an ice bath, cold 10% aqueous sodium bicarbonate solution was added slowly to quench the reaction. The whole mixture was partitioned between ethyl acetate and 10% aqueous sodium bicarbonate solution. The aqueous layer was re-extracted with ethyl acetate. The combined organic layer was washed with brine, dried ($Na_2SO_4$). Removal of the solvent in vacuo afforded the product (2.50 g, 80%).

Example 28

4-(3-(Bromomethyl)phenylthio)-N-(4-morpholinophenyl)pyrimidin-2-amine (Compound 132)

To a stirred mixture of tetrabromomethane (370 mg, 1.12 mmol) and triphenylphosphine (293 mg, 1.12 mmol) in dichloromethane (10 mL), was added (3-(2-(4-morpholinophenylamino)pyrimidin-4-ylthio)phenyl)methanol (400 mg, 1.01 mmol) portionwise. After being stirred at room temperature for 1 hour, another batch of tetrabromomethane (370 mg, 1.12 mmol) and triphenylphosphine (293 mg, 1.12 mmol) was added to the mixture and the whole was stirred at room temperature for 1 hour. All of the volatiles were removed in vacuo, and the residue was flash chromatographed on silica gel using ethyl acetate:dichloromethane (0:100→10:90) as eluant to give the product (208 mg, 45%).

Example 29

2-(1-(3-(2-(4-Morpholinophenylamino)pyrimidin-4-ylthio)benzyl)-1H-imidazol-4-yl)acetonitrile (Compound 128)

To a stirred mixture of 4-(3-(bromomethyl)phenylthio)-N-(4-morpholinophenyl)pyrimidin-2-amine (100 mg, 0.22 mmol) and 4-cyanomethyl imidazole (47 mg, 0.44 mmol) in dimethyl formamide (2 mL), was added cesium carbonate (154 mg, 0.44 mmol) in one portion. The mixture was stirred at room temperature for 16 hours. It was filtered to remove any inorganic material, and the dimethyl formamide solution was concentrated in vacuo. The residue was column chromatographed on the silica gel using methanol:dichloromethane (4:96) as eluant to give the product (50 mg, 47%).

Example 30

2-(1-(4-(2-(4-Morpholinophenylamino)pyrimidin-4-ylthio)benzyl)-1H-imidazol-4-yl)acetonitrile (Compound 90)

In a procedure analogous to Example 29, reaction of 4-(3-(bromomethyl)phenylthio)-N-(4-morpholinophenyl)pyrimidin-2-amine (100 mg, 0.22 mmol) and 1,3-imidazole (30 mg, 0.44 mmol) furnished the product (43 mg, 44%).

Compound Analysis $^1$H NMR data was acquired on a Bruker 300 MHz NMR Spectrometer.

LC-EI-MS and EI-MS

General Parameters:

LC-EI-MS and EI-MS data was acquired on a Waters 2795 Alliance HPLC coupled to a Waters 2996 Photodiode Array Detector and Integrity TMD Electron Impact Mass Spectrometer operating under control of Waters Millenium$^{32}$ software version 4.0 with the settings outlined below.

Mass Spectrometer Parameters:

Helium flow of approximately 0.36 L/min; acquisition mode set to scan; sampling rate of 1 spectra/sec; source temperature 200° C.; nebuliser temperature 80° C.; expansion region temperature 75° C.; mass range m/z 100-550, m/z 100-650 or m/z 100-700 as required.

HPLC Parameters

LC-MS parameters were as described for each of the methods outlined below. EI-MS samples were injected and analysed with no column present, with a solvent flow rate of 0.25 mL/min.

LC-ESI-MS

General Parameters:

LC-ESI-MS data was acquired on a Waters 2695Xe HPLC coupled to a Waters 2996 Photodiode Array Detector and Waters ZQ Mass Spectrometer operating under electrospray ionization conditions with Masslynx software version 4.1 with the settings outlined below.

Mass Spectrometer Parameters:

| Time | % MilliQ water | % ACN | % (0.5% aq formic acid) | Curve |
|---|---|---|---|---|
| 0 | 90 | 0 | 10 | — |
| 0.5 | 90 | 0 | 10 | 6 |
| 7.5 | 0 | 90 | 10 | 6 |
| 10.5 | 0 | 90 | 10 | 6 |
| 11.5 | 90 | 0 | 10 | 6 |
| 14.5 | 90 | 0 | 10 | 6 |

HPLC Parameters:

Were as described for each of the methods outlined below.

Specific LC-MS Method Details

Method A (LC-EI-MS)
Solvent Gradient:

| | |  | |
|---|---|---|---|
| Mass range: | m/z 100-650 | | |
| Scan time: | 0.5 | | |
| Inter scan delay: | 0.1 | | |
| Desolvation gas: | 500 L/h N$_2$ | Capillary: | +3.3 kV |
| Cone Gas: | 100 L/h N$_2$ | Cone Voltage: | +30 V |
| Desolvation Temperature: | 400° C. | Extractor: | 3 V |
| Source Temperature: | 120° C. | RF lens: | 0.0 V |

Flow rate: 0.25 mL/min
Column Heater: 35° C.
Column: one of
    Alltima HP C$_{18}$ 2.1×150 mm, 5 micron
    XTerra MS C$_{18}$, 3.0×100 mm, 3.5 micron
    XBridge C$_{18}$, 3.0×100 mm, 3.5 micron
Method B (LC-EI-MS)
Solvent Gradient:

| Time | % MilliQ water | % ACN | Curve |
|---|---|---|---|
| 0 | 90 | 10 | — |
| 7 | 0 | 100 | 6 |
| 9 | 0 | 100 | 6 |
| 10 | 90 | 10 | 6 |
| 13 | 90 | 10 | 6 |

Flow rate: 0.25 mL/min
Column: one of
    Alltima HP C$_{18}$ 2.1×150 mm, 5 micron
    XTerra MS C$_{18}$, 3.0×100 mm, 3.5 micron
    XBridge C$_{18}$, 3.0×100 mm, 3.5 micron
Method C (LC-ESI-MS)
Solvent Gradient:

| Time | % MilliQ water | % ACN | Curve |
|---|---|---|---|
| 0 | 90 | 10 | 1 |
| 5 | 0 | 100 | 6 |
| 6 | 0 | 100 | 6 |
| 7 | 90 | 10 | 6 |
| 10 | 90 | 10 | 6 |

Flow rate: 0.25 mL/min
    Column: XTerra MS C$_{18}$, 2.1×50 mm, 3.5 micron
Method D (LC-ESI-MS)
Solvent Gradient:

| Time | % MilliQ water | % ACN | % 0.5% formic acid$_{(aq)}$ | Curve |
|---|---|---|---|---|
| 0 | 90 | 0 | 10 | 1 |
| 0.5 | 90 | 0 | 10 | 1 |
| 5.5 | 0 | 90 | 10 | 1 |
| 7.5 | 0 | 90 | 10 | 6 |
| 8.5 | 90 | 0 | 10 | 6 |
| 11.5 | 90 | 0 | 10 | 6 |

Flow rate: 0.25 mL/min
    Column: XTerra MS C$_{18}$, 2.1×50 mm, 3.5 micron
Method E (LC-ESI-MS)
Solvent Gradient:

| Time | % MilliQ water | % ACN | Curve |
|---|---|---|---|
| 0 | 90 | 10 | |
| 7 | 0 | 100 | 6 |
| 9 | 0 | 100 | 6 |
| 10 | 90 | 10 | 6 |
| 13 | 90 | 10 | 6 |

Flow rate: 0.25 mL/min
    Column: one of
    Alltima HP C18, 2.1×150 mm, 5 micron
    XBridge C18, 3.0×100 mm, 3.5 micron
Method F (LC-ESI-MS)
Solvent Gradient:

| Time | % MilliQ water | % ACN | Curve |
|---|---|---|---|
| 0 | 90 | 10 | 1 |
| 5 | 0 | 100 | 6 |
| 6 | 0 | 100 | 6 |
| 7 | 90 | 10 | 6 |
| 10 | 90 | 10 | 6 |

Flow rate: 0.25 mL/min
    Column: Alltima HP C$_{18}$, 2.1×150 mm, 5 micron
Method G (LC-ESI-MS)
Solvent Gradient:

| Time | % MilliQ water | % ACN | % 0.5% formic acid$_{(aq)}$ | Curve |
|---|---|---|---|---|
| 0 | 90 | 0 | 10 | 1 |
| 0.5 | 90 | 0 | 10 | 1 |
| 5.5 | 0 | 90 | 10 | 1 |
| 7.5 | 0 | 90 | 10 | 6 |
| 8.5 | 90 | 0 | 10 | 6 |
| 11.5 | 90 | 0 | 10 | 6 |

Flow rate: 0.25 mL/min
    Column: Alltima HP C$_{18}$, 2.1×150 mm, 5 micron
Method H (EI-MS)
Flow rate: 0.25 mL/min ACN
    Column: None
Method I (LC-ESI-MS)
Solvent Gradient:

| Time | % MilliQ water | % ACN | Curve |
|---|---|---|---|
| 0 | 90 | 10 | |
| 7 | 0 | 100 | 6 |
| 9 | 0 | 100 | 6 |
| 10 | 90 | 10 | 6 |
| 13 | 90 | 10 | 6 |

Flow rate: 0.25 mL/min
    Column: XTerra MS C$_{18}$, 3.0×100 mm, 3.5 micron

Example 31

Enzyme Screening

Compound Dilution
    For screening purposes, compounds (in 100% DMSO) were warmed at 37 degrees for at least 20 minutes before use.

A 20 µm stock was initially made in assay buffer, where the final concentration of DMSO was 0.3%. The stocks were then diluted in 384 well Optiplates (Packard) where the final concentration of the compound was 5 µM.

Tyrosine Kinase Domain Production

Kinase domains were produced using the following procedures:

JAK1

The kinase domain of human JAK1 was amplified from U937mRNA using the polymerase chain reaction with the following primers:

XHOI-J1
[SEQ. ID. NO. 5]
5'-CCG CTC GAG ACT GAA GTG GAC CCC ACA CAT-3'

J1-KPNI
[SEQ. ID. NO. 6]
5'-CGG GGT ACC TTA TTT TAA AAG TGC TTC AAA-3'

The JAK1 PCR products were cloned into the pDest20 destination vector (Gibco). The JAK1 plasmid was then transformed into competent DH10Bac cells (Gibco), and the recombinant baculovirus was prepared via Sf9 insect cell transfection.

JAK2

The kinase domain of human JAK2 was amplified from U937mRNA using the polymerase chain reaction with the following primers:

SALI-jk2
[SEQ. ID. NO. 7]
5'-ACG CGT CGA CGG TGC CTT TGA AGA CCG GGA T-3' jk2-NOTI
[SEQ. ID. NO. 8]
5'-ATA GTT TAG CGG CCG CTC AGA ATG AAG GTC ATT T-3'

The JAK2 PCR products were cloned into the pDest20 destination vector (Gibco). The JAK2 plasmid was then transformed into competent DH10Bac cells (Gibco), and the recombinant baculovirus was prepared via Sf9 insect cell transfection.

JAK3

The kinase domain of human JAK3 was amplified from U937mRNA using the polymerase chain reaction with the following primers:

XHOI-J3
[SEQ. ID. NO. 9]
5'-CCG CTC GAG TAT GCC TGC CAA GAC CCC ACG-3'

J3-KPNI
[SEQ. ID. NO. 10]
5'-CGG GGT ACC CTA TGA AAA GGA CAG GGA GTG-3'

The JAK3 PCR products were cloned into the pDest20 destination expression vector (Gibco). The JAK3 plasmid was then transformed into competent DH10Bac cells (Gibco), and the recombinant baculovirus was prepared via SD insect cell transfection.

HCK:

The kinase domain of Human hemopoietic cell protein-tyrosine kinase (HCK) between L212 and P505 (accession number M16592) was amplified from U937 mRNA using the polymerase chain reaction.

The PCR product was cloned into the pDest20 destination vector (Gibco). The plasmid was then transformed into competent DH10Bac cells (Gibco) to produce a HCK bacmid. The recombinant baculovirus was prepared via Sf9 insect cell transfection with bacmid DNA.

CSF-1R (FMS)

The kinase domain of human CSF1-R from codon 1553 to Q961 was cloned into the pDest20 expression vector (Invitrogen). The CSF1-R plasmid was then transformed into competent DH10Bac cells (Gibco), and the recombinant baculovirus produced prepared for transfection into SD insect cells.

Large Scale Production of Kinase Domains

Baculovirus preparations from each of the constructs were infected into either one or five litres of Sf9 cells (Invitrogen) grown in SF-900 medium (Invitrogen) to a cell density of approximately $1-2 \times 10^6$ cells/ml. Cells were infected with virus at a MOI of 0.8-3.0. Cells were harvested and lysed. Tyrosine kinase domains were purified by affinity chromatography on a glutathione-agarose column (Scientifix Pty. Ltd. catalog #: GSH-200).

FLT-3 tyrosine kinase enzyme was purchased from Upstate Cell Signalling Solutions, CA, USA (flt-3 catalog #: 14-500).

Assay Protocols

Kinase assays were performed in 384 well Optiplates (Packard) using an Alphascreen Protein Tyrosine Kinase PY100 detection kit The compounds were pre-incubated with affinity purified PTK domain in the presence of phosphotyrosine assay buffer (10 mM HEPES, pH 7.5, 100 mM $MgCl_2$, 25 mM NaCl, 200 mM sodium vanadate and 0.1% Tween 20) for 20 minutes. The compounds were then incubated with substrate in the presence of ATP. The substrate used was substrate-1 with the sequence biotin-EGPWLEEEEEAYG-WMDF-$NH_2$ [SEQ. ID. NO. 13] (final concentration 111 µM). For HCK 80 µm ATP was used and incubated for 60 minutes. Alphascreen phosphotyrosine acceptor beads followed by streptavidin donor beads at a concentration of 1/100 in stop buffer were added to each well under subdued light and incubated for 2-3 hours. The Alphascreen plates were read on a Packard Fusion Alpha instrument.

Results

The enzyme assay results for selected compounds are given below in Table 2, where +++ is <100 nM, ++ is <500 nM and + is <1 µM Example 32

Cellular Screening

Compound Dilution

For screening purposes, compounds were diluted in 96 well plates at a concentration of 20 µM. Plates were warmed at 37° C. for 30 minutes before the assay was performed.

Establishment of the TEL:JAK2 Cell Line

The coding region encompassing nucleotides 1-487 of TEL was amplified by PCR using the oligonucleotides 5TEL (5'-GGA GGA TCC TGA TCT CTC TCG CTG TGA GAC-3') [SEQ ID NO 14] and 3TEL (5'-AGGC GTC GAC TTC TTC TTC ATG GTT CTG-3') [SEQ ID NO 15] and U937 mRNA as a template. A BamHI restriction site was incorporated into the STEL primer, and a Sal I restriction site was incorporated into the 3TEL primer. The regions encompassing the kinase domain of JAK2 (nucleotides 2994-3914; JAK2F 5'-ACGC GTC GAC GGT GCC TTT GAA GAC CGG GAT-3' [SEQ ID NO 16]; JAK2R 5'-ATA GTT TAG CGG CCG CTC AGA ATG AAG GTC ATT T-3') [SEQ ID NO 17] and JAK3 (nucleotides 2520-3469; JAK3F 5"-GAA GTC GAC TAT GCC TGC CAA GAC CCC ACG ATC TT-3') [SEQ ID NO 18] were generated by PCR using Taq DNA polymerase (Gibco/BRL) and U937 mRNA as a template. A Sal I restriction site was incorporated into the forward primer of JAK2 and JAK3, a Not I site was incorporated into the JAK2 reverse primer and a Xba I site was added to the reverse primer of JAK3.

A TEL/Jak2 fusion was generated by digestion of the TELPCR product with BamH I/Sal I restriction enzymes, digestion of the JAK2 PCR product with Sal I/Not I restriction enzymes, followed by ligation and subcloning of the ligation product into the mammalian expression Vector pTRE 2 (Clontech), which was prepared by digestion with BamH I-Not I restriction enzymes, to give the TEL/Jak2 fusion plasmid pTELJAK2.

The TEL/Jak3 fusion was prepared by ligation of the JAK3 Sal I/Not I cleaved kinase domain PCR product with the BamH I/Sal I restriction digested TEL product, followed by ligation of the ligation product into the BamH I/Not I digested pTRE2, to give the TEL/Jak3 fusion plasmid pTELJAK3.

The growth factor dependant myelomonocytic cell line BaF3 bearing the pTET-off plasmid (Clontech) was transfected with either pTELJAK2 or pTELJAK3, and the transfected cells were selected for growth-factor independent cell growth. The BaF3 wild-type cells were cultured in DMEM containing 10% FCS, 10% WEHI 3B conditioned medium. The BaF3 TELJAK cells (BafT_J2 or BafT_J2) were cultured in DMEM 10% Tet-System Approved FBS (without WEHI 3B conditioned medium).

Cellular Assays were Performed as Follows:

Cell suspensions were prepared by harvesting cells from culture (the cells used in this test were in late log phase growth with high viability.) Cells were diluted in the appropriate growth medium, as described above, to 1.1× final concentration (from 50,000 cell/mL to 200,000 cell/mL, depending on cell line).

Compounds to be tested were added (10 µL, 10× final concentration) to a flat bottomed 96-well plate. The cellular suspension (90 µL per well) was then added, and the plate incubated for 40 hr at 37° C., 5% $CO_2$. Alamar Blue 10 µL per well was added and the plates returned to the incubator for a further 4-6 hours. The plates were then read at 544 nm Results Cellular assay result are given in table 2 where +++ is <1 µM, ++ is <5 µM and + is <20 µM

TABLE 2

| CmpdNo. | JAK1 IC50_nM | JAK2 IC50_nM | JAK3 IC50_nM | FMS, FLT3, or HCK IC50_nM | BafT_J2 IC50_nM | BAF3wt IC50_nM | BafT_J3 IC50_nM | CTLL2 IC50_nM |
|---|---|---|---|---|---|---|---|---|
| 2 | >1000 | >1000 | +++ | | ++ | ++ | +++ | ++ |
| 3 | >1000 | >1000 | +++ | | | | | ++ |
| 7 | | >1000 | +++ | | + | + | ++ | ++ |
| 8 | | >1000 | +++ | | ++ | + | ++ | + |
| 13 | | >1000 | +++ | | + | >20000 | >20000 | >20000 |
| 16 | | >1000 | +++ | | ++ | + | +++ | ++ |
| 23 | >1000 | >1000 | +++ | | + | + | +++ | +++ |
| 24 | >1000 | ++ | | | + | + | + | + |
| 25 | >1000 | >1000 | +++ | | >20000 | >20000 | +++ | +++ |
| 27 | + | ++ | + | | >20000 | + | + | ++ |
| 31 | | >1000 | +++ | | + | + | +++ | +++ |
| 38 | | | | ++ (FMS) ++ (HCK) | | | | |
| 42 | >1000 | >1000 | +++ | | + | + | ++ | ++ |
| 52 | | >1000 | | ++ (FLT3) | ++ | | ++ | |
| 62 | >1000 | ++ | ++ | +++ (FLT3) | + | + | + | + |
| 67 | + | ++ | ++ | +++ (FLT3) | + | + | + | + |
| 68 | + | +++ | ++ | ++ (FLT3) | + | >20000 | + | >20000 |
| 74 | | >1000 | +++ | | >20000 | >20000 | +++ | ++ |
| 75 | ++ | + | ++ | | + | + | + | + |
| 77 | >1000 | >1000 | +++ | ++ (FMS) | ++ | ++ | +++ | +++ |
| 82 | >1000 | >1000 | +++ | ++ (FMS) | ++ | + | ++ | + |
| 86 | | >1000 | ++ | | + | ++ | ++ | ++ |
| 87 | | >1000 | +++ | | ++ | ++ | +++ | +++ |
| 88 | | >1000 | ++ | | ++ | ++ | ++ | + |
| 90 | | >1000 | ++ | | ++ | + | | ++ |
| 91 | | >1000 | +++ | | + | >20000 | +++ | +++ |
| 97 | | >1000 | +++ | | ++ | + | +++ | +++ |
| 99 | | >1000 | +++ | | >20000 | | +++ | |
| 101 | | >1000 | >1000 | +++ (FMS) | ++ | +++ | +++ | + |
| 104 | | >1000 | +++ | | >20000 | >20000 | ++ | ++ |
| 105 | | >1000 | +++ | | + | >20000 | +++ | + |
| 109 | >1000 | + | ++ | | + | + | + | >20000 |
| 110 | >1000 | >1000 | +++ | | + | + | +++ | ++ |
| 111 | >1000 | >1000 | +++ | | + | + | +++ | ++ |
| 112 | >1000 | >1000 | +++ | | + | >20000 | + | + |
| 117 | | >1000 | ++ | | + | ++ | >20000 | + |
| 118 | | >1000 | +++ | | ++ | >20000 | ++ | >20000 |
| 120 | | >1000 | +++ | | + | >20000 | +++ | ++ |
| 123 | >1000 | >1000 | +++ | | ++ | ++ | ++ | + |
| 124 | | >1000 | +++ | ++ (FMS) | >20000 | >20000 | +++ | +++ |
| 125 | | >1000 | +++ | | + | >20000 | ++ | ++ |
| 126 | | ++ | +++ | | ++ | >20000 | ++ | ++ |
| 127 | | + | ++ | | + | >20000 | + | + |
| 131 | | >1000 | +++ | | + | ++ | ++ | + |
| 135 | | >1000 | ++ | | + | | >20000 | |
| 136 | | >1000 | ++ | | >20000 | >20000 | >20000 | >20000 |

TABLE 2-continued

| CmpdNo. | JAK1 IC50_nM | JAK2 IC50_nM | JAK3 IC50_nM | FMS, FLT3, or HCK IC50_nM | BafT_J2 IC50_nM | BAF3wt IC50_nM | BafT_J3 IC50_nM | CTLL2 IC50_nM |
|---|---|---|---|---|---|---|---|---|
| 148 | | >1000 | ++ | | + | + | + | + |
| 149 | | >1000 | ++ | | ++ | ++ | ++ | + |
| 154 | | >1000 | ++ | | ++ | ++ | ++ | ++ |
| 155 | >1000 | >1000 | +++ | | + | + | + | ++ |
| 156 | >1000 | >1000 | +++ | | ++ | ++ | ++ | ++ |
| 161 | | >1000 | +++ | | >20000 | >20000 | +++ | ++ |
| 162 | ++ | + | +++ | | + | + | ++ | ++ |
| 163 | >1000 | >1000 | +++ | | >20000 | >20000 | +++ | +++ |
| 164 | | >1000 | +++ | | + | >20000 | +++ | +++ |
| 165 | >1000 | >1000 | ++ | | >20000 | >20000 | >20000 | >20000 |
| 166 | | >1000 | ++ | | ++ | + | + | + |
| 168 | | >1000 | +++ | | | | | |
| 169 | >1000 | >1000 | +++ | | | | | |
| 170 | | >1000 | +++ | | | | | |
| 171 | | >1000 | +++ | | >20000 | >20000 | ++ | + |
| 173 | ++ | ++ | +++ | | + | + | +++ | +++ |
| 176 | | + | + | | ++ | ++ | ++ | ++ |
| 188 | | ++ | +++ | | >20000 | >20000 | >20000 | >20000 |
| 189 | | >1000 | ++ | | + | + | + | >20000 |
| 190 | | ++ | +++ | | >20000 | >20000 | >20000 | >20000 |
| 191 | | >1000 | ++ | | ++ | ++ | ++ | ++ |
| 193 | >1000 | >1000 | +++ | | ++ | ++ | +++ | +++ |
| 194 | >1000 | >1000 | +++ | | ++ | ++ | +++ | +++ |
| 195 | | >1000 | +++ | | >20000 | >20000 | + | >20000 |
| 197 | | >1000 | +++ | | >20000 | >20000 | >20000 | >20000 |
| 199 | | + | ++ | | + | + | + | + |
| 201 | >1000 | >1000 | +++ | | ++ | ++ | ++ | ++ |
| 202 | | + | ++ | | ++ | + | ++ | ++ |
| 203 | | + | ++ | | +++ | +++ | +++ | +++ |
| 204 | | + | ++ | | ++ | + | + | + |
| 207 | | >1000 | ++ | | >20000 | | >20000 | |
| 210 | | >1000 | ++ | | >20000 | >20000 | >20000 | >20000 |
| 212 | | ++ | ++ | | >20000 | >20000 | >20000 | >20000 |
| 218 | | >1000 | ++ | | >20000 | >20000 | + | >20000 |
| 219 | | >1000 | ++ | | ++ | ++ | ++ | >20000 |
| 220 | | ++ | +++ | | ++ | ++ | ++ | +++ |
| 221 | | >1000 | ++ | | | +++ | | +++ |
| 222 | | >1000 | ++ | | >20000 | >20000 | >20000 | >20000 |
| 223 | | >1000 | ++ | | ++ | ++ | + | ++ |
| 224 | | + | ++ | | >20000 | + | >20000 | >20000 |
| 225 | | >1000 | ++ | | ++ | ++ | ++ | ++ |
| 226 | | >1000 | ++ | | ++ | | ++ | |
| 228 | | >1000 | +++ | | >20000 | >20000 | >20000 | >20000 |
| 229 | | + | ++ | | + | + | + | + |
| 230 | + | ++ | +++ | | >20000 | >20000 | >20000 | >20000 |
| 231 | >1000 | >1000 | +++ | | + | >20000 | + | + |
| 232 | | >1000 | +++ | | + | | ++ | |
| 233 | | >1000 | +++ | | ++ | ++ | +++ | ++ |
| 235 | | >1000 | +++ | | + | | +++ | |
| 237 | | >1000 | +++ | | ++ | +++ | +++ | +++ |
| 238 | | >1000 | +++ | | ++ | | +++ | |
| 239 | ++ | + | +++ | | ++ | ++ | +++ | +++ |
| 240 | | >1000 | ++ | | ++ | +++ | ++ | ++ |
| 241 | >1000 | >1000 | +++ | | ++ | + | +++ | +++ |
| 242 | | >1000 | ++ | | >20000 | >20000 | + | >20000 |
| 243 | >1000 | >1000 | +++ | | ++ | ++ | +++ | +++ |
| 244 | | ++ | +++ | | ++ | ++ | ++ | ++ |
| 245 | | ++ | ++ | | +++ | +++ | +++ | ++ |
| 246 | >1000 | >1000 | +++ | | ++ | | +++ | |
| 248 | >1000 | >1000 | +++ | | + | ++ | +++ | +++ |
| 249 | | >1000 | +++ | | ++ | ++ | +++ | +++ |
| 251 | | >1000 | +++ | | >20000 | >20000 | >20000 | >20000 |
| 252 | | >1000 | +++ | | >20000 | >20000 | | +++ |
| 253 | | >1000 | +++ | | + | >20000 | +++ | +++ |
| 254 | | >1000 | +++ | | ++ | ++ | +++ | +++ |
| 255 | | + | ++ | | + | + | + | >20000 |
| 259 | | >1000 | +++ | | + | + | +++ | +++ |
| 260 | | >1000 | +++ | | >20000 | >20000 | ++ | ++ |
| 261 | >1000 | ++ | +++ | | >20000 | >20000 | +++ | +++ |
| 262 | | ++ | ++ | | + | >20000 | >20000 | >20000 |
| 263 | | >1000 | ++ | | ++ | ++ | ++ | >20000 |
| 264 | | >1000 | ++ | | ++ | ++ | ++ | ++ |
| 267 | >1000 | >1000 | +++ | | ++ | ++ | +++ | +++ |
| 268 | >1000 | >1000 | +++ | | >20000 | >20000 | +++ | +++ |
| 269 | | >1000 | +++ | | + | | +++ | |
| 276 | | >1000 | +++ | | + | + | +++ | +++ |

TABLE 2-continued

| CmpdNo. | JAK1 IC50_nM | JAK2 IC50_nM | JAK3 IC50_nM | FMS, FLT3, or HCK IC50_nM | BafT_J2 IC50_nM | BAF3wt IC50_nM | BafT_J3 IC50_nM | CTLL2 IC50_nM |
|---|---|---|---|---|---|---|---|---|
| 277 | | >1000 | +++ | | ++ | >20000 | +++ | +++ |
| 278 | | >1000 | +++ | | ++ | | +++ | |
| 279 | | >1000 | +++ | | + | + | + | + |
| 280 | >1000 | >1000 | +++ | | + | + | +++ | +++ |
| 281 | | >1000 | +++ | | + | + | +++ | +++ |
| 282 | | >1000 | +++ | | + | + | +++ | +++ |
| 283 | | >1000 | +++ | | + | + | +++ | +++ |
| 284 | | >1000 | +++ | | + | + | +++ | +++ |
| 285 | >1000 | >1000 | +++ | | ++ | ++ | +++ | +++ |
| 286 | >1000 | >1000 | +++ | | >20000 | >20000 | +++ | +++ |
| 287 | | >1000 | +++ | | >20000 | | + | |
| 288 | >1000 | >1000 | +++ | | + | + | +++ | +++ |
| 289 | | >1000 | +++ | | + | >20000 | ++ | +++ |
| 290 | >1000 | >1000 | +++ | | + | ++ | +++ | +++ |
| 291 | >1000 | >1000 | +++ | | ++ | ++ | +++ | +++ |
| 292 | | >1000 | +++ | | >20000 | >20000 | ++ | ++ |
| 293 | >1000 | >1000 | +++ | | ++ | ++ | +++ | +++ |
| 294 | | >1000 | +++ | | >20000 | >20000 | +++ | +++ |
| 295 | >1000 | >1000 | +++ | | >20000 | >20000 | +++ | ++ |
| 296 | >1000 | >1000 | +++ | | ++ | ++ | +++ | +++ |
| 297 | >1000 | >1000 | +++ | | + | + | +++ | +++ |
| 298 | | >1000 | +++ | | + | + | +++ | +++ |
| 299 | >1000 | >1000 | +++ | | + | + | +++ | +++ |
| 301 | | >1000 | +++ | | + | + | +++ | +++ |
| 306 | >1000 | >1000 | +++ | | >20000 | >20000 | +++ | +++ |
| 307 | | >1000 | +++ | | >20000 | >20000 | + | >20000 |
| 309 | | >1000 | ++ | | ++ | ++ | ++ | +++ |
| 313 | | >1000 | +++ | | >20000 | >20000 | +++ | ++ |
| 315 | | >1000 | +++ | | >20000 | >20000 | +++ | +++ |
| 318 | | >1000 | +++ | | >20000 | + | >20000 | + |
| 328 | | >1000 | +++ | | +++ | ++ | ++ | ++ |
| 331 | | >1000 | ++ | | | | | |
| 332 | | >1000 | +++ | | ++ | ++ | +++ | ++ |
| 340 | >1000 | >1000 | +++ | | + | ++ | +++ | ++ |
| 342 | | >1000 | +++ | | >20000 | >20000 | ++ | + |
| 343 | | >1000 | +++ | | + | + | ++ | ++ |
| 346 | >1000 | >1000 | +++ | | +++ | +++ | +++ | + |
| 347 | | >1000 | +++ | | >20000 | >20000 | +++ | ++ |
| 348 | | >1000 | +++ | | ++ | | ++ | |
| 350 | | >1000 | +++ | | + | >20000 | + | + |
| 352 | | >1000 | +++ | | + | >20000 | + | + |
| 353 | | >1000 | +++ | | + | >20000 | ++ | ++ |
| 354 | | >1000 | +++ | | + | + | + | + |
| 355 | | >1000 | +++ | | + | + | ++ | ++ |
| 356 | | >1000 | +++ | | + | + | ++ | ++ |
| 357 | | >1000 | +++ | | ++ | | ++ | |
| 361 | | >1000 | +++ | | ++ | >20000 | ++ | >20000 |
| 363 | | >1000 | +++ | | | | | |
| 364 | | >1000 | +++ | | ++ | + | +++ | +++ |
| 365 | | >1000 | +++ | | + | + | ++ | + |
| 366 | | >1000 | +++ | | + | + | ++ | ++ |
| 367 | | >1000 | +++ | | + | + | ++ | + |
| 368 | | >1000 | +++ | | + | + | ++ | ++ |
| 370 | | >1000 | +++ | | + | + | ++ | ++ |
| 371 | | >1000 | +++ | | + | + | ++ | ++ |
| 372 | | >1000 | +++ | | ++ | ++ | ++ | ++ |
| 373 | | >1000 | +++ | | ++ | ++ | ++ | ++ |
| 374 | >1000 | >1000 | +++ | | ++ | ++ | +++ | + |
| 378 | | >1000 | ++ | | +++ | +++ | +++ | >20000 |
| 380 | >1000 | >1000 | +++ | | >20000 | >20000 | >20000 | >20000 |
| 381 | | >1000 | ++ | | >20000 | >20000 | + | + |
| 382 | >1000 | >1000 | +++ | | + | + | + | + |
| 383 | | ++ | +++ | | + | + | >20000 | + |
| 384 | | ++ | +++ | | >20000 | >20000 | >20000 | >20000 |
| 385 | >1000 | >1000 | +++ | | >20000 | >20000 | +++ | ++ |
| 386 | | >1000 | ++ | | >20000 | >20000 | >20000 | >20000 |
| 387 | | + | +++ | | >20000 | >20000 | >20000 | >20000 |
| 388 | | ++ | +++ | | ++ | ++ | ++ | ++ |
| 389 | >1000 | >1000 | +++ | | + | + | +++ | +++ |
| 390 | | ++ | +++ | | ++ | ++ | ++ | ++ |
| 393 | | >1000 | +++ | | + | >20000 | +++ | ++ |

Additional Enzyme Screening

Further enzyme assays were conducted at Upstate Biotechnology (Dundee, UK) in the KinaseProfiler™ Assay system.

The general protocol is as follows. All kinases are pre-diluted to a 10× working concentration prior to addition into the assay. The composition of the dilution buffer for the kinases is 20 mM MOPS pH 7.0, 1 mM EDTA, 0.1% β-mercaptoethanol, 0.01% Brij-35, 5% glycerol, 1 mg/ml BSA. All substrates are dissolved and diluted to working stocks in de-ionised water.

The results are outlined in Table 3 expressed as % inhibition.

TABLE 3

| Compound Number | Percent inhibition at 500 nM | | | | | |
|---|---|---|---|---|---|---|
| | Blk(m) | Bmx(h) | BTK(h) | Flt1(h) | Flt4(h) | KDR(h) |
| 23 | 97 | 100 | 84 | | | |
| 25 | 71 | 97 | 83 | | | |
| 42 | 59 | 100 | 100 | | | 100 |
| 51 | 29 | 100 | 100 | | | 100 |
| 59 | 100 | 100 | 100 | | | 100 |
| 71 | 49 | 36 | 27 | | | 90 |
| 74 | 100 | 100 | 100 | | | 100 |
| 77 | 100 | 100 | 100 | | | 100 |
| 87 | 100 | 100 | 100 | | | 100 |
| 97 | 100 | 100 | 100 | | | 100 |
| 99 | 100 | 100 | 100 | | | 100 |
| 104 | 30 | 100 | 73 | | | |
| 105 | 100 | 100 | 100 | | | 100 |
| 110 | 100 | 100 | 100 | | | 100 |
| 111 | 100 | 100 | 100 | | | 100 |
| 112 | 100 | 100 | 100 | | | 100 |
| 115 | 100 | 100 | 100 | | | 100 |
| 118 | 100 | 100 | 100 | | | 100 |
| 120 | 100 | 100 | 100 | | | 100 |
| 123 | 100 | 100 | 100 | | | 100 |
| 124 | 100 | 100 | 100 | 100 | 100 | 100 |
| 125 | 100 | 100 | 100 | | | 100 |
| 126 | 43 | 78 | | 93 | 99 | 95 |
| 131 | 100 | 100 | 100 | | | 100 |
| 352 | 100 | 100 | 100 | | | 100 |
| 353 | 100 | 100 | 100 | | | 100 |
| 356 | 100 | 100 | 100 | | | 100 |
| 350 | 100 | 100 | 100 | | | 100 |
| 351 | 100 | 100 | 100 | | | 100 |
| 354 | 100 | 100 | 100 | | | 100 |
| 201 | 100 | 100 | 100 | | | 100 |
| 161 | 100 | 100 | 100 | | | 100 |
| 357 | 48 | 48 | | 76 | 99 | 95 |
| 233 | 85 | 89 | | 99 | 99 | 98 |
| 162 | 50 | 55 | | 82 | 98 | 95 |
| 163 | 95 | 85 | | 83 | 99 | 92 |
| 237 | 96 | 92 | | 98 | 99 | 97 |
| 165 | 0 | 40 | | 43 | 99 | 86 |
| 164 | 62 | 87 | | 44 | 97 | 83 |
| 364 | 81 | 73 | | 97 | 99 | 96 |
| 135 | 9 | 58 | | 96 | 99 | 95 |
| 235 | 86 | 79 | | 86 | 99 | 96 |
| 238 | 99 | 90 | | 97 | 99 | 95 |
| 307 | 0 | 29 | | 19 | 93 | 72 |
| 168 | 98 | 92 | | 66 | 99 | 96 |
| 170 | 96 | 97 | | 74 | 99 | 97 |
| 241 | 98 | 92 | 88 | 100 | 100 | 97 |
| 280 | 99 | 98 | 97 | 100 | 100 | 97 |
| 285 | 97 | 98 | 91 | 95 | 98 | 94 |
| 173 | 93 | 94 | 93 | 95 | 98 | 96 |
| 239 | 99 | 99 | 97 | 100 | 100 | 96 |
| 243 | 99 | 96 | 97 | 100 | 100 | 97 |
| 286 | 88 | 95 | 74 | 98 | 100 | 94 |
| 288 | 99 | 100 | 98 | 100 | 100 | 94 |
| 340 | 99 | 92 | 97 | 100 | 95 | 94 |
| 374 | 96 | 91 | 96 | 100 | 100 | 96 |
| 291 | 99 | 99 | 95 | 100 | 100 | 96 |
| 246 | 97 | 98 | 97 | 100 | 100 | 93 |
| 267 | 96 | 89 | 94 | 100 | 100 | 94 |
| 290 | 97 | 97 | 94 | 100 | 100 | 95 |

TABLE 3-continued

| Compound Number | Percent inhibition at 500 nM | | | | | |
|---|---|---|---|---|---|---|
| | Blk(m) | Bmx(h) | BTK(h) | Flt1(h) | Flt4(h) | KDR(h) |
| 248 | 92 | 91 | 80 | 95 | 100 | 95 |
| 293 | 30 | 79 | 55 | 79 | 100 | 95 |
| 294 | 37 | 92 | 77 | 94 | 100 | 93 |
| 292 | 10 | 59 | 3 | 67 | 100 | 96 |
| 231 | 82 | 99 | 91 | 95 | 100 | 99 |
| 155 | 40 | 86 | 81 | 74 | 99 | 98 |
| 156 | 41 | 83 | 81 | 80 | 94 | 97 |

Example 33

The effect of the compounds on tumor initiation, progression and metastasis can be evaluated in relevant in vivo animal efficacy models. Models could be human tumor xenografts models in immuno-deficient mice, from human tumor cell lines or preferably from primary or metastatic human tumors. Other models might be human tumor xenografts grown in orthotopic sites, models of disseminated disease and transgenic or labeled tumors models. Models could also include surgical resection of primary tumor and evaluation of metastatic disease.

Models could be selected to ensure that the molecular drug targeted is expressed. Examples of tumors displaying deregulation of the JAK/STAT pathway include prostate carcinoma, breast cancer, colon carcinoma, including leukemia, lymphoma, myeloma, ovarian tumors, melanoma, lung carcinoma, glioma, renal-cell tumors. Efficacy can be measured in these models by various outcomes depending on tumor type (solid, leukemia or metastatic) and might include measure of tumor onset, tumor growth rate, tumor burden, tumor growth delay, tumor cell kill, incidence of metastasis, imaging of tumor and invasiveness/metastasis by various approaches including labeled cells or reagents, survival, angiogenesis, histopathology.

The in vivo animal efficacy models might also be used for determination of the additivity or synergy of the effect of the compounds in combination with other drugs, Rheumatoid arthritis (RA) is a chronic, destructive inflammatory polyarticular joint disease characterised by passive synovial proliferation and subintimal infiltration of inflammatory cells. Although the aetiology remains to be elucidated, it is generally acknowledged that RA is an autoimmune disease and arthritis is a consequence of loss of tolerance against a cartilage specific autoantigen. In this context, animal models have been established that evolves around induction of RA by an autoantigen such as 1. type II collagen-induced arthris (CIA) and 2. a combination of an antigen from gram-ve bacteria (LPS) with a panel of 4 monoclonal antibodies (mAb). A third model of arthritis is the Adjuvant-induced arthritis (AIA) which is performed mainly in rats. The underlying mechanism of AIA is still controversial. However, a 65 kD myobacterial heat shock protein was shown to share a nonapeptide sequence in the core protein molecule of proteoglycan, and suggests that AIA is also a disease inducible by autologous antigen.

In AIA, eight-week old Lewis rats were given Complete Freund's Adjuvant (CFA) prepared by suspending as an emulsion of heat-killed Mycobacterium butyricum in liquid paraffin at 12 mg/ml. CFA-induced arthritis can be stimulated by injection of 50 μl of CFA emulsion intradermally either in to the footpad or to the base of the tail. From day 7 (onset of arthritis), rats are examined daily for clinical arthritic score on a 0-4 scale: 0, normal; 1, minimal swelling; 2, medium swelling; 3, severe swelling; and 4, severe and non-weight bearing. For each limb, the mid-forpaw, the wrist, the joints of the fingers, the midfoot, the ankle and the joints of the digits are scored giving a maximum clinical score of 48 per rat. The animals are sacrificed on day 17 and the hindpaws are amputated and fixed in 7.4% formalin. After decalcification and embedment in paraffin, the limbs are sectioned in a midsagittal plane, stained by eosin and hematoxylin and examined microscopically for pannus formation (cartilage and bone erosion and destruction), vascularity (blood vessel formation by CD31 staining) and mononuclear cell infiltration (T,B and macrophages).

In CIA, DBA/1 mice that bear H-$2^q$ MHC haplotype are used as they are more susceptible to CIA. In general, heterologous collagen is used as they are more immunogenic/arthritogenic tha homologous type II collagen. The mice are primed with an emulsion consisting of bovine type II collagen and Complete-Freund's Adjuvant at a 1:1 ratio (final concentration=2 mg/ml). The emulsion (0.1 ml) is injected into the tail of each mouse approximately 1-2 cm from the base. A whitish bolus beneath the dermis should be visible. A type II collagen booster (200 µg per mouse) is given intraperitoneally in PBS on day 21. High CIA-susceptible mice (DBA/1) generally develop arthritis 4-5 weeks after initial priming. Fully developed arthritis including red and swollen paws, can be observed 3-5 days after the onset and active inflammatory arthritis persists more than 3-4 weeks. Although inflammation will eventually subside, joint damage as seen as ankylosis is permanent. Assessment of CIA symptoms is essentially similar to the AIA model in which clinical signs is assigned clinical score (0-4) based on the severity of the disease. Histological measurements can also be performed on formalin-fixed joints to assess erosin, cellular infiltrates and hyperplasia.

In combined LPS-mAB induced Arthritis, a severe and consistent arthritis can be induced in mice by a combination of LPS and mAB cocktail that recognize individual epitopes clustered within an 83 amino acid peptide fragment located within CB 11 region of type II collagen. This model was developed based on the hypothesis that bacterial toxin(s) absorbed through the GI tract play a synergistic and pathologic role with sub-arthritogenic levels of autoantibodies to type II collagen in triggering RA. The advantages of this model are: 1. synchronized arthritis (100%) is induced rapidly within 7 days 2. a variety of mouse strains can be used as administration of anti-type II collagen mAB cocktail bypasses the requirement for the host's generation of autoantibodies to type II collagen thus arthritis can be induced in mice that do not possess CIA-susceptible MHC haplotypes and 3. ease of administration of mAB and LPS by either i.v. and i.p. routes.

Inflammatory Bowel Diseases (IBD) which includes Crohn's disease (CD) and ulcerative colitis (UC) represents a group of chronic disorders characterized by inflammation of the gastrointestinal tract. CD can affect any part of the digestive track whereas UC affects only the colon and rectum. UC causes inflammation and ulcers, usually in the sigmoid colon and rectum. Cellular infiltrates are complex and pro-inflammatory cytokines are evident in CD and UC.

An experimental model of UC is established in Balb/C mice by administration of dextran sulphate sodium (3% DSS) isolated from *Leuconostoc* spp. into the drinking water. The experiment has a relatively short time-course (8 days) and parameters for assessment of colitis include loss of body weight, stool consistency, rectal bleeding, shortening of colonic length, crypt damage and cytokine analysis of colonic rings.

In CD, Balb/C mice are sensitized at day 0 with 2×50 µl of 5 mg/ml of dinitrofluobenzene (DNFB) epicutaneously to shaved abdomen and feet on two consecutive days. DNFB is typically solubilised in acetone: olive oil (4:1). On day 5, the mice are challenged intracolonically with 50 µl dintrobenzene sulphonic acid (DNS) at 6 mg/ml in 10% ethanol. The mice are sacrificed on day 8. Parameters to be measured include suppression of total blood cell number and cell types, mucosal mast cell protease 1 (MMCP-1) in serum, TNFα level in colon homogenate, stool consistency, vascular permeability and number of colonic patches. Number of neutrophils and mast cells which are indicative of colonic damage and cellular influx will also be assessed by histological and microscopical examinations.

Asthma is restricted to human species, but animal models are often used to investigate particular aspects of this human disease. Bronchial biopsies and bronchoalveolar lavage (BAL) fluid recovered from patients with asthma have been shown to contain an increased number of activated T cells, B cells, eosinophils and mast cells. Many patients with asthma are sensitized and have specific immunoglogulin E (IgE) antibodies to one or more inhalant allergens. Atopy is, considered to be a major cause of asthma. In atopic individuals, inhalation of allergens preferentially induces a T-helper 2 cell (Th2) response. In the majority of current models, mice are sensitized by itraperitoneal (ip) injection of ovalbumin (OVA), often together with a Th2 skewed adjuvant, such as alum. In the classical mouse model for asthma, C57/BL6 mice are actively sensitized on day 0 by ip injection of 10 µg of OVA absorbed onto 1 mg of alum. From day 14-21 the mice are exposed daily to aerosolized OVA over a 30 minute period. On day 22, airway inflammation is apparent. BAL fluid recovered from these animals demonstrate an increase in peri-bronchiolar space consisting of mixed cellular infiltrates of mononuclear cells and eosinophils. OVA-specific IgE antibodies can be demonstrated in the serum of sensitized animals. The mononuclear cell population consists mainly of cells of Th2 phenotype secreting cytokines IL-4 and IL-5. IL-4 promotes isotype switching of B cells towards IgE synthesis and IL-5 influences the production, maturation and activation of eosinophils.

The Compounds can Also be Tested in a Murine Model of JAK2$^{V617F}$-Positive Myeloproliferative Disease (MPD)

Establishment of JAK2$^{V617F}$-Positive MPD

Bone marrow from male 5-Fluorouracil-treated Balb/c mice could be infected with a JAK2-V617F-GFP retrovirus and retroorbitally injected into lethally irradiated female recipients. From day 21 on the mice could be monitored by daily inspection and twice weekly blood counts +FACS for GFP-positive cells. It would be expected that a rise in hematocrit could occur around day 28 and a rise of the white blood cell count around day 40.

Treatment with Compounds

Early Intervention Group: Treatment would start on day 21 with compound or carrier given per oral gavage (12 mice in each group). Mice could be monitored by daily inspection and twice weekly blood counts+FACS for GFP-positive cells. Animals would be sacrificed on day 60 8-12 h after the last drug dose. Moribund mice or mice with a white cell count over 200,000/nl or weight loss >20% could be sacrificed earlier.

Late Intervention Group: Groups of 3 mice could be sacrificed on day 29, 36, 43, 50 and 57 and bone marrow and spleen could be analyzed for reticulin fibrosis. Treatment could start with compound or carrier given per oral gavage as soon as fibrosis is documented in 3/3 mice. Mice could be monitored by daily inspection and twice weekly blood counts +FACS for GFP-positive cells Animals could be sacrificed after 30 days of therapy 8-12 h after the last drug dose. Moribund mice or mice with a white cell count over 200,000/nl or weight loss >20% could be sacrificed earlier. Animals could be subjected to necropsy.

Analysis of Tissues and Survival

Liver and spleen weights could be determined Tissue sections from bone marrow, liver and spleen could be analyzed by HE stain. Marrow and spleens could also be silver-stained to assess reticulin fibrosis. Spleen and marrow cells could be analyzed by FACS for GFP, lineage markers, JAK2 and STAT5 phosphorylation. Blood could be collected by heart puncture and plasma separated and frozen for drug concentration measurement. Survival between groups could be compared with the Kaplan-Meyer method.

Assessment of the Activity of JAK2 Inhibitors in Colony-Forming Assays of Human Hematopoietic Cells Peripheral blood mononuclear cells from patients with MPD (predominantly myelofibrosis) with and without JAK2$^{V617F}$ mutation (N=10 for each) and 5 normal controls (commercial supplier) could be isolated by density gradient centrifugation (Ficoll). CD34+ cells can be selected using commercial kits to enrich for progenitor cells. CD34+ cells can be plated in triplicate in methylcellulose supplemented with fetal bovine serum and cytokines (+/−EPO). After incubation of the plates for 2 weeks erythroid and myeloid colony formation could be assessed under an inverted microscope.

Pulmonary Arterial Hypertension

The compounds of formula I can be tested in the dog model of pulmonary hypertension as described in Gust, R and Schuster, D. P. Experimental Lung Research, 27:1-12, 2001. They can also be tested in a rabbit model of monocrotaline induced pulmonary hypertension. The compounds of formula I can also be tested in humans with pulmonary arterial hypertension. The effect of the compounds of formula I can be tested in humans with pulmonary arterial hypertension by measurement of its acute effects on cardiopulmonary hemodynamics. The effect of the compounds on right ventricular pressures, pulmonary artery pressures, pulmonary vascular resistance, and cardiac output may be determined. The effect of the compounds on the six minute walk time, and maximal oxygen consumption may be determined in humans with PAH. The effect of the compounds on quality of life (as measured by a questionnaire), hospitalization, and survival may be determined in humans with PAH. In humans PAH may be caused by genetic abnormalities (i.e., primary or familial PAH) or secondary causes such as scleroderma, uncorrected congenital heart disease, mixed collagen vascular disorder, hepatitis C, or other liver disease, HIV infection, or hereditary hemorrhagic teleangiectasia. The effect of the compounds may also be tested on human endothelial cells, fibroblasts and/or smooth muscle cell lines: for example, determination of IC50 for STAT3 phosphorylation in human pulmonary artery smooth muscle cell lines. Cell lines from other species, ie, the rat may also be examined. The effect of the compounds on precontracted vascular rings from human blood vessels, or blood vessels from other species, i.e, the rat, may be examined. For example, rat pulmonary artery rings preconstricted with phenylephrine, or endothelin, or serotonin, or vasopressin, angiotensin II, or KCL may be studied to determine the dose response to the compounds for vasorelaxation. Other vasoconstrictors may be examined.

The effect of the compounds on hypoxia induced pulmonary vasoconstriction may be examined. A model of hypoxia induced pulmonary hypertension might include study of rats, such as the Fawn-Hooded rat exposed to low oxygen (i.e., 5 percent oxygen). Another model of hypoxia induced pulmonary hypertension might include the fetal calf maintained in a high altitude chamber.

The effect of the compounds may be examined in transgenic models of pulmonary hypertension: i.e., the BMPR2 knockout mouse treated with IL6, the caveolin1 knock out mouse, or the vasoactive intestinal peptide knockout mouse.

The effect of the compounds on histopathologic changes that occur in both human and animal models of PAH may be measured. For example, the compounds may decrease the extent of plexiform lesions in the pulmonary arterioles of diseased lungs. The plexiform lesion consists of endothelial cells, smooth muscle cells, and fibroblasts which proliferate and obstruct to a varying degree, the pulmonary arteriolar lumen. All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for the treatment of a kinase associated disease, wherein said method comprises administering to a subject in need of such treatment a therapeutically effective amount of:

(a) a compound of formula I:

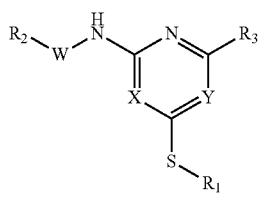

wherein:

X is N and Y is $CR_3$;
wherein each $R_3$ is independently hydrogen, $C_{1-6}$alkyl, $C_{2-6}$alkenyl, hydroxyl, halogen, nitro, substituted or unsubstituted amino, cyano, trifluoromethyl, methoxy, trifluoromethoxy, aryl, or substituted or unsubstituted 5 or 6 membered heterocyclyl containing 1 to 2 N atoms;

$R_1$ is aryl; heterocyclyl; $C_{1-6}$alkyl; or aryl substituted with one or more substituents $R_9$ or R;
wherein each $R_9$ is independently substituted or unsubstituted $C_{1-6}$alkyl, OH, $OC_{1-6}$alkyl, CN, $SR_7$, CHO, $CO_2R_7$, $COR_7$, $CONR_5R_6$, $CONR_5R_7$, $NR_5COR_7$, $NR_5R_6$, or $NR_5COOR_7$, or a heterocyclyl optionally substituted with 1 to 4 substituents selected from the group consisting of $NH_2$, CN, OH, $CO_2R_7$, $CH_2CN$, and 5 membered N-containing heterocyclyl; and
wherein $R_5$ and $R_6$ are each independently H, $C_{1-6}$alkyl, $C_{1-6}$alkylCN, $C_{3-8}$cycloalkyl, aryl, heterocyclyl, $C_{1-6}$alkylene, cycloalkyl, substituted or unsubstituted $C_{1-6}$alkylene, $SO_2C_{1-6}$alkyl, or $C_{1-6}$alkylene heterocyclyl; or $R_5$ and $R_6$ together with the nitrogen to which they are attached form a 4 to 8 membered ring having 1 to 3 heteroatoms independently selected from the group consisting of $NR_8$, O, and $S(O)_m$, wherein m is 0, 1, or 2, and wherein the ring may be optionally substituted with $C_{1-6}$alkyl or $NR_5R_6$;
wherein $R_8$ is H, $C_{1-6}$alkyl, $C_{2-6}$alkyleneOH, $C_{2-6}$alkyleneNR_5R_6, $C_{3-8}$cycloalkyl, aryl, heterocyclyl, $C_{1-6}$alkylenecycloalkyl, $C_{1-6}$alkylenearyl, $C_{1-6}$alkyleneheterocyclyl, or $C_{1-6}$alkyleneCN, $R_7$ is H, substituted or unsubstituted $C_{1-6}$alkyl, substituted or unsubstituted $OC_{1-6}$alkyl, substituted or unsubstituted $SC_{1-6}$alkyl, CNOH, $C_{1-6}$alkyleneCN, substituted or unsubstituted $C_{3-8}$cycloalkyl, substituted or unsubstituted aryl, substituted or unsubstituted heterocyclyl, $C_{1-6}$alkylenecycloalkyl, $C_{1-6}$alkylenearyl, $C_{1-6}$alkyleneheterocyclyl, $C_{2-6}$alkenyl, $C_{2-6}$alkynyl, $NR_5R_6$, $C_{1-6}$alkyleneNR_5R_6, or $C_{1-6}$alkyleneOR_5;
each R is $C_{1-6}$alkyleneR_9 or $OC_{1-6}$alkyleneR_9 (except when $R_9$ is $NR_5R_6$ or $OC_{1-6}$alkyl, then R is $OC_{2-6}$alkyleneR_9); or
$R_9$ and R together with the groups to which they are attached form a substituted or unsubstituted 5 or 6 membered N-containing heterocyclyl;

W is absent, CO, $SO_2$ or $C_{1-6}$alkylene;
$R_2$ is aryl; imidazolyl; (methylenedioxy)phenyl; or aryl substituted with one or more substituents selected from the group consisting of an N-containing 5 or 6 membered heterocyclyl; substituted or unsubstituted $OC_{1-6}$alkyl; $NR_5COR_7$ wherein in this instance only, $R_5$ is H and $R_7$ is $C_{1-6}$alkyl, $C_{2-6}$alkenyl, $C_{2-6}$alkynyl, $CH_2CN$, or CN; $NH_2$; halo; $CO_2R_7$; $SO_2NR_5R_6$; $NO_2$; $NHSO_2Me$; $CHOHCF_3CH_3$; $CH_2NHSO_2Me$; OH; and SH;
wherein each alkenyl or alkynyl is optionally substituted with 1 to 3 substituents independently selected from the group consisting of $C_{1-6}$alkyl, $CO_2R_7$, $CONR_5R_6$, aryl, heterocyclyl, $C_{1-6}$alkylene OH, and $C_{1-6}$alkyleneNH_2; and each heterocyclyl is independently a 5 to 7 membered saturated or unsaturated heterocyclyl having 1 to 4 heteroatoms independently selected from the group consisting of N, O, S, and $SO_2$;

provided that at least one of $R_1$ and $R_2$ is substituted with a substituent selected from the group consisting of:

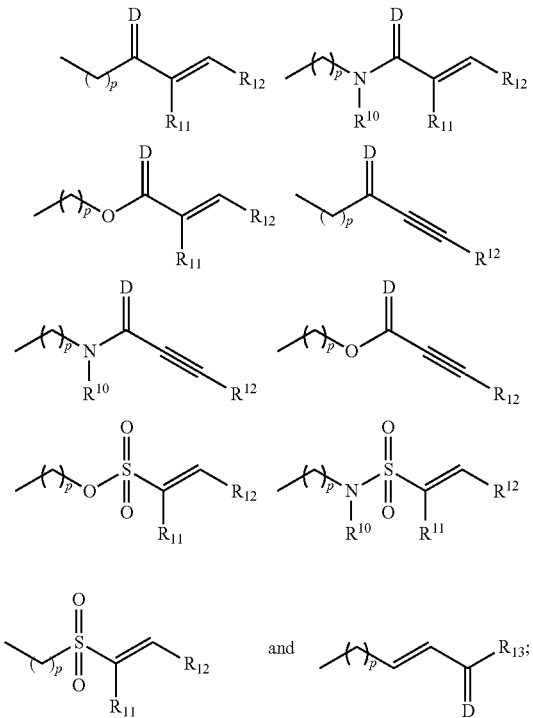

wherein

D is O or N;

$R_{10}$ is H or substituted or unsubstituted $C_{1-4}$alkyl;

$R_{11}$ and $R_{12}$ are each independently H, substituted or unsubstituted $C_{1-4}$alkylN$R_{14}R_{15}$, $C_{1-4}$alkylOR$_8$, or substituted or unsubstituted aryl, or $R_{11}$ and $R_{12}$ are joined to form a substituted or unsubstituted 5 to 8 membered ring optionally containing one or more heteroatoms selected from the group consisting of O, S, $SO_2$, and N$R_{10}$;

$R_{13}$ is OH, OC$_{1-4}$alkyl, or N$R_{14}R_{15}$;

p is 0, 1, 2, 3, or 4; and $R_{14}$ and $R_{15}$ are each independently H, or substituted or unsubstituted $C_{1-4}$alkyl, or $R_{14}$ and $R_{15}$ are joined to form a substituted 3-8 membered ring optionally containing one or more heteroatoms selected from the group consisting of O, S, $SO_2$ and N$R_{10}$;

or a salt and/or isomer thereof; or (b) a pharmaceutical composition comprising a compound of formula I or a salt and/or isomer thereof.

2. The method of claim 1, wherein the compound of formula I has the formula Ia

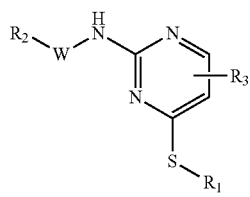

wherein W, $R_1$, $R_2$ and $R_3$ are as defined in claim 1.

3. The method of claim 1, wherein the compound of formula I has the formula Ib

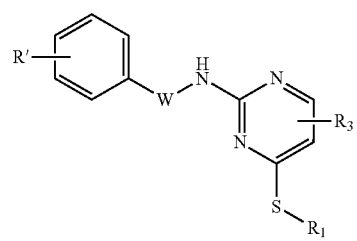

wherein W, $R_1$ and $R_3$ are as defined in claim 1, and R' is H, R, or $R_9$, wherein R and $R_9$ are as defined in claim 1.

4. The method of claim 1, wherein the compound of formula I has the formula Ic

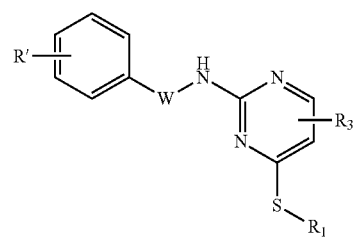

wherein W and $R_3$ are as defined in claim 1;
R' is H, R or $R_9$, wherein R and $R_9$ are as defined in claim 1, and
$R_1$ is phenyl substituted as defined in claim 1.

5. The method of claim 1, wherein W is absent, CO or $C_{1-6}$alkylene.

6. The method of claim 1, wherein $R_3$ is H; $C_{1-6}$alkyl; halo; $C_{2-6}$alkenyl; amino which may be substituted with $C_{2-6}$alkenyl; cyano; nitro; methoxy; aryl; or 5 or 6 membered heterocyclyl containing 1 or 2 N atoms which may be substituted with trimethylcarboxy.

7. The method of claim 1, wherein the therapeutically effective amount of said compound is administered using an implant, wherein said implant comprises a compound of claim 1 or a pharmaceutical composition comprising a compound of claim 1.

8. A method of claim 1, wherein the kinase associated disease is an immunological disease, an inflammatory disease, a hyperproliferative disease, a viral disease, a metabolic disease or a vascular disease.

9. A method for suppressing the immune system of a subject, wherein said method comprises administering a therapeutically effective amount of a compound of claim 1 or a pharmaceutical composition comprising a compound of claim 1.

10. A method of inhibiting a kinase in a cell, wherein said method comprises contacting the cell with a compound of claim 1.

* * * * *